US012644088B2

(12) United States Patent
Yeo et al.

(10) Patent No.: US 12,644,088 B2
(45) Date of Patent: Jun. 2, 2026

(54) SYSTEMS, METHODS, AND DEVICES FOR ELECTROPORATION OF CELL-CONTAINING FLUID

(71) Applicants: LIFE TECHNOLOGIES CORPORATION, Carlsbad, CA (US); LIFE TECHNOLOGIES HOLDINGS PTE LTD, Singapore (SG)

(72) Inventors: Steven Huei Yeo, Singapore (SG); Siu Wee Hon, Singapore (SG); Han Wei, Singapore (SG); Yvonne Peck, Singapore (SG); Way Xuang Lee, Singapore (SG); Benyong Shi, Singapore (SG); Chee Wai Chan, Singapore (SG); Beng Heng Lim, Singapore (SG); Dhanaraj Shanmugam, Singapore (SG); Stacey Mei Lin Teo, Singapore (SG); Jun Yan Tham, Singapore (SG); Kok Shyong Chong, Singapore (SG); Li Yang Lim, Singapore (SG); Michael Gordon, San Diego, CA (US); Nektaria Andronikou, San Diego, CA (US); Chris Rossman, San Diego, CA (US); Xavier De Mollerat Du Jeu, Carlsbad, CA (US); Ulrich Forke, San Diego, CA (US)

(73) Assignees: Life Technologies Corporation; Life Technologies Holdings PTE Ltd, Singapore (SG)

( * ) Notice: Subject to any disclaimer, the term of this patent is extended or adjusted under 35 U.S.C. 154(b) by 1003 days.

(21) Appl. No.: 17/079,100

(22) Filed: Oct. 23, 2020

(65) Prior Publication Data

US 2021/0123009 A1 Apr. 29, 2021

Related U.S. Application Data

(60) Provisional application No. 62/926,078, filed on Oct. 25, 2019.

(51) Int. Cl.
*C12M 1/00* (2006.01)
*C12M 1/06* (2006.01)
(Continued)

(52) U.S. Cl.
CPC ............ *C12M 35/02* (2013.01); *C12M 23/14* (2013.01); *C12M 23/44* (2013.01); *C12M 27/02* (2013.01);
(Continued)

(58) Field of Classification Search
CPC ...... C12M 35/02; C12M 23/14; C12M 23/44; C12M 27/02; C12M 29/00; C12M 41/12;
(Continued)

(56) References Cited

U.S. PATENT DOCUMENTS

| | | | |
|---|---|---|---|
| D249,708 S | 9/1978 | Smith et al. | |
| 4,800,163 A | 1/1989 | Hibi et al. | |

(Continued)

FOREIGN PATENT DOCUMENTS

| | | |
|---|---|---|
| CN | 104403943 A | 3/2015 |
| CN | 208250332 U | 12/2018 |

(Continued)

OTHER PUBLICATIONS

Maxcyte: "ExPERT GTx Manual", EX-SS-GTX Rev.C, 2019, 2 pages.

(Continued)

*Primary Examiner* — Liban M Hassan
(74) *Attorney, Agent, or Firm* — Matthew J. Hierholzer

(57) ABSTRACT

Electroporation cartridges for single use electroporation as well as electroporation cartridges for automated batch pro-
(Continued)

cessing, electroporation instruments and systems and methods of electroporation using these devices and systems. Electroporation cartridges include an electroporation chamber defined by an elongate body, a first electrode at a proximal end and a second electrode at a distal end of a chamber. Electroporation systems include one or more components including a pulse generator, compartments for placing either flow-through or single use electroporation cartridges, components for storage of cells, cooling and pre-cooling mechanisms, removably insertable modular casings having compartments for holding and arranging electroporation system and reagent components, one or more pumps for moving sample through the system, and processors and controllers.

12 Claims, 103 Drawing Sheets

(51) Int. Cl.
*C12M 1/34* (2006.01)
*C12M 1/36* (2006.01)
*C12M 1/42* (2006.01)
*C12M 3/00* (2006.01)

(52) U.S. Cl.
CPC ............ *C12M 29/00* (2013.01); *C12M 41/12* (2013.01); *C12M 41/48* (2013.01)

(58) Field of Classification Search
CPC ...... C12M 41/48; C12M 23/42; C12M 23/38; C12M 33/04; C12M 41/00; C12M 41/44; C12N 15/87
See application file for complete search history.

(56) References Cited

U.S. PATENT DOCUMENTS

| | | | |
|---|---|---|---|
| D325,881 S | 5/1992 | Brayton et al. | |
| 5,650,305 A | 7/1997 | Hui et al. | |
| D414,270 S | 9/1999 | Escoffier | |
| 6,969,604 B1 * | 11/2005 | Yakovenko | C12M 35/02 435/288.1 |
| D516,732 S | 3/2006 | Sakurai et al. | |
| 7,141,425 B2 | 11/2006 | Dzekunov et al. | |
| D564,100 S | 3/2008 | O'Banion et al. | |
| 7,704,727 B2 | 4/2010 | Siebenkotten et al. | |
| D621,523 S | 8/2010 | Onuma et al. | |
| 7,771,984 B2 | 8/2010 | Dzekunov et al. | |
| D757,958 S | 5/2016 | Murray et al. | |
| 9,340,842 B2 | 5/2016 | Arnold et al. | |
| 9,382,510 B2 | 7/2016 | Chen | |
| 9,546,350 B2 | 1/2017 | Dzekunov et al. | |
| D822,224 S | 7/2018 | Luoma, II et al. | |
| D852,979 S | 7/2019 | Liu et al. | |
| 10,336,996 B2 | 7/2019 | Altrogge et al. | |
| 10,376,889 B1 | 8/2019 | Masquelier et al. | |
| 10,435,713 B2 | 10/2019 | Bernate et al. | |
| D877,924 S | 3/2020 | Kocher et al. | |
| D888,984 S | 6/2020 | Solakian | |
| D890,361 S | 7/2020 | Nuesch et al. | |
| D901,677 S | 11/2020 | Hong et al. | |
| D901,711 S | 11/2020 | Galen et al. | |
| D907,793 S | 1/2021 | Chang et al. | |
| D907,797 S | 1/2021 | Zergiebel | |
| D927,014 S | 8/2021 | Turner | |
| D944,410 S | 2/2022 | Luther et al. | |
| D965,170 S | 9/2022 | Lim et al. | |
| D965,816 S | 10/2022 | Luther et al. | |
| D983,396 S | 4/2023 | Chan | |
| D987,076 S | 5/2023 | Williamson et al. | |
| 2002/0068338 A1 | 6/2002 | Nanda et al. | |
| 2005/0282200 A1 | 12/2005 | Dzekunov et al. | |
| 2005/0282283 A1 * | 12/2005 | Vozza-Brown | C12M 35/02 435/459 |
| 2010/0196998 A1 | 8/2010 | Jarvis et al. | |
| 2011/0065171 A1 | 3/2011 | Dzekunov et al. | |
| 2012/0003740 A1 | 1/2012 | Vozza-Brown et al. | |
| 2012/0244593 A1 * | 9/2012 | Huang | C12N 15/87 435/173.6 |
| 2013/0052711 A1 | 2/2013 | Chen | |
| 2013/0261499 A1 | 10/2013 | Kissinger et al. | |
| 2014/0062489 A1 * | 3/2014 | Pindiprolu | G01N 13/00 324/347 |
| 2014/0220665 A1 | 8/2014 | King et al. | |
| 2016/0298074 A1 | 10/2016 | Dai | |
| 2017/0283761 A1 | 10/2017 | Corso | |
| 2017/0335269 A1 | 11/2017 | Chen | |
| 2018/0051243 A1 | 2/2018 | Hogan et al. | |
| 2018/0237765 A1 | 8/2018 | Walters et al. | |
| 2019/0002814 A1 | 1/2019 | Masquelier et al. | |
| 2019/0225928 A1 | 7/2019 | Masquelier et al. | |
| 2023/0110090 A1 | 4/2023 | Ling et al. | |
| 2023/0369815 A1 | 11/2023 | Ben Shoshan et al. | |
| 2024/0150699 A1 | 5/2024 | Wei et al. | |

FOREIGN PATENT DOCUMENTS

| | | | |
|---|---|---|---|
| CN | 208577721 U | 3/2019 | |
| CN | 109679844 A | 4/2019 | |
| CN | 208883899 U | 5/2019 | |
| CN | 209243072 U | 8/2019 | |
| CN | 209243073 U | 8/2019 | |
| CN | 305512379 | 12/2019 | |
| CN | 214361426 U | 10/2021 | |
| EP | 0785987 A2 | 7/1997 | |
| EP | 1766057 A2 | 3/2007 | |
| EP | 1766057 B1 | 12/2014 | |
| JP | 2017104073 A | 6/2017 | |
| JP | 1719808 | 7/2022 | |
| JP | 1723773 | 9/2022 | |
| WO | WO-9612006 A2 | 4/1996 | |
| WO | WO-2006112870 A1 * | 10/2006 | C12M 35/02 |
| WO | WO-2018064463 A1 | 4/2018 | |
| WO | WO-2019076353 A1 | 4/2019 | |
| WO | WO-2019126212 A1 | 6/2019 | |

OTHER PUBLICATIONS

PCT/US2020/057138, Partial Search Report, Feb. 12, 2021, 9 pages.

PCT/US2020/057138, Search Report and Written Opinion, Apr. 6, 2021, 17 pages.

Facebook, "Bio-diagnostics SDN Bhd," Aug. 15, 2023, [Retrieved on Aug. 14, 2024], 1page, Retrieved from Internet: URL: https://www.facebook.com/permalink.php/story_fbid=627681559471071&id=100066876961417.

Maxcyte, "Understanding Flow Electroporation," Jun. 27, 2023, 1 page, [Retrieved on Aug. 14, 2022], at youtube.com. Retrieved from Internet: URL: https://www.youtube.com/watchv=BXXCenQGVC0.

Microbe Notes, "Microinjection," Aug. 15, 2023, [Retrieved on Aug. 14, 2022], at microbenotes.com. Retrieved from Internet: URL: https://www.facebook.com/permalink.php/story_fbid=627681559471071&id=100066876961417.

Researchgate, "In Vivo Dna Electro transfer for Immunotherapy for Cancer and Neurodegenerative Diseases," Mar. 2013, 1 page, [Retrieved on Aug. 14, 2022], at researchgate.net Retrieved from Internet: URL: https://www.researchgate.net/figure/Fig-1-Most-advanced-devices-for-intramuscular-and-intradermal-EP-The-EP-based-DNA_fig1_232282033.

* cited by examiner

*960*

Determine, by way of a conductivity sensor, the conductivity of the sub-volume within the electroporation chamber of the electroporation cartridge.  *962*

Based on the determined conductivity, determine a voltage drop across the electroporation chamber.  *964*

Determine the resistance in the electroporation circuit between the capacitor and the electroporation chamber.  *966*

Charge the capacitor to a voltage level above the determined drop in voltage across the electroporation chamber to compensate for the additional resistance between the capacitor and the electroporation chamber.  *968*

Iteratively ramp charger voltage based on a previous input voltage and a corresponding previous measured actual voltage as applied to the electroporation chamber.  *970*

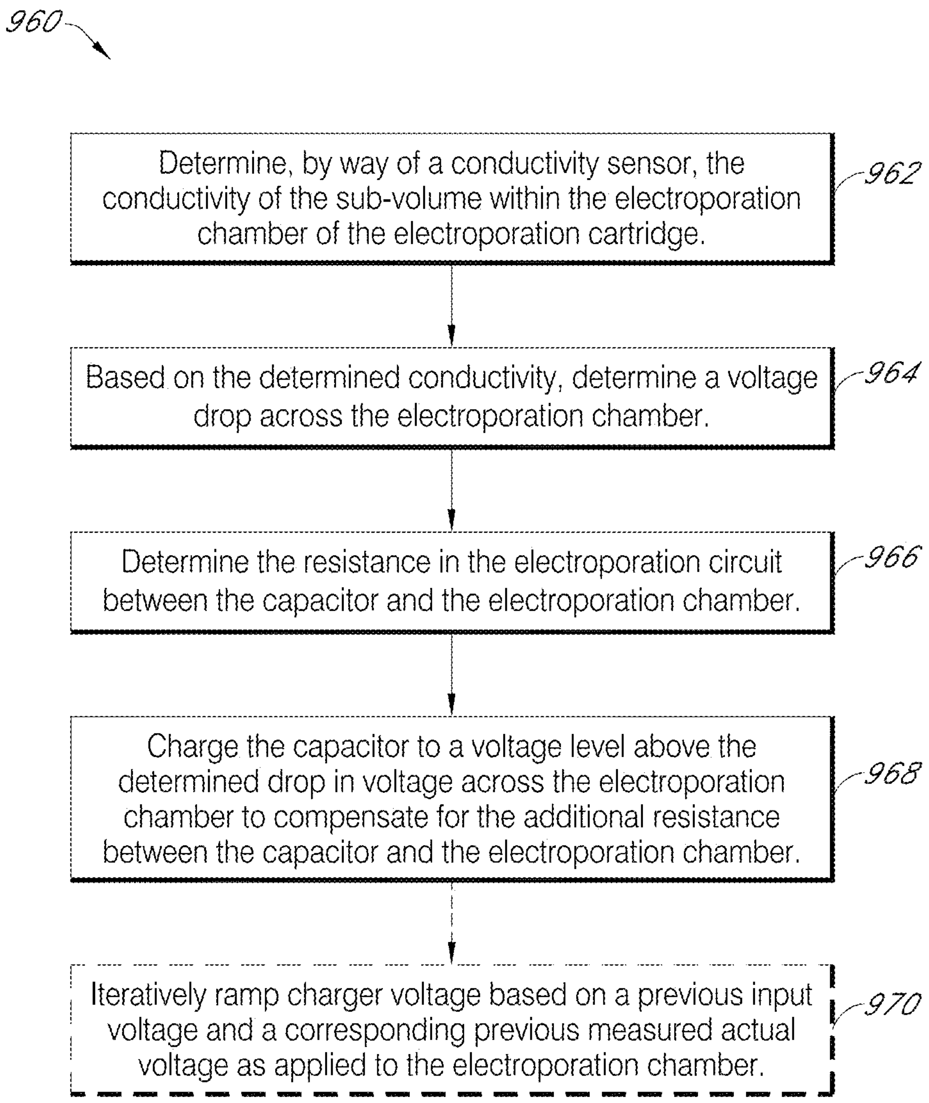

FIG. 26

SYSTEMS, METHODS, AND DEVICES FOR ELECTROPORATION OF CELL-CONTAINING FLUID

BACKGROUND

Technical Field

This disclosure generally relates to systems, devices, and methods for treating cells with transient electric fields. More specifically, the present disclosure relates to systems, devices, and methods for automated electroporation of cell-containing fluid, including single and automated batch electroporation systems, devices and methods.

Related Technology

Since at least as early as the 1970's, scientists have been using electroporation as a technique for inserting molecules into animal or plant cells. By exposing cells to transient electric fields, particularly short duration, high voltage electrical fields, cellular membranes become permeable to molecules in the surrounding media, allowing cellular uptake of target macromolecules—typically proteins and nucleic acid. When the voltage and duration of exposure to electric fields is controlled appropriately, electroporated cells are able to recover membrane permeability and normal functionality. However, overexposure to electric fields—whether for extended periods of time or at too high of a voltage, can permanently disrupt the electrical potential and/or membrane integrity of the cell, leading to cell death.

Traditionally, cellular electroporation has been implemented using specialized cuvettes containing electrodes positioned relative to one another so as to create a uniform electric field therebetween. For example, electroporation cuvettes known in the art include two flat plate electrodes attached to opposite walls of a rectangular cuvette or chamber. A suspension of cells to be electroporated is combined with an electroporation target and placed in the cuvette where an electric field pulse of high voltage and short duration is applied through the electrodes. Most commercially available electroporation cuvettes such as this are limited in capacity and can only process small amounts of cell suspension at a time, typically less than one milliliter.

However, this configuration has been preferred and retained over time because of its high efficiency and ability to maintain a more standard distribution of current through the affected media by producing a uniform electric field. Uniform electric fields help to normalize electroporation efficiency by reducing current hot spots, which could damage or destroy the cells, and by reducing current cold spots, which lead to low electroporation efficiency. However, the strength of a uniform electric field is dependent upon the potential difference, or voltage, between the electrodes and the distance between the electrodes. Increasing the distance between the electrodes weakens the electric field. Although this can be compensated for by increasing the voltage, the delicate nature of live cells has traditionally set the limits at which the voltage and/or distance can be increased between electrodes while maintaining a uniform electric field of sufficient strength to efficiently electroporate cells.

For example, to maintain a uniform electric field between two electrodes when the physical distance between the electrodes is increased, the voltage must be increased. Increasing the voltage causes the electrodes to generate more heat, which is transferred to the cell-containing fluid. This is particularly problematic in continuous flow protocols where a combination of voltage, pulse duration, and number of pulses, together with the starting temperature of the sample, quickly result in sample temperatures exceeding 60° C. or even localized vaporization of a portion of the cell-containing sample. As expected, cell viability is negatively impacted by increased temperatures, particularly when those temperatures are prolonged or within ranges incompatible with living cells. Heating and electrical discharge through an aqueous solution (i.e., almost all cell-containing fluid and/or electroporation media) can also cause bubble formation through localized vaporization of water molecules and/or through electrolysis of water molecules to form oxygen and hydrogen gas. The presence of bubbles can cause the breakdown of electrical conductivity and result in arcing, which among other things, reduces electroporation performance and can harm or destroy the sample. Accordingly, the volume of cell-containing fluid that can be electroporated has traditionally been limited.

By limiting the volume of cuvettes, it has previously been impractical to scale this type of electroporation model due to the manually intensive process of loading and unloading cuvettes. Further, maintenance of sterility is essential for nearly all applications of electroporation of large volumes of cells, and repeated loading of a cuvette and pooling of the electroporated cells is especially impractical and prone to contamination. While this method of electroporation is convenient and simple and has met the needs of many researchers carrying out small scale electroporation of cells, additional methods are needed, especially methods that could conveniently facilitate the electroporation of large volumes of cells while maintaining a sterile environment.

Electroporation of large volumes of cells in a closed sterile system would enable the use of electroporation for cell-based therapy of humans. In an attempt to address this, some continuous flow electroporation systems have been created and generally consist of parallel electrodes between which the cell containing fluid is continuously and steadily flowed until the entire volume of cells has passed through the high voltage electric fields. Problematically, however, repeated application of high voltage pulses to the electrodes of continuous flow systems resulted in the generation of too much heat. Some systems have compensated for this using cooling means to prevent the electrodes and the cell suspension from reaching too high a temperature.

Nevertheless, these continuous flow systems suffer from a lack of efficiency and reliability. For example, the hydrodynamic flow of the cell containing fluid through the electroporation chamber of continuous flow devices does not result in every cell traveling through the chamber and between the electrodes at the same rate. The rate of flow is higher away from the chamber walls compared to the rate near the chamber walls. A cell that flows between the electrodes toward the center of the fluid flow will pass between the electrodes in less time and may receive an inefficiently low number of pulses, while a cell that flows near a wall may take longer to pass between the electrodes and thereby receive too many pulses. As such, the most continuous flow systems are inherently flawed and inefficient as there are subpopulations of cells that either fail to be sufficiently electroporated by passing by the electrodes too quickly or become damaged or destroyed from overexposure to high voltage electric fields by passing too slowly by the electrodes.

Between imprecise and uneven electroporation of cells passing by the electrodes and the continuous application of an electrical field through the cell containing fluid, which causes bubble formation and excessive heat, continuous flow electroporation systems have failed to achieve sufficient throughput and efficiency to meet the need in both R&D and commercial cell therapies to transfect cells quickly and efficiently. Indeed, electroporation has to date failed to compete commercially with viral transfection, which is the most efficient and widely utilized technology. There are, however, inherent risks with using viruses to perform transfection on cells that may eventually be put back into a patient.

Accordingly, there are a number of disadvantages and problems that can be addressed for automating the electroporation of cells, and there is an outstanding need for systems, devices and methods, that can automate the process of electroporation with high efficiency, particularly those that can do so in a manner that reduces the likelihood of contamination and/or arcing caused by bubble formation within the processed cell-containing fluid.

BRIEF SUMMARY

Implementations of the present disclosure solve one or more of the foregoing or other problems in the art with systems, devices, and methods for electroporating a cell-containing fluid. The terms “cell-containing fluid” and “sample” are used interchangeably herein.

In particular, one exemplary embodiment includes an electroporation cartridge having an electroporation chamber defined by an elongate body, a first electrode disposed at a proximal end of the electroporation chamber, and a second electrode disposed at an opposite, distal end of the electroporation chamber. In some embodiments, at least one of the first electrode or the second electrode is moveable between a capped position for electroporation and an uncapped position for loading a sample for a single use or automated batch processing and/or the electroporation cartridge is configurable between sealed and unsealed states.

In one aspect, an elongate body of the disclosure can comprise, be made of or include one or more of a non-conductive plastic, a glass, and/or a ceramic and is configured to receive a cell-containing liquid to be electroporated within the electroporation chamber defined by the elongate body. For example, an electroporation chamber of the disclosure can comprise, be made of or includes a glass and/or a ceramic. As an additional example, the electroporation chamber can comprise, be made of or include polycarbonate and/or other non-conductive irradiation-stable plastic.

In one aspect, at least a portion of an electroporation chamber of the disclosure is tapered between the first electrode and the second electrode. When present, the tapered portion of the electroporation chamber does not substantially interfere with generation of a uniform electric field between the first and second electrodes.

Additionally or alternatively, an electroporation chamber of the disclosure has a uniform cross section along a length of the reaction chamber. The uniform cross section can, in some instances, extend an entire length of the electroporation chamber between the first and second electrodes such that the electroporation cartridge is configured to produce a uniform electric field within the electroporation chamber. For example, an electroporation chamber of the disclosure can be a cylindrical cavity defined by the elongate body such that the uniform cross section is a circle.

In one aspect, an electroporation cartridge of the disclosure includes a proximal sidewall defined between a proximal opening of the elongate body and an inflection point on the sidewall defining the electroporation chamber, the proximal sidewall narrowing from a first diameter defined by the proximal opening to a second, smaller diameter defined at a position distal to the inflection point.

In one aspect, a first electrode includes a bulbous extension. The bulbous extension can, in one aspect, have a substantially flat distal surface. Preferably, however, the bulbous extension has a distal surface with a convex or angled contour and is operable to displace one or more bubbles associated with a cell-containing liquid to be electroporated within the electroporation chamber upon securing the first electrode within the electroporation chamber or otherwise sealing the electroporation chamber. In either embodiment, the bulbous extension can be separated from a base portion of the first electrode by a narrow stem.

In one aspect, an electroporation cartridge of the disclosure includes a sealing member disposed between the first electrode and a proximal surface of the elongate body, the sealing member being operable to form a fluid tight connection between the first electrode and the elongate body. The first electrode can additionally include a first electrode flange, and the elongate body can include a proximal body flange. The proximal body flange can be oriented in a plane substantially parallel to the first electrode flange with the sealing member disposed between the first electrode flange and the proximal body flange, forming a fluid tight connection therebetween.

In one aspect, a first electrode is operable to configure an electroporation cartridge between sealed and unsealed states and can do so without an additional removable cap piece.

In one aspect, the first electrode is, itself, a cap. In one aspect, the first electrode is, itself, a removable cap.

In one aspect, an electroporation cartridge of the disclosure includes a removable cap secured to the first electrode. The removable cap can include a coupling member for selectively securing the first electrode to the elongate body.

In one aspect, the diameter of a proximal end of the second electrode is substantially equal to a cross section of the electroporation chamber. Additionally, or alternatively, the second electrode can include a protruding portion that extends into the electroporation chamber from a distal end of the elongate body and can have, for example, a complementary shape to the inner surface of the elongate body defining the electroporation chamber. Additionally, or alternatively, the second electrode can include a first sealing member disposed between the second electrode and a distal surface of the elongate body, the first sealing member operable to form a fluid tight connection between the second electrode and the distal surface of the elongate body. For example, the second electrode can include an electrode flange and the elongate body can include a distal body flange oriented in a plane substantially parallel to the electrode flange, and the sealing member can be positioned between the electrode flange and the distal body flange to form a fluid tight connection therebetween. Additionally or alternatively, the second electrode can include or be associated with a second sealing member disposed about the protruding portion of the second electrode and positioned distal to the proximal surface of the second electrode, the second sealing member being operable to form a fluid tight connection between the protruding portion and an inner surface of the elongate body defining the electroporation chamber.

In some aspects, the proximal surface of the second electrode includes a flat, uniform surface and/or the proximal surface of the second electrode can be orthogonal to a longitudinal axis of the electroporation chamber.

In one aspect, an electroporation cartridge of the disclosure includes a fixing pin associated with the second electrode and configured to secure the second electrode to the elongate body. For example, the second electrode can define a channel configured in size and shape to receive the fixing pin and can be aligned with a pair of apertures defined by the sidewall of the elongate body so as to receive the fixing pin and thereby secure the second electrode at a fixed position relative to the elongate body. The channel can be formed through a central region of the protruding portion of the second electrode distal to the first sealing member and/or second sealing member.

In one aspect, a volume of the electroporation chamber is less than about 5 mL, preferably less than about 3 mL, more preferably less than about 1 mL or between about 100 μL-1 mL.

In one aspect, an electroporation cartridge of the disclosure includes a volume reducing sleeve configured in size and shape to fit within the electroporation chamber. The volume reducing sleeve defines a secondary electroporation chamber having a smaller volume than the electroporation chamber and a distal opening configured to interface with the second electrode when secured within the electroporation chamber.

In one aspect, a volume reducing sleeve includes air vents disposed adjacent to the proximal end of the volume reducing sleeve that are configured to allow air to pass therethrough during introduction or extraction of the volume reducing sleeve with an electroporation chamber of the disclosure and prevent formation of a vacuum between the secondary electroporation chamber and the electroporation chamber, thereby allowing the electroporated cell-containing fluid to fill the secondary electroporation chamber upon introduction of the volume reducing sleeve and to exit the secondary electroporation chamber upon introduction upon extraction of the volume reducing sleeve.

A volume reducing sleeve of the disclosure can additionally include a radial sealing member configured to secure the volume reducing sleeve within an electroporation chamber of the disclosure. The radial sealing member can form a fluid tight seal with the sidewall defining the electroporation chamber to prevent leakage of cell containing fluid within the secondary electroporation chamber through the distal opening of the volume reducing sleeve.

The first electrode can be configured to selectively associate with and form a fluid tight seal with the volume reducing sleeve.

An electroporation cartridge of the disclosure, in some embodiments, can have a space defined between an outer surface of the volume reducing sleeve and the inner sidewall of the elongate body to form a fluid overfill space configured to receive a volume of overfill displaced by the first electrode upon sealing the electroporation chamber.

In one aspect, the electroporation cartridge includes a fluid overfill space associated with a proximal region of the electroporation chamber and configured to receive a volume of overfill displaced by the first electrode upon sealing the electroporation chamber.

In one aspect, an electroporation cartridge of the disclosure is a flow-through electroporation cartridge. A flow-through electroporation cartridge can include a port associated with the first electrode that defines a lumen within the first electrode such that the lumen is fluidically connected to the electroporation chamber. Alternatively, a flow-through electroporation cartridge of the disclosure can include a port associated with a proximal portion of the elongate body that is configured to exhaust displaced air from the electroporation chamber when the electroporation chamber is being filled and/or introduce filtered or purified air into the electroporation chamber when the electroporation chamber is being drained. In some instances, a flow-through electroporation cartridge includes a chamber inlet and a chamber outlet that are each fluidically connected to the electroporation chamber. One or more of the chamber inlet or chamber outlet can be disposed above a proximal surface of the second electrode and/or a lumen of the chamber inlet and/or chamber outlet can be substantially parallel to the proximal surface of the second electrode. Additionally, or alternatively, one or more of the chamber inlet or chamber outlet can be associated with a plug and/or valve to control an inward flow of cell-containing fluid to be electroporated within the electroporation chamber and/or to control an outward flow of electroporated cell-containing fluid from the electroporation chamber.

Electroporation cartridges disclosed herein can include a fluid overfill space associated with the first electrode and/or the elongate body that is configured to receive a volume of overfill displaced from the electroporation chamber when filling the electroporation chamber and/or when sealing the electroporation chamber with the sealing cap.

An exemplary electroporation system configured to provide flow-through electroporation of a sample includes a modular casing having a plurality of compartments for holding and arranging a plurality of electroporation system components. An electroporation system of the disclosure can include one or more pumps configured for moving a sample through the system, and an electroporation compartment configured to receive a flow-through electroporation cartridge configured for holding a sub-volume of the sample within an electroporation chamber for electroporation of the sub-volume. An electroporation system of the disclosure can further include tubing routed through the casing so as to fluidically connect the plurality of electroporation system components between an inlet and an outlet.

In one aspect, an electroporation system of the disclosure includes a bag compartment configured for receiving and supporting an input bag and/or output bag. A bag compartment can include an insert that is slidably connected to the bag compartment so as to be capable of being selectively drawn out from the casing or enclosed within the casing and may include one or more magnetic latches for holding the bag compartment in an enclosed position within the casing. In one aspect, an electroporation system includes one or more hooks on which to hang one or more bags outside of the casing.

In one aspect, an electroporation system of the disclosure includes one or more features for regulating the temperature of the sample via cooling and/or heating (e.g., according to a predetermined target temperature). For example, an electroporation system can include a cooling module in thermal contact with the electroporation chamber and configured to regulate the temperature of the electroporation chamber. A cooling module, in some embodiments, can include a ceramic block cooled via thermoelectric cooling. Other embodiments of cooling modules used in systems and devices of the present disclosure can additionally or alternatively utilize air cooling, liquid cooling, or other temperature regulating mechanisms known in the art. As described below, though such components are described herein as "cooling modules" based on their typical function, they may also be configured to provide heat in applications where such heating is desired.

In one aspect, an electroporation system of the disclosure includes a mixer reservoir disposed downstream of an inlet and upstream of an electroporation cartridge, the mixer reservoir comprising a mixing element configured to provide mixing to a portion of a sample contained within the mixing reservoir. A mixing element can be formed as a mixing blade or other mixing device that avoids contact of magnetic containing parts with a sample fluid.

In one aspect, a mixer reservoir includes a mixer magnet assembly mechanically coupled to the mixing element, the mixer magnet assembly being disposed so as not to contact the portion of the sample contained within the mixer reservoir. For example, a mixer reservoir may have a cover, and a mixer magnet assembly can be disposed at or near the cover. An electroporation system of the disclosure can further comprise a mixer driver having a magnet magnetically coupled to the mixer magnet assembly and configured to indirectly drive rotation of the mixer magnet assembly via magnetic connection to the mixer magnetic assembly.

In one aspect, an electroporation system of the disclosure can comprise or include a sample input assembly configured to aid in transfer of sample between an input and the mixer reservoir. A sample input assembly, in some embodiments, includes a main section of tubing disposed between the input and the mixer reservoir, and an intermediate section of tubing coupled to the main section of tubing in a manner that allows air to pass from the intermediate section of tubing to the main section of tubing, the intermediate section of tubing extending from the main section of tubing to a terminal end. The terminal end of the intermediate section of tubing has access to air (e.g., an air reservoir or a filter open to the atmosphere), and the intermediate section thereby allows passage of air into the main section of tubing upon sufficient pressure drop in the main section of tubing. For example, when an input container coupled to the inlet is empty or nearly empty of its contents, continued pumping will cause the pressure in the main section of tubing to drop, which in turn will cause air to be drawn into the main section of tubing from the intermediate section of tubing.

In one aspect, an electroporation system of the disclosure includes a chamber sealing assembly operatively coupled to the electroporation chamber and configured to regulate pressure within the chamber during electroporation and thereby limit bubble formation. A chamber sealing assembly can comprise one or more linear actuators configured to advance plungers toward or retract plungers away from the chamber to thereby open and close corresponding ports to regulate fluid flow through the chamber and pressure within the chamber.

In one aspect, an electroporation system includes a pre-cooling assembly disposed upstream of the electroporation chamber and configured for regulating the temperature of a sub-volume of the sample prior to electroporation of the sub-volume. In some embodiments, a pre-cooling assembly can comprise or include a cooling block and a section of tubing disposed within or adjacent to the cooling block. In some embodiments, a cooling block can be cooled via thermoelectric cooling, for example. In other embodiments a cooling block can additionally or alternatively utilize air cooling, liquid cooling, or other temperature regulating mechanisms known in the art. As described below, though such components are described herein as "pre-cooling modules/assemblies" based on their typical function, they may also be configured to provide heat in applications where such heating is desired. An electroporation system of the disclosure can also include a flexible biasing element that biases a cooling block against the section of tubing disposed within or adjacent to the cooling block.

In one aspect, an electroporation system of the disclosure can comprise one or more flow sensors configured for detecting flow (or the absence thereof) through particular sections of the tubing. A flow sensor may be disposed between the mixer reservoir and the electroporation chamber. In some non-limiting embodiments, flow sensors can be ultrasonic sensors, for example.

In one aspect, a casing of an electroporation system of the disclosure is configured to route one or more sections of tubing in a path, such as along the exterior of the casing, that provides visual indication of flow through the section of tubing.

In one aspect, a casing of an electroporation system of the disclosure includes one or more handles. In non-limiting embodiments, the one or more handles may include a handle having a catch configured to engage with an instrument panel to attach the instrument panel to the casing.

In one aspect, an electroporation system of the disclosure includes an electroporation cartridge attachment feature coupled to the electroporation cartridge and configured to allow selective attachment and detachment of the electroporation cartridge to the casing. The attachment feature may include a flexible biasing element that biases the electroporation cartridge toward the cooling module.

In one aspect, an electroporation system of the disclosure comprises or includes a capping mechanism. A capping mechanism is configured to engage with an inserted electroporation cartridge and is configured to actuate so as to move one of the electrodes of the electroporation cartridge between a capped position for electroporation and an uncapped position for venting. An electroporation cartridge of the disclosure, in some embodiments, may comprise or include a spring mechanism that allows overtravel of the capping mechanism relative to the displacement of the electrode moved as a result of actuation of the capping mechanism.

In one aspect, an electroporation cartridge of the disclosure comprises one or more bellows structures each configured to encase a moveable component of the electroporation chamber.

In one aspect, an electroporation system of the disclosure includes an electroporation assembly electrically coupled to the electroporation chamber of the electroporation cartridge. In some embodiments, an electroporation assembly includes a conductivity sensor for measuring conductivity across the electroporation chamber. In some embodiments, an electroporation assembly is communicatively coupled to a controller having one or more processors and one or more hardware storage devices.

In one aspect, a controller is configured to implement a method for determining the conductivity of a sub-volume within an electroporation chamber of the disclosure and to charge a capacitor accordingly in order to increase repeatability and/or accuracy of the delivered electroporation pulses across electroporation of a sample volume (such as in a single-use electroporation cartridge of the disclosure) or across successive sub-volumes (such as in a flow-through electroporation cartridge of the disclosure).

In one aspect, a controller is configured to implement a method for predicting the risk of arcing during electroporation through determining a predicted temperature increase of the sub-volume within an electroporation chamber of the disclosure. A controller, in some embodiments, may determine, by way of the conductivity sensor, the conductivity of the sub-volume within an electroporation chamber of the disclosure. A controller, in some embodiments, may then (or subsequently) determine a predicted temperature increase of the sub-volume based on the determined conductivity, an intended pulse voltage, and an intended pulse duration. The controller may then send an arc risk alert if the predicted temperature increase leads to a temperature of the sub-volume that is greater than a predetermined threshold temperature, such as about 60° C. or about 70° C. In some embodiments, a controller may additionally cause the electroporation system to drain the sub-volume from the electroporation chamber to preserve the sample.

In one aspect, a controller is configured to implement a method for predicting the risk of arcing during electroporation through determining the presence of a bubble within an electroporation chamber of the disclosure. In this aspect, the controller may determine, by way of the conductivity sensor, the conductivity of the sub-volume within the electroporation chamber. Then, if the determined conductivity falls below a pre-determined threshold indicative of the presence of one or more bubbles within the electroporation chamber, the controller may send an arc risk alert. The controller may additionally cause the system to drain the sub-volume from the electroporation chamber to preserve the sample.

In one aspect, a controller is configured to implement a method for determining a calibrated step volume to be moved by the system between each electroporation event, corresponding to a fill volume of the electroporation chamber. In this aspect, the controller may determine a number, N, of revolutions of a drive pump required to move a sample volume sufficient to fill the tubing disposed between the flow sensor and the electroporation chamber, as well as fully filling the electroporation chamber. The number N thus represents the volume between the flow sensor and the outlet of the electroporation chamber. Determining that the electroporation chamber has been filled may be accomplished by way of the conductivity sensor.

The controller may then cause the electroporation chamber to be drained, and then may cause the drive pump to reverse the sample by a fixed number, k, of revolutions to a point upstream of the flow sensor, the fixed number, k, representing the volume between the point upstream of the flow sensor and the inlet of the electroporation chamber. The controller may then determine a number, x, of revolutions of the drive pump required to move the sample from the point upstream of the flow sensor to the flow sensor, the number, x, representing the volume between the point upstream of the flow sensor and the flow sensor. The number (k−x) thus represents the volume between the flow sensor and the inlet of the electroporation chamber, and the number N−(k−x) represents the fill volume of the electroporation chamber.

In another aspect, a controller is configured to implement a method for determining a calibrated step volume to be moved by the system between each electroporation event into a flow-through electroporation chamber, corresponding to a fill volume of the flow-through electroporation chamber. In one embodiment, such a method can comprise a first fill of a flow-through electroporation chamber till the sample makes contact (touches) the top electrode (first electrode as described in some embodiments) of the electroporation chamber. At this time (i.e., during the first fill), the electroporation system monitors a drop in the electrical resistance in the electroporation chamber from several thousand ohms to a stable value in the range of from about 600-800 ohms. The first fill is stopped when this stable electrical resistance value is reached.

In some embodiments, for the second fill (and subsequent fills) the gross filling sample volume is derived from a combination of empirical data and theoretical calculation. Accordingly, for a second fill (and subsequent fills), the electroporation system (for e.g., a controller therein) determines a number of revolutions, "$N_{rev}$," i.e., number of revolutions of a drive pump that are required to move a sample volume sufficient to fully fill the electroporation chamber (i.e., the number of revolutions are counted from the time a sample fluid enters an electroporation chamber from a fixed entry point till the sample fluid makes contact with the top electrode (reaches its sample volume). In addition, an empirical determination of the inner tubing diameter "$d_i$" of the pump tubing and the number of rollers of the pump "n" are made. In a non-limiting example, the pump can be a peristaltic pump, which in some embodiments can have six rollers (e.g., n=6).

Determining the $N_{rev}$ value comprises measuring (e.g., empirically or by other ways) one or more of the following: revolutions of a peristaltic pump needed to fill an electroporation chamber from an entry point till it reaches the top electrode (which corresponds to the drop in resistance of the sample fluid to 600-800 ohms); inner diameter "$d_i$" of tubing in the pump; number of pump rollers "n"; volume of fluid per one complete revolution of the pump ("a" μL); fluid volume per one roller movement "b" μL; smallest diameter of the electroporation chamber area where the electroporation sample resides; and/or electrical resistance or conductivity (using a voltmeter, a conductivity sensor, etc.) of the fluid in the electroporation chamber followed by theoretical calculations to arrive at $N_{rev}$.

Following this, is a step of measuring electrical resistance after capping the top electrode after the second fill (and subsequent fill); if the electrical resistance is within the stable value range determine from the first fill (i.e., in the range of from about 600-800 ohms), then the fill is complete and one can proceed to electroporate the sample. However, if after the second fill, the electrical resistance is not within the stable value range determine from the first fill (i.e., not in the range of from about 600-800 ohms), then the step of uncapping the top electrode and fine filling the electroporation chamber with a fluid by an additional $n_{rev}$ amount ($n_{rev}$ of the pump) is performed. This is followed by measuring the electrical resistance after capping the top electrode after the fine fill. If the electrical resistance is within the stable value range determine from the first fill (i.e., in the range of from about 600-800 ohms), then the second fill is complete and one can proceed to electroporate the sample. If not, repeat the file fill and electrical resistance steps above till the electrical resistance is within the stable value range determine from the first fill (i.e., in the range of from about 600-800 ohms). Subsequent fills (third fill, fourth fill and so on) are done for pump revolutions of $N_{rev}+n_{rev}$ x (number of tries of the fine fill). In some embodiments, the stable value of electrical resistance is about 700 ohms, such as for example in the range of 650-750 ohms and any values therebetween.

In one embodiment, $N_{rev}$ is calculated as follows: in one embodiment system of the disclosure, having a peristaltic pump with six rollers and a tubing having an inner diameter 2.4 mm, empirical data of 172 μL of fluid was dispensed per full complete revolution of the pump. From empirically determined data, 28 μL of fluid was dispensed per rotation movement by one roller distance (in this case, 60 degree) of the pump. This was followed by a theoretical calculation to determine the volume of fluid the electroporation chamber can contain. With a nominal diameter of 6.4 mm (2r, where r=radius of the electroporation chamber), with a lower limit of 6.3 mm and an upper limit of 6.5 mm, together with the height of the electroporation chamber being 30 mm (h), using the formula of $\pi r^2 h$, the nominal sample volume was determined to be 965 μL with lower limit at 935 μL and upper limit at 995 μL. Variation of height (h), with the design tolerance of 0.2 mm is deemed to be insignificant as it contributes to at a maximum of 74, variations. To reduce sample loss from gross fill due to overfilling of the chamber, lower limit of the chamber diameter 6.3 mm was used in the calculation. Based on the calculated volume of 935 μL divided by the empirical data of 172 μL, the peristaltic pump revolution was determined to be 5.4, however to introduce a convex meniscus, a round up to 5.5 revolution was recommended. Therefore, in this case, "$N_{rev}$" equals 5.5 revolution. The difference in chamber diameter from 6.3 mm to 6.5 mm resulted in about 30 μL sample volume difference for every 0.1 mm diameter change. This is quite close to the empirical data of 28 μL of fluid that was dispensed per rotation movement by one roller distance (in this case, 60 degree) of the pump, which is term as fine fill "$n_{rev}$" in the equation. Upon the gross fill of 5.5 revolution ($N_{rev}$), instrument will read the conductivity and if the fill is incomplete, the fine fill "$n_{rev}$" will commence. Depending on the number of tries, "x", for the fine fill, the second fill (and subsequent fills) will be made up of "$N_{rev}$ $n_{rev}$ x".)

Accordingly, systems, methods, and devices for automated electroporation of cell-containing fluid are disclosed.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims or may be learned by the practice of the disclosure as set forth hereinafter.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope. The disclosure will be described and explained with additional specificity and detail through the use of the accompanying drawings in which:

FIGS. 11A-11D illustrate example embodiments of electroporation systems or electroporation instruments, wherein FIG. 11A shows one embodiment of an electroporation instrument; FIG. 11B shows another embodiment of an electroporation instrument having a lid in an open position; FIG. 11C depicts one embodiment of an electroporation system comprising an electroporation instrument and a removably attachable modular casing that can comprise various electroporation components including cells and reagents; and FIG. 11D illustrates yet another embodiment of an electroporation instrument having a lid;

FIG. 26 illustrates a method for generating repeatable and consistent electrical pulses across the electroporation chamber, according to one embodiment;

DETAILED DESCRIPTION

Figure 1A:
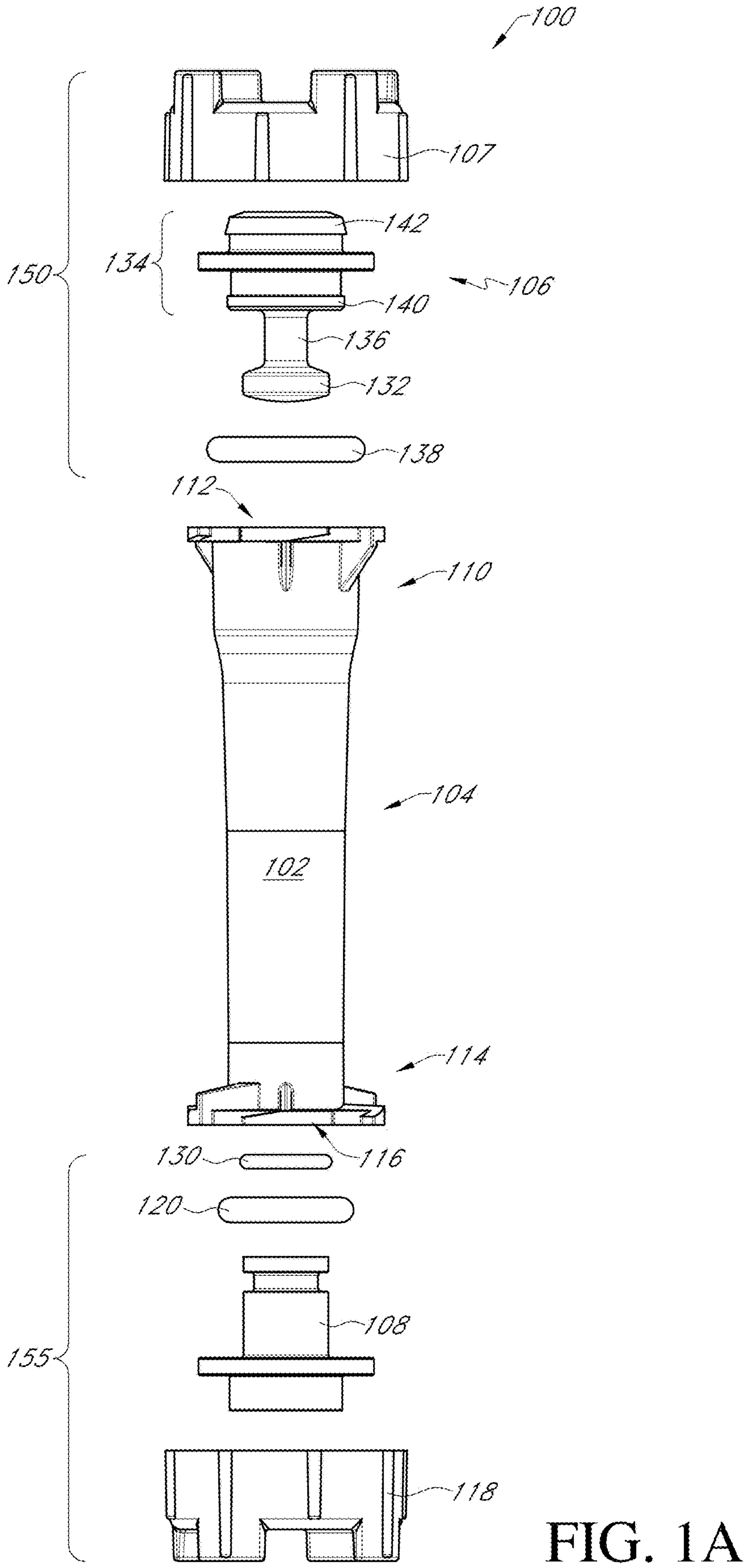
FIG. 1A is an exploded view of an exemplary single use electroporation cartridge, in accordance with some embodiments of the present disclosure.

Before describing various embodiments of the present disclosure in detail, it is to be understood that this disclosure is not limited to the parameters of the particularly exemplified systems, methods, apparatus, products, processes, and/or kits, which may, of course, vary. Thus, while certain embodiments of the present disclosure will be described in detail, with reference to specific configurations, parameters, components, elements, etc., the descriptions are illustrative and are not to be construed as limiting the scope of the claimed invention. In addition, the terminology used herein is for the purpose of describing the embodiments and is not necessarily intended to limit the scope of the claimed invention.

Furthermore, it is understood that for any given component or embodiment described herein, any of the possible candidates or alternatives listed for that component may generally be used individually or in combination with one another, unless implicitly or explicitly understood or stated otherwise. Additionally, it will be understood that any list of such candidates or alternatives is merely illustrative, not limiting, unless implicitly or explicitly understood or stated otherwise.

In addition, unless otherwise indicated, numbers expressing quantities, constituents, distances, or other measurements used in the specification and claims are to be understood as being modified by the term "about," as that term is defined herein. Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

Any headings and subheadings used herein are for organizational purposes only and are not meant to be used to limit the scope of the description or the claims.

Overview and Advantages of Exemplary Electroporation Cartridges

Embodiments of the present disclosure relate to electroporation systems and their various components including several types of electroporation chambers, electroporation devices, electroporation cartridges, electroporation modules, module casings, electroporation instruments and electroporation systems including systems comprising computer processors, user interfaces and computer implemented methods.

Embodiments of the present disclosure related to electroporation systems and related instruments and devices such as electroporation cartridges, and/or electroporation chambers useful for single electroporation experiments. Embodiments of the present disclosure related to electroporation systems and instruments for non-automated electroporation.

Embodiments of the present disclosure related to high-throughput electroporation systems and related instruments and devices such as electroporation cartridges, and/or chambers and/or electroporation casings/modules. Embodiments of the present disclosure related to electroporation systems and instruments for automated, high-throughput electroporation.

As discussed above, there are a number of disadvantages and problems that can be addressed in the field of electroporation. Embodiments of the disclosure address a number of disadvantages and problems in the field of automated, high throughput electroporation as well as in single electroporation applications. For example, embodiments of the present disclosure provides devices, instruments, systems and methods capable of performing electroporation in a functionally closed, sterile pathway that provide one or more advantages including minimizing or substantially reducing arcing, minimizing or substantially reducing bubble formation and associated arcing in cell-containing fluid, greatly improving and maximizing transfection efficiency, recovery efficiency of transfected cells, providing uniform electric fields for efficient electroporation, etc.

In some embodiments, systems, devices, instruments and methods of the disclosure combine the advantages of continuous flow electroporation with batch or static volume electroporation, particularly the ability to automatedly electroporate large volumes of cells in a sterile, closed system while minimizing arcing due to bubble formation within the cell-containing fluid and maximizing recovery efficiency.

Embodiments of the present disclosure solve one or more of the foregoing problems in the art of automated electroporation. For example, FIGS. 1A-6D, FIGS. 10A and 10B, FIGS. 11A-D and the corresponding description illustrate various electroporation devices, such as, single use electroporation cartridges, and electroporation instruments and systems that enable high efficiency electroporation. In other examples, embodiments depicted in FIGS. 7A-9, FIGS. 10A-22S and their corresponding descriptions illustrate various electroporation devices, such as, flow-through electroporation cartridges, electroporation modules, electroporation instruments and systems that enable high efficiency electroporation of large volumes of cell containing fluid using an automated batch process. Exemplary methods utilizing one or more of the electroporation cartridges are provided in FIGS. 23-33 and the corresponding description.

Advantageously, the disclosed systems, devices (such as single use and flow-through electroporation cartridges), and methods reduce bubble formation in a number of ways, including, for example, pressurizing the electroporation chamber prior to electroporation, which can make it more energy intensive (and thereby more difficult or less likely) to vaporize the aqueous cell containing fluid or cause electrolysis of water molecules into oxygen and hydrogen gas. Further, single use and flow-through electroporation cartridges of the present disclosure additionally cause any bubbles that do form during processing to be directed away from the electrode surface thereby further reducing the likelihood of arcing. With less bubbles forming or collecting on or near the electrode surface, embodiments of the present disclosure allow for less arcing to occur and maximizes recovery efficiency of each sample.

The disclosed flow-through devices, modules and systems further provide the benefit of automating the manual process of loading and unloading sample into/out of an electroporation cuvette, a process where many have tried and failed. Instead of continuous processing, which has been done in prior art systems and which is prone to lower electroporation efficiency, systems, cartridges and methods of the present disclosure enable automated batch electroporation, which combines the advantages of continuous flow electroporation with the advantages of batch or static volume electroporation while minimizing the disadvantages inherent to each. For example, the devices and systems disclosed herein provide a sterile, closed system, which eliminates (or significantly reduces) the risk of sample contamination previously associated with batch or static processing techniques. Preferably, the devices and systems disclosed herein are made from materials that are compliant with ISO (International Organization for Standardization) guidelines and are suited for use in cell and gene therapy applications.

Exemplary Electroporation Cartridges

As discussed above, there are a number of disadvantages to electroporation systems known in the art. In particular, arcing during electroporation is undesirable as it affects transfection efficiency and cell viability. Systems and devices are needed that minimize or prevent arcing in electroporation cartridges and electroporation chambers made for single use. Systems and devices are needed that minimize or prevent arcing within a continuous flow or continuous batch electroporation process.

One of the main causes of arcing is the presence of bubbles at or near the electrode surface and/or within the path of the current generated by application of high voltage across the cell-containing media during electroporation. Under high voltage applications like electroporation, nearly any bubble of significant size will result in arcing. It is known that bubbles form as a result of heat generated from electrical discharge through an aqueous cell containing solution. This intense, often repeated heating can also cause bubble formation through localized vaporization of water molecules. The electrical discharge through the cell containing solution that occurs during electroporation can cause electrolysis of water molecules, forming oxygen and hydrogen gas—another source of bubbles during electroporation.

Figure 1B:
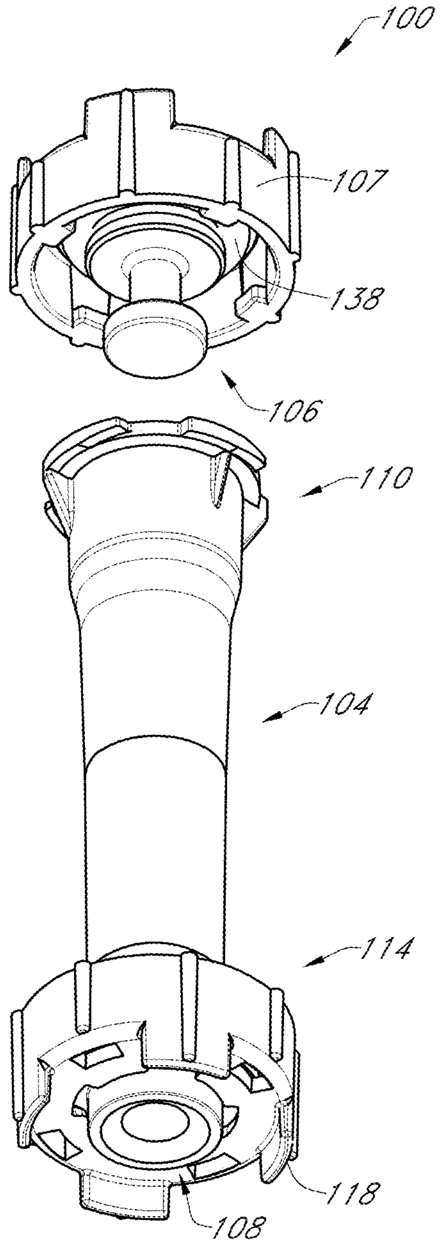
FIG. 1B is a bottom perspective view of the exemplary single use electroporation cartridge of FIG. 1A shown partially assembled and in an uncapped position, according to one embodiment of the disclosure.
Figure 1C:
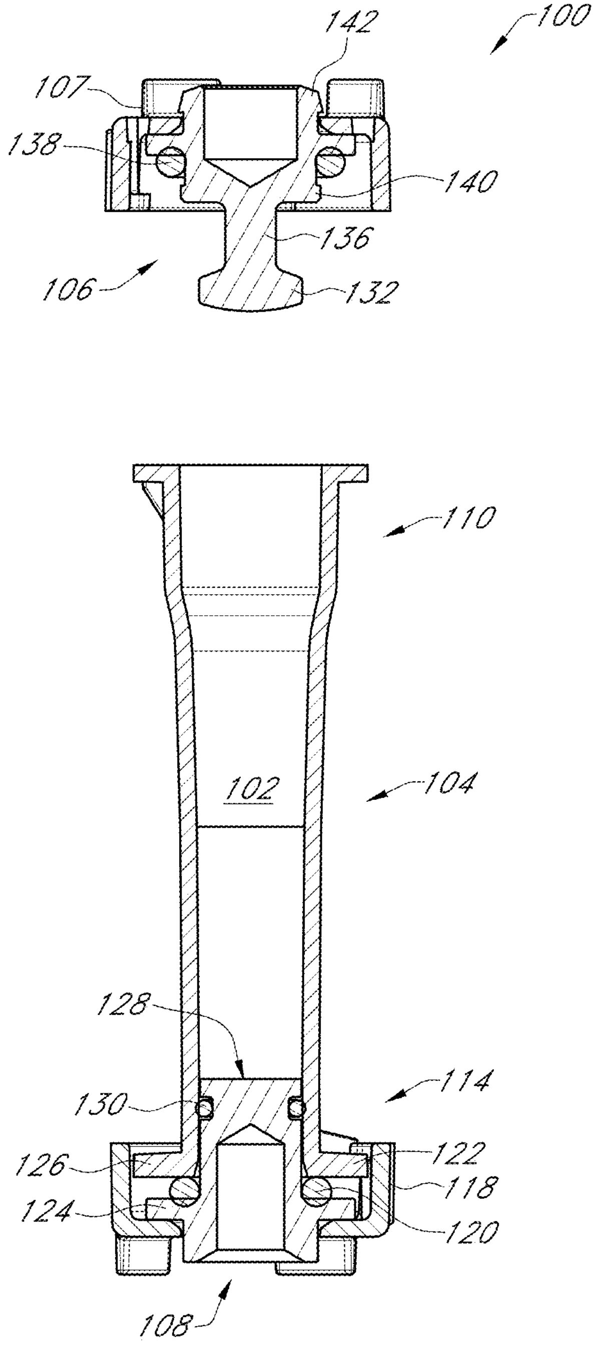
FIG. 1C is a front view of a longitudinal cross section of the partially assembled, uncapped electroporation cartridge of FIG. 1B.
Figure 1D:
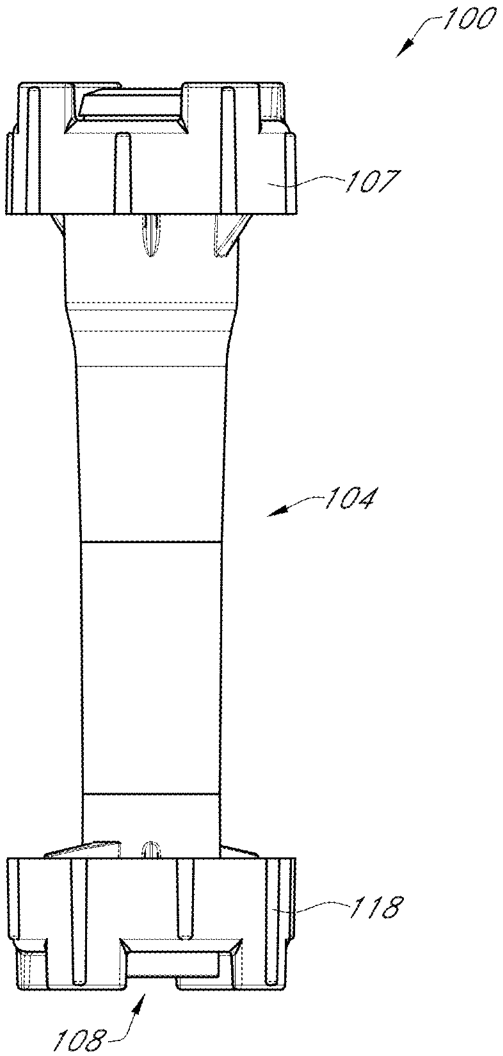
FIG. 1D is a front view of the exemplary single use electroporation cartridge of FIG. 1A shown assembled and in a capped position.
Figure 1E:
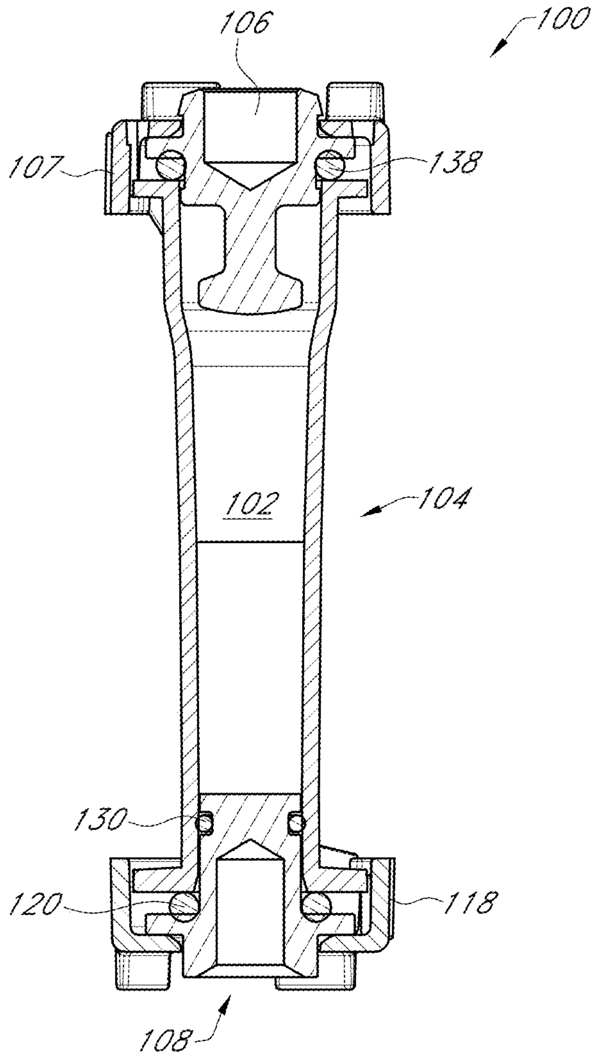
FIG. 1E is a front view of a longitudinal cross section of the assembled and capped electroporation cartridge of FIG. 1D.

Embodiments of the present disclosure include electroporation cartridges, associated systems, and methods for using the same that enable a reduction of bubble formation during electroporation, even at large volumes that would traditionally cause arcing (e.g., 1 mL or greater). An exemplary single use electroporation cartridge is illustrated in FIGS. 1A-1E, where FIG. 1A provides an exploded view of the components of the exemplary electroporation cartridge, FIGS. 1B and 1C show the electroporation cartridge of FIG. 1A in a partially assembled and an uncapped position, and FIGS. 1D and 1E show surface shaded and cross-sectional views of the assembled cartridge in a capped position. The illustrated single use electroporation cartridge, along with other single use electroporation cartridges described herein, may include one or more security features for ensuring that they are only used a single time. For example, a single use electroporation cartridge may include a locking feature, breakaway feature, and/or other mechanical feature that does not allow reuse of the electroporation cartridge after it has been inserted and removed from the electroporation system. Single use of the single use electroporation cartridges may additionally or alternatively be ensured electronically, such as through an electronic tag or code associated with each single use electroporation cartridge and scanned/logged by the electroporation system.

According to one embodiment, as shown in FIGS. 1A-1E, the electroporation cartridge 100 includes an electroporation chamber 102 defined by an elongate body 104, a first electrode 106 disposed at a proximal end 110 of the electroporation chamber 102, and a second electrode 108 disposed at an opposite, distal end 114 of the electroporation chamber 102, wherein at least one of the first electrode 106 or second electrode 108 is moveable between a capped position for electroporation and an uncapped position for loading a sample (e.g., as shown between FIGS. 1B, 1C, 1D, and 1E). As particularly shown in FIG. 1A, the elongate body has two open ends—a proximal end 110 defining a proximal opening 112 and a distal end 114 defining a distal opening 116—where first electrode 106 and second electrode 108 are installed, respectively. According to one embodiment, first electrode 106 is associated with a removable cap 107 that allows for selective association of first electrode 106 with elongate body 104. In some embodiments, second electrode 108 of cartridge 100 is inserted into the distal opening 116 of elongate body 104 where it is secured in place by distal cap 118. In some embodiments, second electrode 108 is secured within and/or in association with distal end 114 of elongate body 104 by distal cap 118 via a locking feature to prevent the lower cap from being removed. This can advantageously act to reduce potential confusion about which end a user is to be using for adding and/or removing cell containing fluid for electroporation and also provides the benefit of a modular construction that can be partially assembled to create a more structurally secure cartridge.

As shown in FIG. 1C, second electrode 108 additionally comprises a first sealing member 120 disposed between the second electrode 108 and a distal surface 122 of elongate body 104, the first sealing member operable to form a fluid tight connection between second electrode 108 and distal surface 122 of elongate body 104. In some instances, the fluid tight connection is provided by compressing a sealing member (e.g., an O-ring or other gasket) between an electrode flange 124 and a distal body flange 126 oriented in a plane substantially parallel to the electrode flange 124. In some embodiments, distal cap 118 locks into association with the elongate body with the sealing member 120 disposed between the electrode flange 124 and the distal body flange 126, forming the fluid tight connection therebetween.

With continued reference to FIG. 1C, in some embodiments, second electrode 108 can include a protruding portion 128 that extends into electroporation chamber 102 from distal end 114 of elongate body 104 to define the bottom of electroporation chamber 102. In some embodiments, second electrode 108 can additionally include a second sealing member 130 disposed about the protruding portion 128 and positioned distal to the proximal surface of the second electrode where it forms a fluid tight connection with the interior sidewall of the electroporation chamber 102. Whereas the first sealing member 120 forms a fluid tight seal between second electrode 108 and elongate body 104 via compression of distal cap 118 to seal the distal end of the electroporation chamber 102 from the outside environment, the second sealing member 130 forms a fluid tight connection between the protruding portion 128 of second electrode 108 and the interior sidewall of the electroporation chamber 102 to minimize dead volume by creating a seal closer to the wetted proximal surface of the second electrode 108 to prevent fluid from seeping around the second electrode 108.

In some embodiments, such as that illustrated in FIG. 1C, a circumference of the protruding portion 128 can have a shape complementary to the contour of the inner surface of the elongate body 104 that defines electroporation chamber 102 such that a diameter of the proximal end of second electrode 108 is substantially equal to a cross section of electroporation chamber 102. Additionally, the proximal surface of the second electrode can be a flat, uniform surface positioned orthogonal to a longitudinal axis of the electroporation chamber.

By including one or more of the foregoing structural features in the shape and/or location of the second electrode with respect to the electroporation chamber, certain benefits can be derived. For example, generation of a uniform electric field is one factor for successful and efficient electroporation. To have a uniform electric field, it is advantageous for the opposing first and second electrodes to be substantially parallel and having essentially the same cross-sectional geometry as the electroporation chamber. A uniform electric field is most effectively generated within an electroporation chamber having a uniform cross section (e.g., a constant diameter). Accordingly, in some embodiments, the electroporation cartridges disclosed herein can include an electroporation chamber having a uniform cross section along a length of the reaction chamber. The uniform cross section may extend an entire length of the electroporation chamber between the first and second electrodes such that the electroporation cartridge is configured to produce a uniform electric field within the electroporation chamber disposed between the first and second electrodes. As a non-limiting example of the foregoing, the electroporation chamber may be defined as a cylindrical cavity having a circular cross section extending along the entire length of the cylindrical cavity between the first and second electrodes.

Alternatively, the uniform cross section may extend along a length less than the entire length of the electroporation chamber. In such embodiments, at least a portion of the electroporation chamber can be tapered between the first electrode and the second electrodes. Preferably, the tapered portion of the electroporation chamber does not substantially interfere with generation of a uniform electric field between the first and second electrodes. For the purposes of this disclosure, the tapered portion of the electroporation chamber does not substantially interfere with generation of a uniform electric field if the electric field generated between the opposing first and second electrodes is defined by field lines that are substantially parallel and equally spaced within a 10% degree of tolerance. For clarity, a taper within the electroporation chamber can include a narrowing of a proximal sidewall defined between the proximal opening of the elongate body and an inflection point on the sidewall defining the electroporation chamber such that the proximal sidewall narrows from a first diameter defined by the proximal opening to a second, smaller diameter defined at a position distal to the inflection point.

It should be appreciated that the presence of a taper or uniform cross section along an entire length of the electroporation chamber can affect the methods available to manufacture the electroporation chamber efficiently and/or cost-effectively. Preferably, the elongate body and/or electroporation chamber is made of or includes a non-conductive irradiation-stable plastic, ceramic, and/or glass. For example, the elongate body and/or electroporation chamber can be made of polycarbonate or another non-conductive gamma-stable plastic. Alternatively, glass and ceramic are both electrically insulative and thermally more conductive than polycarbonate; advantageously, both materials can be mass produced with zero draft sidewalls and provide a constant cross section.

In some embodiments, the chamber is made of material that can be sterilized by one or more of steam sterilization, flash sterilization, hydrogen peroxide sterilization, vaporized hydrogen peroxide sterilization, gamma ray sterilization, peracetic acid sterilization, ethylene oxide sterilization, chlorine dioxide gas sterilization, electron beam sterilization, or the like, without compromising the functionality of the chamber (e.g., without reduction in electroporation efficiency or impacting cell viability).

As provided by the foregoing, a uniform electric field can be generated between two opposing electrodes having cross sections that are close to the shape and size of the uniform cross section of the electroporation chamber. The inventors found, however, that when making various cartridges having these features and geometry, air tended to be trapped more easily when sealing the chamber. Trapped air can cause the breakdown of electrical conductivity within the electroporation chamber and result in arcing, which negatively affects the electroporation process and performance.

To overcome the air trap problem, the electroporation cartridges disclosed herein make use of surface tension at liquid to air interfaces where there is greater attraction of liquid molecules to each other than to the molecules in the air. This results in formation of a convex shaped meniscus, and upon capping the top electrode, the liquid is displaced around the electrode so that no air is trapped between the sample and the distal surface of the first electrode. To encourage this, the distal portion of first electrode 106 can have a bell shape or bulbous protrusion 132 separated from a base region 134 by a narrow stem 136, as shown in FIG. 1A-1E. The bulbous protrusion 132 can have a smaller diameter than the cross section of the electroporation chamber 102 so as to form a gap therebetween. This gap between the bulbous protrusion and the chamber body allows small bubbles to exit the electroporation volume. The narrow stem 136 can allow for a greater volume of air in the proximal portion of the chamber, which can serve as a compressible volume during electroporation to minimize the pressure buildup within the chamber caused by the partial vaporization of the sample.

The bell or bulbous shape of the distal end of the first electrode can provide additional advantages during electroporation. Bubbles can form during electroporation by electrolysis and/or vaporization of water. The bulbous extension can be operable to displace one or more bubbles generated during electroporation so that they are removed from the electrode surface before agglomerating into a bubble of sufficient size to cause arcing. For example, the bulbous extension may have an arcuate or convex surface that encourages any bubbles rising from the electroporation volume to pass along the surface of bulbous extension and rise to the sample-air interface proximate the stem.

Further, it was beneficially found that under higher pressures, the intensity of vaporization could be decreased, leading to smaller and/or less bubble formation during electroporation. By making the electroporation chamber sealed prior to electroporation, the release of energy and electrolysis occurring during electroporation will make the chamber behave like a pressure chamber. Any increase in pressure within the chamber will delay the formation of bubbles reaching a significant size that could result in arcing.

Accordingly, in some embodiments, such as that shown in FIG. 1A-1E, the first electrode 106 is associated with a sealing member 138 operable to form a fluid tight connection between the first electrode and the elongate body 104. In some embodiments, the axial compression for maintaining the fluid tight seal can be provided by the removable cap 107 associated with the first electrode 106. In some embodiments, the removable cap 107 is threadedly sealed to the elongate body 104, though it should be appreciated that other forms of connection are contemplated herein (e.g., friction fitting, snap fitting, etc.). As shown in FIG. 1A-1E, each of the caps 107, 118 feature flanges that extend beyond the outer surfaces of the electrodes. These flanges can provide the additional balance and stability to the device, such as when placed on a flat surface. Absent the illustrated flanges, the narrow footprint and the midline center of gravity of the cartridge is likely to make the cartridge unstable.

Because the first electrode 106 is removed by the user during normal operation, there may be a tendency for the sealing member to be lost or disassociated with the electrode when uncoupled from the elongate body. To prevent this, the electrode may include a retaining feature 140 proximal to the stem 136 that is configured to allow the sealing member 138 to stretch over the retaining feature 140 but then be retained thereby adjacent to the sealing surface of the first electrode 106. This sealing surface creates a functionally closed system at the upper end of the chamber when the cap 107 is associated therewith.

In some embodiments, the first electrode 106 can additionally include a cap retaining feature 142 to prevent the end cap from separating from the electrode once installed. The cap retaining feature 142 may act as a barb for a snap fit, may threadedly secure to the cap, or may be retained thereby by any other means known in the art. Notably, in some embodiments, it may be beneficial to secure the first electrode to the cap in such a way that the cap rotate independently from the first electrode so that the associated sealing member only receives axial compression.

In some embodiments, the electrodes 106, 108 are made from, or plated with, a conductive material that does not negatively impact cells by introducing harmful or toxic elements either passively or during electroporation. For example, plating the electrode in pure gold can provide an electrode with beneficial conductive properties that is unlikely to introduce harmful or toxic elements into the electroporation media. Further, it should be appreciated that the electrodes 106, 108 can be connected to a high voltage circuit and either may act as the anode or cathode or may alternate between the two, depending on the electroporation protocol. Alternatively, other non-toxic and/or non-reactive metals or materials can be used, as known in the art.

In some embodiments, the volume within an electroporation chamber of the present disclosure is larger when compared to prior art electroporation cuvettes. In some embodiments, electroporation chambers, have an internal volume from about 10 mL to about 1 mL. In some embodiments, electroporation chambers, have an internal volume from about 1 mL to about 100 μl.

In some embodiments, exemplary electroporation chambers of the present disclosure can have a volume less than about 5 mL, preferably less than about 3 mL, or in some embodiments, less than about 4 mL, less than about 2 mL, or less than about 1 mL. In some embodiments, where the internal volume of an electroporation chamber is from about 10 mL to about 1 mL, at these volumes and at the preferred range of voltage for electroporating most cellular samples, the distance between the first and second electrodes is between about 20 mm-100 mm, e.g., between about 30 mm-50 mm, between about 40 mm-70 mm, and/or between about 60 mm and about 100 mm.

In another exemplary embodiment, the volume of the electroporation chamber is about 1 mL or between about 100 μL-1 mL. In some embodiments, at this volume and at the preferred range of voltage for electroporating most cellular samples, the distance between the first and second electrodes is between about 20 mm-40 mm, e.g., between about 22 mm-38 mm, between about 25 mm-35 mm, and preferably about 30 mm. Having an electroporation chamber configured to this size is advantageous because a standard 1 mL pipette can easily enter the body of the 1 mL electroporation chamber and thus aspirate nearly 100% of the electroporated sample and no specialized equipment is necessary beyond that which is commonly used for moving such volumes of fluid about in a laboratory or clinical setting.

Volume Reducing Sleeve

In some instances, the volume of sample is less than 1 mL. If the distance between the two electrodes remains unchanged, then the diameter of the chamber must be greatly reduced to accommodate the smaller volume. Problematically, existing standard pipette tips are not likely to fill or drain a smaller volume chamber.

Embodiments of the present disclosure include adaptors for the electroporation cartridges described above with respect to FIG. 1A-1E. In principle, the elongate body is fit with a volume reducing sleeve which forms a fluid tight connection with the second (bottom) electrode and defines an inner, secondary electroporation chamber having lesser volume than that defined by the original elongate body 104. In this way, the electroporation cartridges above can be easily adapted for smaller volume samples while preserving the benefits and advantages of the original design.

FIGS. 2A-2F illustrate an exemplary embodiment of the electroporation cartridge of FIG. 1A-1E configured with a volume reducing sleeve. As shown in these Figures, the volume reducing sleeve defines a secondary electroporation chamber of about 200 μL in volume. It should be appreciated, however, that this volume is exemplary in nature and that other volumes are contemplated herein and can be made by adjusting the cross-sectional circumference of the volume reducing sleeve. For example, a 1 mL elongate body may be able to support volumes between 100 μL and 1 mL using different sized sleeves. In particular, a smaller volume sleeve, such as a 100 μL sleeve, can be made by reducing the cross-sectional circumference of the sleeve. Alternatively, a larger volume sleeve, such as a 200 μL, 250 μL, 400 μL, 450 μL, or 500 μL sleeve, can be made by increasing the cross-sectional circumference of the volume reducing sleeve.

Figure 2A:
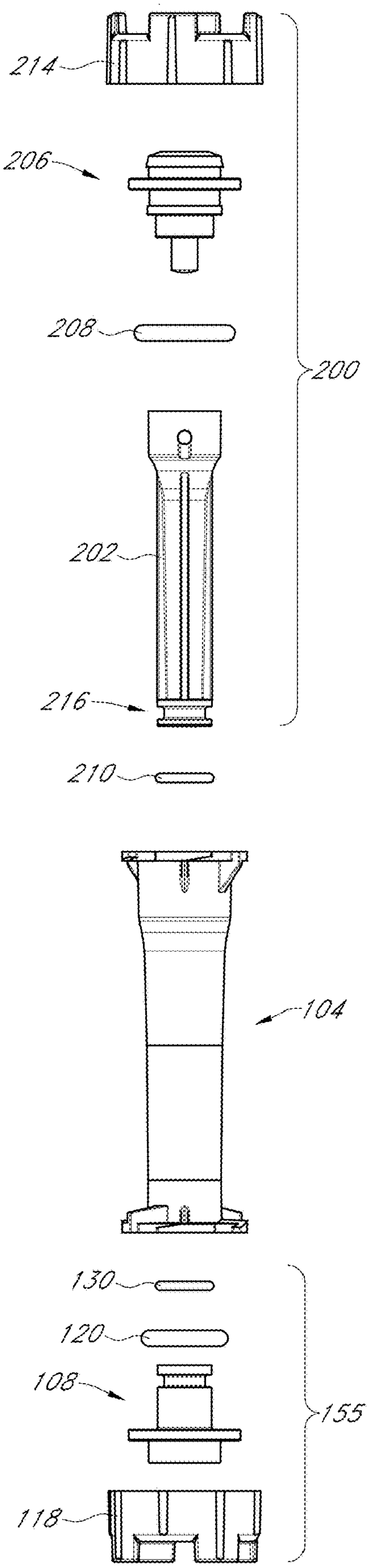
FIG. 2A is an exploded front view of an exemplary single use electroporation cartridge having a volume reducing sleeve in accordance with some embodiments of the present disclosure.
Figure 2B:
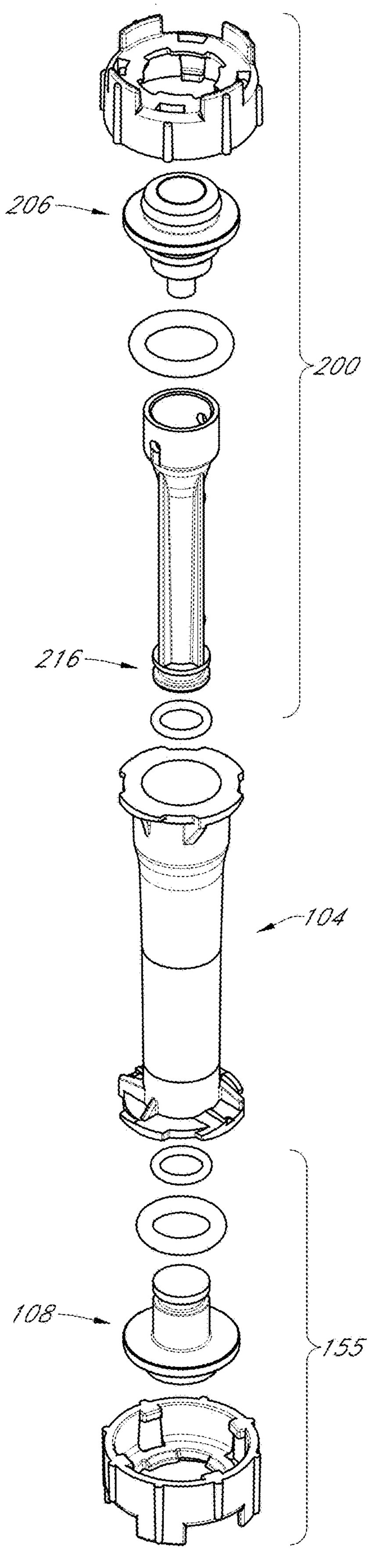
FIG. 2B is an exploded top perspective view of the exemplary single use electroporation cartridge and volume reducing sleeve of FIG. 2A.
Figure 2C:
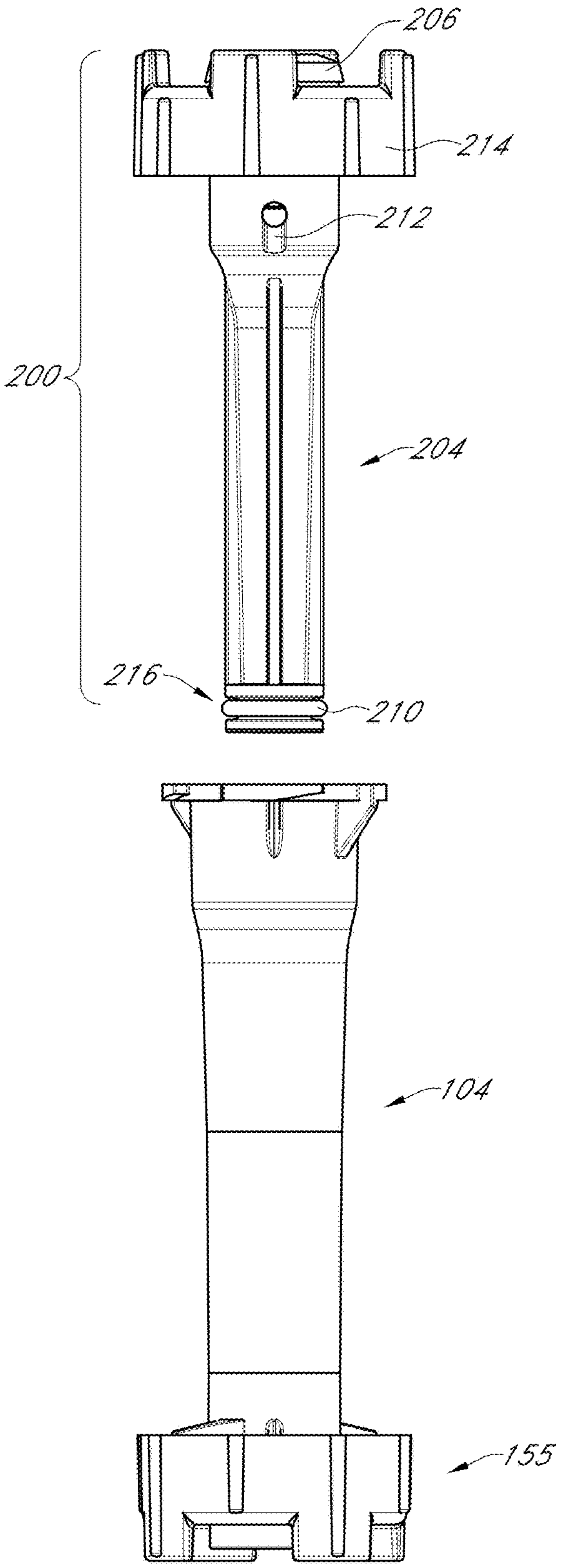
FIG. 2C is a front view of the exemplary single use electroporation cartridge of FIG. 2A shown with the electroporation cartridge partially assembled and in an uncapped position with the volume reducing sleeve being associated with the removable cap.
Figure 2D:
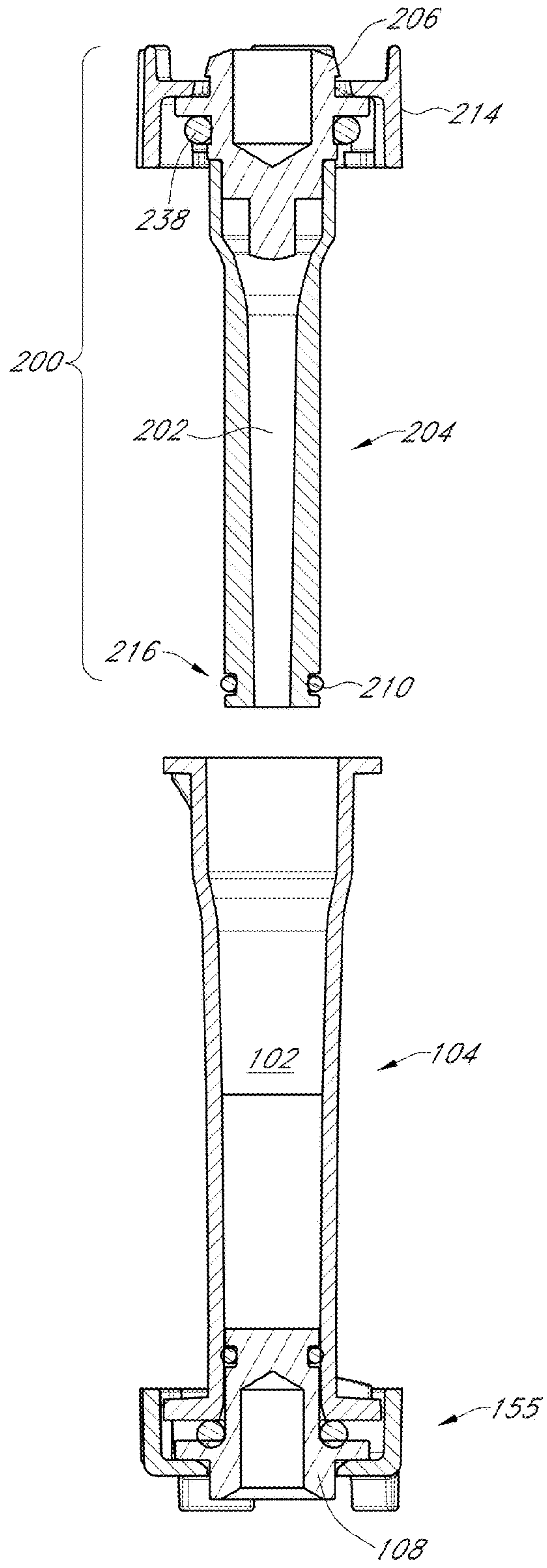
FIG. 2D is a front view of a longitudinal cross section of the partially assembled and uncapped electroporation cartridge and volume reducing sleeve of FIG. 2C.
Figure 2E:
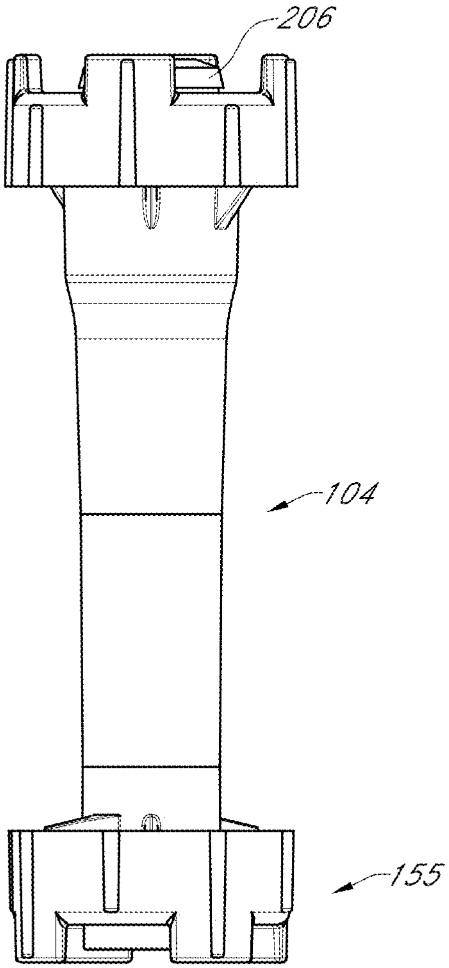
FIG. 2E is a front view of the exemplary single use electroporation cartridge of FIG. 2A shown assembled and capped.
Figure 2F:
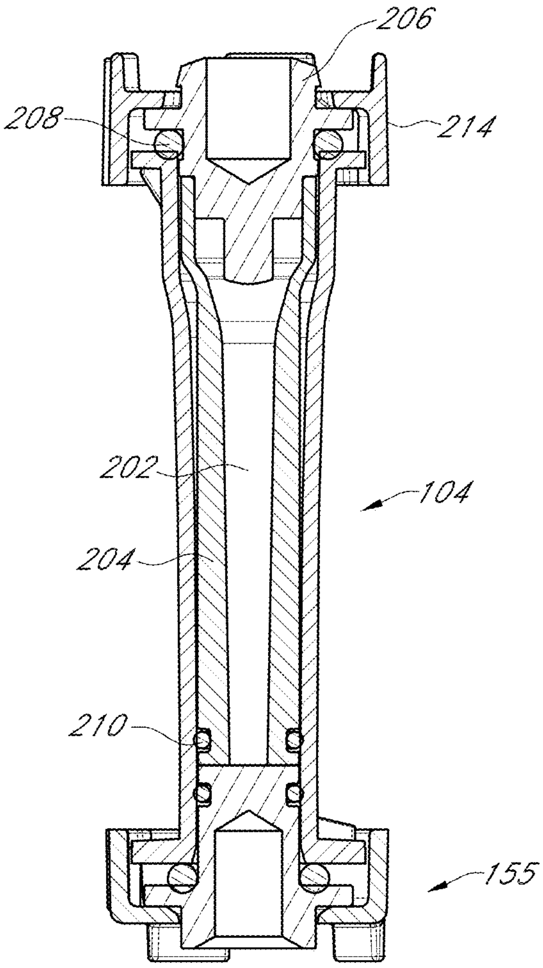
FIG. 2F is a front view of a longitudinal cross section of the assembled and capped electroporation cartridge of FIG. 2E, which illustrates the volume reducing sleeve disposed within the chamber defined by the elongate body of the cartridge to form a reduced volume electroporation compartment between the opposing electrodes.

Referring now to FIG. 2A-2F, illustrated in FIGS. 2A and 2B are exploded views of an exemplary single use electroporation cartridge and volume reducing sleeve. FIGS. 2C and 2D show the cartridge and sleeve of FIGS. 2A and 2B in an assembled and uncapped position, and FIGS. 2E and 2F illustrate the cartridge and sleeve of FIGS. 2A and 2B in an assembled and capped position.

In the embodiments shown in FIG. 2A-2F, the sleeve assembly 200 replaces the standard upper electrode assembly 150 (comprising the removable cap 107, first electrode 106, and sealing member 138) of the 1 mL single-use cartridge illustrated and described in FIG. 1A-1E. The lower electrode assembly 155 (comprising the distal cap 118, second electrode 108, and sealing members 120, 130 of FIG. 1A-1E) remains unchanged. In essence, the internal volume of the secondary electroporation chamber 202 defined by the sleeve 204 is 200 μL (or other defined volume less than 1 mL as disclosed herein) and preferably mimics the geometry of the 1 mL chamber.

Referring to FIGS. 2C and 2D, the lower electrode assembly 155 is shown coupled to the elongate body 104 to seal a distal portion of the elongate body from the environment, as described above. The sleeve assembly 200 is assembled in FIGS. 2C and 2D, and notably, the sleeve electrode 206 can be associated with the removable cap 207 in the same or similar way as described above. Further, the proximal sealing member 238 of the sleeve assembly 200 can also be held in place by a retention member and can be configured to form a fluid tight connection with the respective electrode and elongate body flanges, as described above.

In some embodiments, the sleeve 204 can additionally include a radial sealing member 210 that seals against the inside surface of the elongate body 104. The radial sealing member 210 forms a fluid tight seal with the sidewall defining the electroporation chamber 102 to prevent leakage of cell containing fluid from the secondary electroporation chamber 202 through the distal opening of the volume reducing sleeve and into the electroporation chamber 102. The distal end of the sleeve 204 may include a groove 216 for receiving and/or aligning the radial sealing member 210. In an embodiment, the bottom surface of the sleeve is flat to minimize dead volume by occupying any areas where fluid may get trapped.

In operation, a user places the desired volume of sample in the elongate body 104, as they ordinarily would using the cartridge 100 of FIG. 1A-1E, followed by placement of sleeve 204 into elongate body 104. When inserted into the elongate body 104, the sleeve 204 displaces any additional fluid into the hollow center of the sleeve. The sleeve has been designed such that 200 μL of volume fully wets the lower surface of the sleeve electrode 206. The sleeve assembly 200 includes air vents 212 to allow air to escape the secondary electroporation chamber 202 during insertion. The air vents 212 additionally allow the electroporated sample to remain inside the elongate body 104 when the sleeve 204 is removed following electroporation. The vacuum created within the chamber during removal of the sleeve 204 pulls the electroporated sample out of the secondary electroporation chamber 202 and into the elongate body 104. This design allows a user to aspirate and dispense a smaller volume (e.g., 200 μL) into the elongate body 104, as before, with standard pipettes and without special techniques. It also allows for high voltage electroporation of small volumes while maintaining “capillary-style” geometry. In some embodiments, slots may also be present near the air vents to ensure that the air vents do not become impeded. Such slots can be useful during removal of the sleeve when the vent holes are very close to the inside surface of the elongate body.

The volume reducing sleeve 200 can be made of or include a non-conductive plastic, glass, or ceramic and may include any of the other structural features described above with respect to the elongate body and/or electroporation chamber 102 defined thereby. Additionally, the sleeve body can be injection molded and may have external ribs for rigidity and for guiding the sleeve during insertion/removal.

In some embodiments, the sleeve 204 is fixed to the sleeve electrode 206 by means of adhesives, welding, or geometric (physical) locking features to form a single piece sleeve assembly 200. In such an embodiment, the sleeve 204 is introduced into the elongate body 104 when the proximal cap 214 is secured to the elongate body 104. Similar to the first electrode 106, the sleeve electrode 206 can be made from, or plated with, a conductive material that does not negatively impact cells by introducing harmful or toxic elements either passively or during electroporation. For example, plating the electrode in pure gold can provide an electrode with beneficial conductive properties that is unlikely to introduce harmful or toxic elements into the electroporation volume. Further, it should be appreciated that the sleeve electrode 206 can be connected to a high voltage circuit and may act as the anode or cathode or may alternate between the two, depending on the electroporation protocol. It should be further appreciated that the sleeve electrode 206 can include the same or similar structural features (scaled appropriately to fit the reduced cross section of the sleeve) described above with respect to the bulbous protrusion 132, stem 136, and base region 134 of the first electrode 106 to mitigate bubbles and beneficially decrease a likelihood of arcing during electroporation.

Figure 3:
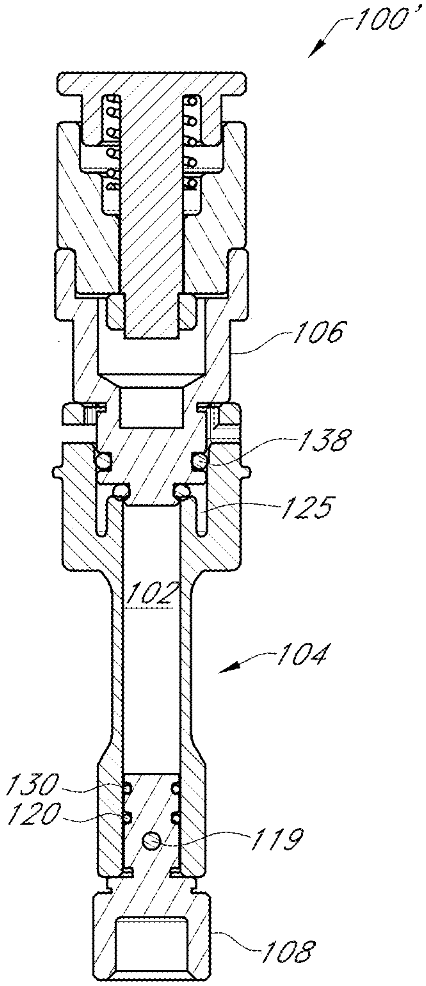
FIG. 3 is a front view of a longitudinal cross section of another single-use electroporation cartridge in accordance with some embodiments of the present disclosure.

Referring now to FIG. 3, illustrated is a longitudinal cross section of yet another embodiment of a single use electroporation cartridge 100' having additional features. For example, the electroporation chamber 102 of the chamber body 104 is sealed at a lower portion by two sealing members—a first proximal sealing member 120 and a reserve sealing member 130. The first proximal sealing member 120 forms a fluid tight seal with the inner surface of the chamber body 104 while the reserve sealing member 130, which also forms a fluid tight seal with the inner surface of the chamber body 104, is provided as a backup seal to prevent any leakage from the first proximal sealing member 120.

The cartridge 100' additionally includes a fixing pin 119 to secure the second electrode to the elongate body 104. This can beneficially prevent the second electrode from being displaced when pressure is applied to the chamber 102. To accommodate the fixing pin 119, the second electrode 108, in some embodiments, defines a channel configured in size and shape to receive the fixing pin and can be aligned with a pair of apertures defined by the sidewall of the elongate chamber body 104 that are also configured to receive and/or hold the fixing pin 119, thereby securing the second electrode at a fixed position relative to the chamber body 104.

In some embodiments, cartridge 100' of FIG. 3 can additionally include a fluid overfill space 125 operable to receive a volume of overfill displaced from the electroporation chamber when sealing the electroporation chamber with the sealing cap and/or first electrode. Sealing member 138, similar to that described above, can also be present to form a fluid tight connection between the first electrode 106 and the elongate body/chamber body 104.

Figure 4:
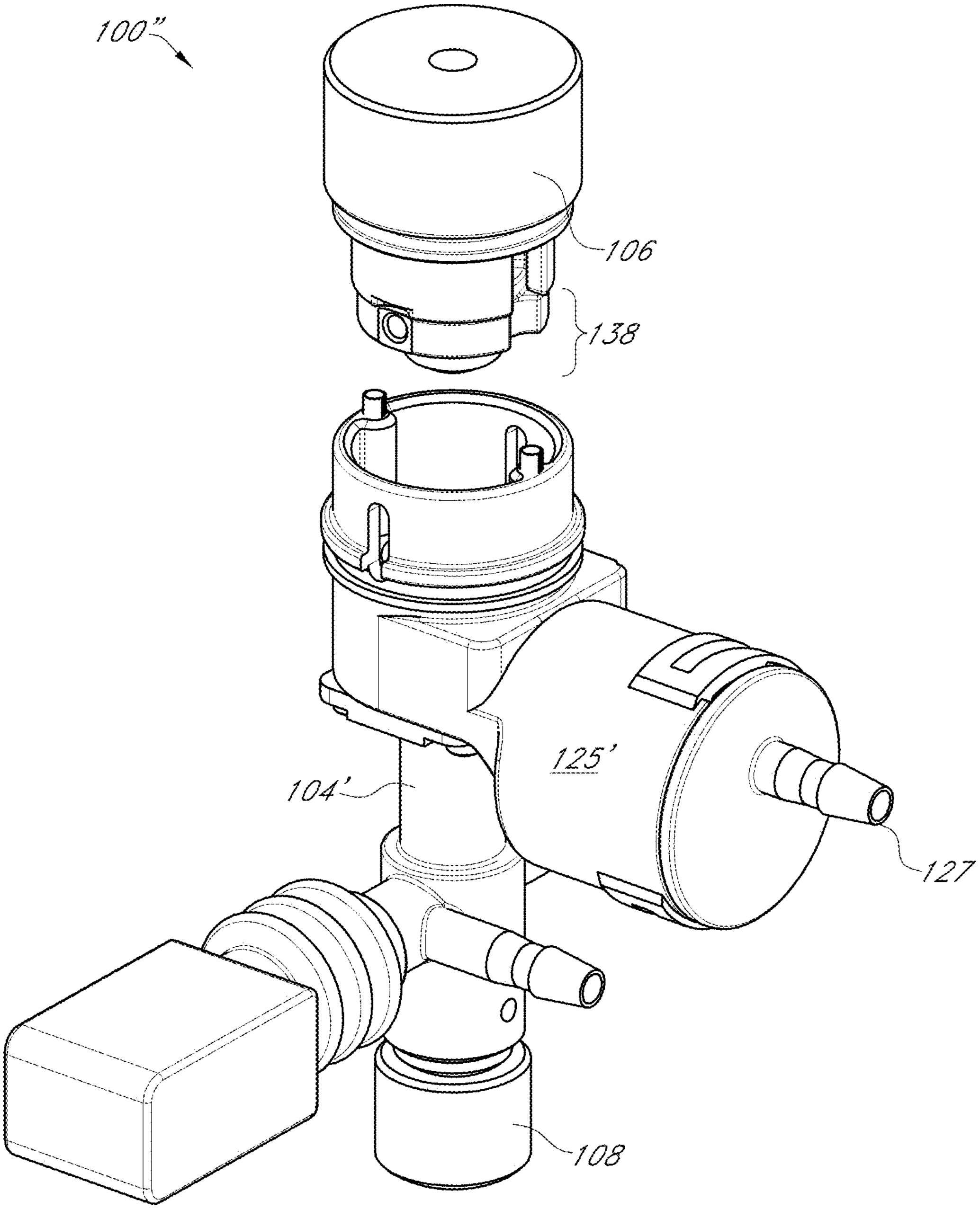
FIG. 4 is a perspective view of another exemplary single use electroporation cartridge having an electrode cap in accordance with some embodiments of the present disclosure.

Referring now to FIG. 4, another embodiment of an exemplary single use cartridge 100" can include a fluid overfill reservoir 125' that can be attached to a proximal outlet of the associated electroporation chamber 104'. The fluid overfill reservoir 125' can include a port 127 that aligns with a filtered air source and/or tubing associated therewith to assist in the forming and breaking a vacuum seal within the electroporation chamber 104' in between iterative rounds of filling, electroporating, and draining cells within the chamber 104'.

As additionally exemplified by the cartridge 100" of FIG. 4, the top electrode 106 can function as a selectively movable cap operable to position the cartridge 100" in a capped and uncapped position. When in an uncapped position, the electrode 106 is moved away from the proximal end of the electroporation chamber 104', allowing the distal sealing member 138 associated therewith to disengage the proximal end of the electroporation chamber 104' and thereby break any fluid tight seal formed therebetween. The top electrode 106 can be moved back toward the proximal end of the electroporation chamber 104' where it presses the distal sealing member 138 against the proximal end of the electroporation chamber 104' to reform the fluid tight seal therebetween. In this example embodiment, top electrode 106 can be used without an associated removable cap piece to form, break, and reform a fluid tight seal with the electroporation chamber and iteratively place the electrode into contact with cell containing fluid to be electroporated.

While not shown in FIG. 4, it should be appreciated that single use or flow-through devices may similarly include a top electrode that is operable to seal and unseal the electroporation chamber without the use of an associated removable cap piece.

Figure 5:
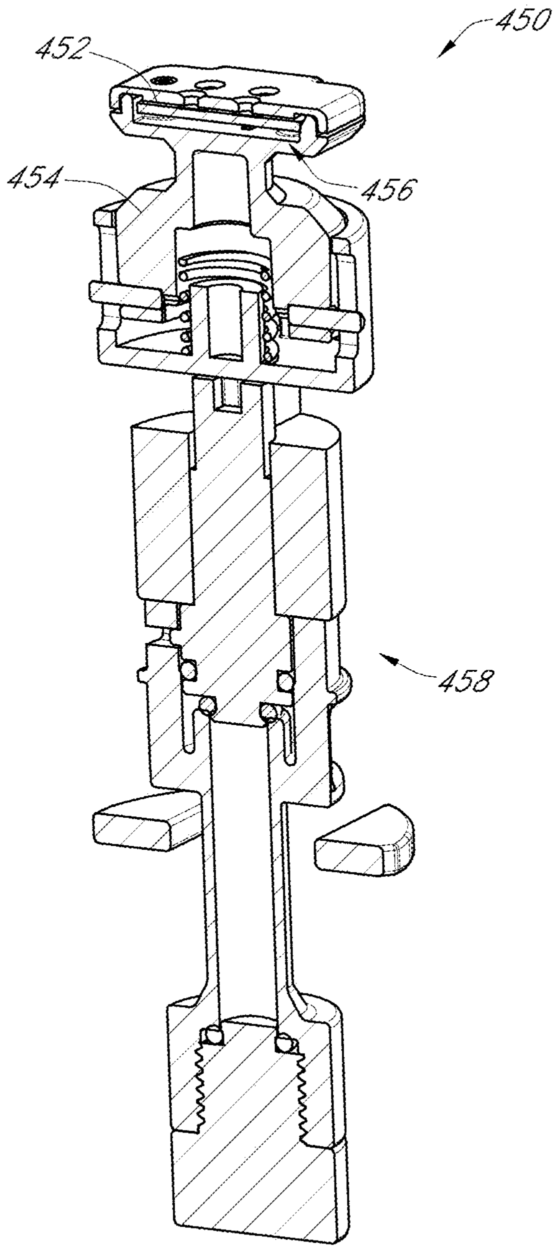
FIG. 5 is a cross-section of another exemplary single use electroporation cartridge having an authentication chip associated with the electrode cap in accordance with some embodiments of the present disclosure.

Referring now to FIG. 5, illustrated is a cross-section of an exemplary single use electroporation cartridge 450. The components and functionality of cartridge 450 may be similar to the cartridge 100' of FIG. 3, described above, with the addition of an authentication chip 452 in association with an electrode cap 454. The authentication chip 452 can be any form of authentication or use-limiting device known in the art and can impart any of a number of desired functionalities to the disclosed cartridges and systems.

For example, the authentication chip can be, or include, non-volatile memory, which can be used to embed manufacturing characteristics and operating parameters, data storage, security, or to manage limited use or reuse of the associated cartridge. This can beneficially protect against use of unauthorized aftermarket consumables and/or ensure authenticity and use of cartridges made by the original equipment manufacturer. Non-volatile memory can also provide the added functionality of allowing factory calibration of the cartridge such that it can communicate a given run protocol to the electroporation system to which it is associated during use. In this way, the cartridge may specify one or more runtime parameters of the electroporation system and/or can be optimized for use with various cell type(s) or electroporation target(s).

Authentication chips can take a variety of forms and may, in some instances, depend on the type of sterilization protocol (if any) used in manufacturing and/or packaging the cartridges. In general, gamma radiation—a common sterilizing agent in manufacturing of medical or laboratory grade equipment—is directly incompatible with semiconductor devices that traditionally incorporate floating-gate memory technologies used in many nonvolatile memories, such as erasable programmable read-only memory (EPROM), electrically erasable programmable read-only memory (EEPROM), and flash memory. In embodiments where sterilization via gamma radiation is desired, alternative non-floating-gate technologies can be used, including those user-programmable nonvolatile memory devices known in the art.

Other forms of authentication chips can be used and are within the scope of this disclosure. For example, simple electronics can be used as a reliable method for limiting cartridges to a single use or a prescribed number of uses. In an exemplary use, a cartridge utilizing a fuse-incorporated circuit within the authentication chip can be associated with an electroporation system. After running a given electroporation protocol with the associated cartridge, the electroporation system can send a high current through the authentication chip to blow the fuse. If the cartridge is removed and later reconnected, the lack of electrical continuity through the fuse can be a signal to the associated electroporation system to remain inactive, can prevent the system from completing a requisite circuit for functionality, or the like.

Alternative authentication chips also include radiofrequency identification (RFID) tags. An RFID tag can be associated with each cartridge and when the cartridge is loaded into a compatible electroporation system that has an RFID reader, the RFID tag can communicate information to the electroporation system that is relevant to the given cartridge. In this way, RFID tags can beneficially provide both use-limiting and counterfeit prevention capabilities. For example, the RFID tag can include the type of cartridge associated therewith, the number of times the cartridge can/has been used, a key or manufacturer specific authentication, or the like.

With continued reference to FIG. 5, authentication chip 452 can be housed within a space 456 formed by electrode cap 454. Access to the chip (e.g., for communicating with the electroporation system) can be achieved through contactless communication protocols or through one or more pin ports formed within electrode cap 454.

FIG. 6A-6D illustrate various views of another exemplary single use electroporation cartridge 460 having an authentication chip 465 housed within electrode cap 462. As illustrated in the cross-section of FIG. 6D, authentication chip 465 rests within a recess formed by a lower portion 478 of electrode cap 462 and is retained therein by an upper portion 476 of electrode cap 462. The upper portion 476 can, in some embodiments, be secured to the lower portion 478 in a manner that prevents tampering or otherwise removing authentication chip 465 from electrode cap 462 following manufacturing.

The cartridge 460 of FIG. 6A-6D is illustrated as having a plurality of pin ports 464 formed in the upper portion 476 of electrode cap 462. The number and orientation of pin ports 464 can change and, in some embodiments, can correspond to the number and/or orientation of pins associated with the connector/bus of the electroporation system that contacts and communicates with the authentication chip. For example, the authentication chip illustrated in FIG. 6A-6D includes six pin ports 464 that correspond to and mate with six pins of the connector/bus of the electroporation system (not shown). In some embodiments, the number of pin ports may be less or may be non-existent, such as when the authentication chip is an RFID tag. It should be appreciated, therefore, that the electrode cap can be configured in any manner to accommodate the desired authentication chip and communicator/bus associated with the paired electroporation system.

With continued reference to 6A-6D, the body 466 of the cartridge 460, in some embodiments, can include one or more stabilizers 468. The illustrated embodiment depicts two stabilizers 468. In some embodiments, stabilizers 468, themselves, can be sized and shaped to more easily manipulate the cartridge 460 and may include one or more gripping members 470 to assist the user in securely grasping and maneuvering the cartridge 460. For example, when loading the cartridge 460 into the electroporation system, a user can grasp the stabilizers 468 (e.g., at the gripping members 470) and easily maneuver the cartridge 460 into position. Similarly, the stabilizers 468 can be used to remove the cartridge 460 from the electroporation system after being used. The gripping members 470 can include one or more protrusions extending from the surface of the stabilizers 468, as shown, or can include other contours in the surface of the stabilizers 468. In some embodiments, the gripping members may additionally, or alternatively, include a different material (e.g., rubber or silicone) designed to increase the friction between the user's grip and the stabilizers.

The stabilizers can additionally, in some embodiments, include feet 472 positioned at the same elevation as the base (or second electrode) of the cartridge 460, thereby providing an effectively wider base to support the cartridge 460. The feet 472 can act to stabilize the cartridge when placed, for example, on a benchtop or other flat surface, preventing the cartridge 460 from being knocked over by a glancing blow or otherwise increasing the stability of the cartridge in a standing position.

Figure 6A:
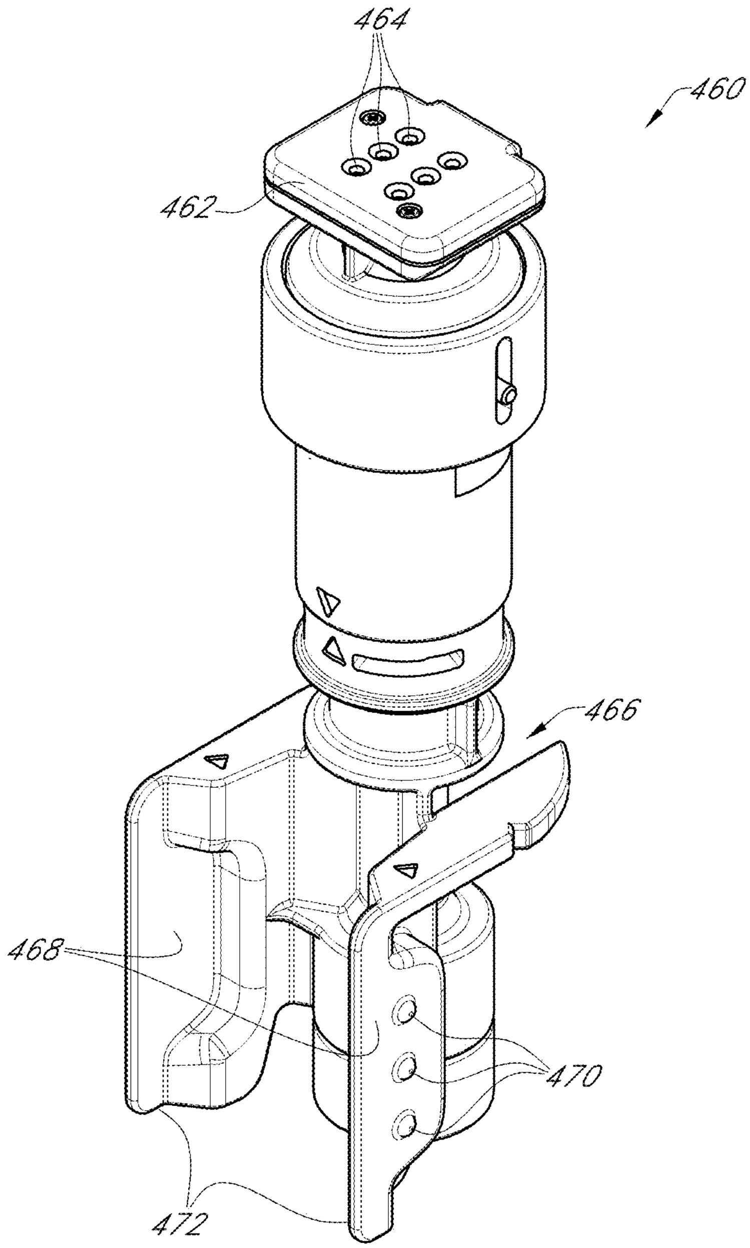
FIG. 6A is a perspective view of another exemplary single use electroporation cartridge having an authentication chip associated with the electrode cap and a gripping member associated with the chamber body in accordance with some embodiments of the present disclosure.
Figure 6B:
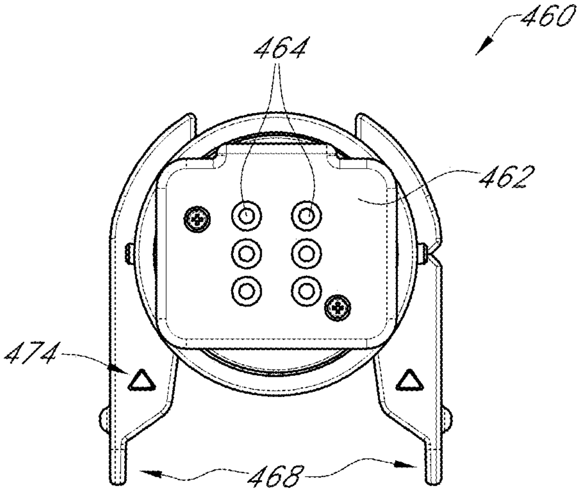
FIG. 6B is a top view of the single use electroporation cartridge of FIG. 6A.
Figure 6C:
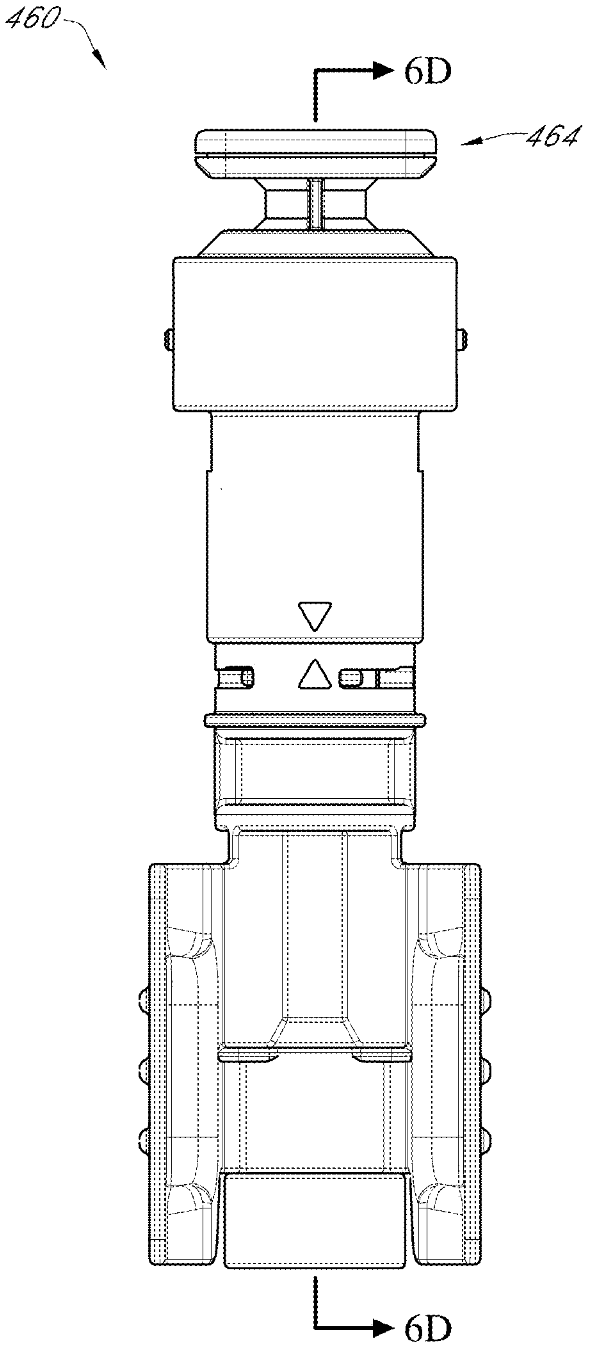
FIG. 6C is a front plan view of the single use electroporation cartridge of FIG. 6A.
Figure 6D:
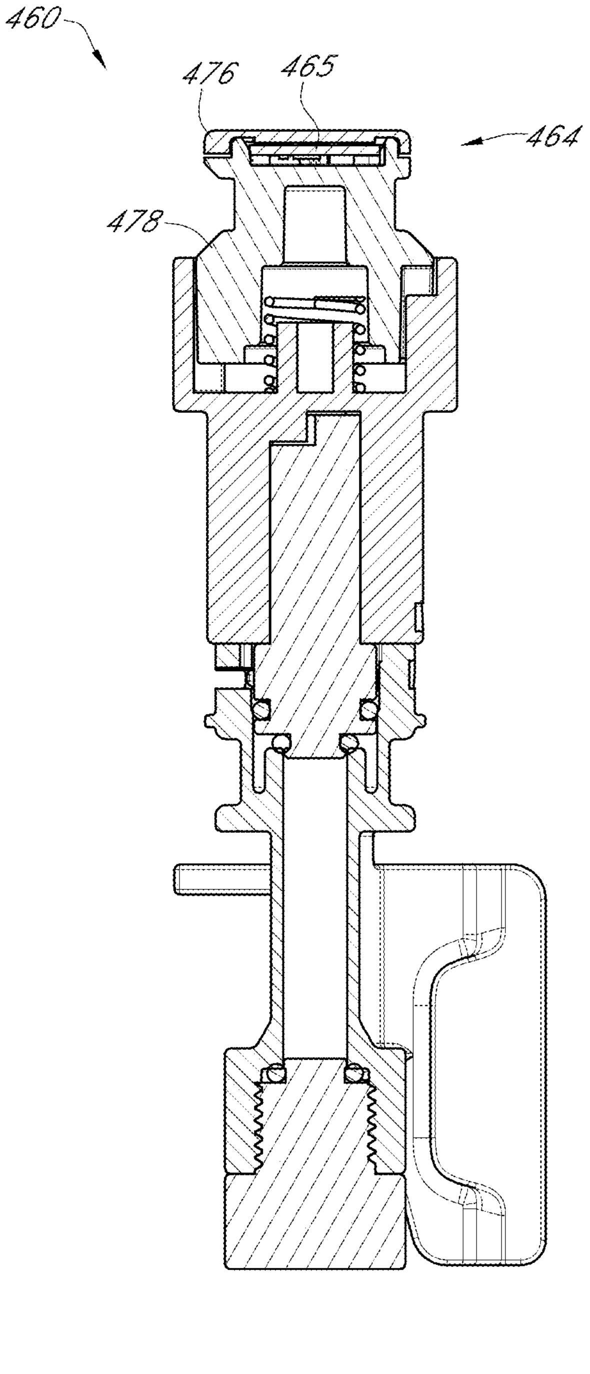
FIG. 6D is a cross-sectional view of the single use electroporation cartridge of FIG. 6C (taken along plane 6D as illustrated in FIG. 6C)

As shown in FIG. 6B, the stabilizers may additionally include signals or signs 474 to passively communicate the orientation or directionality of the cartridge 460 when inserted or otherwise associated with the electroporation system. Although FIG. 6B depicts the signs 474 as arrows, it should be appreciated that other signals, signs, or designations can be placed thereon as known in the art.

In some embodiments, electroporation cartridges, for example, those depicted and described in FIGS. 1-5, FIGS. 6A-6D (as well as in FIG. 9 and FIGS. 22A-22S described later in the description) are designed to form a convex meniscus when a fluid is dispensed into these cartridges. In some embodiments, formation of a convex meniscus in electroporation cartridges of the present disclosure (as opposed to concave meniscus formed in several prior art electroporation cartridges) prevents bubble from being trap during the capping or sealing of the chambers. In some embodiments, formation of a convex meniscus in electroporation cartridges of the present disclosure (as opposed to concave meniscus formed in several prior art electroporation cartridges) substantially reduce bubble from being trap during the capping or sealing of the chambers.

Figure 7A:
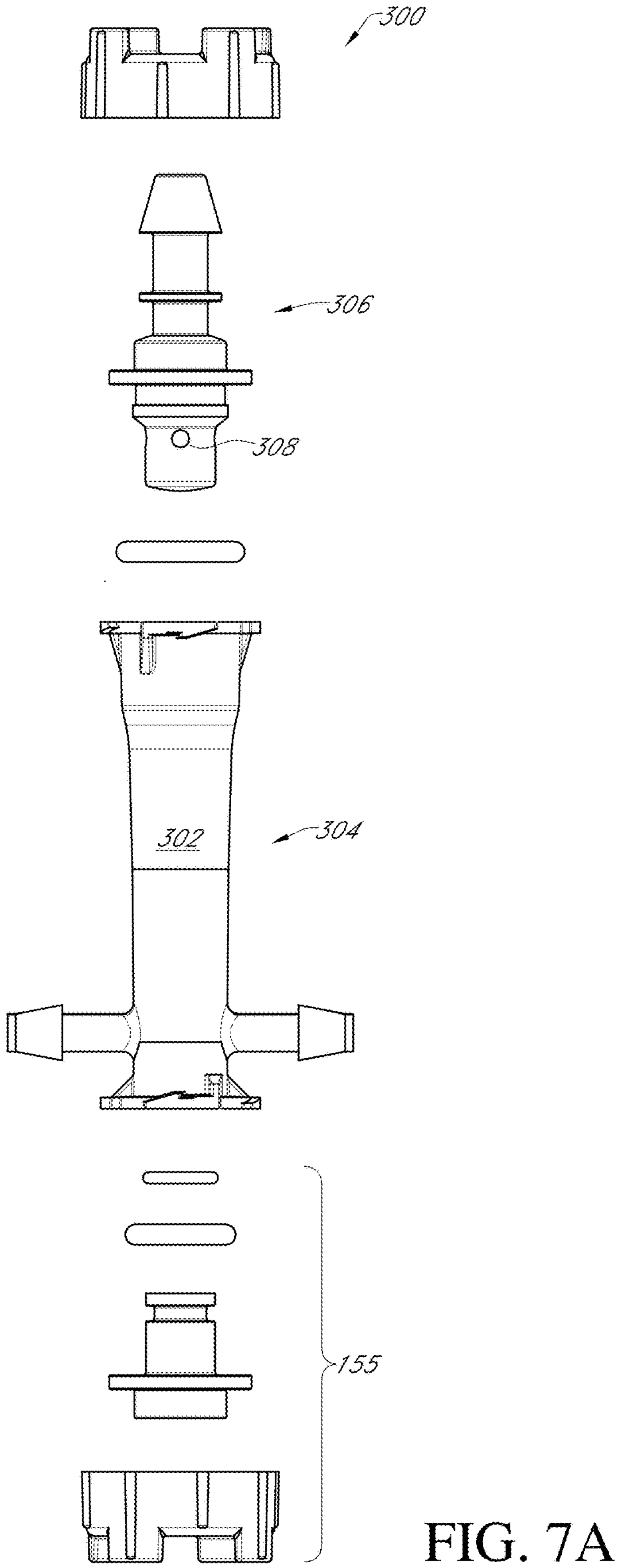
FIG. 7A illustrates an exploded front view of an exemplary flow-through electroporation cartridge with the cartridge body being illustrated as transparent for ease of viewing and description herein, in accordance with some embodiments of the present disclosure.
Figure 7B:
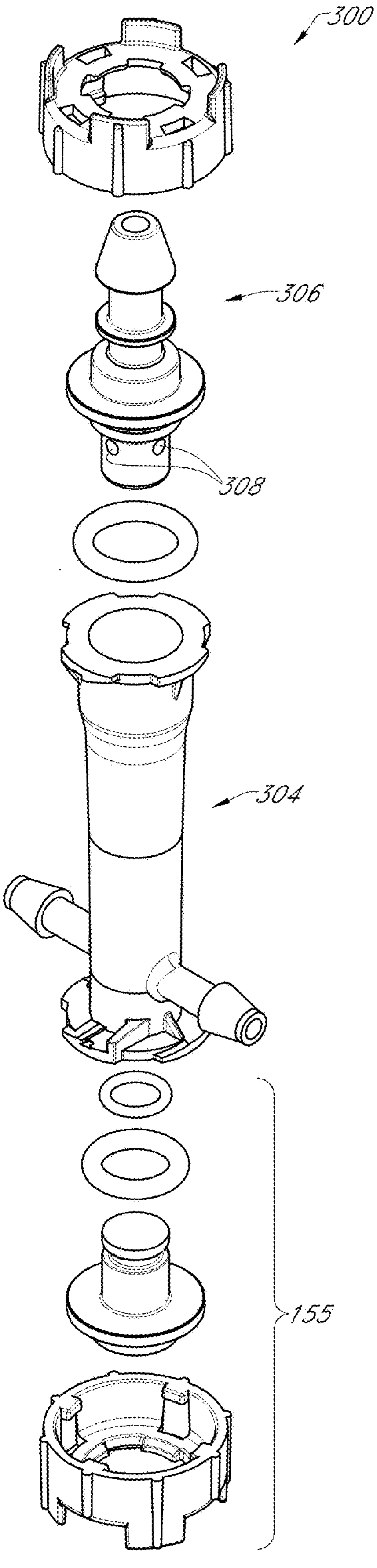
FIG. 7B is a top perspective view of the exploded flow-through electroporation cartridge of FIG. 7A.
Figure 7C:
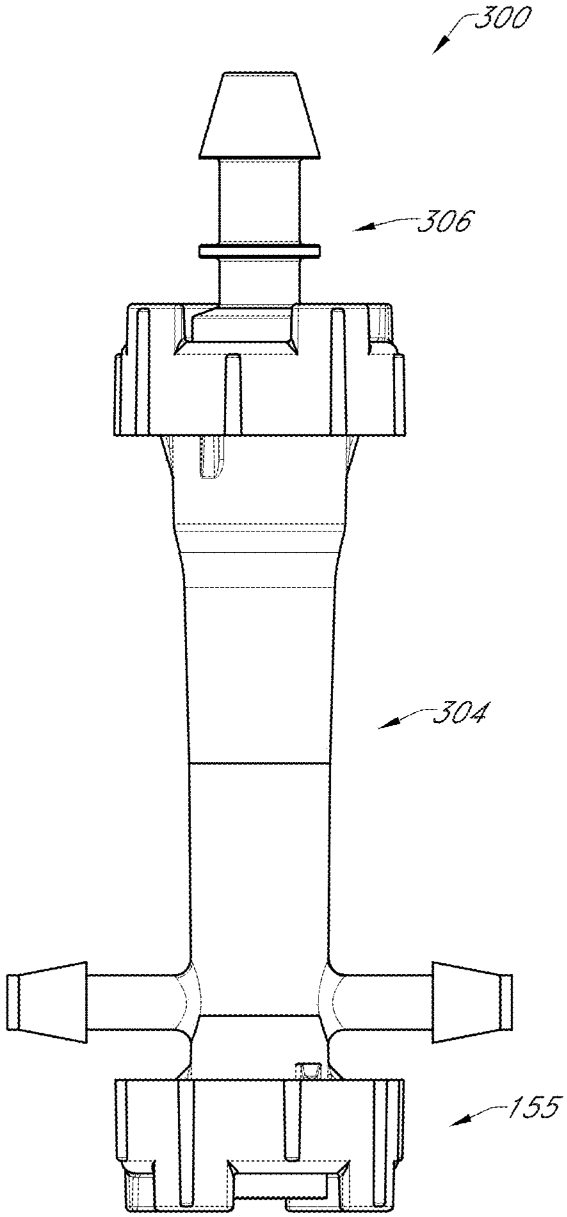
FIG. 7C is a front view of the exemplary flow-through electroporation cartridge of FIG. 7A shown assembled and with the cartridge body being surface shaded instead of transparent.
Figure 7D:
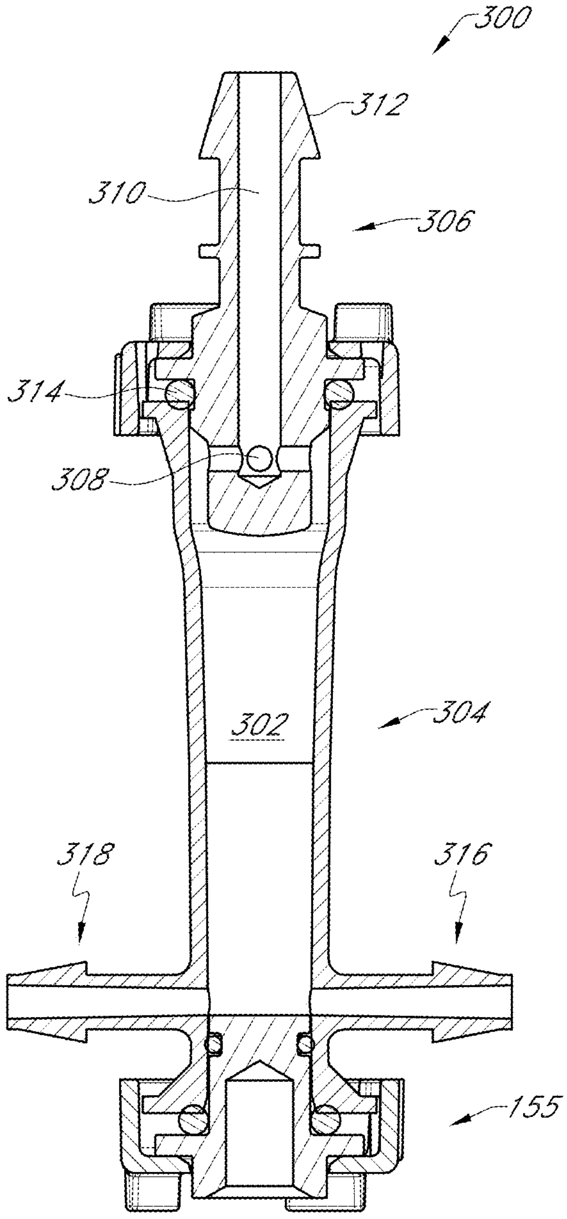
FIG. 7D is a front view of a longitudinal cross section of the assembled flow-through electroporation cartridge of FIG. 7C, the cross section bisecting the port associated with the first electrode as well as the chamber inlet and outlet.

Some embodiments of electroporation cartridges described herein can be implemented within a continuous batch processing system, described in greater detail below. One such embodiment is disclosed in FIG. 7A-7D. FIGS. 7A and 7B illustrate exploded views of an exemplary flow-through electroporation cartridge 300 with FIGS. 7C and 7D showing the flow-through electroporation cartridge 300 in an assembled configuration. As shown in FIG. 7A-7D, the flow-through electroporation cartridge 300 includes the same or similar components as described above with respect to the electroporation cartridge of FIG. 1A-1E. However, instead of being a single (or limited batch use) electroporation cartridge requiring manual manipulation in between individual electroporation events, the flow-through electroporation cartridge 300 shown in FIG. 7A-7D can be used to iteratively electroporate successive samples without user intervention. Such flow-through electroporation cartridges can be used to process tens to hundreds of milliliters of sample in a single or even multiple different runs.

As shown in FIG. 7A-7D, the chamber body 304 of the continuous flow cartridge 300 includes a flow-through electrode 306 inserted into the upper open end of the chamber body 304. Similar to the other electrodes disclosed herein, the flow-through electrode 306 is made from, or plated with, a conductive material like gold that does not negatively impact cells by introducing harmful or toxic elements. The flow-through electrode 306 is operable for connection to a high voltage circuit and may act as an anode, a cathode, or may alternate between the two. The flow-through electrode 306, in some embodiments, additionally includes the bell or bulbous protrusion having a slight convex curvature to assist bubbles with exiting the electroporation volume by moving them radially outward and away from the distal electrode surface to thereby reduce a likelihood of arcing during electroporation.

In some embodiments, the flow-through electrode 306 can have additional physical features to accommodate the continuous-flow functionality. For example, one or more apertures or thru-holes 308 can be formed by the flow-through electrode 306 that are axially perpendicular to the flow-through electrode 306. The thru-holes 308 can intersect a blind hole or lumen 310 that is axial to the flow-through electrode 306 (see FIG. 7D). The thru-holes 308 and lumen 310 can function as vents to allow filtered air to exit and enter the chamber when filling and removing fluid from the electroporation chamber 302, respectively. When the chamber 302 is filling with fluid to be electroporated, the air that is in the chamber 302 exits the chamber 302 through these thru-holes 308 and lumen 310. When electroporated fluid is pumped out of the chamber 302, filtered air enters the chamber 302 through these thru-holes 308 and 310 to prevent a vacuum from forming within the chamber 302. In some embodiments, such as that shown in FIG. 7A-7D, the upper section of the flow-through electrode 306 is shaped as a barb or port 312 to help maintain sterility. A tube may be installed on this port and either fitted with a micron filter to vent the chamber to atmosphere. Port 321 can be connected to a sterile air source or to an air filter. During electroporation, pressure buildup can be dissipated through the thru-holes 308 and lumen 310. Similar to other electrodes disclosed herein, flow-through electrode 306, in some embodiments, is associated with a cap such that it can rotate independently and so that the sealing member 314 only (or predominantly) receives axial compression.

The flow-through electroporation cartridge 300 can additionally include a chamber inlet 316 and a chamber outlet 318 fluidically connected to the electroporation chamber 302. The chamber inlet 316 can be fluidically connected to a source of cell containing fluid to be electroporated, and through the action of one or more pumps in the system, the chamber inlet 316 can be used to move said fluid into the electroporation chamber 302. Conversely, the chamber outlet 318 can be fluidically connected to an output reservoir of electroporated cells, and through the action of one or more pumps associated with the system, the chamber outlet 318 can be used as an egress point for electroporated cells from the electroporation chamber 302. The chamber inlet 316 and chamber outlet 318 can be associated with a plug and/or valve to control an inward flow of cell-containing fluid to be electroporated within the electroporation chamber and/or to control an outward flow of electroporated cell-containing fluid from the electroporation chamber, respectively. In some embodiments, the chamber inlet/outlet can be positioned above a proximal surface of the second electrode and/or the lumen of the chamber inlet/outlet can be substantially parallel to the proximal surface of the second electrode.

Figure 8A:
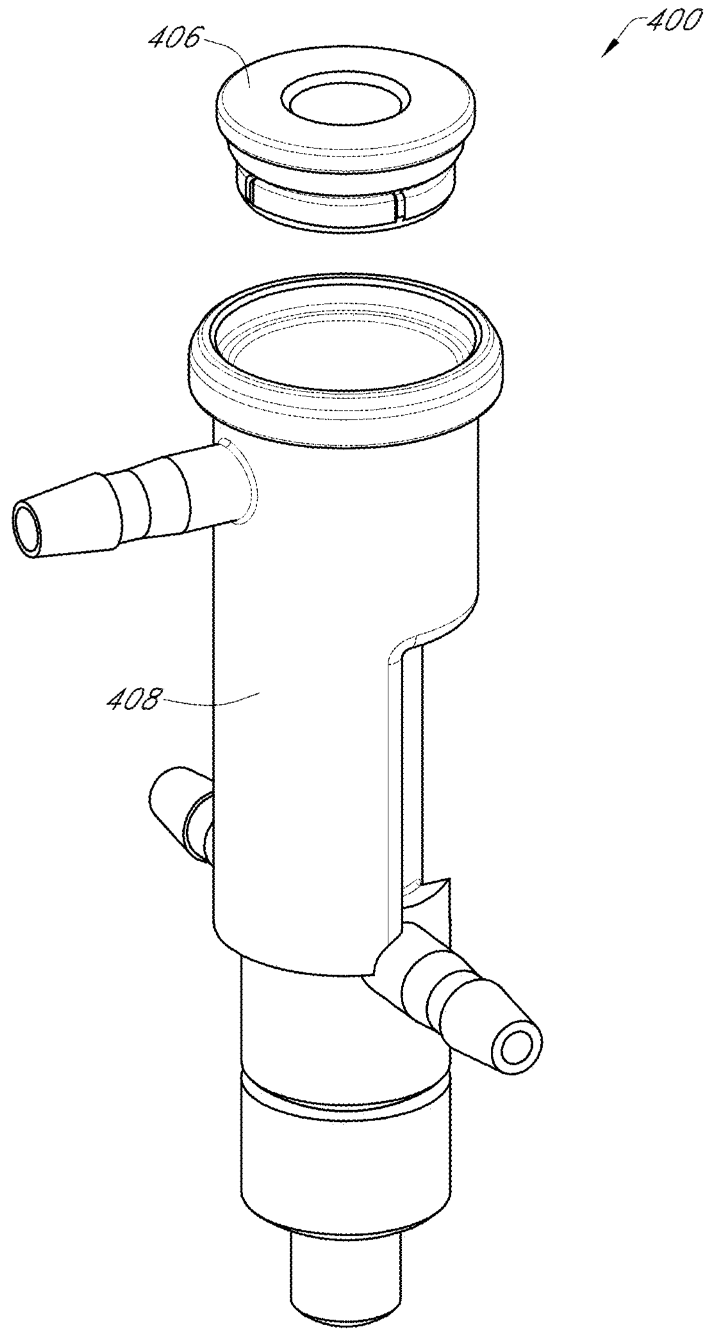
FIG. 8A is a top perspective view of another embodiments of a flow-through electroporation cartridge wherein the illustrated flow-through electroporation cartridge comprises a reservoir integrated with the chamber body and is shown partially assembled with the top sleeve cap exploded away from the chamber body.
Figure 8B:
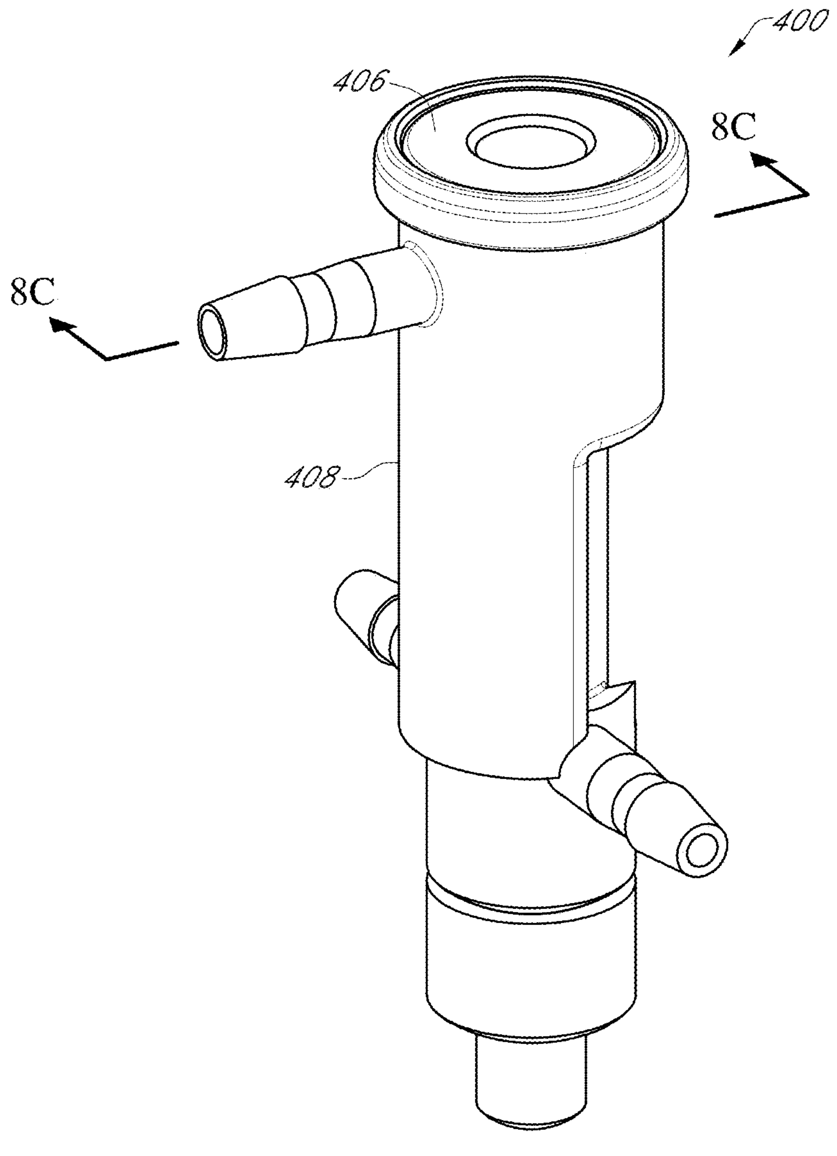
FIG. 8B is a top perspective view of the flow-through electroporation cartridge of FIG. 8A in a partially assembled state, the top sleeve cap being associated with a proximal opening of the chamber body.
Figure 8C:
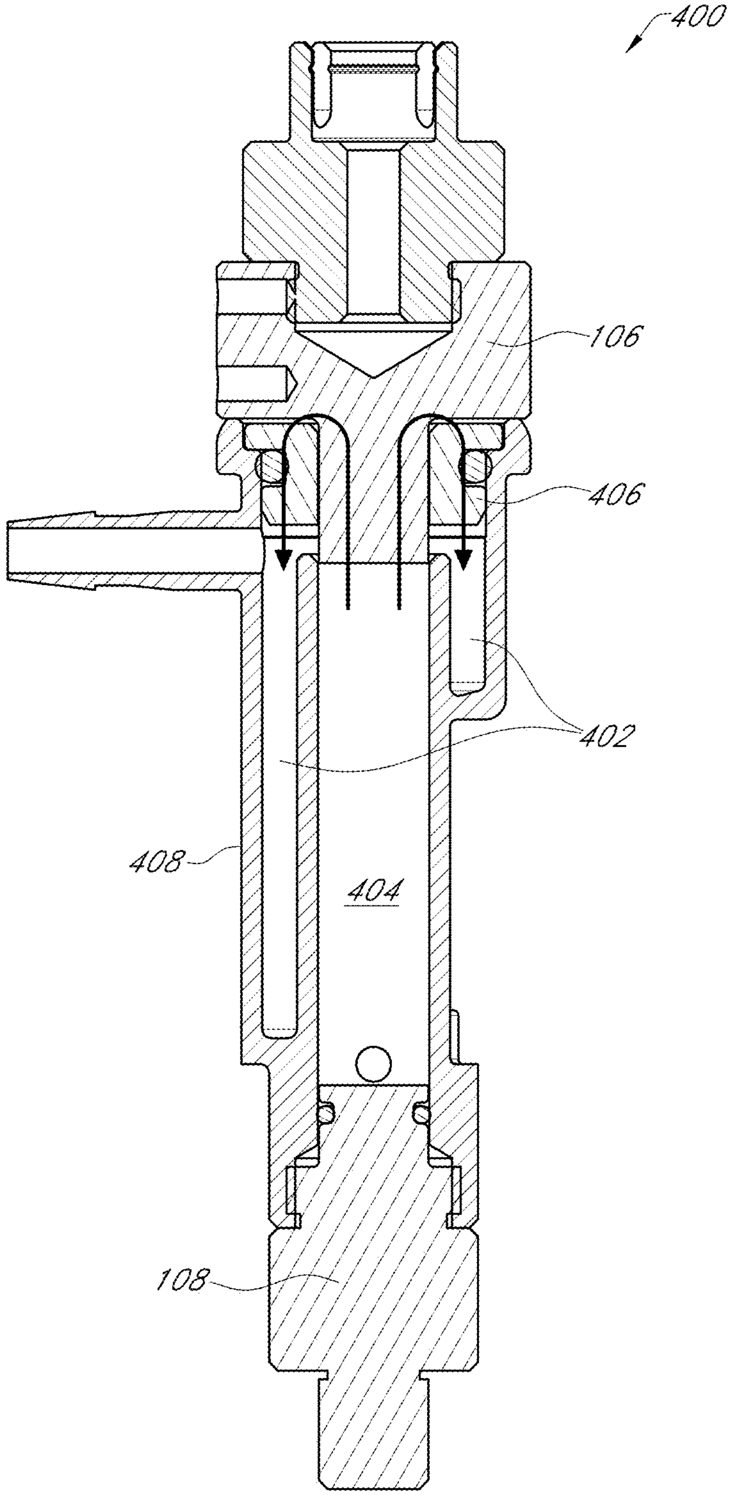
FIG. 8C is a longitudinal cross section of the flow-through electroporation cartridge of FIG. 8B (taken along the plane 8C as illustrated in FIG. 8B), the illustrated flow-through electroporation cartridge being shown with a top electrode associated therewith; the arrows shown in the drawing illustrate overflow fluid being discharged from the electroporation chamber in response to be collected in the associated reservoir.

Referring now to FIG. 8A-8C, illustrated, is another embodiment of a flow-through electroporation cartridge 400 having an inlet and outlet and having a reservoir 402 integrated with the electroporation chamber body 404. In an exemplary operation, fluid to be electroporated is filled within the chamber body 404 using a standard pipette and an electrode adaptor 406 can be fitted over the opening thereof. An electrode 106 can be fitted into the adaptor to seal the chamber 408 (see, for example, FIG. 8C). The fluid can be overfilled within the chamber, forming a convex meniscus at a top portion of the chamber 404. Insertion of the electrode can then cause the fluid overfill to pour out of an adjacent opening and into the reservoirs 402, ensuring a properly wetted electrode (e.g., as shown in FIG. 8C, which is a cross-section of the flow-through electroporation cartridge of FIG. 8B taken along the plane A). The arrows shown in FIG. 8C illustrate overflow fluid being discharged from the electroporation chamber in response to be collected in the associated reservoir.

Figure 9:
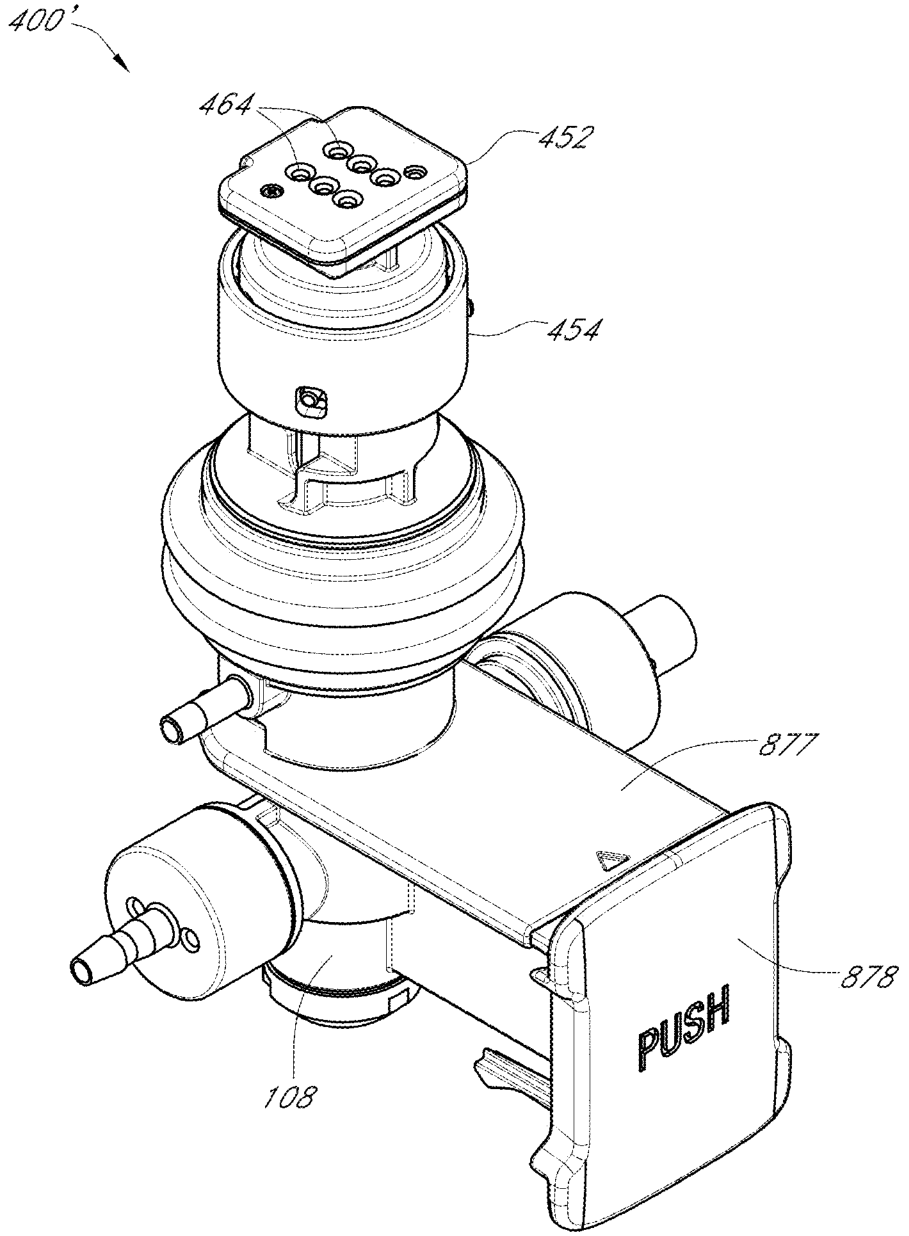
FIG. 9 is another embodiment of a flow-through electroporation cartridge according to some embodiments of the disclosure.

Referring now to FIG. 9, illustrated is an exemplary flow-through electroporation cartridge 400' having an inlet and outlet. The components and functionality of cartridge 400' are similar to the cartridge 400 of FIG. 8A-C, described above, with the addition of an authentication chip 452 in association with an electrode cap 454. The authentication chip 452 can be any form of authentication or use-limiting device known in the art and can impart any of a number of desired functionalities to the disclosed cartridges and systems. Several examples of authentication chips, described in sections above, can be used here as well. Several aspects and additional embodiments of electroporation cartridge and how it functions for refilling and electroporating batches of cells are described ahead in FIGS. 22A-22S.

Overview of Electroporation System

The following provides an initial overview of an exemplary electroporation system and corresponding process for electroporating a sample. As will be appreciated, embodiments described herein provide for effective electroporation of relatively high volumes of sample, and are capable of providing high electroporation efficiency, high cell viability, and a safe and relatively straightforward user experience, among other benefits. As will be seen in the more detailed description below, systems may be functionally closed such that all contact parts are closed off from the ambient environment, thus limiting potential contamination and also enhancing safe operation of the device. Further, as detailed below, disclosed systems are capable of recovering sample in the case of a system error, overly high temperature reading, arc risk reading, and/or other warning event. In the case of such an event, for example, the relevant sub-volume(s) of the sample may be pumped out of an electroporation chamber and back into a mixing reservoir, or even back into the sample input bag from which it originated.

Figure 10A:
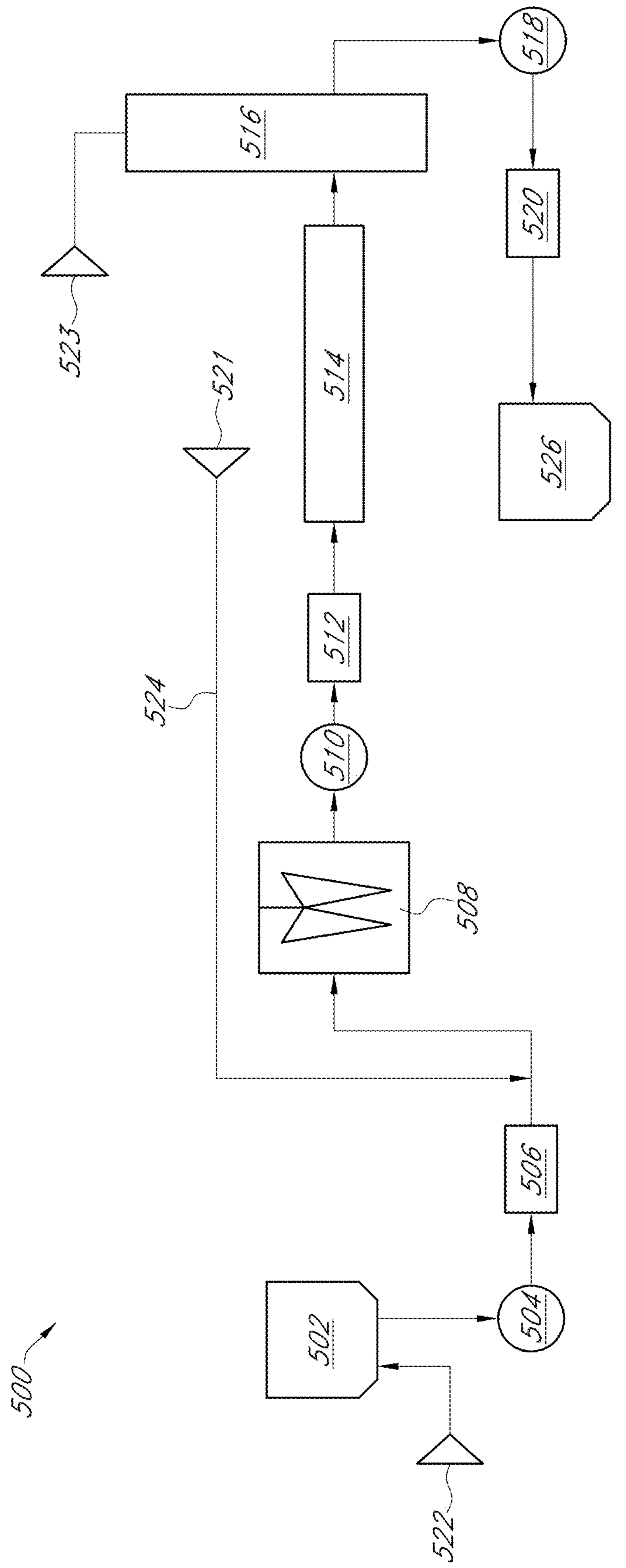
FIG. 10A schematically illustrates one embodiment of an electroporation process flow through an exemplary electroporation system of the disclosure.

FIG. 10A schematically illustrates the process of an exemplary flow-through electroporation system 500. FIG. 10A is intended to provide an overview of an exemplary process flow that the systems described herein may be utilized to perform. The various electroporation system components that can be included within the system 500 will be described in greater detail below. It will be understood that the various alternative embodiments of the different electroporation system components may be combined together in various ways to construct an electroporation system such as generally shown in FIG. 10A.

In the illustrated system 500, an input bag 502 including a sample may be fluidically attached to a first pump 504. The first pump 504 is configured to drive fluid flow from the input bag 502 to a mixer reservoir 508. A first flow sensor 506 may be positioned between the pump 504 and the mixer reservoir 508 to enable the system to determine when fluid is flowing through the corresponding section of tubing. The mixer reservoir 508 is fluidically attached to a second pump 510. The second pump 510 is configured to drive fluid flow from the mixer reservoir 508 to an electroporation cartridge 516. In some embodiments, the electroporation cartridge can be a flow-through electroporation cartridge, such as any of the flow-through electroporation cartridges described above (see, e.g., FIGS. 7A-9 and in FIGS. 22A-Q described ahead).

As shown, in some embodiments, a second flow sensor 512 and/or a pre-cooling module 514 (also referred to a pre-cooling assembly) can be disposed between second pump 510 and electroporation cartridge 516. As described in greater detail below, a pre-cooling module is beneficially provided upstream from electroporation cartridge 516 in order to assist in lowering the temperature of passing sample to lower temperatures (e.g., toward a target temperature) more suitable for electroporation and less prone to bubble formation (or otherwise regulating temperature of the passing sample via heating if needed).

As shown in FIG. 10A, the electroporation cartridge 516 is fluidically connected to a third pump 518 configured to drive sample fluid out of the electroporation cartridge 516 and toward an output, such as output bag 526. A third flow sensor 520 may be disposed between the third pump 518 and the output bag 526.

In operation, the electroporation cartridge 516 operates to provide an electroporation pulse to a portion of the sample contained therein. The terms "sub-volume" and "sample sub-volume" will be used herein to refer to the discrete portion of the sample contained within the electroporation cartridge 516 at any given time, to distinguish from the greater overall volume of sample intended to be processed by the system 500. System 500 beneficially operates to move a series of successive sub-volumes through the electroporation cartridge 516 without requiring removal of the electroporation cartridge 516 from electroporation of one sub-volume to the next.

This system 500 beneficially enables effective electroporation of relatively high-volume samples. For example, a single "run" which electroporates several successive sub-volumes of until the overall sample volume has been electroporated, may process an overall sample volume of about 5 mL up to about 25 mL, or even up to about 50 mL. Sample volumes even greater than 50 mL could also plausibly be processed with limited additional setup, the limit being only that most standard sample bags are not sized to be that large. Thus, the system is capable of processing even higher volumes so long as the input and output containers are configured to accommodate such volumes.

As shown, the system 500 may also include one or more air filters or other air venting devices to provide air venting and to assist in movement of the sample fluid through the system. For example, a vent line and/or air filter 522 may be coupled to the input bag 502, and a vent line and/or air filter 523 may be coupled to the electroporation cartridge 516. A vent line and/or air filter 521 may also connect to an intermediate section of tubing 524 extending off of a main section of tubing between the first pump 504 and the mixer reservoir 508. As explained in greater detail below, this feature may be utilized to determine and/or control when sample transfer from the input bag 502 to the mixer reservoir 508 has occurred.

While specific examples of the foregoing components will be described in greater detail below, it will be understood that alternative embodiments of the electroporation components may additionally or alternatively be included. For example, while the pumps may be described as peristaltic pumps, other embodiments may include one or more gear pumps, diaphragm pumps, rotary displacement pumps, pneumatic pumps, in-line pumps, other types of pumps, or other suitable fluid displacement mechanisms known in the art. Further, while three pumps are shown in this particular example, other embodiments may include a fewer or greater number of pumps.

By way of further example, while the flow sensors may be described as ultrasonic sensors, other embodiments may include one or more rotameters, spring and piston flowmeters, turbine/paddle sensors or other positive displacement meters, vortex metes, Pitot tubes, Hall effect sensors, or other suitable flow sensors known in the art. Further, while three flow sensors are illustrated in this particular example, other embodiments may include a fewer or greater number of flow sensors. Moreover, while input containers and output containers are described in the following examples as being bags, other suitable sample containers may also be utilized so long as their contents are able to be effectively transferred from the input container into the electroporation system and then out into the output container.

Further, while the cooling module and pre-cooling module components described herein are described in the context of cooling, it will be understood that they may also, at least in some embodiments, be operated to heat the samples and/or sample sub-volumes. For the sake of convenience, because the typical operation will benefit from cooling more than heating, these components will be referred to herein as "cooling" or "pre-cooling" modules. This, however, should not be taken as limiting their ability to provide heating in addition to or as an alternative to the ability to provide cooling.

In addition, while the particular examples described herein illustrate a single system with a single input bag, other implementations may utilize more than one system and/or more than one input bag per system in order to treat higher volumes through parallel operation.

Figure 10B:
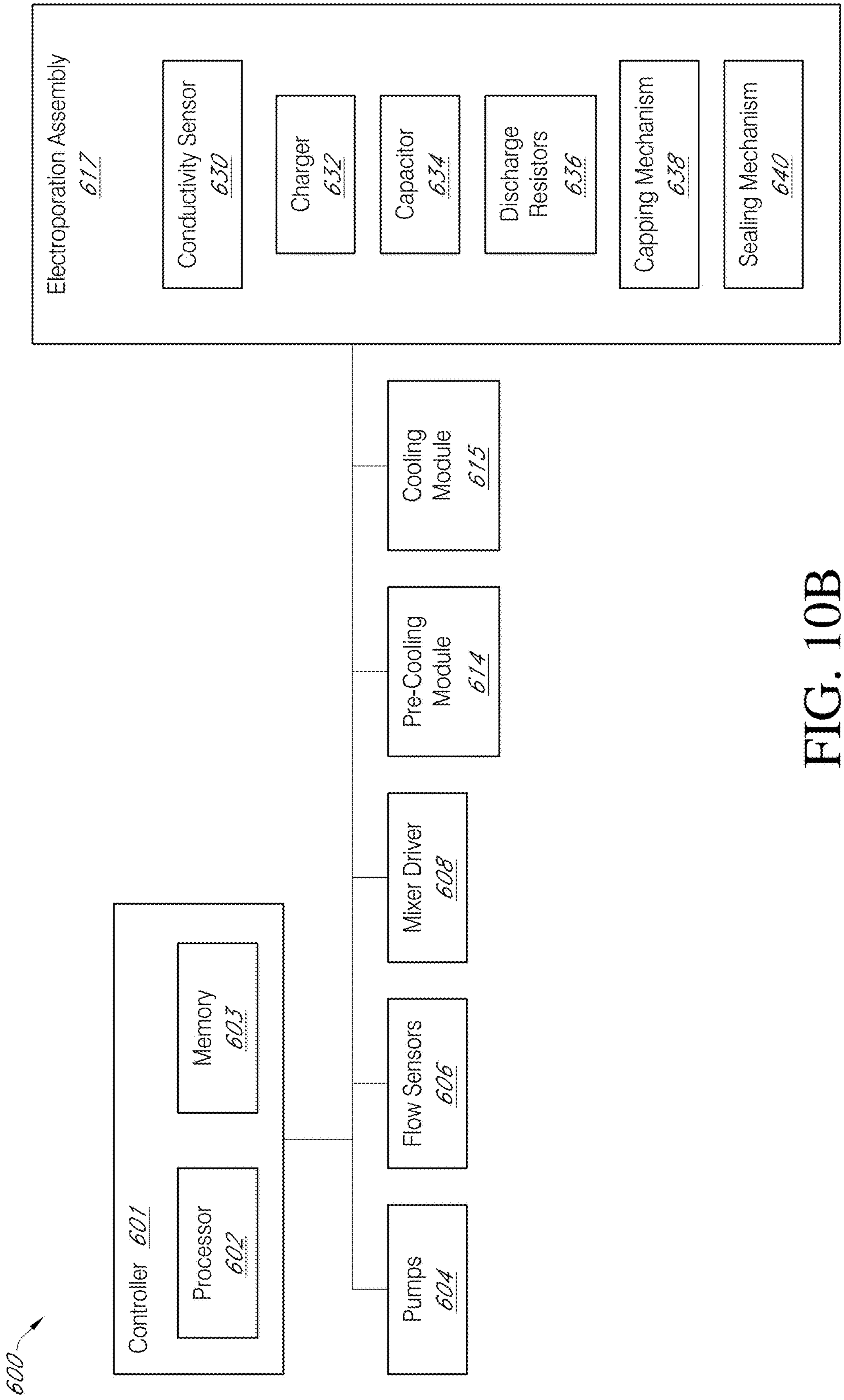
FIG. 10B illustrates one embodiment of a control system configured to be communicatively coupled to one or more components of an electroporation system of the disclosure and configured to provide one or more computer-implemented process control methods for the system.

FIG. 10B illustrates a control system 600 (used interchangeably herein with the terms "computer system" and "computing system") that may be included as part of an electroporation system. For example, the control system 600 form part of and/or may be communicatively coupled to one or more components of the electroporation system 500 illustrated in FIG. 10A or with any of the other electroporation systems described herein.

The control system 600 includes a controller 601 that has one or more processors 602 and one or more hardware storage devices (for holding memory 603). The controller 601 is communicatively coupled to one or more of the various electroporation components of the electroporation system so as to receive data and/or send instructions to the one or more electroporation components. As shown, the controller 601 may be communicatively coupled to the pumps 604, flow sensors 606, mixer driver 608 (for controlling mixing in the mixer reservoir), pre-cooling module 614, cooling module 615, and an electroporation assembly 617.

The controller 601 operates to provide control over the various, linked electroporation components. For example, the controller 601 may be configured to: control actuation, direction, and/or speed of the pumps 604; receive flow data from the flow sensors 606; control actuation, direction, and/or speed of the mixer driver 608 to thereby correspondingly control mixing in the mixer reservoir; and control temperature in the pre-cooling module 614 and/or cooling module 615.

The electroporation assembly 617 includes various components configured to interact with the electroporation cartridge. As shown, the electroporation assembly 617 may include a conductivity sensor 630 configured to measure the conductivity across an electroporation chamber of an electroporation cartridge. As explained in greater detail below, the controller may utilize information from the conductivity sensor to control one or more electroporation parameters, such as whether or not to deliver a pulse and the targeted voltage for delivering the pulse.

The electroporation assembly 617 also includes components that make up the electroporation circuit configured for generating and delivering the electrical pulse to the electroporation chamber. These components include a charger 632 configured to act as a voltage source for charging the capacitor 634 and one or more discharge resistors 636 and/or other safety components configured to allow safe discharge of the capacitor when not immediately discharged for normal operation. Additional or alternative circuit components, as are known in the art, may be included for generating and delivering an electrical pulse across the electroporation chamber.

The electroporation assembly 617 may also include a capping mechanism 638 configured to mechanically engage with an electroporation cartridge when the electroporation cartridge is properly inserted into the electroporation assembly 617. As explained in greater detail below, in some embodiments, capping mechanism 638 operates to move the electroporation cartridge between a capped state, in which electroporation can occur, and an uncapped state, in which venting and fluid movement out of and into the electroporation chamber can occur. A sealing mechanism 640 may operate in conjunction with the capping mechanism 638 to seal and unseal the electroporation chamber as the system moves from electroporation of one sub-volume to the next.

Various exemplary electroporation components will now be described in greater detail. Any of the following embodiments may be incorporated into the electroporation system 500 and/or control system 600.

Figure 11A:
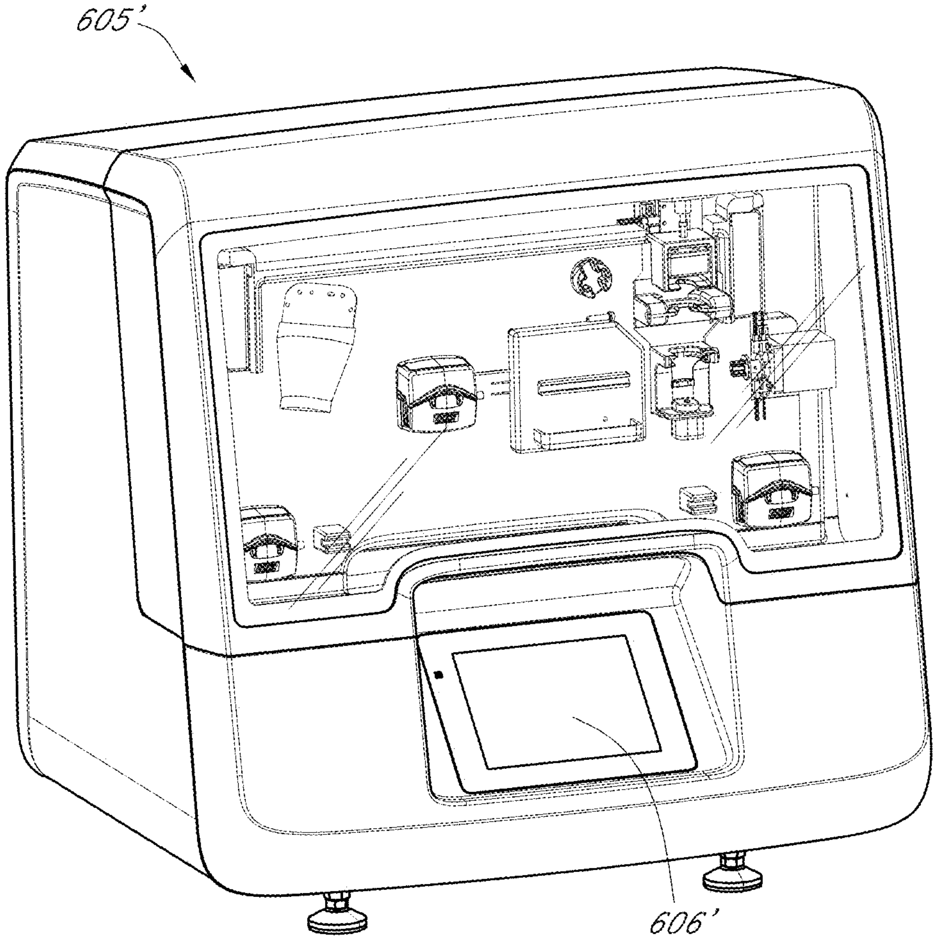
Figure 11B:
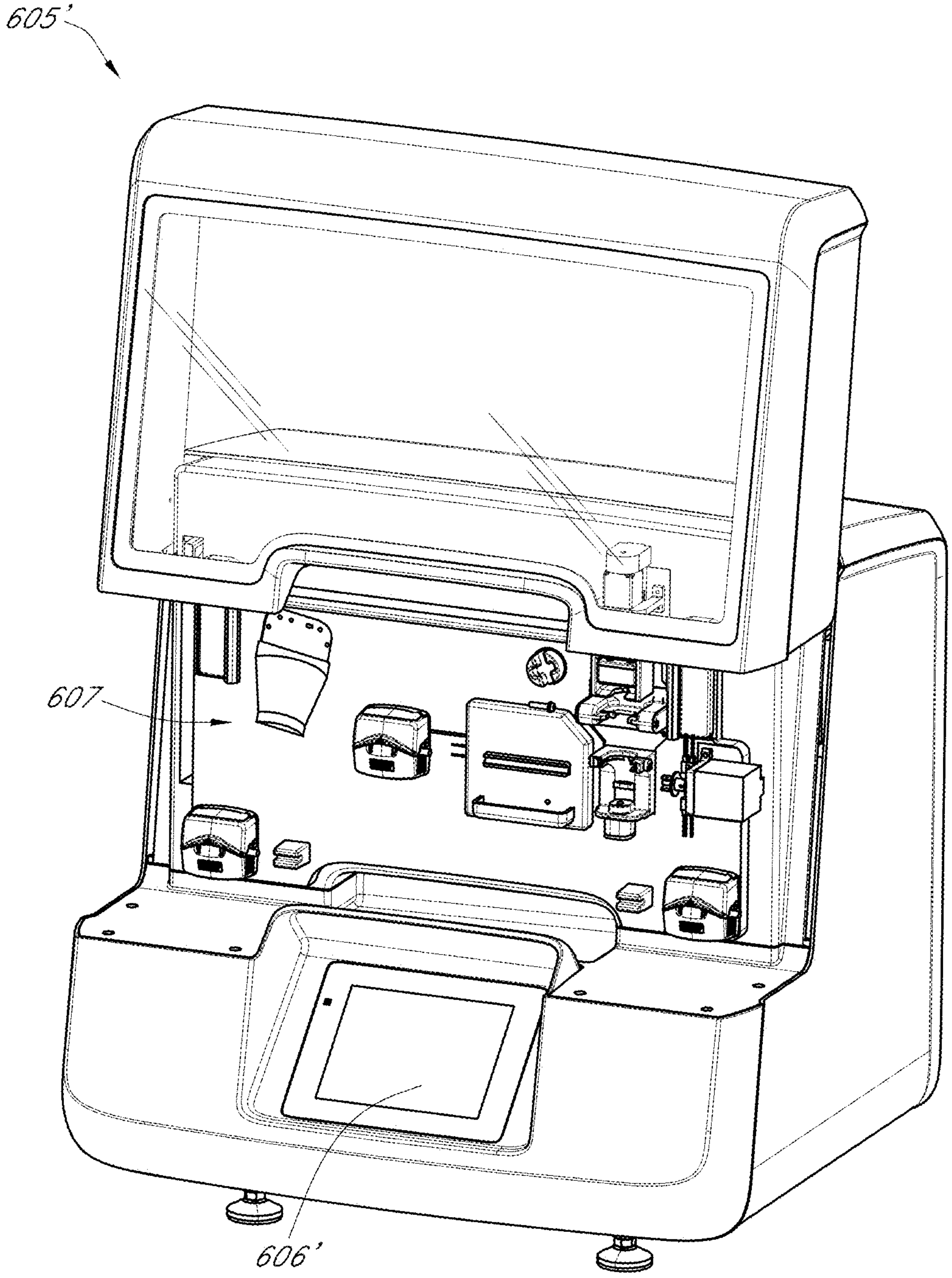

FIGS. 11A-11D illustrate example embodiments of an electroporation system of the disclosure. FIG. 11A and FIG. 11B show an exemplary electroporation system/instrument 605', according to one embodiment, comprising one or more components of electroporation system 500 and one or more components of electroporation system 600 (components of system 500 and system 600 are shown but not numbered). The embodiment shown in FIG. 11A comprises a door that can be closed while the electroporation is in progress and an user-interface panel 606' that can allow a user to select electroporation parameters, run protocols, monitor progress of a run, receive any error messages to correct potential issues etc. via a graphical user interface and computer implemented methods.

Electroporation system/instrument 605' of FIGS. 11A and 11B, in one embodiment, can comprise one or more components including: at least one or more pumps, at least one or more sensors for sensing liquids (e.g., such as but not limited to ultrasonic sensors), at least a cell mixer mechanism and/or an area to removably insert a cell mixer, an area to removably insert an electroporation chamber (e.g. a single use electroporation chamber for a single electroporation run, or a flow-through chamber for a batch/continuous electroporation), corresponding electric pins (such as but not limited to high voltage electric pins to make electric contact with electrodes located in the inserted electroporation chambers), an authentication chip reader (configured to read chips on electroporation chambers), one or more bubble sensors, one or more pre-cooling chambers or modules, a shell or placeholder to insert a modular casing having various electroporation device components (such as but not limited to, an instrument panel or a modular casing such as 700, 701, 703, 800 or 803 described in FIGS. 12A-G and 13A-C), pressure sensors, locking mechanisms to clamp in a modular casing and/or an electroporation chamber; handles for easy insertion and removal of modular casing and/or electroporation chambers, stopcocks and placement mechanisms, air filters, tubes for sample flow from one component to another, tubes for air flow, one or more stopcocks for controlling air flow and/or liquid flow, sterile air sources and/or air filters, vents, valves, rotating mechanisms to open or close chambers or inlets and outlets for cells, pressure sensing mechanisms, conductivity sensors, hooks or drawers to attach sample input bags and sample output bags (the bags containing cells in fluid before and after electroporation respectively), components of processor systems (e.g., computer controllers and processors) to sense, control and operate one or more or all of the foregoing (some these components are shown on the inner surface 607 but not expressly labeled or called out in FIGS. 11A and 11B). Some of the components listed above can be present inside a housing of 605' while some of the components may be present on an inner face such as 607 of system/instrument 605'.

In some embodiments, the one or more pumps of system 605' can comprise for example, a first pump (e.g., a peristaltic pump) to transfer sample, such as a sample comprising cells to be electroporated from a input bag/reservoir, to a cell mixer, and a second pump, (e.g., a peristaltic pump) to transfer processed sample, such as a sample comprising electroporated cells from an electroporation chamber to an output bag/reservoir, to a cell mixer.

In some embodiments, system 605' can comprise a precooling module located just before cells enter an electroporation chamber so that cells are cooled to an optimal temperature. In some embodiments, an additional precooling module can be located in the area where an electroporation cartridge is removably inserted into the instrument. Precooling modules are described in sections supra.

Figure 11C:
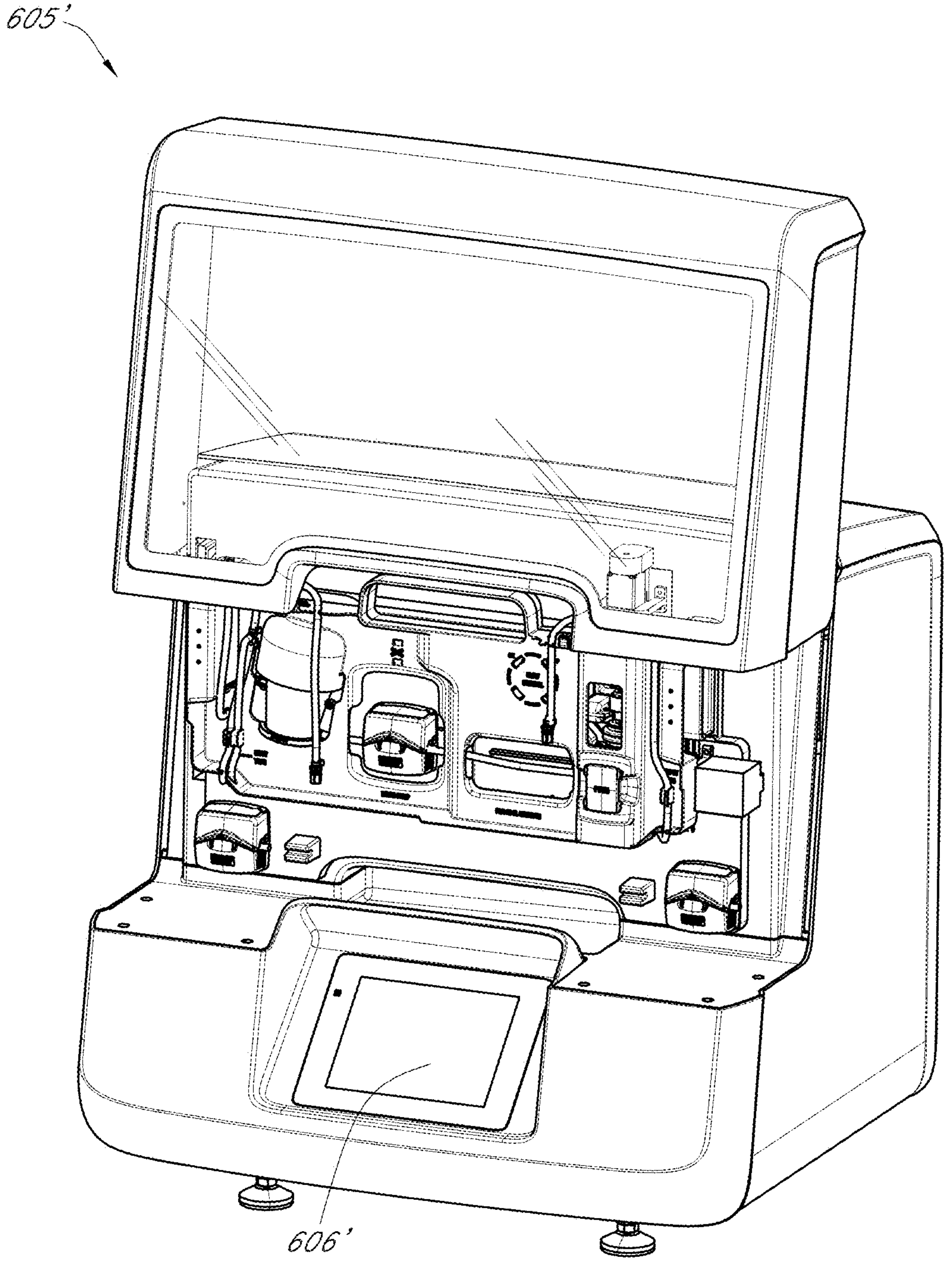

FIG. 11C shows an example electroporation system comprising an electroporation instrument of FIG. 11A and a removably attachable modular casing (which can be similar to 700, 701, 703, 800, 801, 803 etc.) for arranging various electroporation components (additional details of modular casings are provided in FIGS. 12A-G, FIGS. 13A-C and FIGS. 15A-15I below). Modular casings are amenable to using a flow-through electroporation chamber to process large volumes of sample for electroporation by electroporating small batches of samples at a time.

Figure 11D:
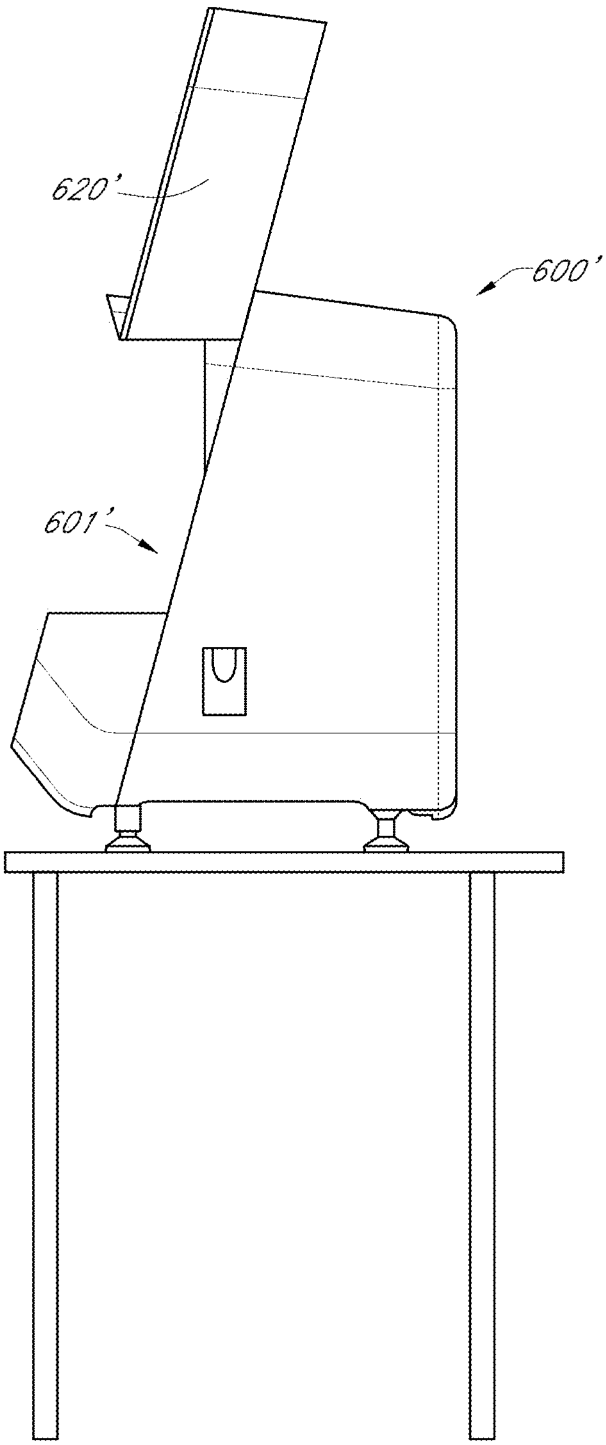

Electroporation instruments and systems 605' and/or 600' typically have a lid to allow a user to close the system while electroporation is carried out. FIG. 11B depicts an embodiment having a sliding lid in an open position. FIG. 11D illustrates another embodiment of an electroporation instrument having a different lid that can swing open upward. Various other lid types can be used. Lids can provide safety from the high electrical voltages used to a user as well as can provide a sterile environment In some embodiments of an electroporation system 605' or 600', a modular casing with multiple components is not required, for example, where a single use electroporation chamber is used. In such a system configured for a single electroporation event (in contrast to the batch processing/continuous flow), 605' or 600' can comprise components of an electrical pulse generator, bubble sensors, conductivity sensors, fluid sensors, pressure sensors, a precooling module to cool the electroporation chamber directly and a slot to insert an electroporation chamber with appropriate electrical contacts (such as high voltage pins) available to provide an electrode pulse to the electrodes inside the electroporation chamber, locking mechanisms to clamp in the electroporation chamber, air filters, computer controllers and processors and optionally a user interface. A single use electroporation chamber can be placed into the corresponding slot for receiving the electroporation chamber and be connected to electrode contacts and other components inside the electroporation instrument to perform electroporation.

Electroporation Systems and Modular Casings

Figure 12A:
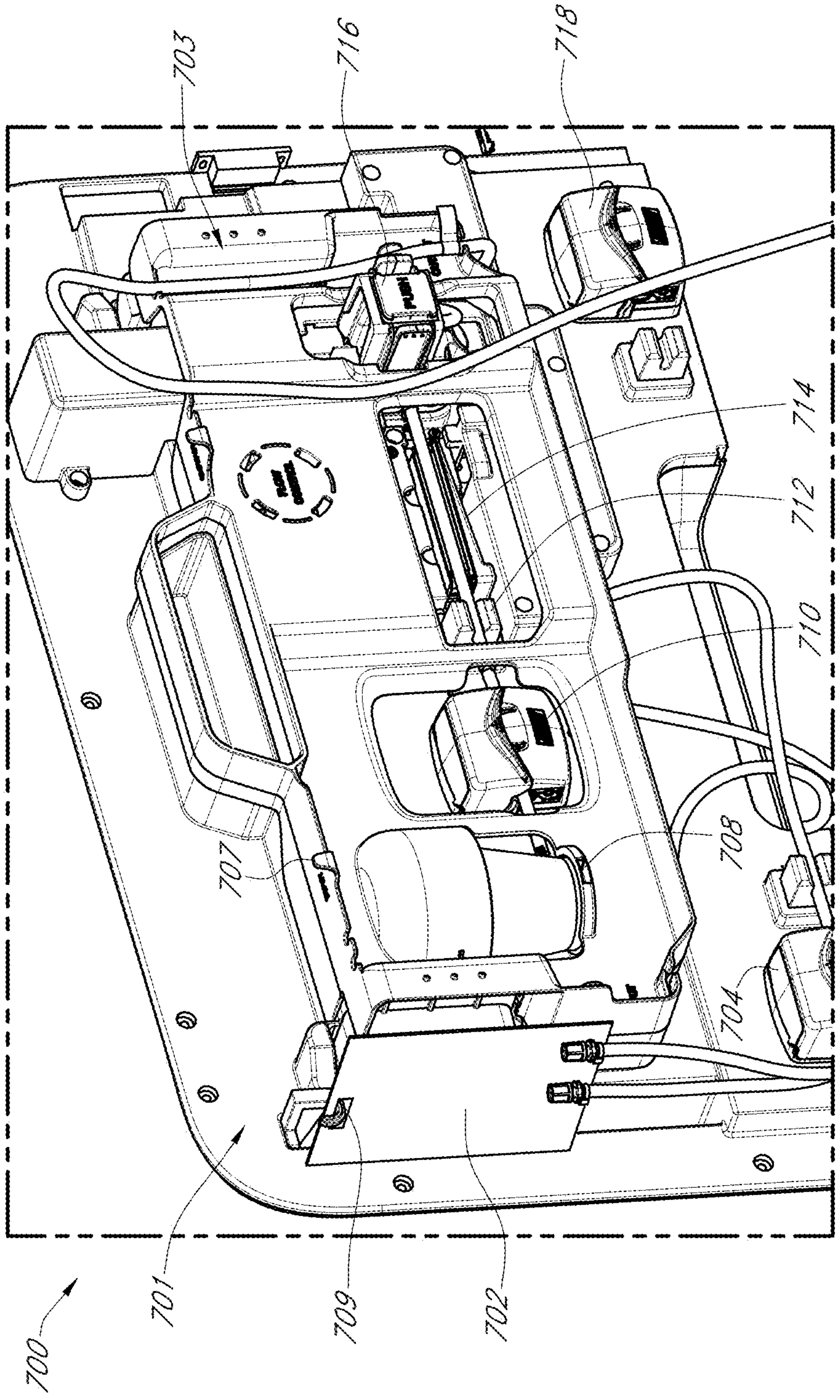
FIG. 12A illustrates one example embodiment of a modular casing for arranging various electroporation components that can be selectively attached and detached to an electroporation instrument.

FIG. 12A illustrates one example embodiment of an electroporation system 700 that includes a modular casing 703 and an instrument panel 701. Casing 703, in some embodiments is attached to instrument panel 701 and can be detached from instrument panel 701 (see FIG. 12A). Many conventional electroporation systems require the use of multiple consumable components and are plagued by easily tangled tubes and bags that get in the way of the other components, making setup and operation complicated. The modular casing 703 is intended to beneficially arrange the different electroporation components and tubing into one place in an organized and easily managed arrangement. This, along with other design features of the systems described herein, aid in reducing errors and maximizing electroporation efficiency. For example, the design of the electroporation cartridges described herein beneficially reduces user touchpoints where mistakes or issues may occur.

As shown in FIG. 12A, casing 703 is selectively attachable/detachable from the instrument panel 701. Casing 703 may include one or more attachment features that engage with instrument panel 701 and allow selective attachment. Casing 703 may attach to one side of instrument panel 701, as shown. Additionally, or alternatively, instrument panel 701 can be configured to enclose all or a portion of casing 703.

FIG. 12A (as well as FIG. 11C (which comprises an instrument panel/modular casing similar to 701/703) show an exemplary arrangement of various electroporation components. Input bag 702 is fluidically coupled, via tubing, to first pump 704. First pump 704 drives sample fluid from input bag 702 through first flow sensor 706 and into mixer reservoir 708. Second pump 710 then drives the sample fluid from mixer reservoir 708 through a second flow sensor 712, through a pre-cooling module 714, and into the electroporation chamber of electroporation cartridge 716. Following electroporation of a sample sub-volume, a third pump then drives fluid out of the electroporation chamber, through a third flow sensor (not shown in this view) and toward an output chamber (e.g., output bag) (not shown in this view).

As shown, casing 703 and instrument panel 701 may each separately include one or more hooks or other attachment features for supporting the input bag 702 and optionally an output bag as well. In the illustrated embodiment, input bag 702 may be attached to a casing hook 707 during movement and loading of casing 703 onto instrument panel 701. After attachment, input bag 702 may be moved to an instrument hook 709 to move it out of the field of view of the other electroporation components and/or better position the bag for the transfer and electroporation processing.

A modular casing of the disclosure, with components of the system 700, can be removably placed into an electroporation instrument 600' or system 605' (such as those described in FIGS. 11A-11D). encased within an outer shell or lid 720 that can be manually opened and closed to access the instrument panel (e.g., upward away from the base of the system or slide upward or slid/opened to the side) to reveal and allow access to these components, as shown in FIG. 11A. In some embodiments, the lid 720 is rotatable about a hinge to reveal and allow access to the internal components of the system 700.

Figure 12B:
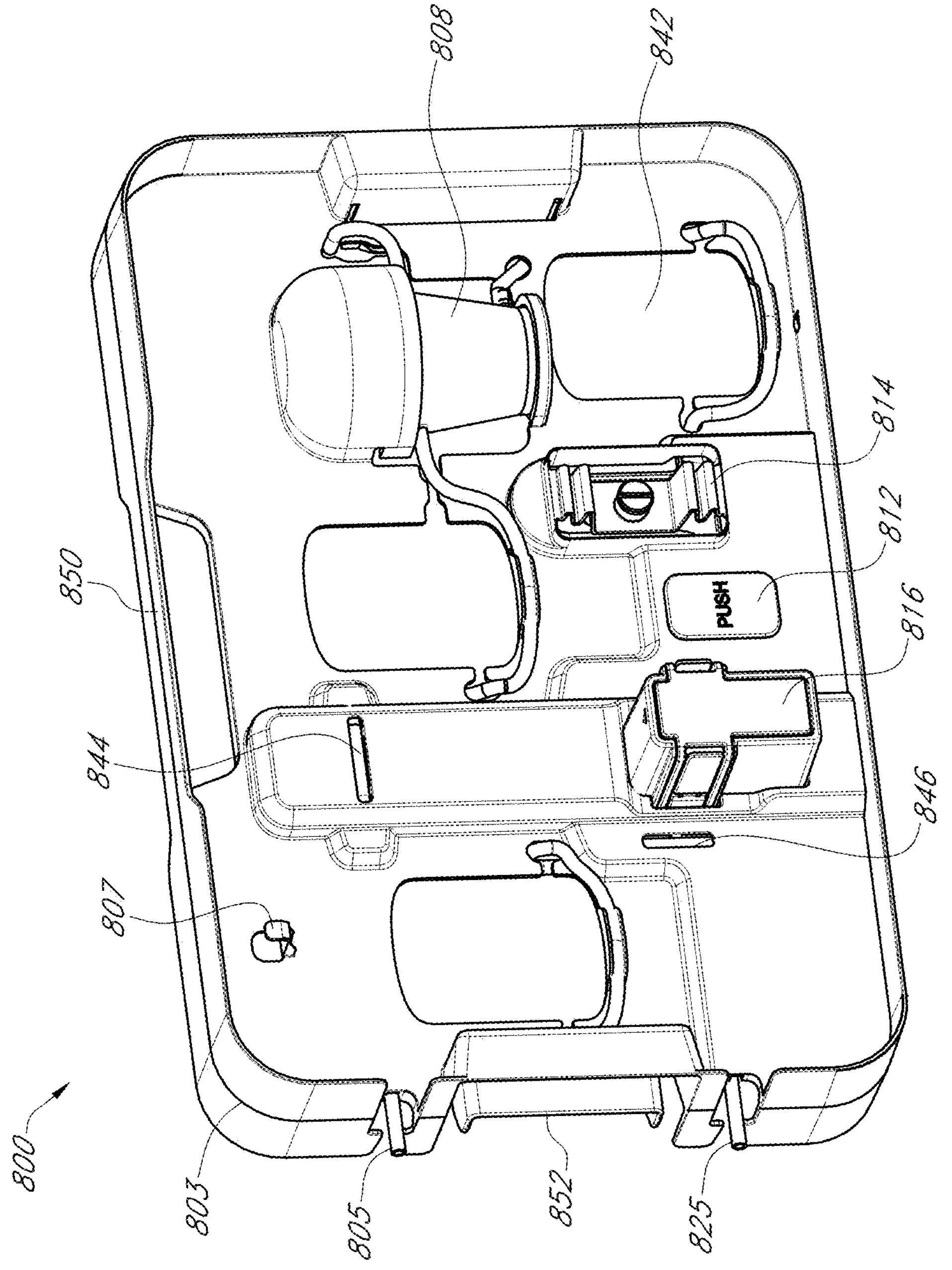
FIGS. 12B-12E illustrate another example embodiment of a modular casing for arranging various electroporation components that can be selectively attached and detached to an electroporation instrument.
Figure 12C:
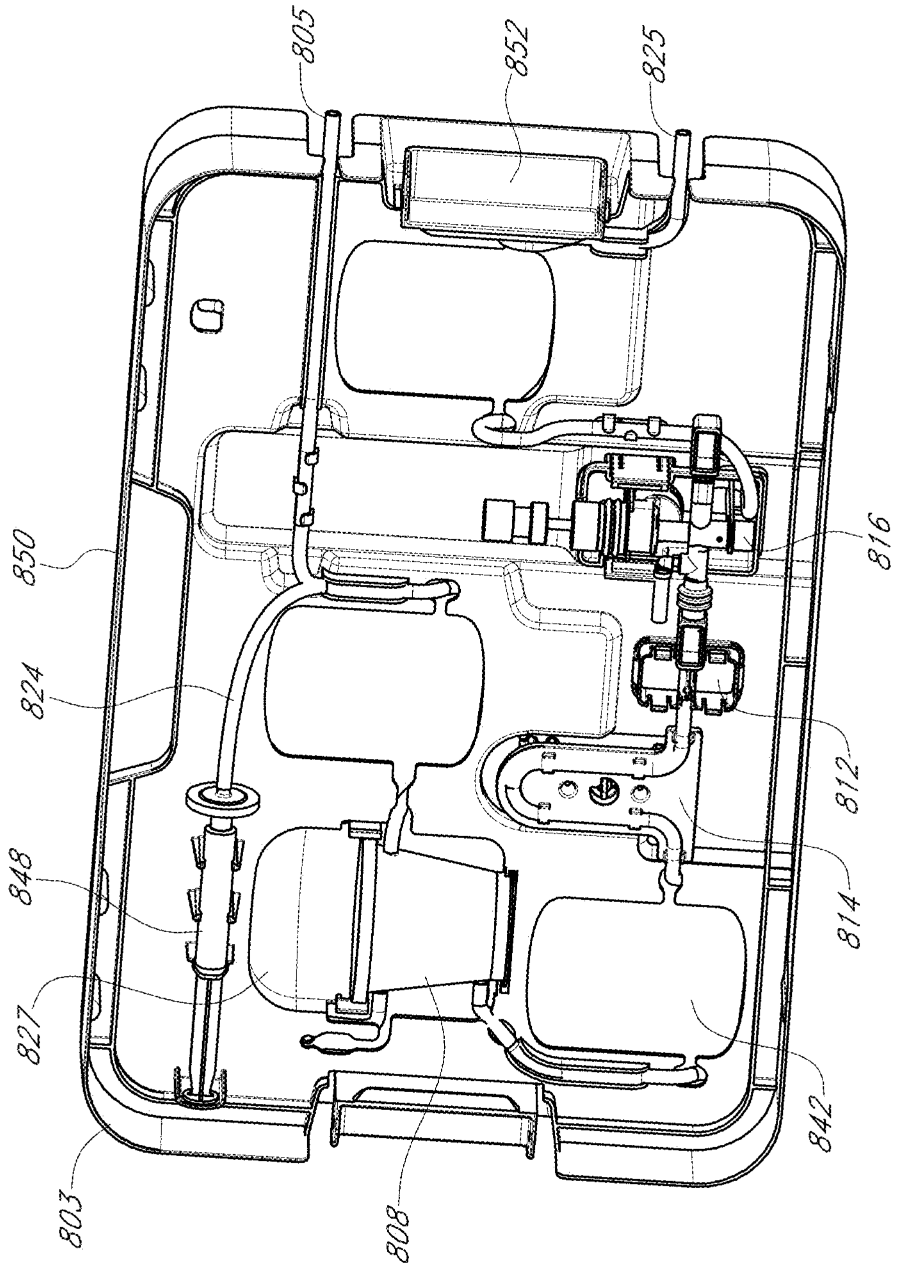
Figure 12D:
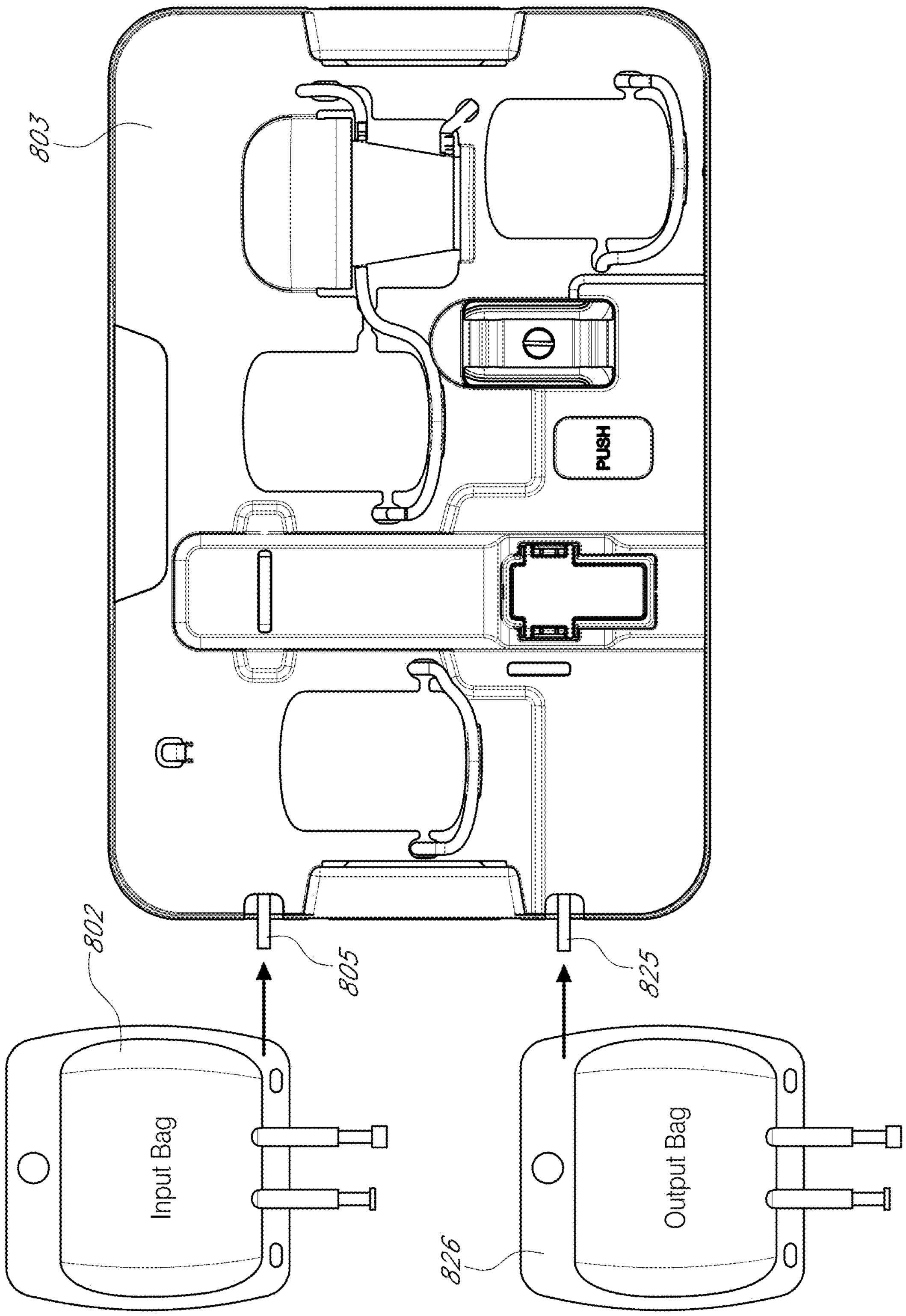
Figure 12E:
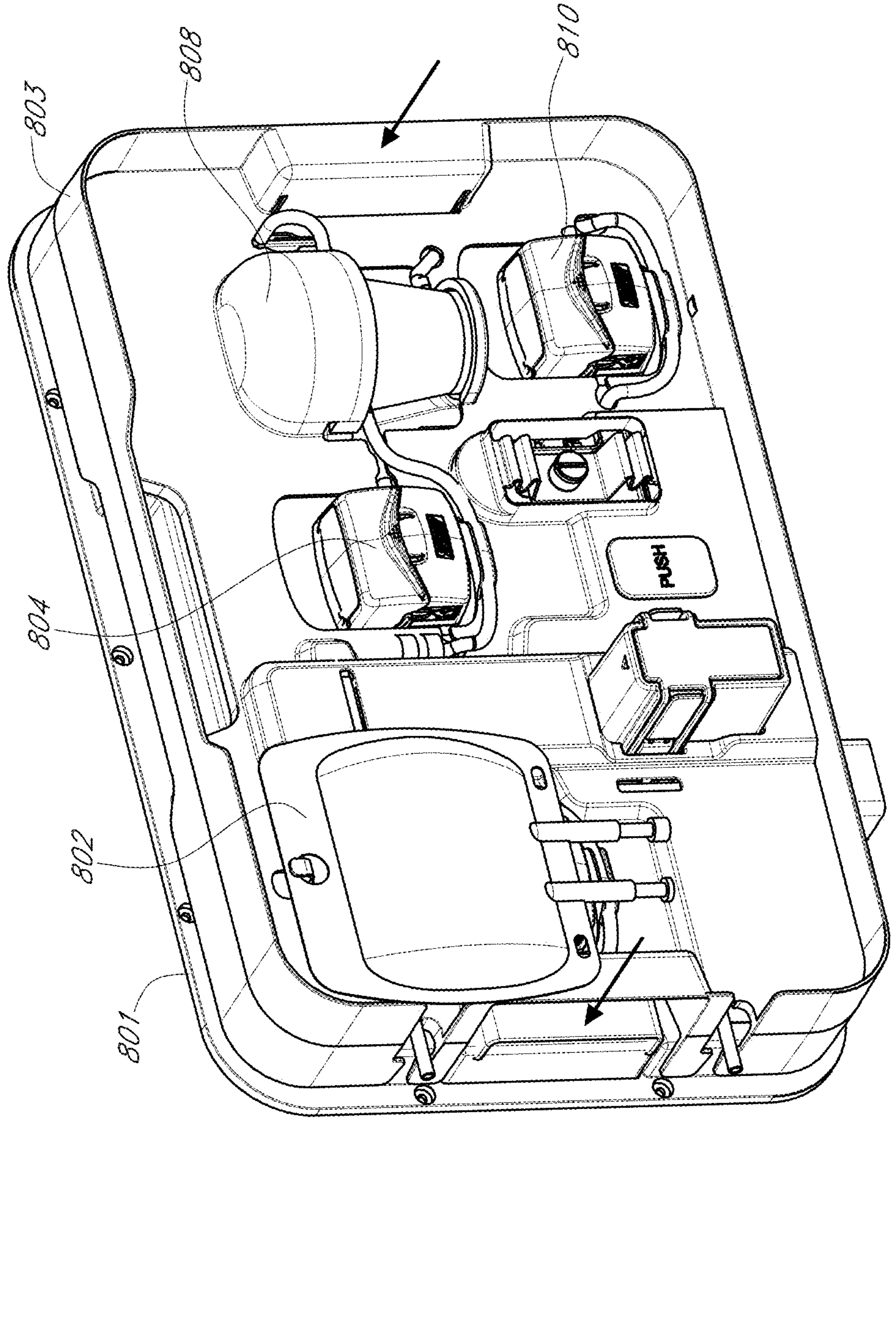

FIGS. 12B-12E further illustrate a slightly different embodiment of an electroporation system 800 having a casing 803 configured for attachment to a corresponding instrument panel 801. FIG. 12B illustrates a back side of the casing 803, FIG. 12C illustrates a front side of the casing 803, FIG. 12D illustrates attachment of input and output bags to the tubing of the casing 803, and FIG. 12E illustrates attachment of the casing 803 to an instrument panel 801.

As with the system 700, the system 800 includes a casing 803 and tubing that is routed through the casing 803 from an inlet 805 (configured for attachment to an input bag 802) to an outlet 825 (configured for attachment to an output bag 826). The tubing connects to a mixer reservoir 808, a pre-cooling module 814, one or more flow sensors 812, and the electroporation cartridge 816. The tubing also passes through one or more cutout sections of the casing that allow visualization of flow (flow indicators 844 and 846). The casing 803 may also include one or more side handles 852 and one or more upper handles 850 to assist in moving and handling the casing 803 (e.g., from the lab bench to the instrument panel 801).

The casing 803 includes an arrangement of compartments 842 that correspond to the arrangement of pumps (e.g., pumps 804 and 810, other pumps not shown) on the instrument panel so that the pumps are received into the compartments 842 when the casing 803 is attached to the instrument panel 801 (shown in FIG. 12E). As best shown in FIG. 12C, the casing 803 also includes a mixer compartment 827 configured to provide space adjacent to the mixer reservoir 808 for receiving the corresponding mixer driver, which is attached to the instrument panel 801.

As visible in FIG. 12C, the system 800 may also include an air reservoir 848 pneumatically coupled to an intermediate section 824 of tubing disposed between the inlet 805 and the mixer reservoir 808. As described in greater detail below, the air reservoir 848 is configured to provide air to the intermediate section of tubing after a sample has been drawn into the mixer reservoir.

Figure 12F:
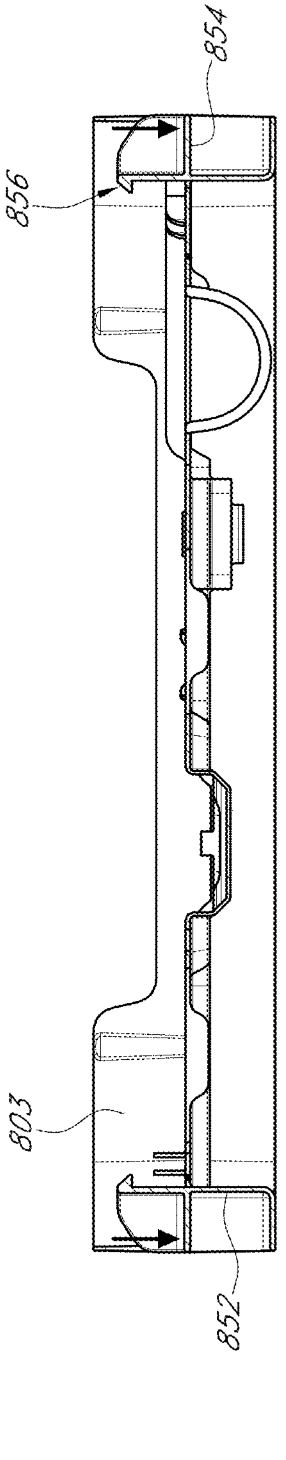
FIGS. 12F and 12G show different views of the empty modular casing of FIG. 12B-12E and illustrates an attachment feature that enables removable attachment of the casing to an electroporation instrument.
Figure 12G:
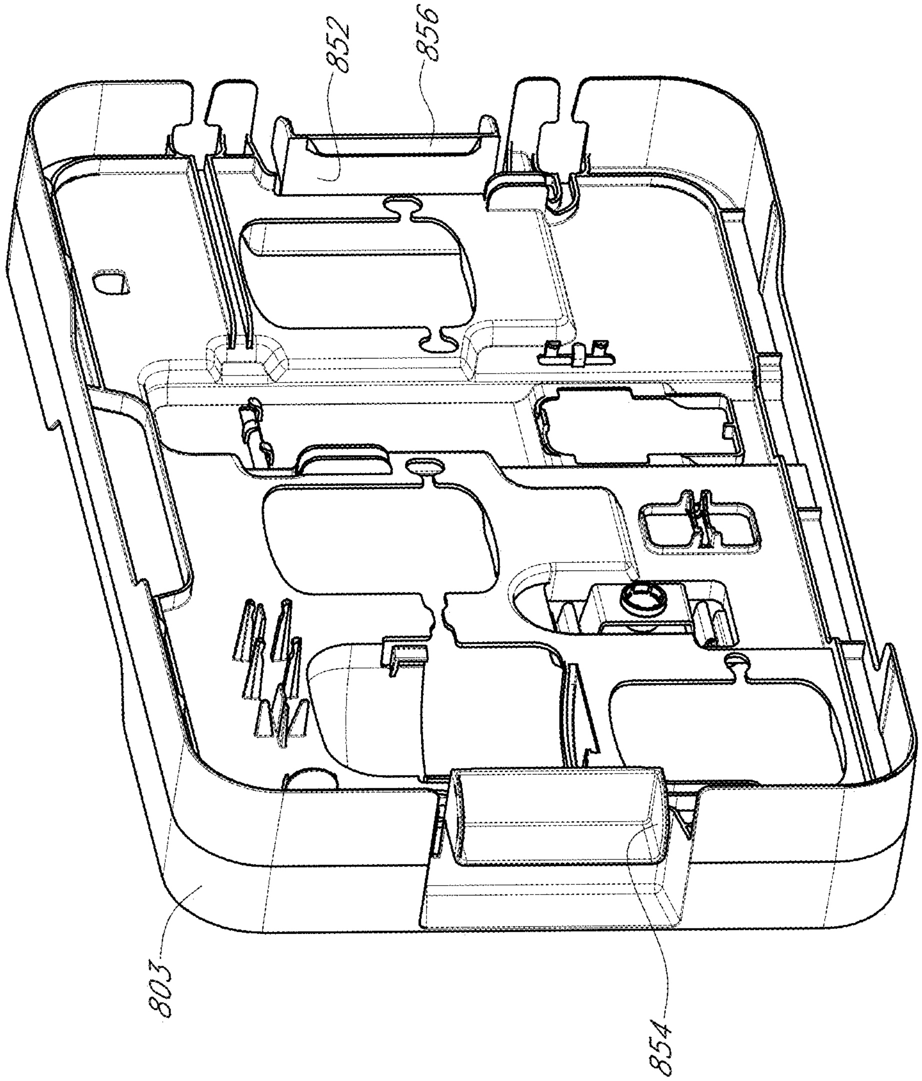

FIGS. 12F and 12G illustrate different views of the casing 803 to show one embodiment of an attachment feature that enables attachment of the casing 803 to the instrument panel 801. In this embodiment, the side handles 852 are flexible and include catches 856 that can engage with corresponding structure of the instrument panel 801. The handles 852 may be biased toward a neutral, straight position and configured to flex when gripped and pulled outwardly. As shown in FIG. 12G, a user may position his/her fingers on a grip surface 854, and by pulling on the grip surface 854, cause the handle 852 to flex outwardly. Upon release of the handles 852, the handles 852 will move back to the neutral position, allowing the catches 856 to move inward to engage with the instrument panel. Other embodiments may additionally or alternatively include other attachment features known in the art, including latches, alignment pins, hooks, clamps, and the like.

Figure 13A:
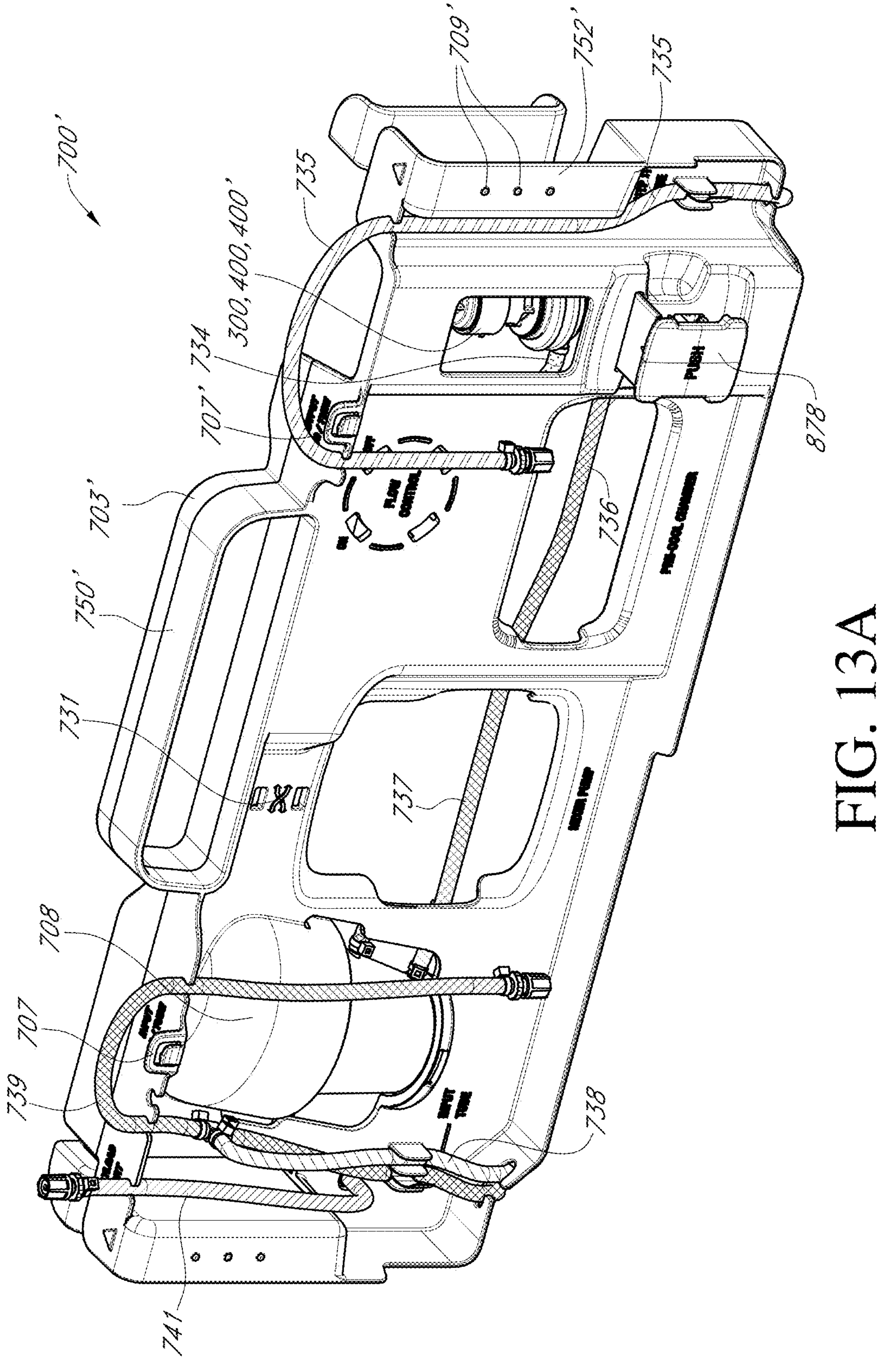
FIG. 13A illustrates yet another embodiment of a modular casing for arranging various electroporation components that can be selectively attached and detached to an electroporation system/instrument.
Figure 13B:
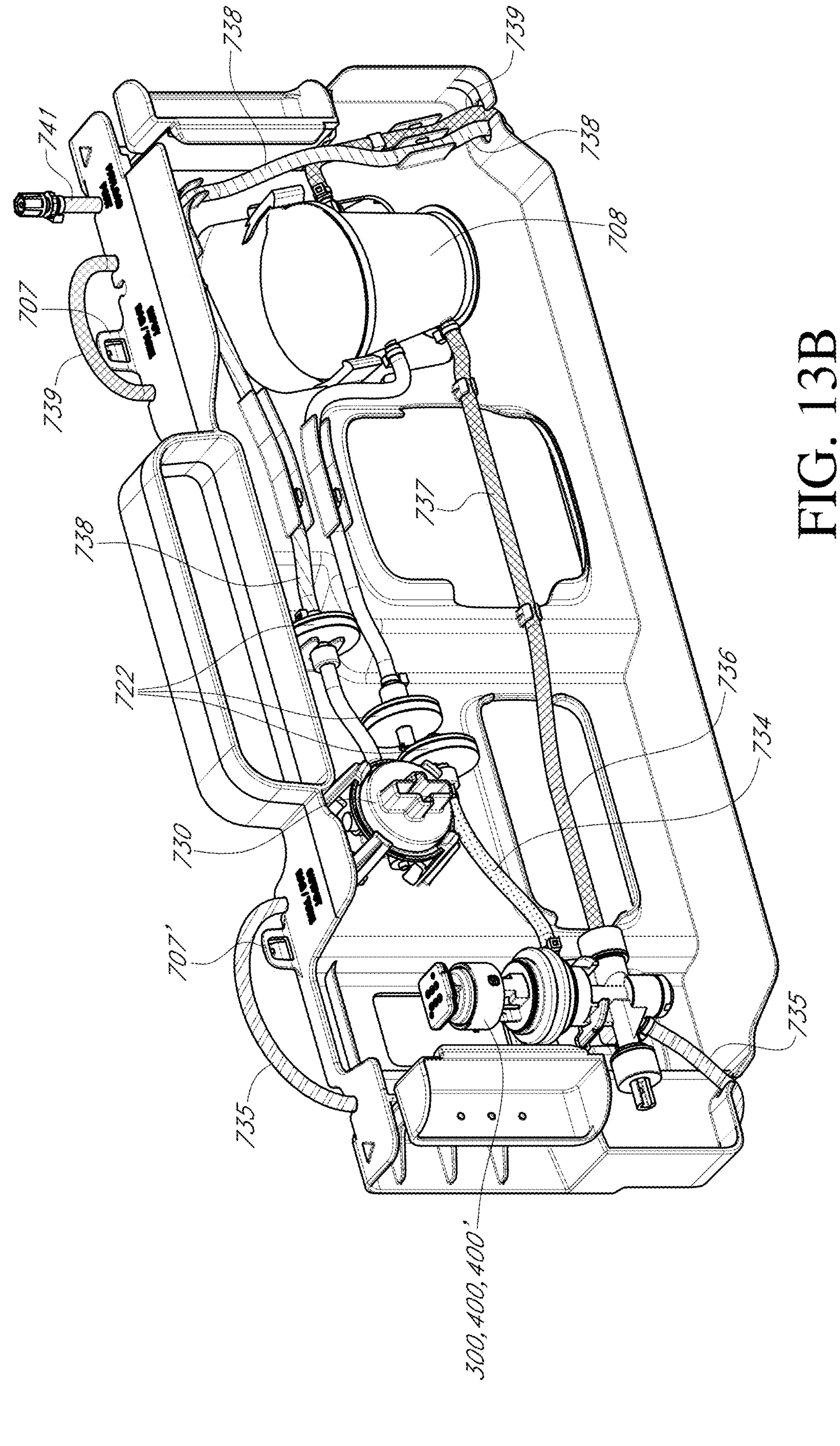
FIG. 13B illustrates a back view of the modular casing of FIG. 13A.
Figure 13C:
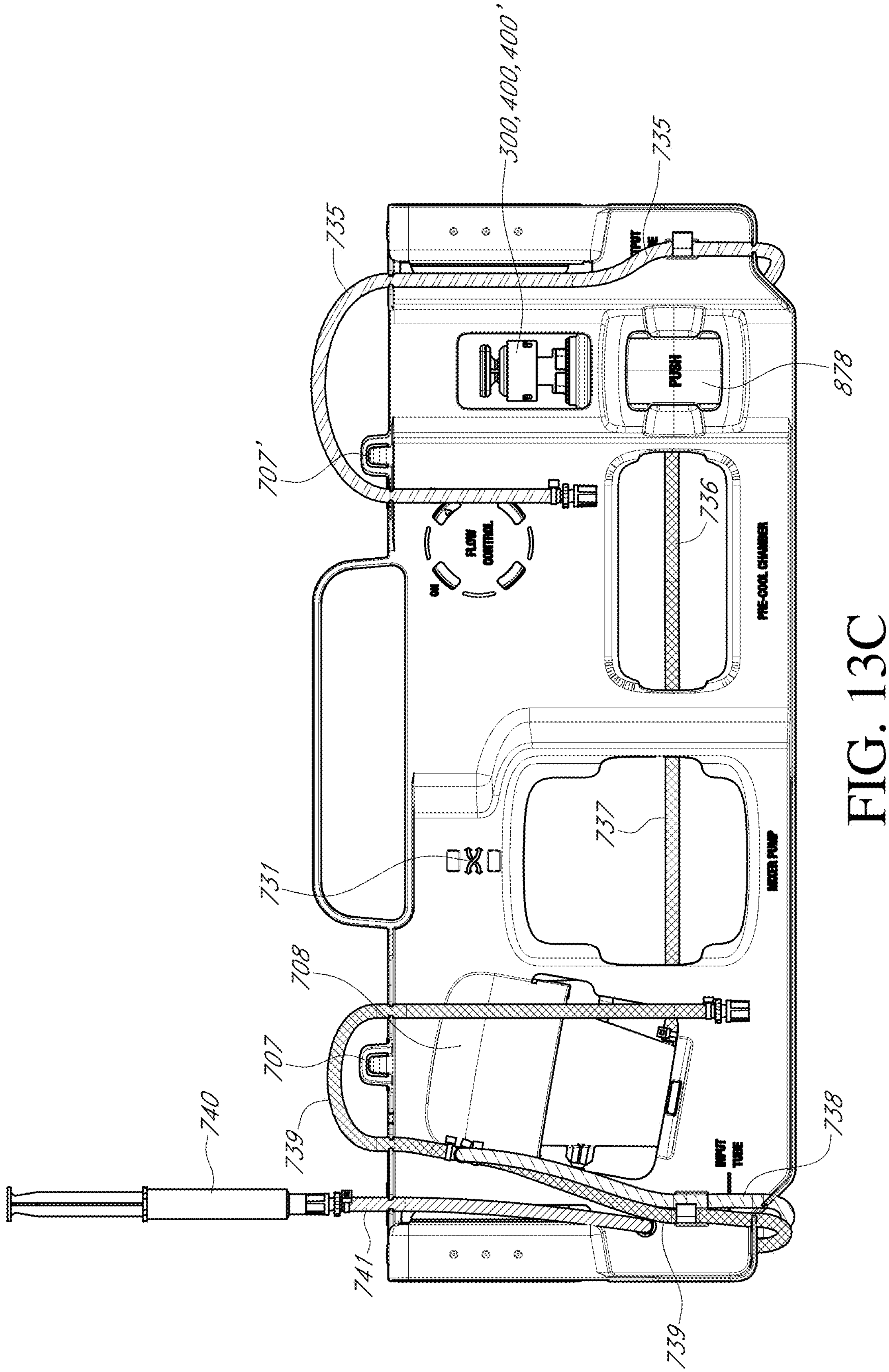
FIG. 13C illustrates one embodiment of an additional electroporation component that can be attached to a modular casing of the disclosure to keep a solution/payload/reagent available for manual dispensing into the electroporation cell mixer chamber as and when needed.

FIGS. 13A-13C illustrate embodiments of another exemplary modular casing that can be attached into an electroporation instrument/system such as 605' or 600'. FIG. 13A illustrates a front view of modular casing 700' for arranging various electroporation components that can be selectively attached and detached to an electroporation instrument. FIG. 13B illustrates a back view of the modular casing 700' (of FIG. 13A) showing additional components.

As with the system 700, the system 700' includes a casing 703' and tubing that is routed through the casing 703' from an inlet tube 739 configured for attachment to an input bag (not shown) where input bag is to be placed on input bag hook 707. Input tubing 739 connects to a cell mixer reservoir 708, then continues through a first pump (pump not shown since it is located on a surface of an instrument/system such as 605'/600'), to tube 737 (which is the tube exiting from mixer reservoir 708) which can be seen through a slot in modular casing 708' for a mixer pump (mixer pump not shown), depicted as mixer tube 737, which then continues through a pre-cooling module as pre-cool tube 736 (pre-cooling module not shown since it is located on a surface of an instrument/system such as 605'/600', however perspective view of a precooling module 714' can be seen in FIG. 17C supra), although a slot in the casing for precooling module 714' is shown, and the tube continues to an electroporation cartridge such as 300, 400 or 400' (which is placed/housed in an electroporation cartridge retainer 878) and then to an outlet tube 735 (configured for attachment to an output bag (not shown). Output bag is to be attached to output bag hook 707'. The tubing, in some instances, passes through one or more cutout sections of the casing that allow visualization of flow. The casing 703' may also include one or more side handles 752' that may have grippers such as 709' and one or more upper handles 750' to assist in moving and handling the casing 703' (e.g., from the lab bench to an instrument/system 605' or 600' or an instrument panel on an instrument/system such as 701 or 801).

As depicted in the embodiments of FIGS. 13A and 13B, cell mixer reservoir 708 is placed tilted in the modular casing. A tilted cell mixer 708 has been shown by the inventors to provide an unexpectedly surprising reduction of sample loss by reducing or preventing sample from being trapped in cell mixer 708. In some embodiments, cell mixer 708 is tilted at an angle of from about 5 degrees to about 20 degrees and any value in between. In some embodiments, a cell mixer 708 is tilted by an angle of about 10 degrees, such as about 8 degrees, about 8.5 degrees, about 9 degrees, about 9.5 degrees, about 10 degrees, about 10.5 degrees, about 11 degrees, about 12 degrees etc.

As shown in FIGS. 13A, 13B and 13C, system 700' can include an air reservoir (not expressly shown) pneumatically coupled to an intermediate section of tubing, air inlet tube 738, disposed between sample inlet tube 739 and mixer reservoir 708. Air reservoirs configured to provide air to the intermediate section of tubing after a sample has been drawn into the mixer reservoir are described elsewhere in this application in detail.

FIG. 13B depicts the placement of air inlet tube 738 over mixer reservoir 708 going through several air filters 722 to a stopcock (not expressly shown) that has a stopcock adaptor 730 that retains the stopcock on the modular casing 700'. Working of stopcock and stopcock adaptor 730 are describes in sections supra. Icon 731 can be used as an visual indicator to a user of the airflow direction. Air inlet tubes connecting to air filters 722, allow air exchange to different zones to allow fluid to flow, and/or to avoid pressure built-up within a mixer chamber or an electroporation chamber.

FIG. 13C illustrates an embodiment of modular casing 700' wherein an additional input chamber 740 (e.g. payload chamber) with its own additional input tube 741 is provided to add one or more additional components to a sample. Input tube 741 can have an inlet into mixer reservoir 708 in addition to the inlet of sample inlet tube 739. In one example, the additional material can comprise a payload (such as a material to be electroporated into a cell (e.g. nucleic acid, DNA, RNA, a protein, a drug or any other molecule or material that is desired to be electroporated into a cell), that is to be added later and not to be exposed to the cells or other contents of a cell bag during setup and assembly of the electroporation system before performing electroporation). In some non-limiting embodiments, an additional input chamber 740 can be a syringe containing an additional material that can be manually injected into the cell mixer, when and as needed (as depicted in FIG. 13C). However, other chambers such as input bags, containers and the like may be used as chamber 740.

Electroporation cartridges 300, 400 or 400' are inserted into the slot on an instrument via a cartridge casing 878. Casing 878 and its functioning is described ahead in FIGS. 19A-19C.

Bag Compartment

Figure 14A:
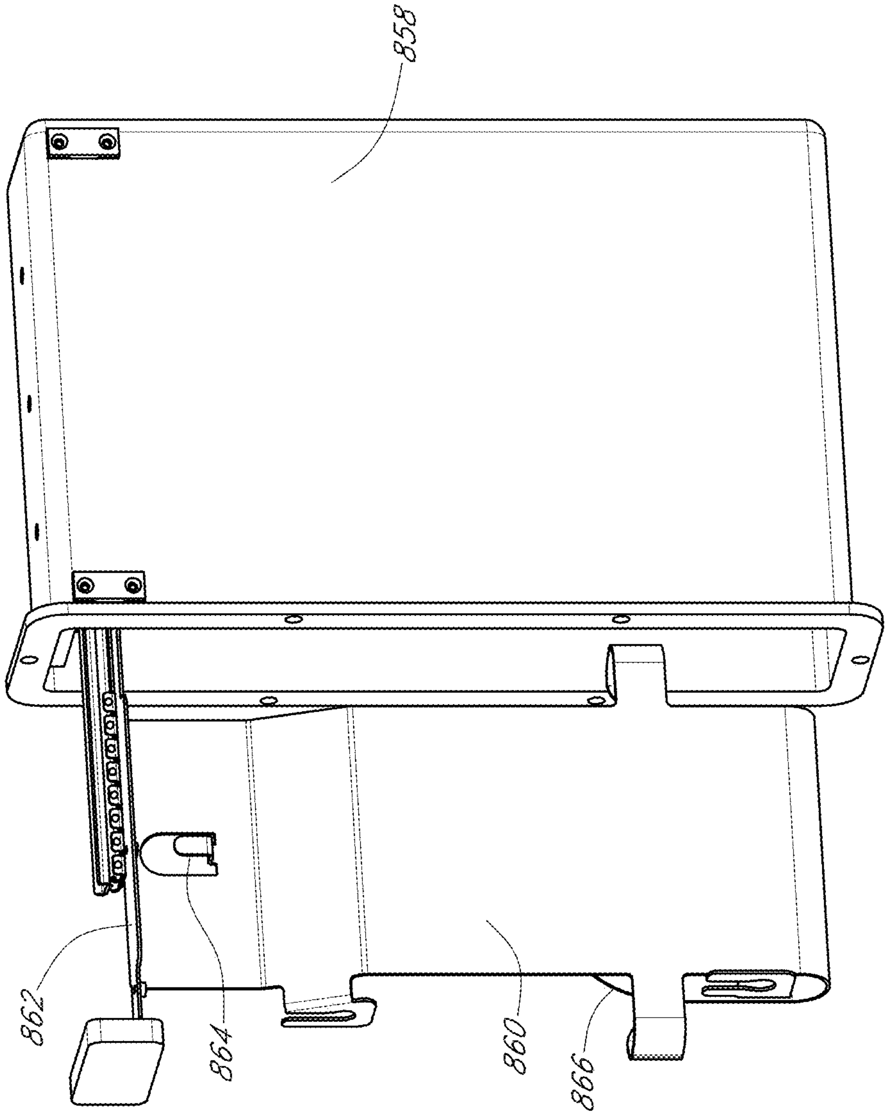
FIGS. 14A and 14B illustrate one example of a bag compartment that may be incorporated into an electroporation system/instrument as described herein.
Figure 14B:
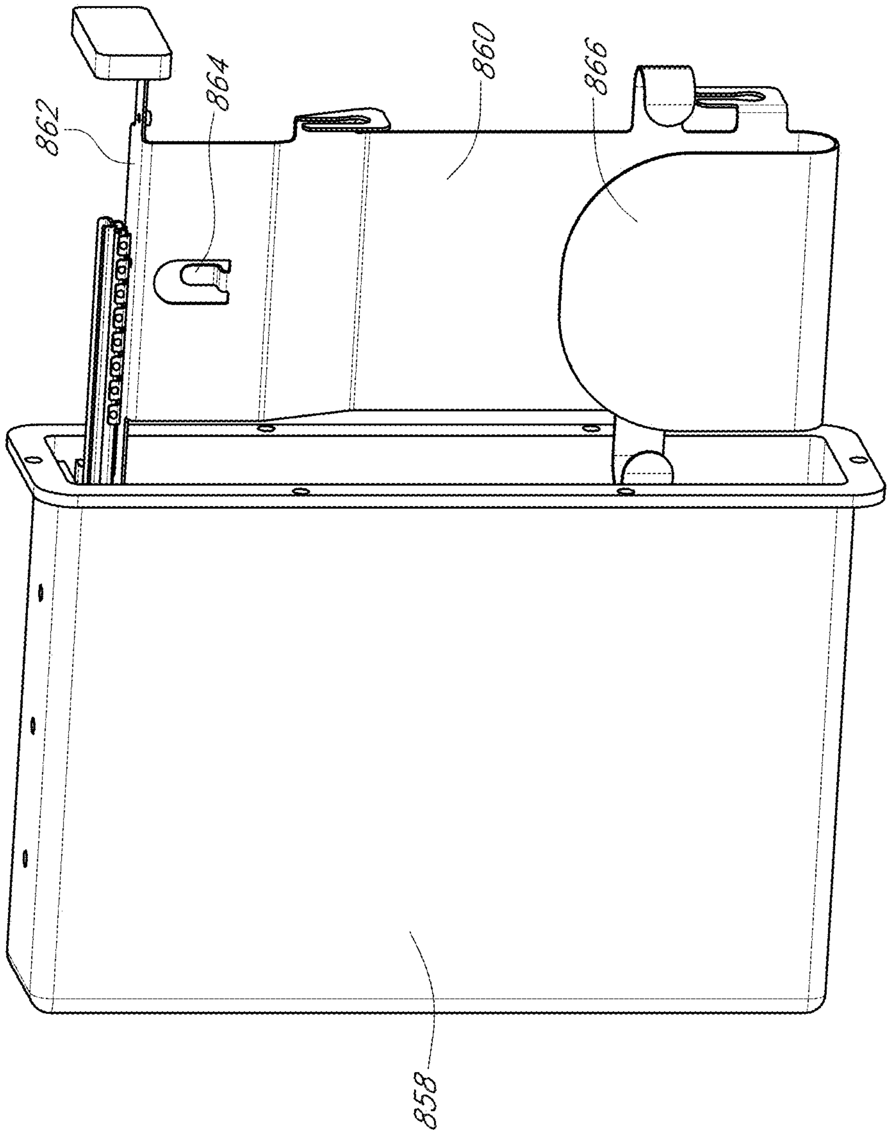

FIGS. 14A and 14B illustrate one example of a bag compartment 858 that may be incorporated into an electroporation system as described herein. During use, sample container bags should be supported in an upright position with ports facing downwards to minimize residual fluid (for the input bag) and to minimize bubble accumulation (for the output bag). Preferably, the bags are also able to fit within a small footprint to keep the size of the device down and to minimize obstructing the view of the other components of the system. Further, it is beneficial, though not necessary, to enclose the bags during use of the system to prevent them from being handled by the user during the high voltage electroporation operation.

In the illustrated bag compartment 858 (the remainder of the casing removed for clarity), an insert 860 is slidably connected to the bag compartment 858 so as to be capable of being selectively drawn out from the casing or enclosed within the casing. The insert 860 may be connected to the bag compartment 858 via a track and rail system 862, for example. The insert 860 may include a hook 864 or other suitable attachment feature for supporting an input bag, and a support 866 for supporting an output bag. The bag compartment 858 may include one or more latches (e.g., magnetic latches), clamps, stops, and the like for holding the insert 860 in a desired position.

Input Sample Transfer

Figure 15A:
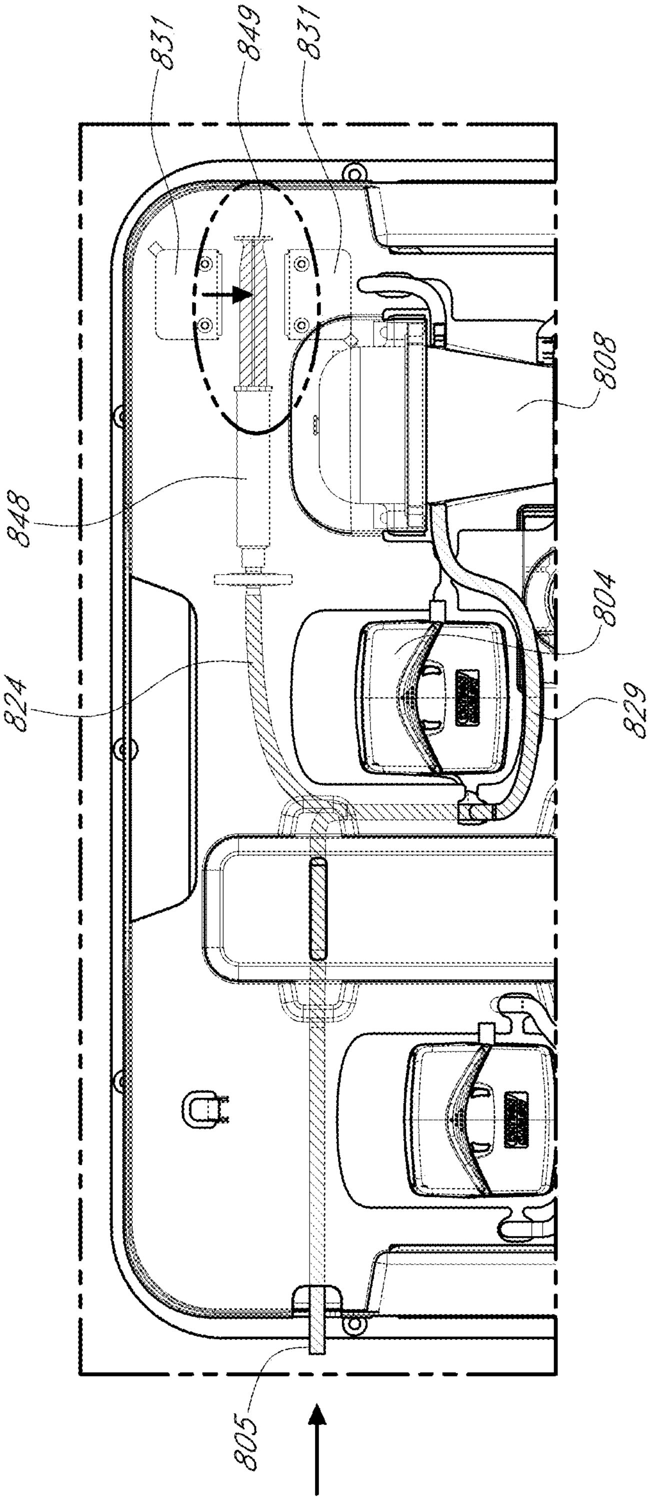
FIGS. 15A-15C illustrate one example of a sample transfer assembly configured to provide effective transfer of sample fluid from an input container to the mixer reservoir and to the electroporation chamber, according to one embodiment of the disclosure.
Figure 15B:
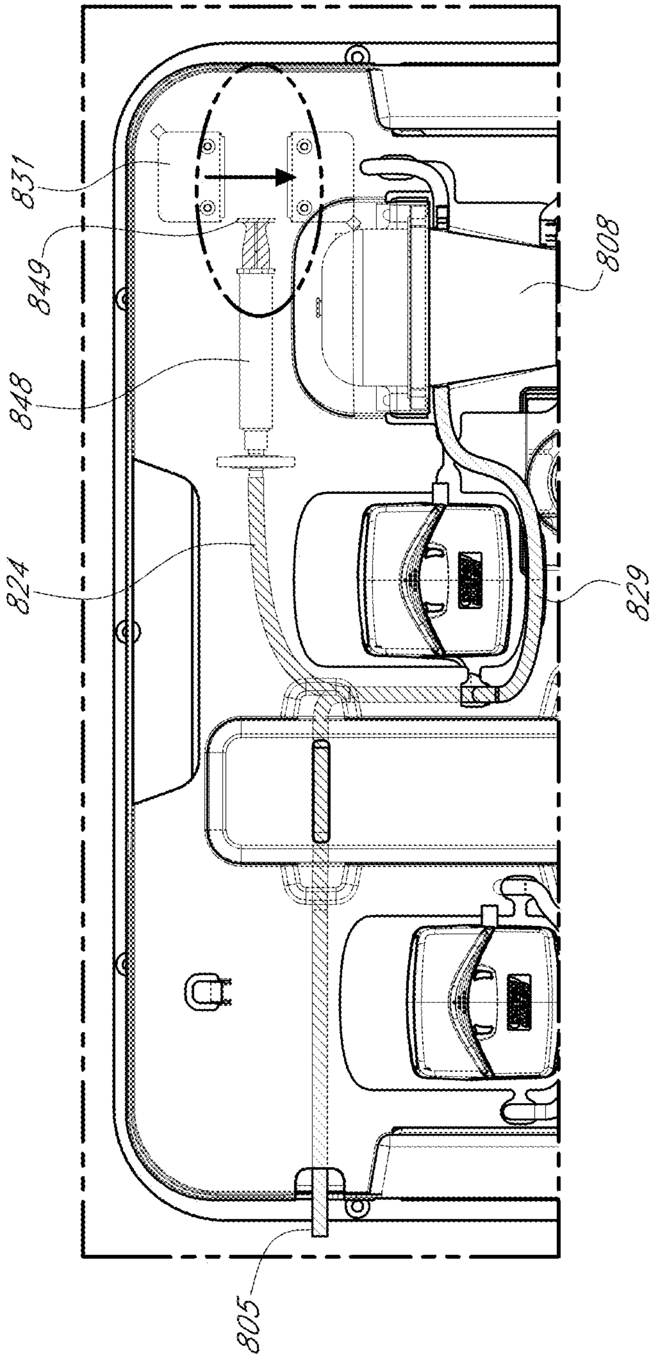
Figure 15C:
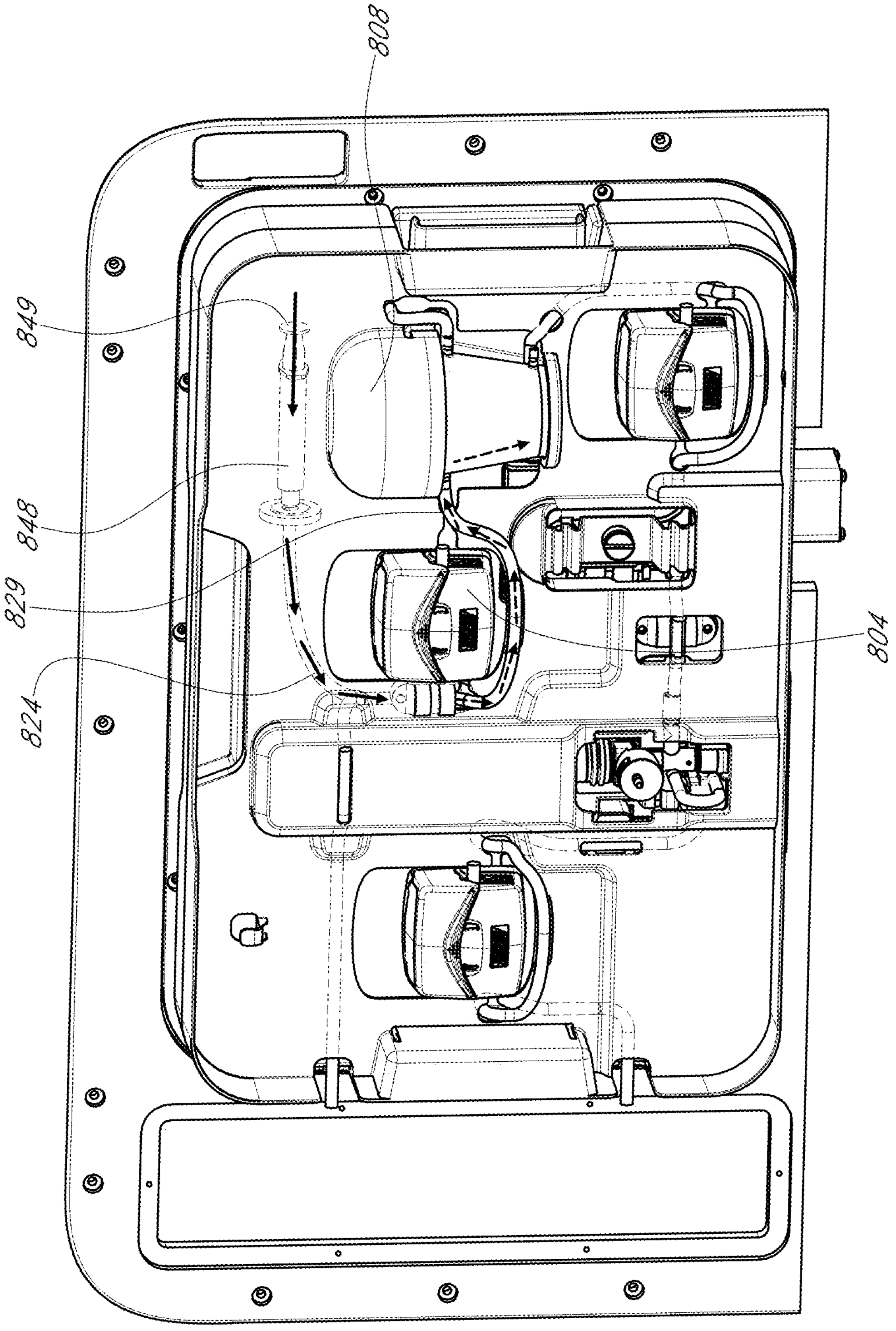

FIGS. 15A through 15C illustrate one example of an assembly configured to provide effective transfer of sample fluid from an input bag to the mixer reservoir 808. Sample inputs may vary from process to process based on sample type, sample volume, sample fluid characteristics (e.g., viscosity), and bag type. It is therefore beneficial to be able to accurately determine when the sample fluid has been fully transferred from the input bag to the mixer reservoir. In addition, it is desirable to minimize sample loss due to residual amounts remaining in the bag and/or in the tubing between the bag and the mixer reservoir 808.

The illustrated transfer assembly is configured to indicate when an input bag is substantially emptied of sample fluid and to allow the controller to configure the process controls accordingly. The transfer assembly is also configured to minimize sample waste by clearing the tubing between the inlet 805 and the mixer reservoir 808 of sample at the end of the sample transfer process.

FIG. 15A illustrates the sample transfer assembly prior to the end of sample transfer, and FIGS. 15B and 15C illustrate the sample transfer assembly at the end of sample transfer. In FIG. 15A, air has not yet passed from the air reservoir 848 through the intermediate section 824 of tubing into the main section 829 of tubing. That is, while sample fluid is being transferred from the inlet 805 to the mixer reservoir 808 through the main section 829 of tubing, the air reservoir 848 will remain full.

As shown in FIGS. 15B and 15C, once the input bag is nearly emptied, continued operation of the pump 804 will further lower the pressure within the tubing, which in turn will pull air out of the intermediate section 824 of tubing and into the main section 829 of tubing. This additional bolus of air will help to flush/clear the main section 829 of tubing of residual sample to help maximize the amount of sample carried to the mixer reservoir 808.

The air reservoir 848 may also be associated with a sensor (e.g., proximity sensor) that senses when the volume of the air reservoir has been reduced, thereby signaling progression or completion of the sample transfer process. In the illustrated embodiment, a plunger 849 moves as the air reservoir 848 is depleted, and motion of the plunger 849 thus indicates the pressure within the main section 829 of tubing and thereby indicates progression of the sample transfer process.

Other embodiments may additionally or alternatively utilize other means for determining the progression or completion of the sample transfer process. For example, the electroporation system 600' or 605' shown in FIGS. 11A through 11B omits the syringe and plunger arrangement of the system 800. Instead, the system 700 includes an intermediate section of tubing that extends from the main section of tubing and terminates in an air filter that is open to the atmosphere. Air flow within the intermediate section of tubing may be controlled by regulating how open the intermediate section of tubing is, such as by using a pinch mechanism to open/close the intermediate section of tubing. As with the system of FIGS. 15A and 15B, when pressure in the main section of tubing gets sufficiently low near the end of the sample transfer process, air may be drawn into the main section of tubing through the intermediate section of tubing. As indicated above, the system 700 also includes a first flow sensor 706 disposed between the input and the mixer reservoir 708 to aid in determining when sample transfer has completed.

Figure 15D:
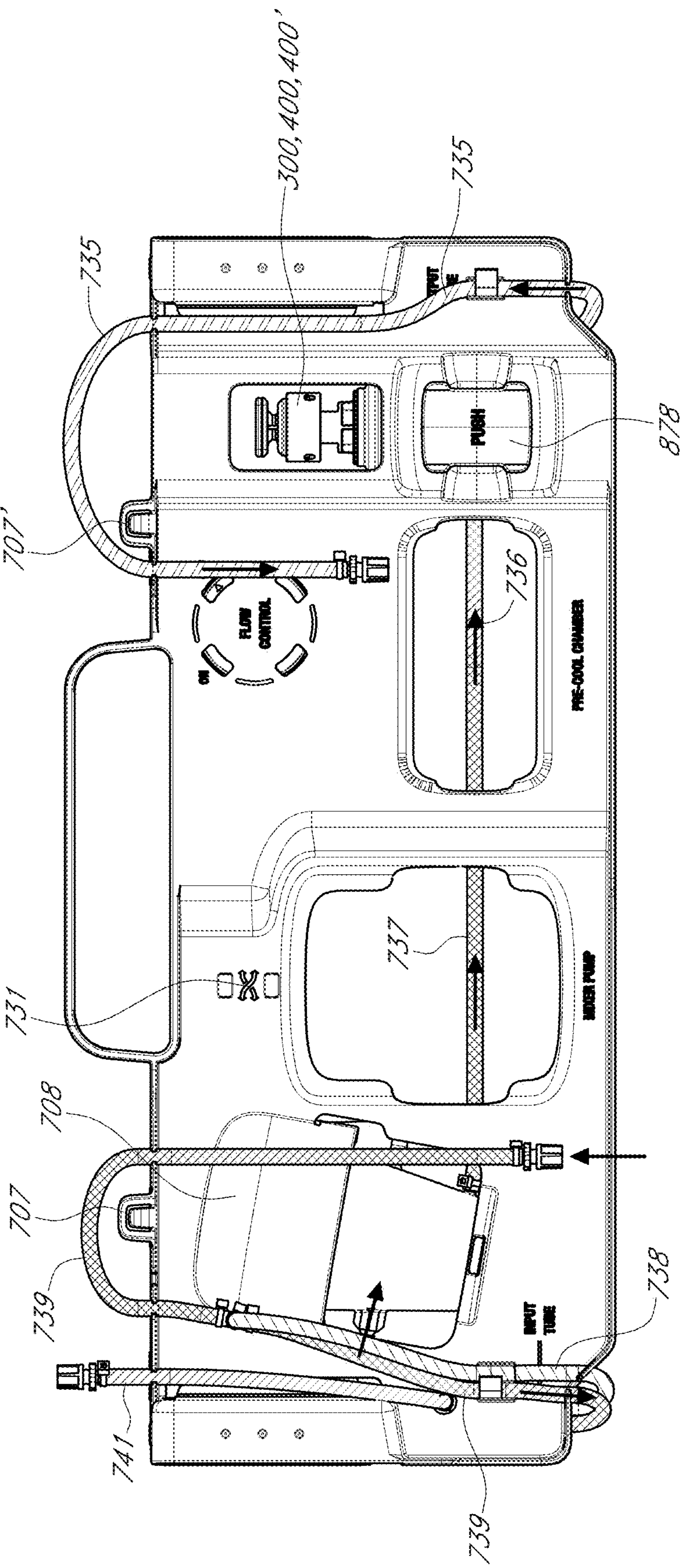
FIGS. 15D-15E illustrates one example of a sample transfer assembly showing the path of flow of sample fluid from an input container into an input tube to a cell mixer reservoir and to an electroporation chamber via various tubes and components of the electroporation system, according to one embodiment of the disclosure.
Figure 15E:
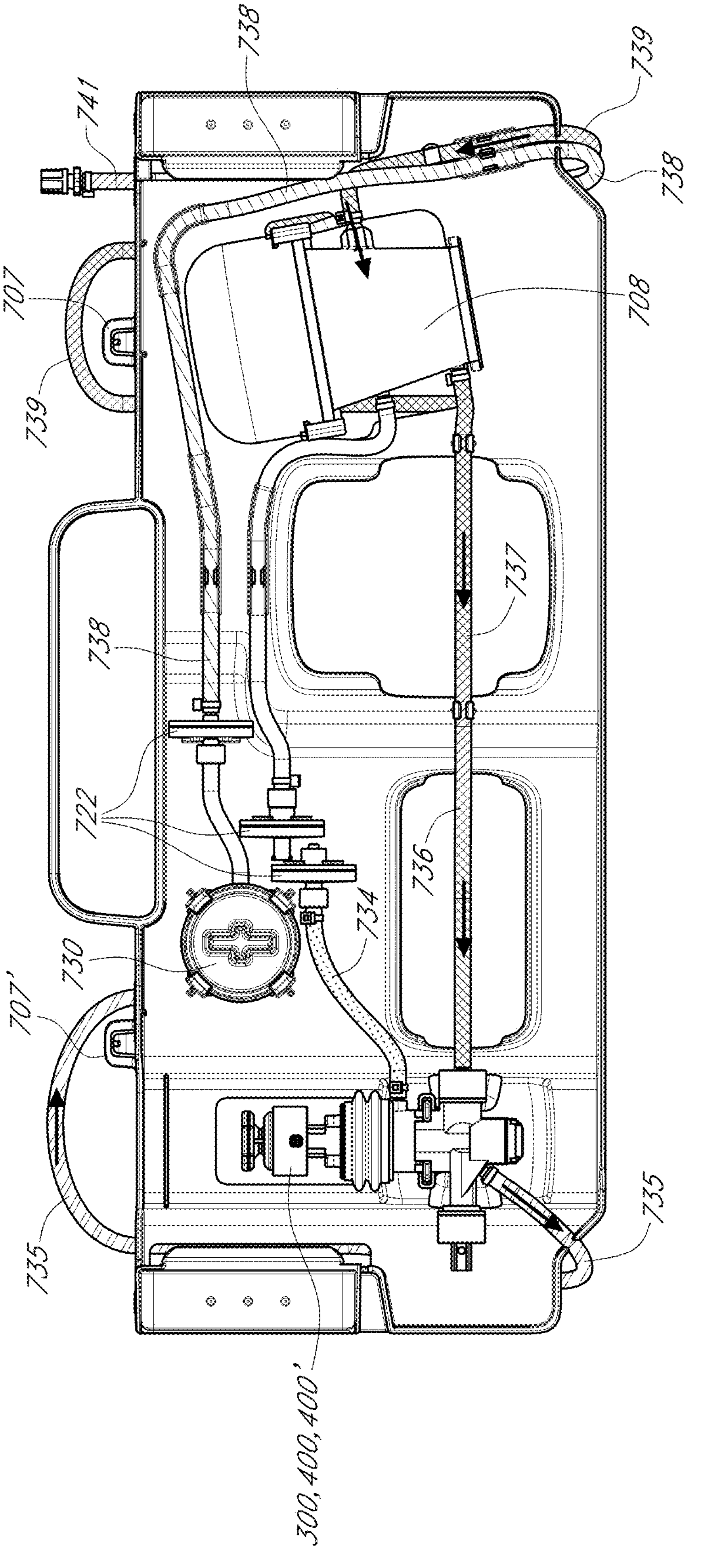

FIGS. 15D-15E illustrate one example embodiment of sample flow through a modular casing as shown in system 700' of FIGS. 13A-13C. Similar part numbers have similar functions as in FIGS. 13A-13C. The arrows depicted in different sections of tubes in FIGS. 15D and 15E depict the flow of sample (such as sample comprising cells in fluid with material to the electroporated) though modular casing system 700' shown through the front view (FIG. 15D) and the back view (FIG. 15E) of modular casing 700'. For example, as depicted by an arrow, sample can enter inlet tube 739 and through an inlet into mixer reservoir 708 (see arrows in FIGS. 15D and 15E into 708) and exit through an outlet in 708 (see FIG. 15E) and continue through mixer tube 737 through mixer pump (pump not shown) and through pre-cooling chamber (not shown) via tube 736 and enter into an inlet into electroporation chamber 300, 400 or 400'. Additional payload can be loaded via an input device 740 (such as a syringe) to manually dispense payload into sample in the mixer reservoir 708. After electroporation of the sample, electroporated sample exits electroporation chamber 300, 400 or 400' via an outlet, see arrow in outlet tube 735 in FIG. 15E. Electroporated sample continues through outlet tube 735 which in the embodiment of FIG. 15E continues toward the top of electroporation chamber and casing 700' to enter an outlet bag (not shown) which can be hung on hook 707'.

Figure 15F:
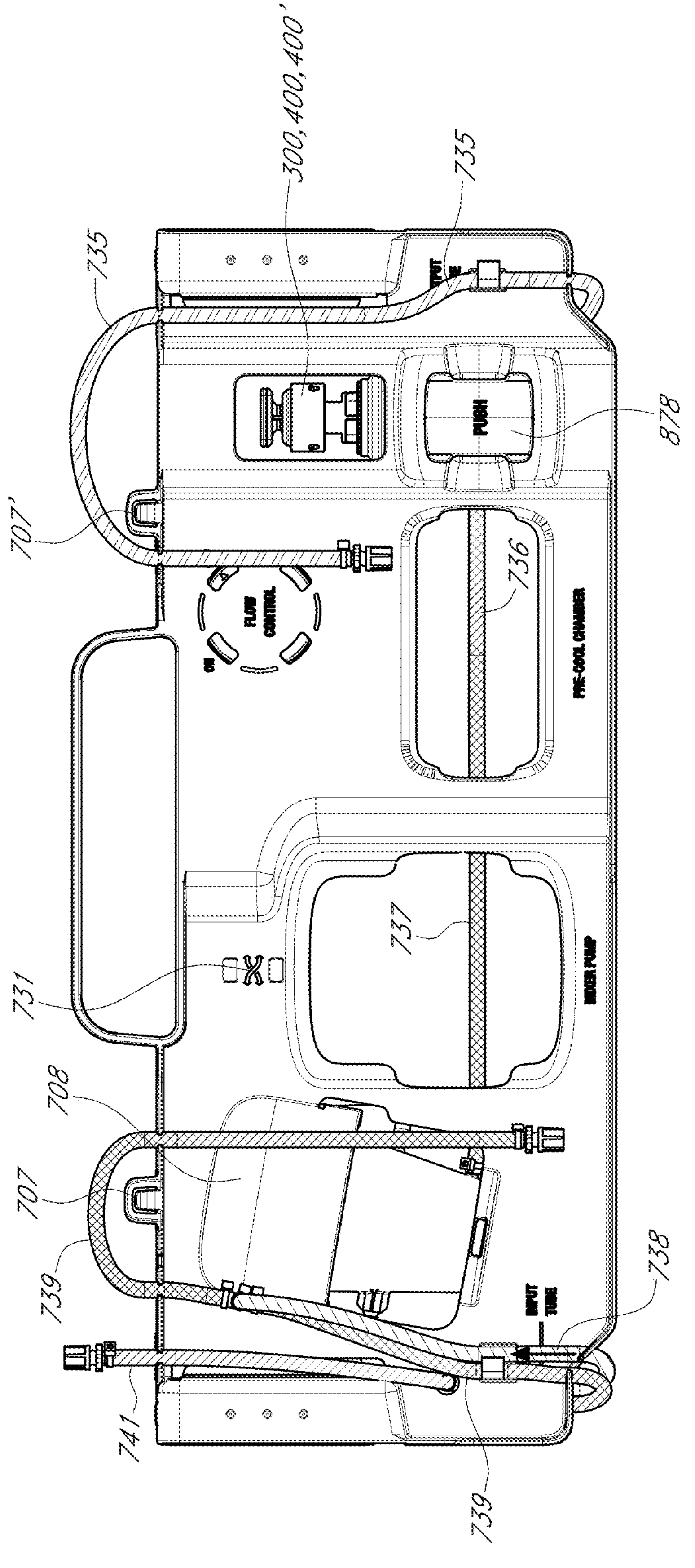
FIGS. 15F-15G illustrate one example of a sample transfer assembly showing the path of flow of air during the flow of sample fluid from an input tube to an electroporation chamber, according to one embodiment of the disclosure.
Figure 15G:
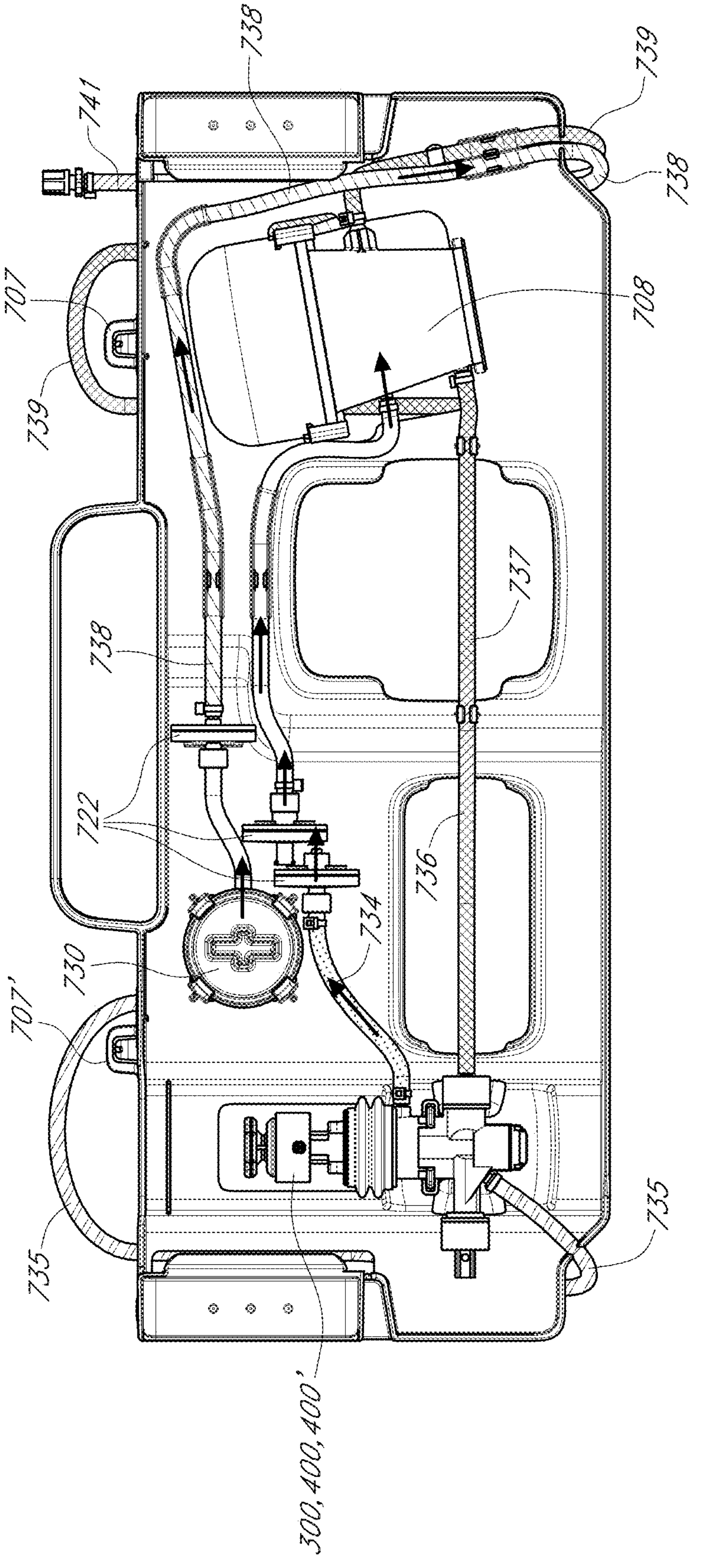

FIGS. 15F-15G illustrate one example embodiment of air flow through a modular casing as shown in system 700' (of FIGS. 13A-13C). The arrows depicted in different sections of tubes depict the flow of air though the modular casing system 700' and show entry of air into air inlet tube 738 (see FIG. 15F). FIG. 15G shows arrows of airflow through tube 738 and tube 734 (tube exiting electroporation chamber 300, 400 or 400' during filling and subsequent filling of the chamber via air filters 722 as well as via stopcock 731 located behind stopcock retainer 730.

Figure 15H:
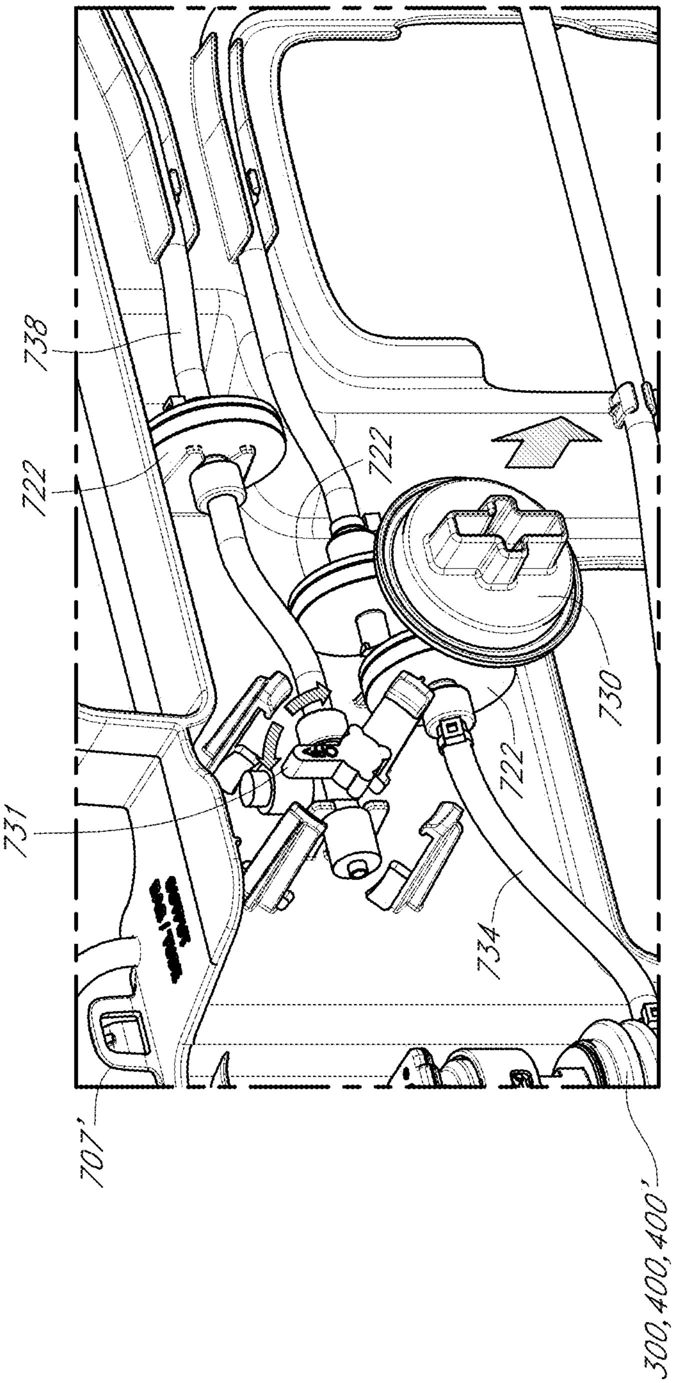
FIG. 15H illustrates one example of an air flow control assembly comprising air filters, tubes and a stopcock of an electroporation system/casing module, according to one embodiment of the disclosure.

FIG. 15H shows additional details of the stopcock mechanism for air flow and the shaded arrows depict the rotation of the stopcock. The instrument's driver rotates stopcock 731 90 degree clockwise to allow air exchange, and back to original position (0 degrees) to stop air exchange. This allows input pump (or first pump) to work where the air would push the sample/liquid from tube 737 to the subsequent stage which is mixer reservoir 708 and from there to mixer pump via mixer tube 737. Stopcock adapter 730 functions as a retainer to hold stopcock 731 on the casing module 700'. Stopcock adaptor 730 also functions as an easier lead-in for a user to load it correctly into the stopcock drive on an instrument such as 605' or 600'.

Figure 15I:
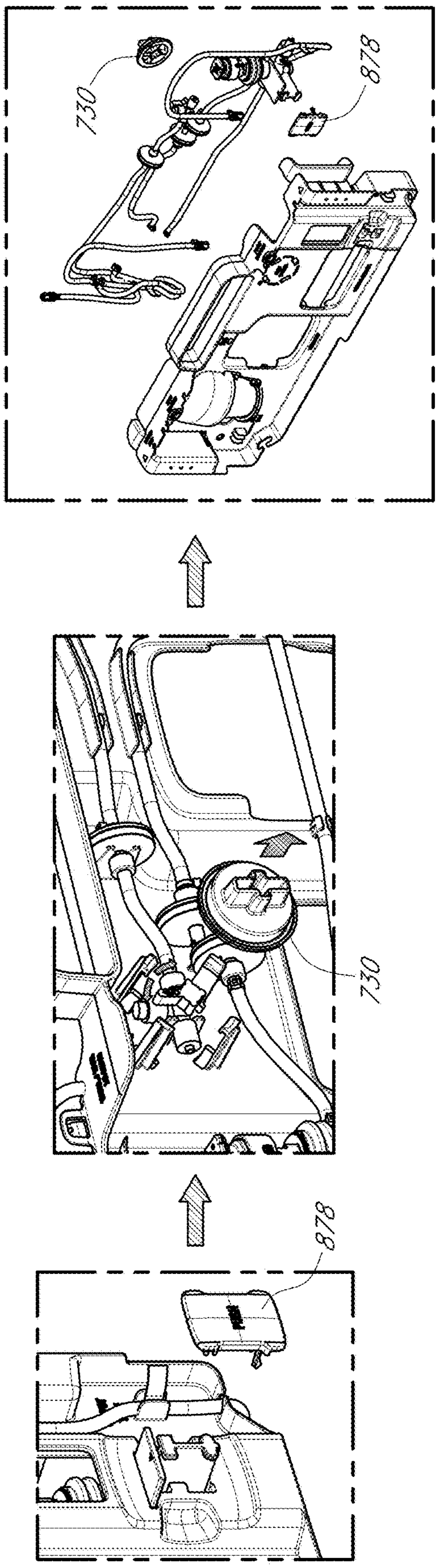
FIG. 15I illustrates steps of disassembly of an electroporation casing module from an electroporation instrument, according to one embodiment of the disclosure.

FIG. 15I depicts three steps to remove a modular casing 700' from an instrument or system 600' or 605 and comprise the steps of: removing the electroporation chamber by first removing the knob of cartridge retainer 878; then removing stopcock adaptor 730; and then removing modular casing 700' using the handles and grips (if present) to remove this away from system 605' or instrument 600'.

Mixer Reservoir

Figure 16A:
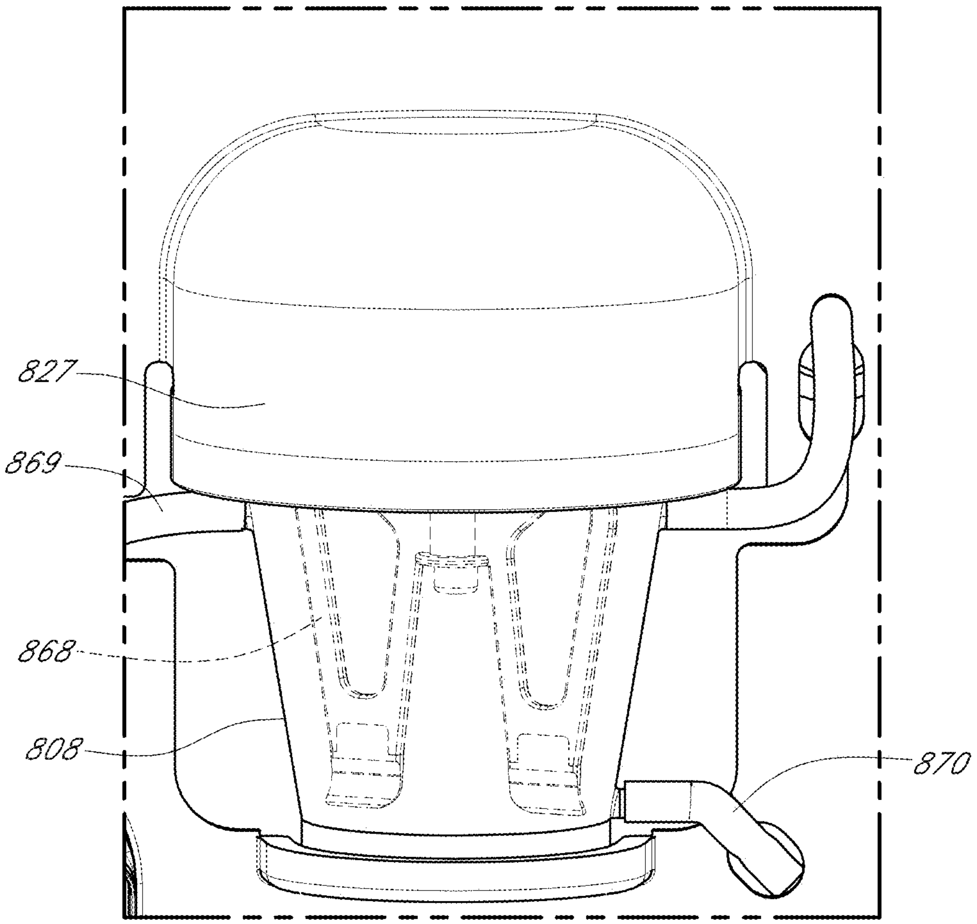
FIGS. 16A and 16B illustrate expanded views of an exemplary mixer reservoir configured to hold transferred sample and to maintain the sample in homogenous suspension while successive sub-volumes of the sample are passed to the electroporation cartridge for electroporation, according to some embodiments.
Figure 16B:
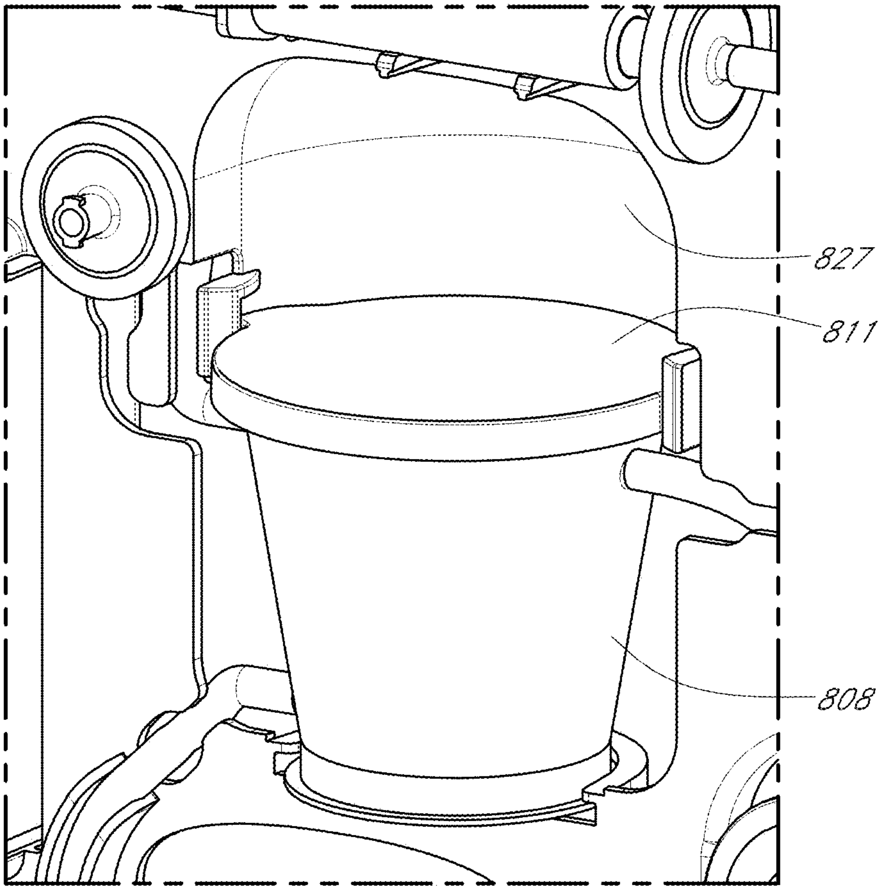

FIGS. 16A and 16B illustrate expanded views of an exemplary mixer reservoir 808. The mixer reservoir 808 beneficially functions to keep the sample fluid (e.g., containing cells) in homogenous suspension while successive sub-volumes of the sample are electroporated and moved to the output bag. The inclusion of a mixer reservoir 808 beneficially allows for the use of a wide variety of input bag types. Because bags can vary according to volume, shape, rigidity, and the like, attempts to transfer directly to the electroporation cartridge from the bag itself can lead to non-uniform cell densities from sub-volume to sub-volume, cell settling, plugging of tubing lines, and other undesirable issues. These issues are bypassed by moving the sample volume to the mixer reservoir 808.

As shown in FIG. 16A, the mixer reservoir 808 may include a mixer element 868. The mixer element 868 is preferably configured as a blade (as shown), impeller, or the like, as opposed to a free-moving element such as a magnetic stir bar. Centrifugal stirrers are also less preferred because they tend to concentrate cells in the outer portions of the circulating fluid.

Preferably, magnetic elements do not contact the sample fluid. The mixer element 868 thus preferably does not include a magnetic material but is formed from a medical-grade polymer or other suitable material. The mixer element (not shown in FIG. 16B) may couple to a mixer magnet assembly located in a cover 811. A mixer driver (not shown, part of instrument panel) is received into the mixer compartment 827 when the casing is attached to the instrument panel. The mixer driver includes one or more magnets that magnetically couple to the mixer magnet assembly and thereby indirectly drive rotation of the mixer magnet assembly via the magnetic connection.

The illustrated mixer reservoir 808 includes a reservoir input 869 and reservoir output 870. As shown, the reservoir input 869 is preferably disposed at an upper section of the mixer reservoir 808 so that incoming sample fluid can run down the inner side surface of the mixer reservoir 808 before collecting at the bottom. This configuration tends to limit the formation of bubbles upon entry to the mixer reservoir 808.

Cooling Mechanisms

Figure 17A:
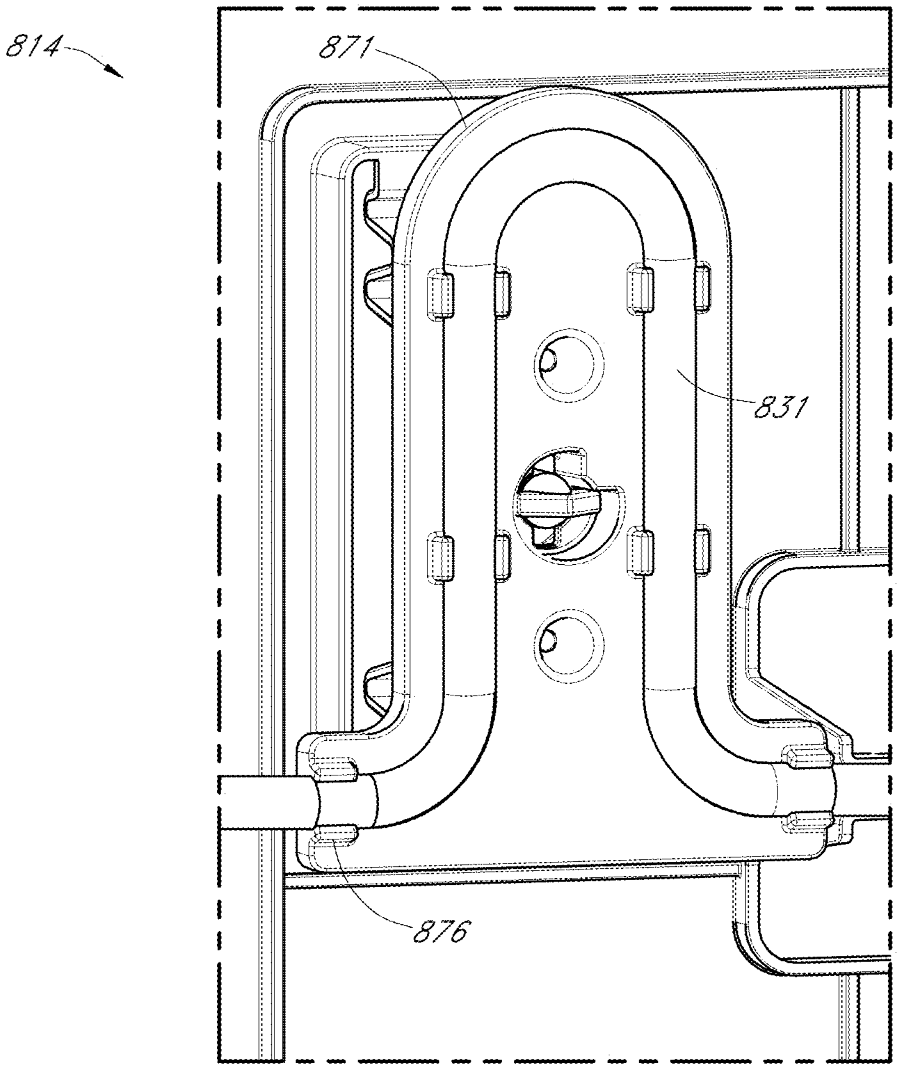
FIGS. 17A, 17B and FIG. 17C illustrate example embodiments of pre-cooling modules disposed upstream from the electroporation cartridge and configured to cool passing sample prior to electroporation.
Figure 17B:
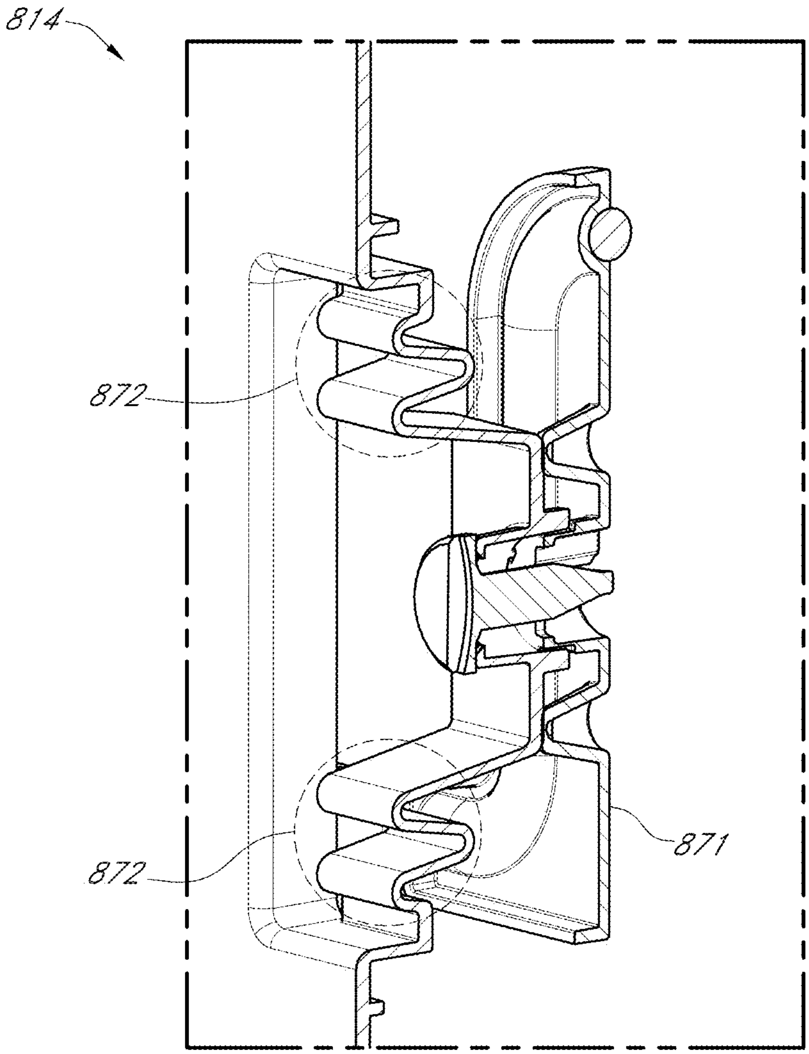

FIGS. 17A and 17B illustrate one embodiment of a pre-cooling module 814. In this embodiment, a pre-cool section 831 of tubing upstream from the electroporation chamber is contacted with a cooling block 871, by one or more attachment clamps 876. Other modes of attachment can be used and clamps 876 are one example embodiment. Cooling block 871 can be a ceramic block or can comprise any other material capable of effective thermal communication and heat transfer with the pre-cool section 831 of tubing. Cooling block 871 can be cooled according to methods known in the art, preferably via thermoelectric cooling. Other embodiments may additionally or alternatively utilize air cooling, liquid cooling, or other temperature regulating mechanisms known in the art.

In the illustrated embodiment, the pre-cool section 831 of tubing is disposed in a looped or serpentine arrangement. This beneficially provides greater contact between the pre-cool section 831 of the tubing and the cooling block 871, allowing for greater heat transfer to occur. However, it has been found that a looped or serpentine arrangement may also lead to the generation of bubbles, which can negatively impact subsequent electroporation of the sample sub-volume. Thus, some embodiments maintain the pre-cool section 831 of tubing in a substantially straight line, such as in the pre-cooling module 714 of the embodiment of FIG. 12A and the pre-cooling module 814 of the embodiment of 12B.

As shown in FIG. 17B, the pre-cooling module 814 can further include a flexible biasing element 872. In this embodiment, flexible biasing element 872 is disposed on the side of the cooling block 871 opposite the pre-cool section 831 of tubing. The flexible biasing element 872 includes features that bias against the cooling block 871 and tend to press the cooling block 871 against the pre-cool section 831 of tubing, thus assisting in maintaining good thermal contact between cooling block 871 and the pre-cool section 831 of tubing.

Figure 17C:
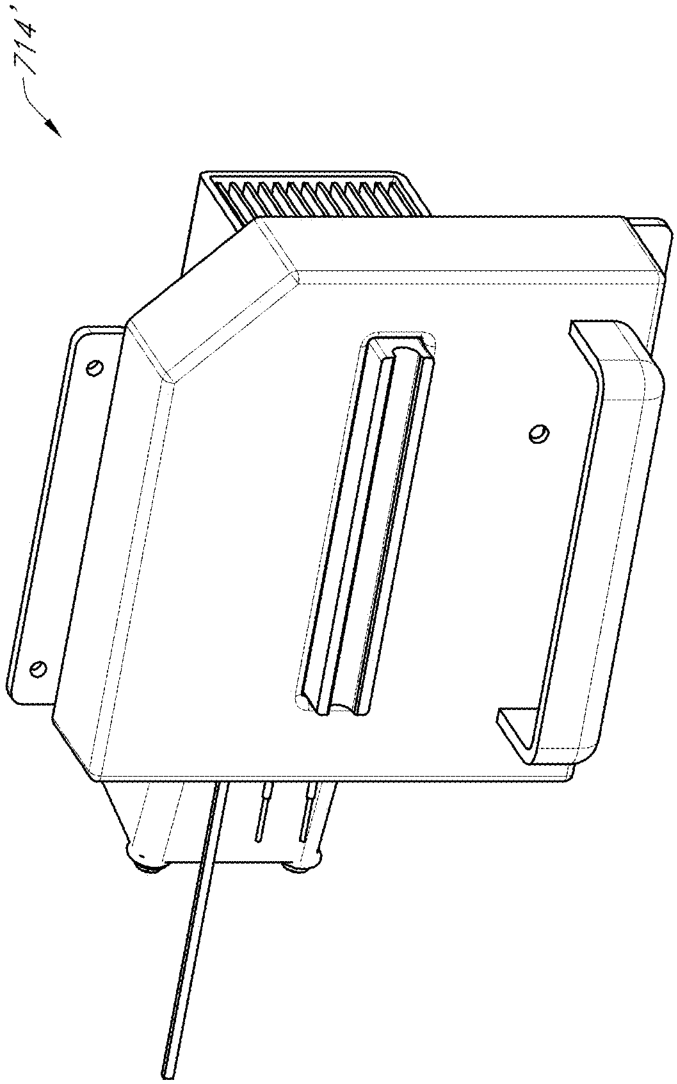

FIG. 17C illustrates a perspective view if an embodiment of a pre-cooling module 714 as shown in FIG. 12A. A section of tubing with sample (such as 831 in FIG. 12 A or 737 in FIGS. 13A-13C) in a substantially straight line move through pre-cooling module 714 to cool sample prior to electroporation.

Figure 17D:
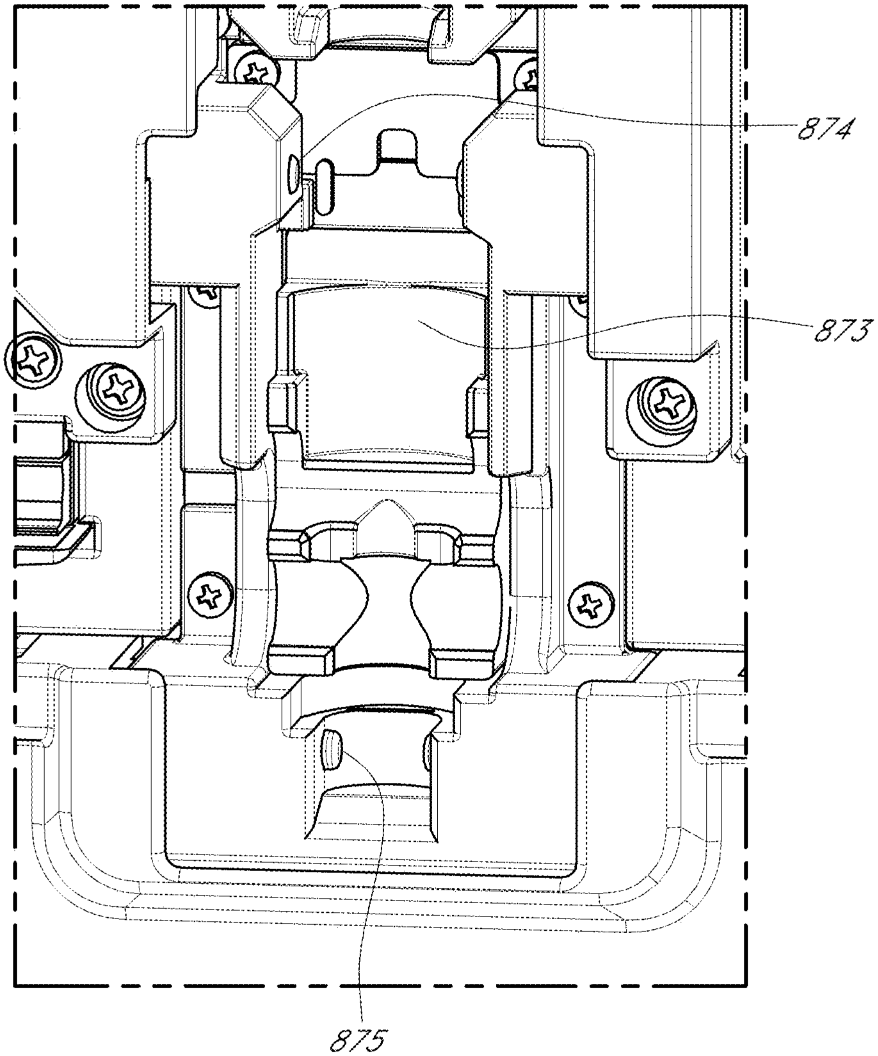
FIG. 17D illustrates an example of a cooling module configured to cool the electroporation chamber itself.

FIG. 17D illustrates an example of a cooling module 873 configured to cool an electroporation chamber of the disclosure. The illustrated cooling module 873 is configured in size and shape to receive the corresponding electroporation chamber portion of an electroporation cartridge of the present disclosure. FIG. 17D also shows upper electrode contacts 874 and lower electrode contacts 875 which are positioned to contact the corresponding upper and lower electrodes of an inserted electroporation cartridge. As with the pre-cooling module, the cooling module 873 can comprise a ceramic block or other suitable heat transfer material and may operate via thermoelectric cooling and/or other cooling methods known in the art (e.g., air cooling and/or liquid cooling).

Figure 18A:
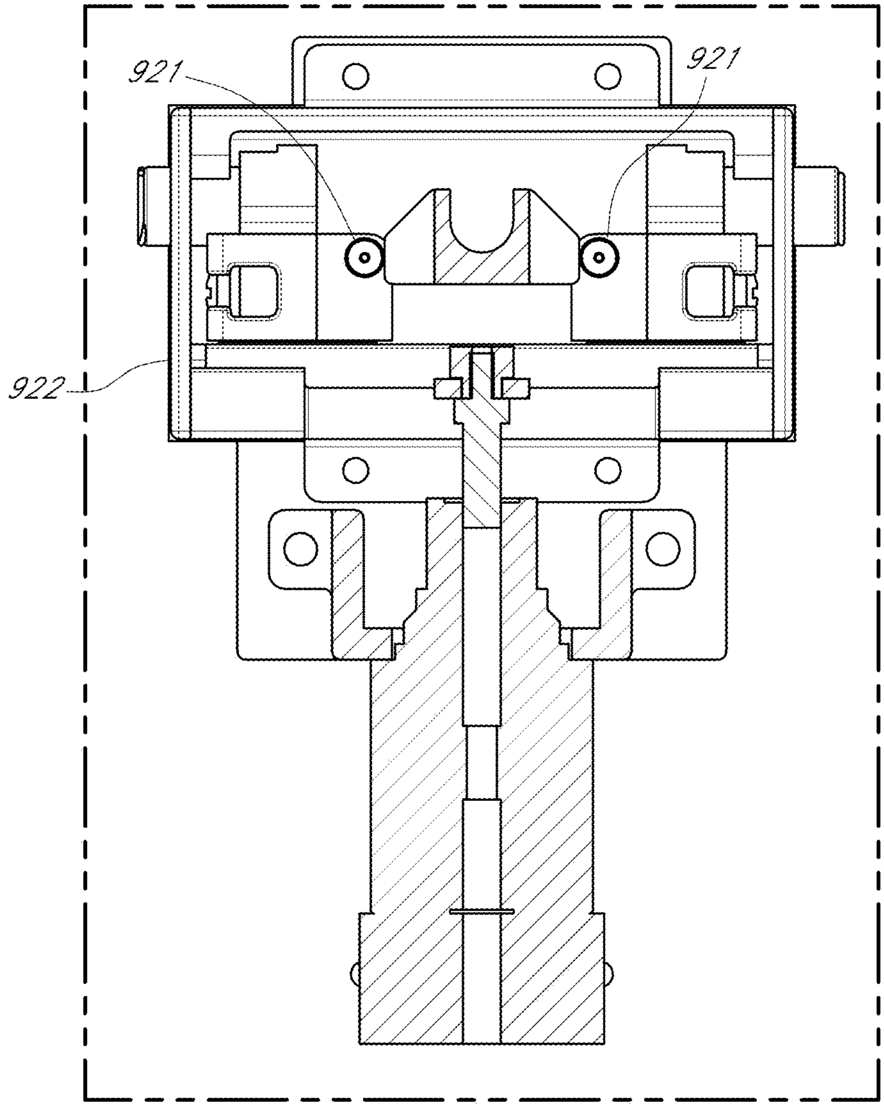
FIGS. 18A and 18B illustrate an example of high voltage touch pins of an electroporation instrument of the disclosure disengaging with an example electroporation chamber.
Figure 18B:
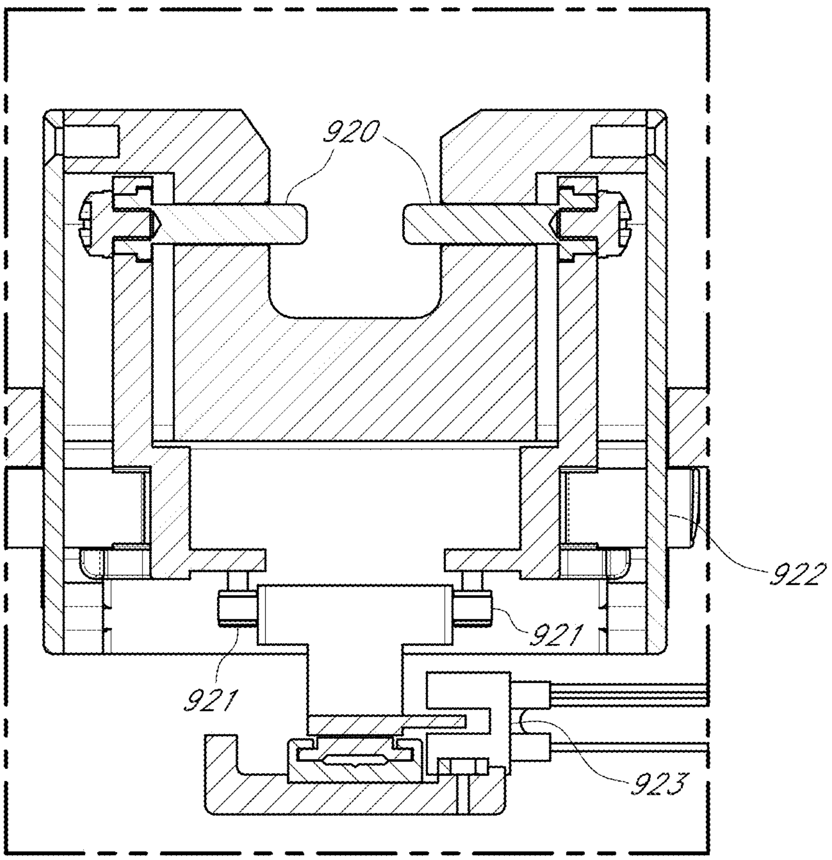
Figure 18C:
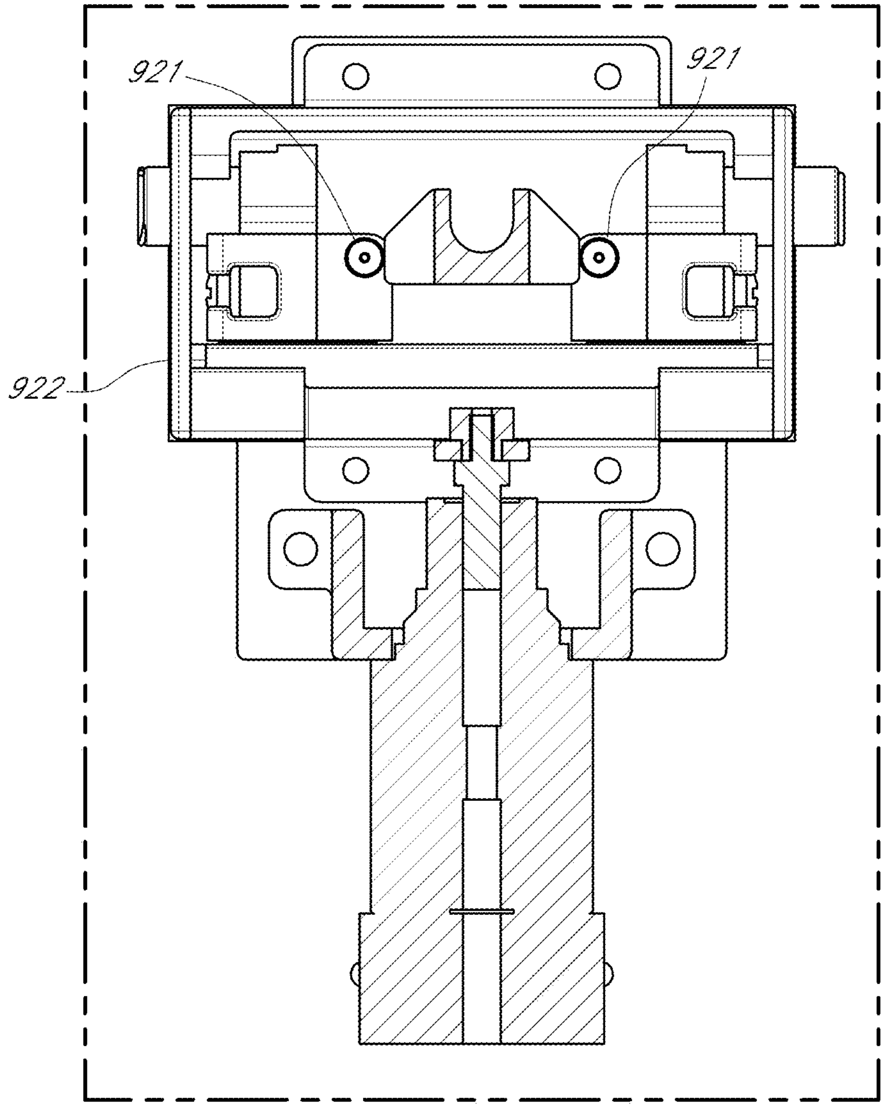
FIGS. 18C and 18D illustrates an example of high voltage touch pins of an electroporation instrument of the disclosure engaging with an electroporation chamber.
Figure 18D:
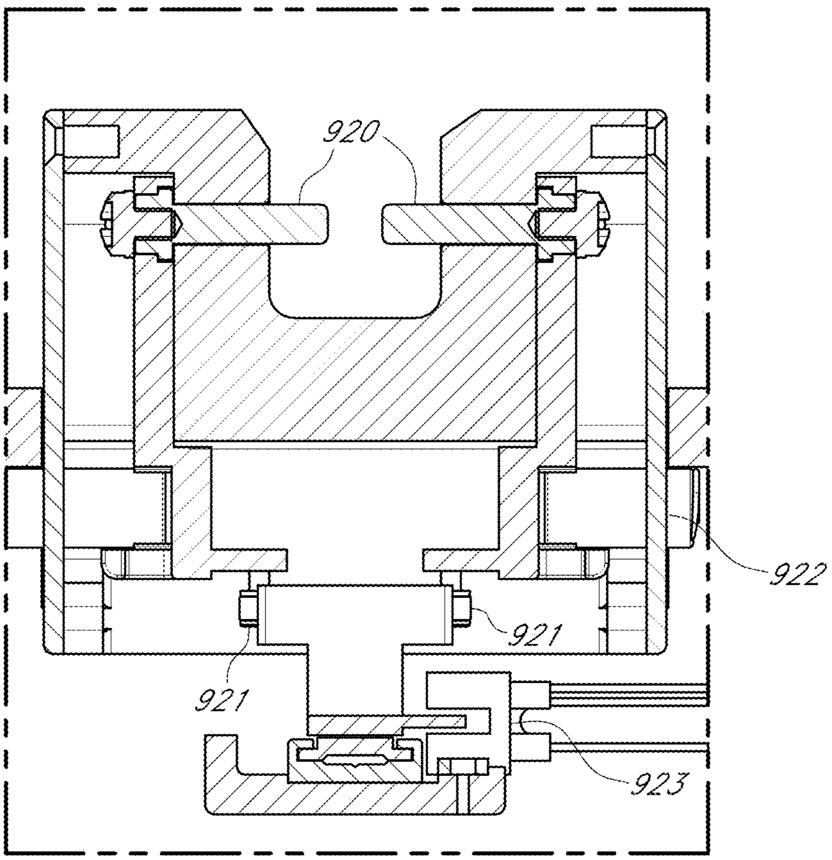

FIGS. 18A and 18B illustrate an example of high voltage touch pins of an electroporation instrument of the disclosure disengaging with an example electroporation cartridge. FIG. 18A depicts a back cross section view of an electroporation instrument or system showing the area where an electroporation cartridge can be removably placed (cartridge not expressly shown). Cams 921 in the engaged portion are shown in FIG. 18A. FIG. 18B shows the corresponding area in a top cross section view and depicts high voltage pins 920 of the system where an electroporation cartridge can be removably placed just where the ends of the high voltage pins end. Springs 922 and Sensor 923 are also depicted. Linear actuator stroke is about 10 mm. FIG. 18B shows high voltage pins 920 disengaged from the electroporation cartridge when cams 921 are engaged. FIGS. 18C and 18D illustrates an example of high voltage touch pins of an electroporation instrument of the disclosure engaging with an electroporation chamber. FIG. 18C depicts a back cross section view of the electroporation instrument or system showing the area where an electroporation cartridge can be removably placed (cartridge not expressly shown). Cams 921 in the disengaged portion are shown in FIG. 18C which correspond to the engagement of high voltage pins 920 with an electroporation cartridge. FIG. 18D shows the corresponding area in a top cross section view and depicts high voltage pins 920 of the system engaging with an electroporation cartridge (cartridge not depicted). Linear actuator stroke is about 2 mm.

Electroporation Cartridge Attachment Features

Figure 19A:
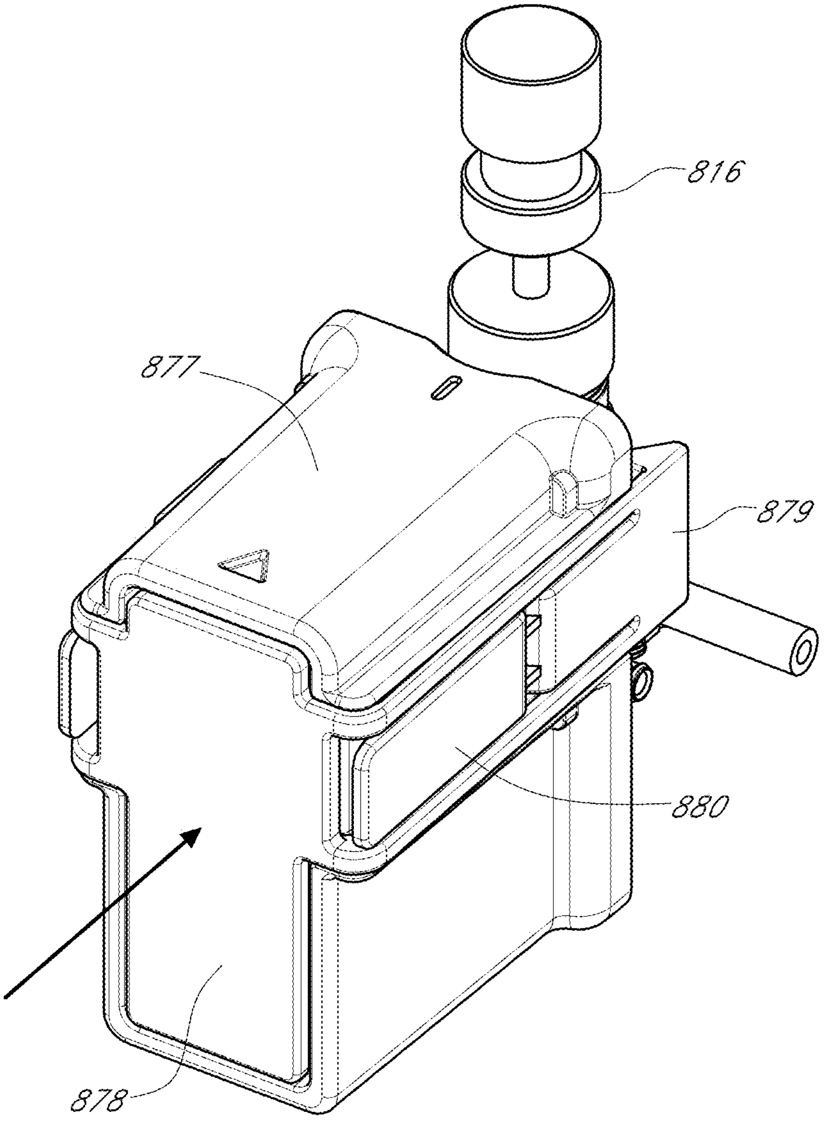
FIGS. 19A-19C illustrate an embodiment of an electroporation cartridge attachment feature configured to enable attachment of the cartridge in the appropriate position in the cooling module.
Figure 19B:
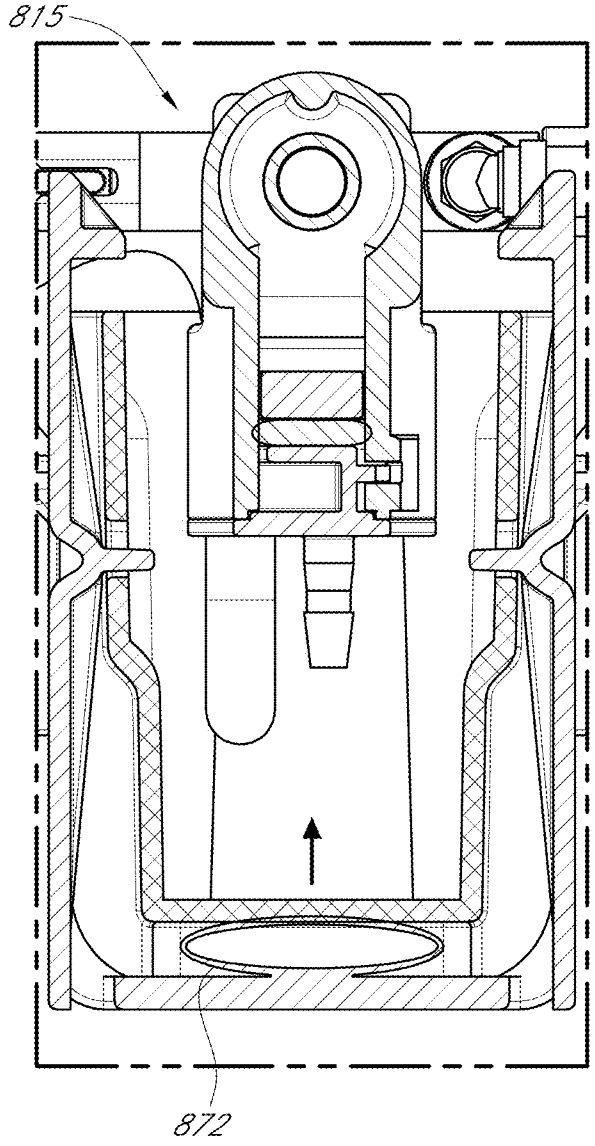
Figure 19C:
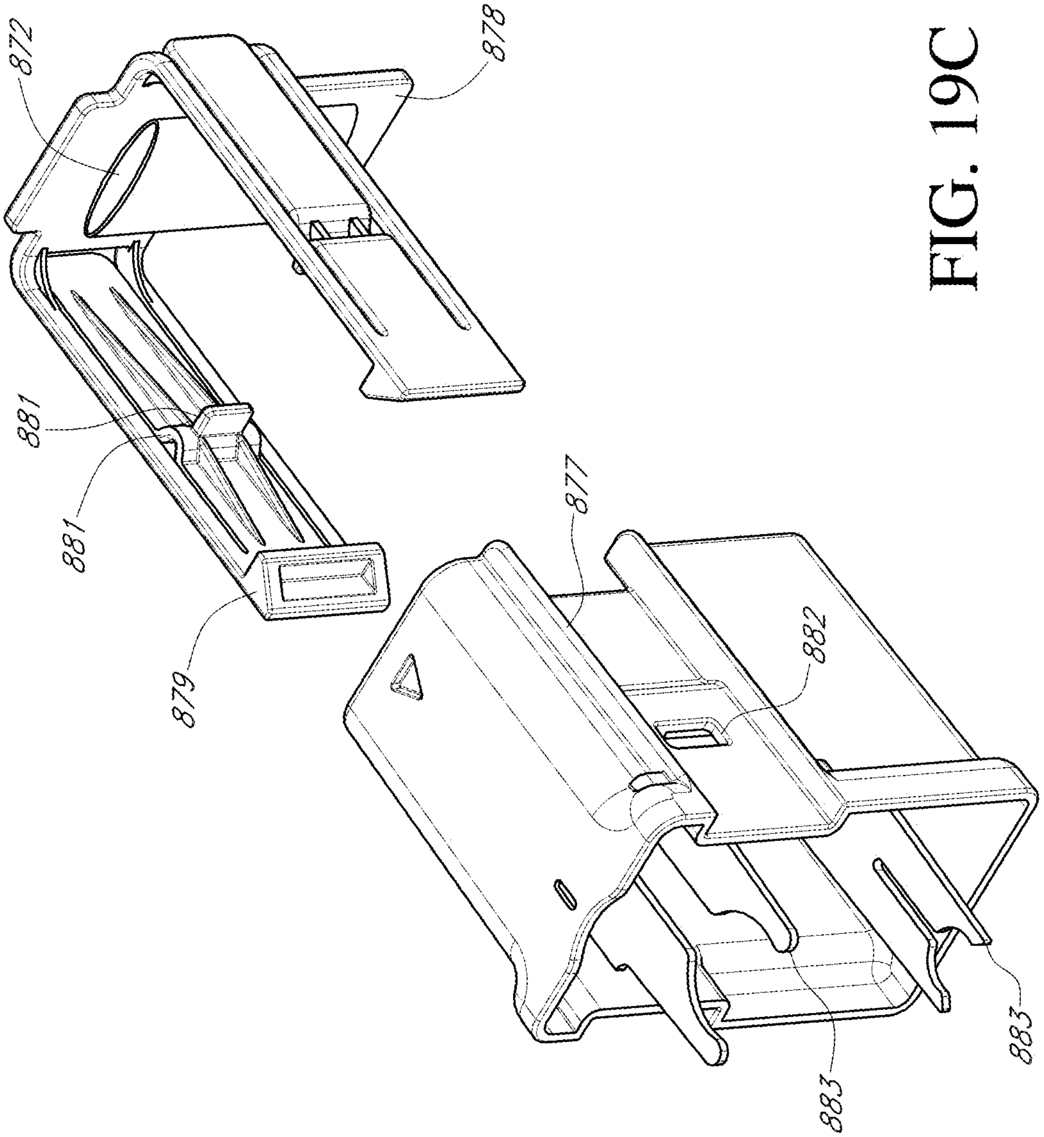

FIGS. 19A, 19B and 19C illustrate an embodiment of an electroporation cartridge attachment feature configured to enable attachment of an electroporation cartridge in the appropriate position in cooling module 815. In the illustrated embodiment, the electroporation cartridge 816 includes a cartridge body 877 and a retainer 878. The cartridge body 877 is adapted to attach to the electroporation cartridge 816 by way of one or more clasps 883. The retainer 878 then attaches to the cartridge body 877. The retainer 878 includes two catches 879 that extend past the cartridge body 877 when the retainer 878 is attached to the cartridge body 877, and can engage with corresponding structure of the cooling module 815 to thereby hold the cartridge body 877 and the electroporation cartridge 816 in place within the cooling module 815.

As shown, the retainer 878 may also include a flexible biasing element 872 configured to bias the cartridge body 877 and electroporation cartridge 816 toward the cooling module 815. The flexible biasing element 872 beneficially accounts for differences in part tolerances and ensures that small differences are compensated for such that the electroporation cartridge 816 is brought into effective thermal contact with the cooling module 815 regardless.

The attachment feature is also configured to allow for selective disengagement and removal of the electroporation cartridge. Pressing inward on the proximal sections 880 of the retainer 878 causes the catches 879 to flex outwardly to allow removal from the cooling module 815. The tabs 881 of the retainer 878 fit into corresponding slots 882 of the cartridge body 877 to enable the user to pull the full cartridge out from the cooling chamber upon disengaging the catches 879.

Electroporation Chamber Capping Mechanisms

Figure 20A:
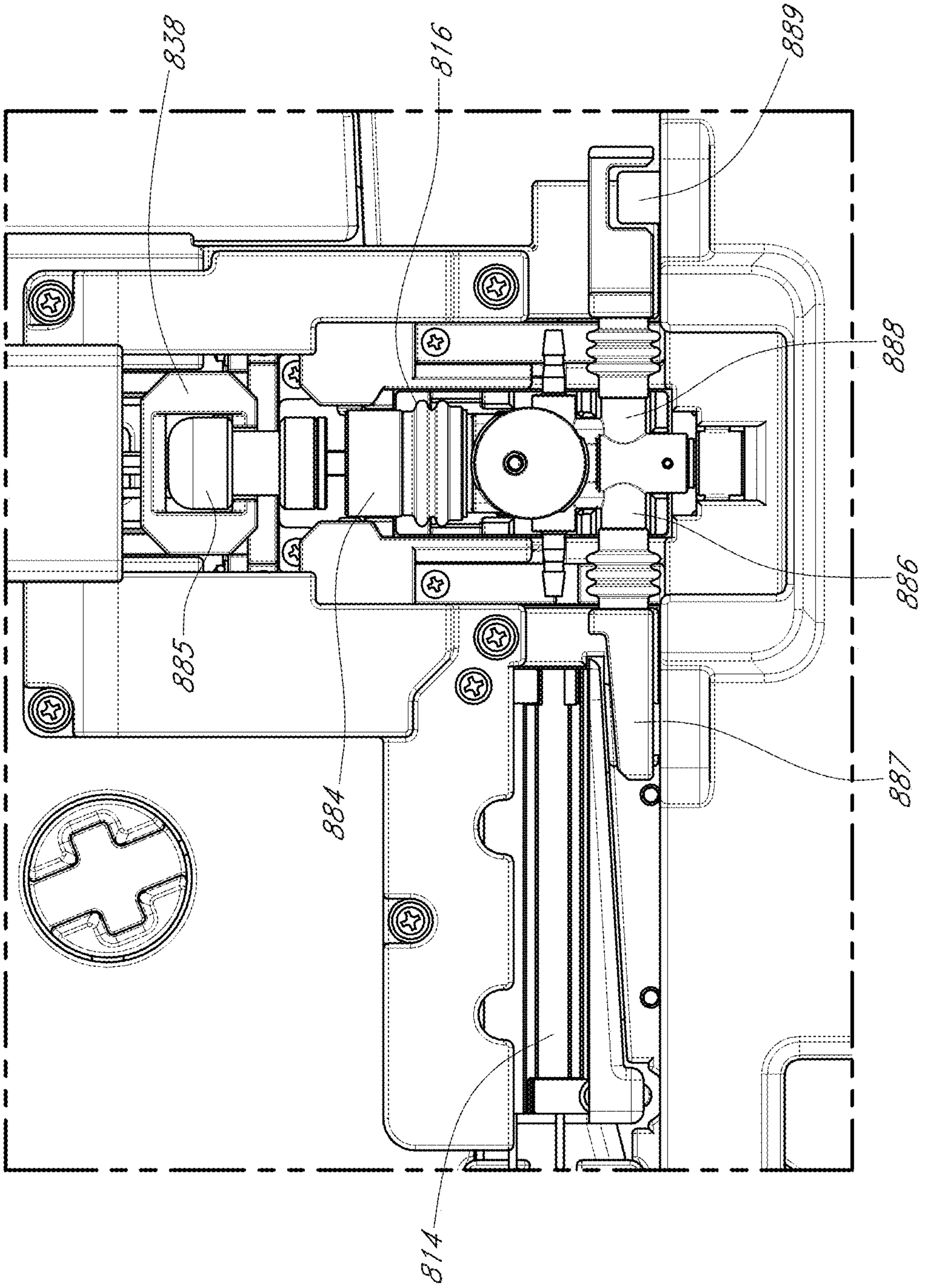
FIGS. 20A-20C illustrate operation of a capping mechanism to move an electroporation cartridge between a capped state in preparation for electroporation and an uncapped state in preparation for filling or draining of the corresponding electroporation chamber, according to some embodiments.
Figure 20B:
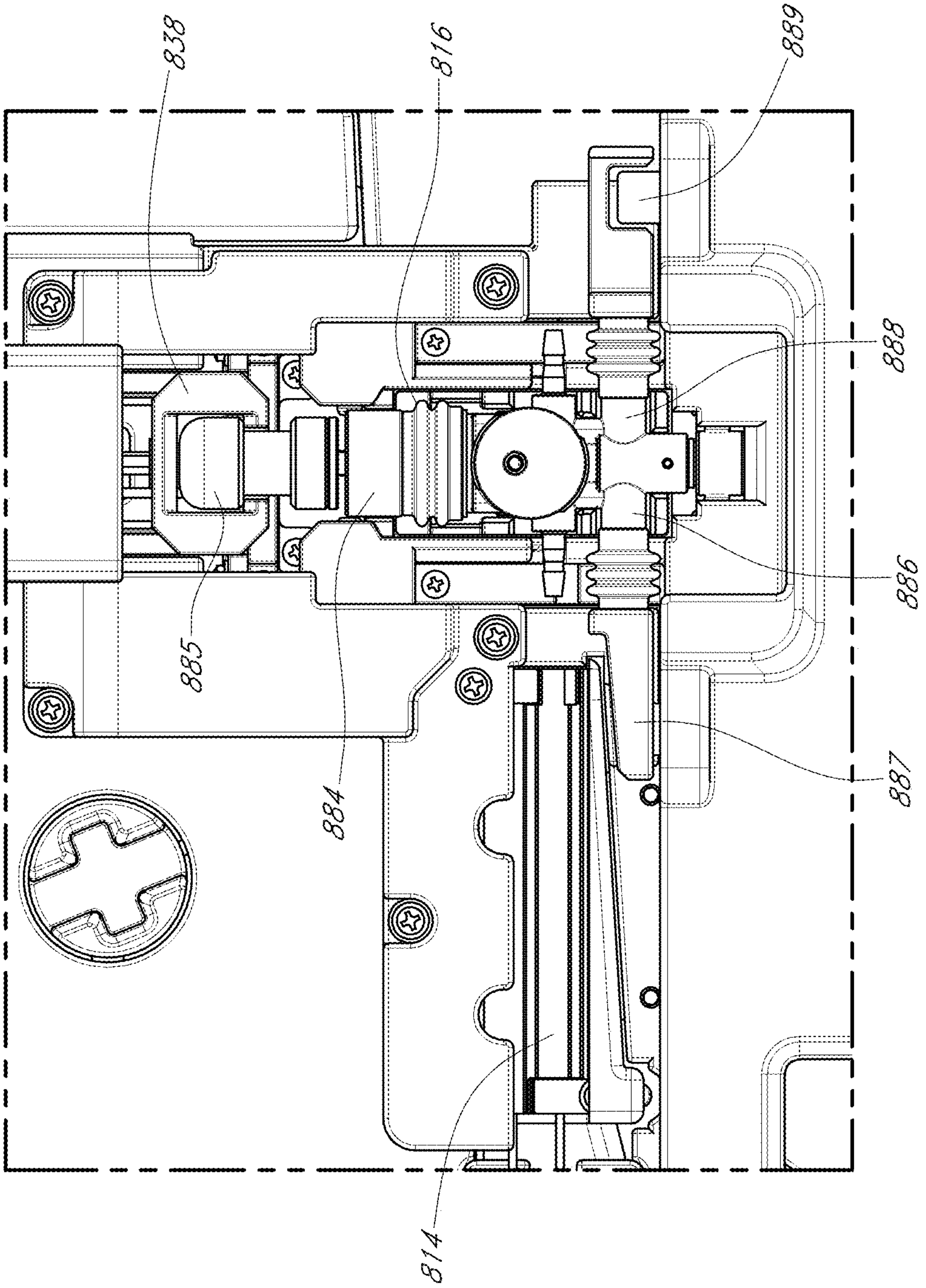
Figure 20C:
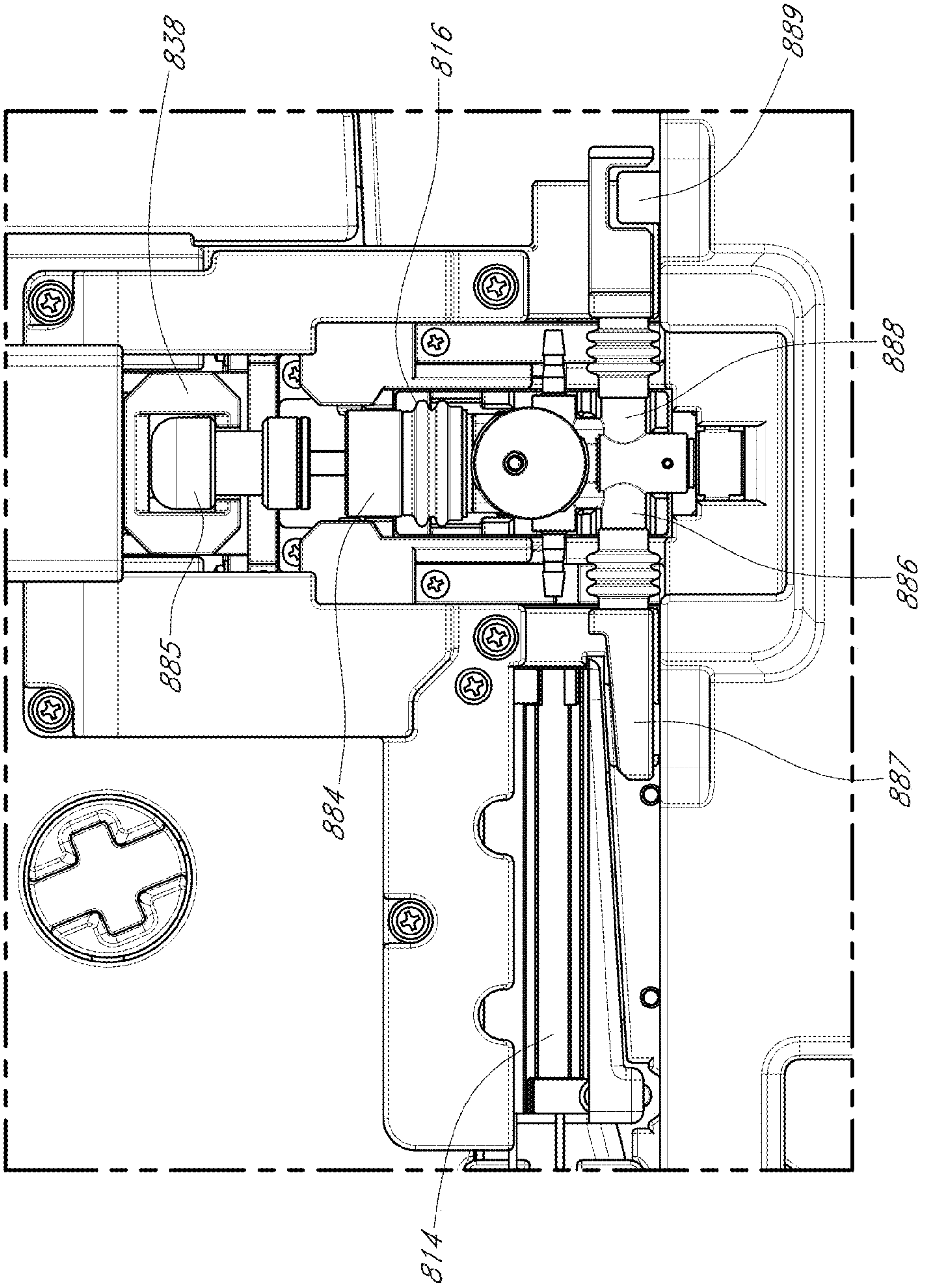

FIG. 20A through 20C illustrate operation of a capping mechanism 838 to move the electroporation cartridge between a capped state in preparation for electroporation and an uncapped state in preparation for filling or draining of the electroporation chamber. The capping mechanism 838 functions as a linear actuator that engages with a cap 885 of the electroporation cartridge 816. The cap 885, in turn, is coupled to the upper electrode 884 of the electroporation cartridge, so that movement of the capping mechanism 838 controls upward and downward movement of the upper electrode 884.

FIG. 20A through 20C also show chamber inlet plunger 886, controlled by chamber inlet driver 887, and the chamber outlet plunger 888, controlled by chamber outlet driver 889. FIG. 20A shows the upper electrode 884 in an uncapped position, the inlet plunger 886 in a retracted, open position, and the outlet plunger 888 in an advanced, closed position. FIG. 20A represents the relative positions of these components during a filling operation.

FIG. 20B shows the upper electrode 884 in a closed position, the inlet plunger 886 in an advanced, closed position, and the outlet plunger 888 remaining in the advanced, closed position. FIG. 20B represents the relative positions of these components when in a sealed state in preparation for an electroporation operation.

FIG. 20C shows the upper electrode 884 in an uncapped position, the inlet plunger 886 remaining in an advanced, closed position, and the outlet plunger 888 moved to a retracted, open position. FIG. 20C represents the relative positions of these components during a drain operation, such as following electroporation of the sub-volume within the electroporation chamber.

Figure 21:
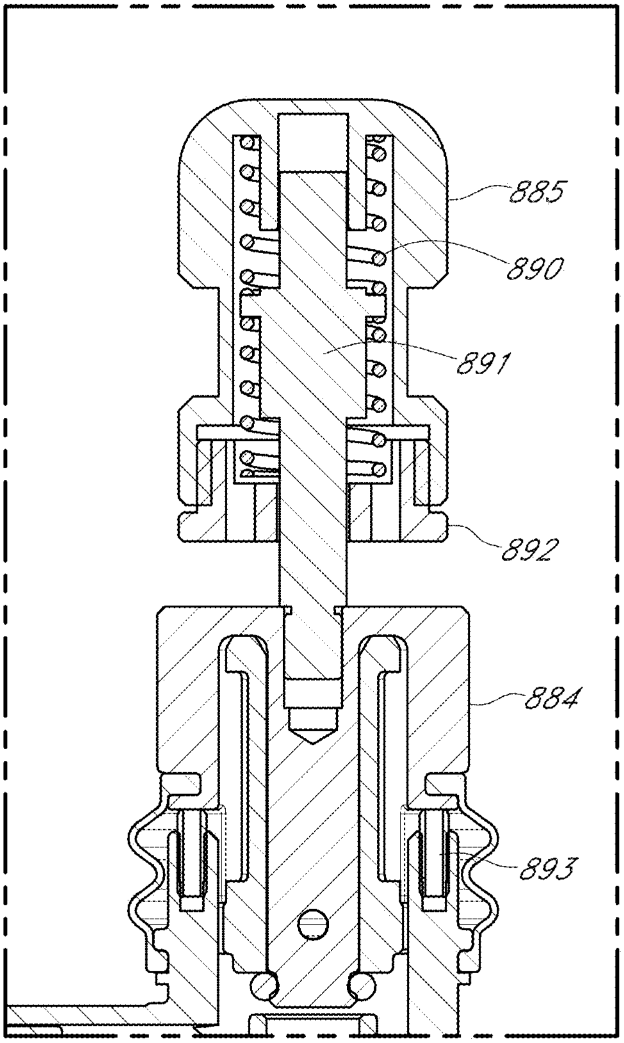
FIG. 21 illustrates a capping mechanism and its operation in conjunction with the cap of an electroporation cartridge, illustrating the functionality of a spring-based mechanism that allows for overtravel of the capping mechanism to ensure that the electrode is fully moved to the desired position despite different cartridge dimensional tolerances, according to some embodiments.

FIG. 21 illustrates the capping mechanism (element 838 in FIG. 20A-20C) and its operation in conjunction with the cap 885 (shown in cross section) in further detail. As shown, the cap 885 includes a spring 890 disposed within a spring chamber, and a elongate member 891 that is mechanically associated with the spring 890 such that linear movement of the elongate member 891 can transfer to the spring 890 and such that forces stored in the spring 890 can transfer to the elongate member 891. For example, as shown, the elongate member 891 may include a flange sized to extend outward and engage with the coils of the spring 890, while the remainder of the elongate member 891 extends through the inner lumen of the spring 890.

The elongate member 891 extends from the cap 885 and mechanically couples to the upper electrode 884. When the cap 885 is moved in response to actuation of the capping mechanism 838, and if there is no resistance, the linear motion causes the elongate member 891, and thus the upper electrode 884, to move accordingly. Once the electrode 884 tops out or bottoms out, however, the elongate member 891 will no longer be able to move. At that point, continued motion of the cap 885 causes the spring 890 to deform. That is, the spring 890 allows for overtravel of the cap 885 after the upper electrode 884 has reached a terminal upper or lower position. The mechanically allowed overtravel ensures that the electrode 884 is moved to the proper position despite actuation drift and/or potential tolerance differences from one electroporation cartridge to the next.

As shown, the upper limit of the electrode 884 may be defined by a hard stop 892. An upper portion of the electroporation chamber may similarly function as a hard stop representing the lower limit of the electrode 884. Some embodiments may include one or more spring pins 893 disposed at the upper portion of the electroporation chamber in order to define a "home" or position useful during initial calibration of the instrument. The spring pins 893 are configured so that the downward force during the initial downward movement of the upper electrode 884, as assisted by force from the spring 890 from an amount of overtravel of the cap 885, overcomes and presses the spring pins 893 down and allows the electrode 884 to reach the fully capped position.

Electroporation Chamber Sealing Mechanisms

Figure 22A:
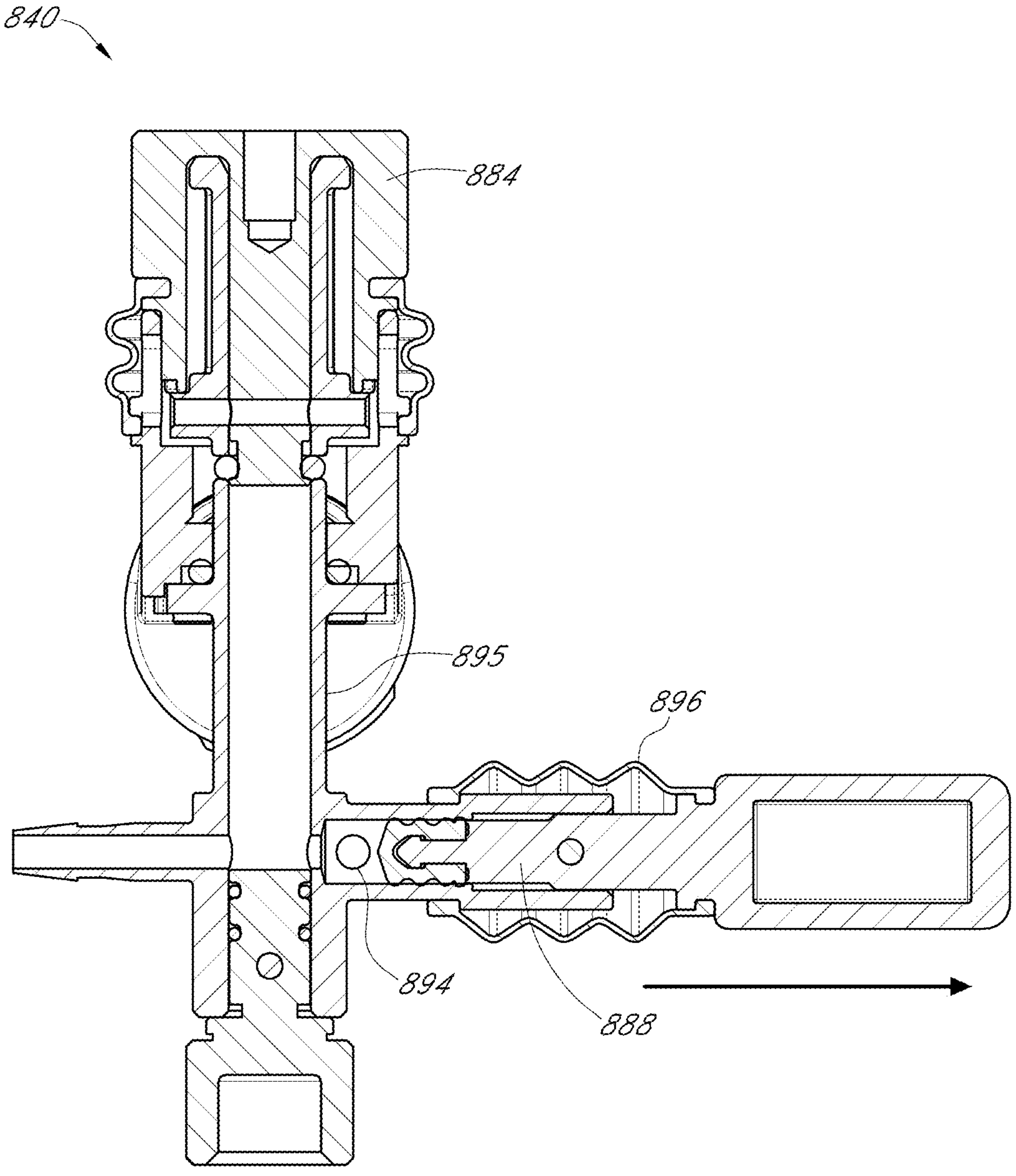
FIGS. 22A-22E illustrate examples of sealing mechanisms and associated components of an electroporation cartridge of the disclosure in greater detail, according to some embodiments.
Figure 22B:
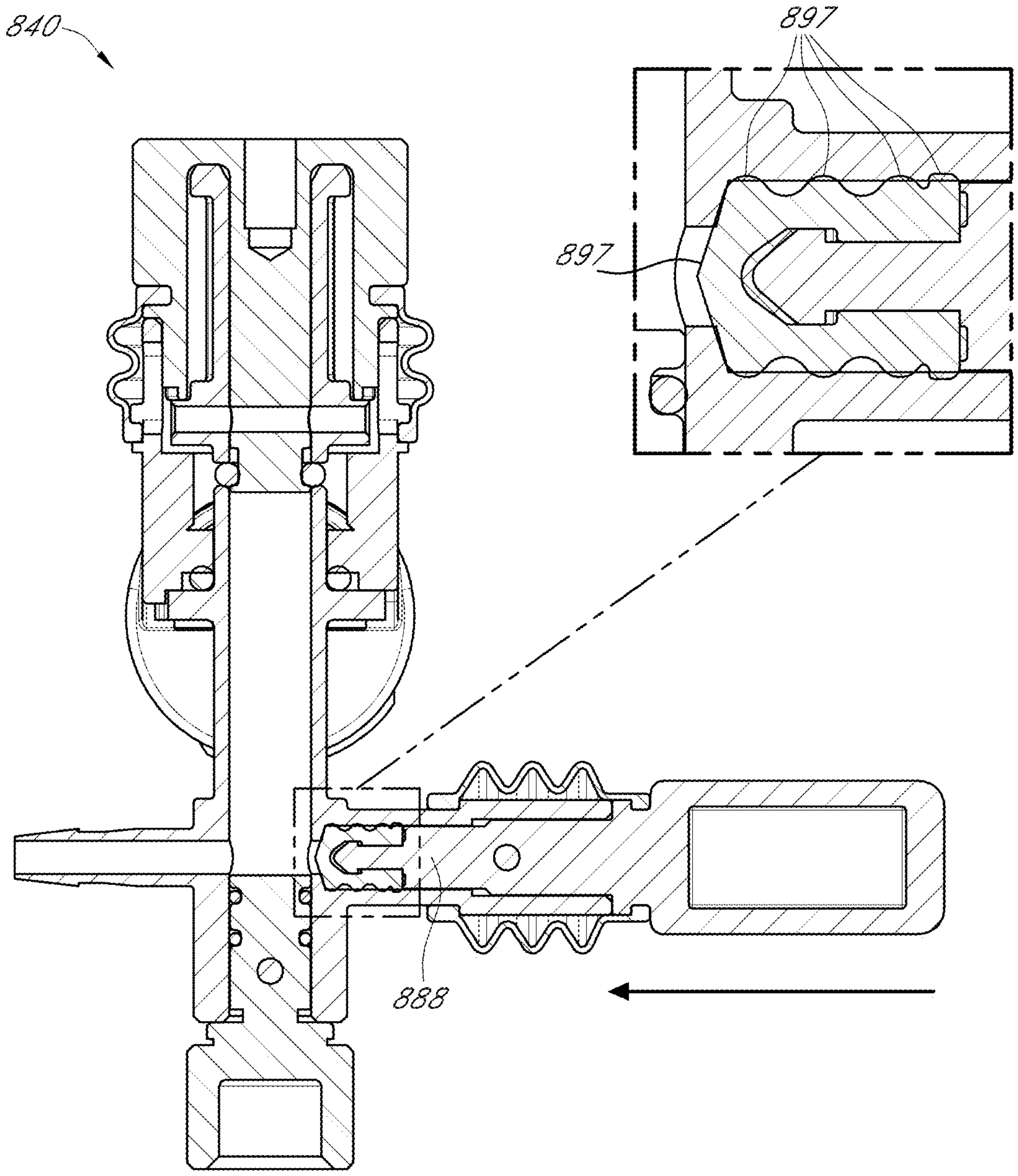

FIGS. 22A and 22B illustrate an example of the sealing mechanism 840 in greater detail. Providing effective sealing of the electroporation chamber 895 beneficially minimizes bubble formation and associated arcing during electroporation. The ability to maintain higher relative pressures within the electroporation chamber 895 reduces vaporization of the fluid (i.e., raises the boiling point of the fluid) and may also reduce the growth rate of oxygen and hydrogen bubbles formed as a result of electrolysis of water in the sample fluid.

The outlet plunger 888 is shown here for illustration, but the inlet plunger 886 may be configured similarly. When the plunger 888 is in the retracted position, as shown in FIG. 22A, an outlet port 894 is revealed, allowing fluid to drain out of the electroporation chamber 895. On the other hand, when the plunger 888 is in the advanced position, as shown in FIG. 22B, the outlet port 894 is sealed off, preventing passage of fluid out of the electroporation chamber.

The inlet plunger 886, outlet plunger 888, and/or outer portion of the upper electrode 884 may also be covered by a bellows 896. The bellows 896 beneficially function to encase moving parts of the device and assist in isolating the interior environment to minimize the possibility of particulates entering electroporation chamber 895.

The detail view of the outlet plunger 888 shown in FIG. 22B illustrates that the plunger may include a rubber cap 897 for forming a watertight seal with the outlet channel. Alternative embodiments may additionally or alternatively include other sealing members, such as one or more O-rings. Movement of the inlet plunger 886 and outlet plunger 888 may be controlled by respective linear actuators/drivers 887, 889 (see FIGS. 20A-20C).

Figure 22C:
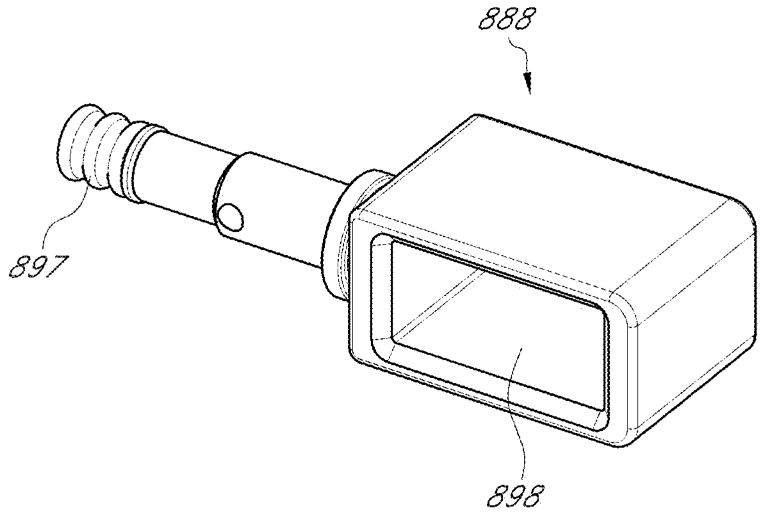

FIG. 22C illustrates another view of the plunger 888, showing the rubber cap 897 at a first end and an attachment 898 at a second end. The attachment is configured for engaging with the corresponding outlet driver 889 so that motion of the drive can be mechanically transferred to the plunger 888. The attachment 898 may be configured as an aperture, as shown here, or alternatively may be configured as a clasp, clamp, magnetic coupling, or other suitable mechanical linkage.

Figure 22D:
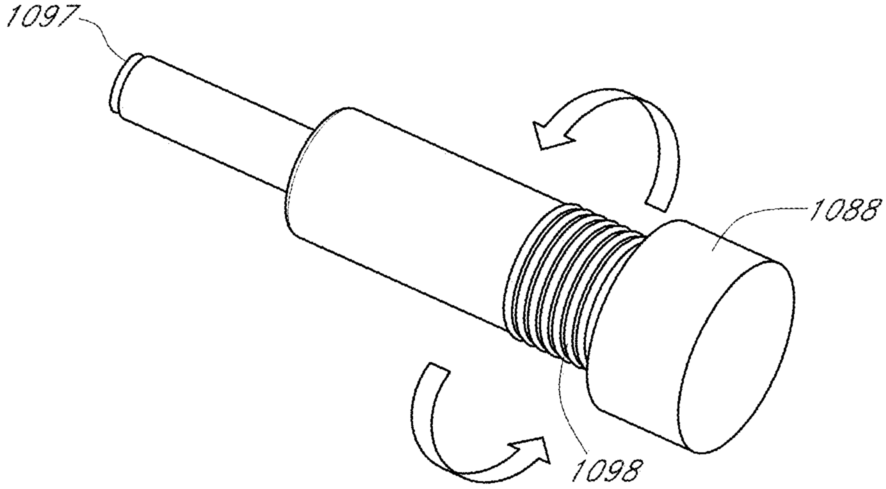

FIG. 22D illustrates an alternative embodiment of a plunger 1088 having a threaded portion 1098 and being configured to transfer rotational motion to linear movement. The plunger 1088 may have an O-ring seal member 1097, as shown, or alternatively may have a rubber cap, such as in other plunger embodiments, or other suitable sealing members. Other means for providing controlled linear motion of a plunger may additionally or alternatively be included. For example, some embodiments may include a track and rail assembly, a worm gear assembly, or a pneumatically or hydraulically powered actuator.

Figure 22E:
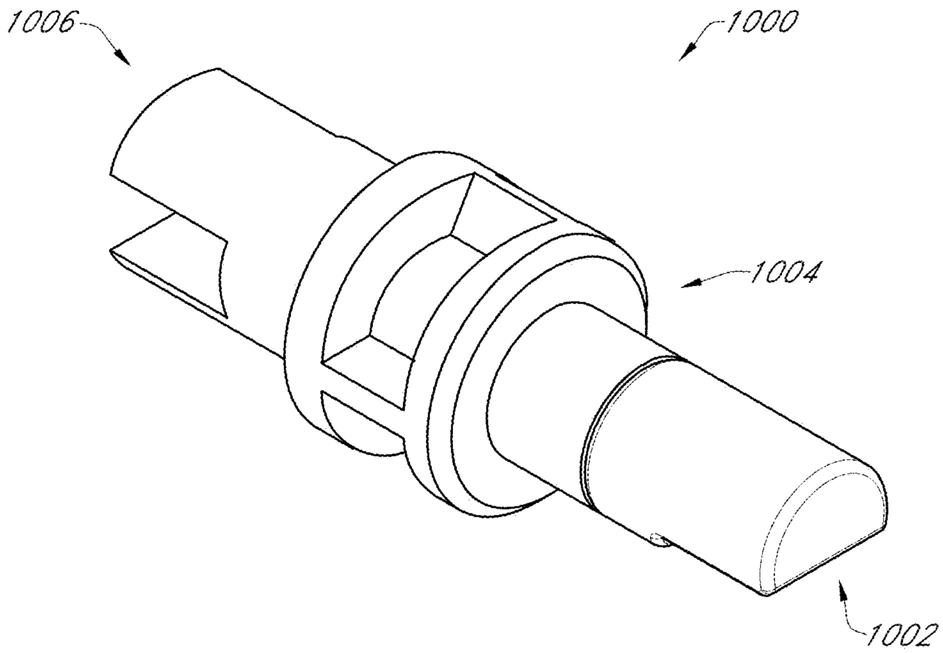
Figure 22F:
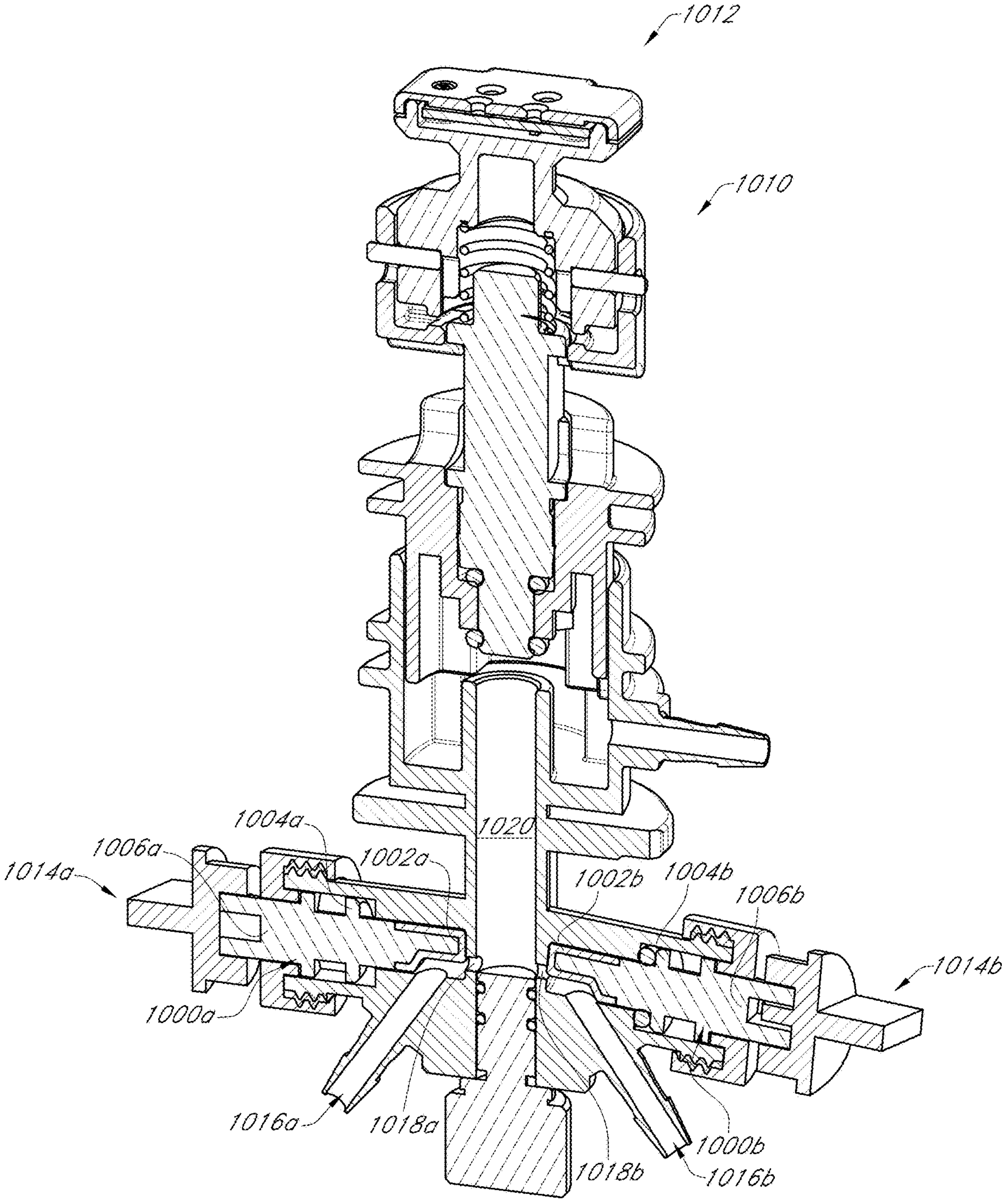
FIGS. 22F and 22G illustrate an exemplary flow-through electroporation cartridge that includes a sealing mechanism as depicted in FIG. 22E associated with the inlet and outlet ports and in various open and closed configurations, according to some embodiments.
Figure 22G:
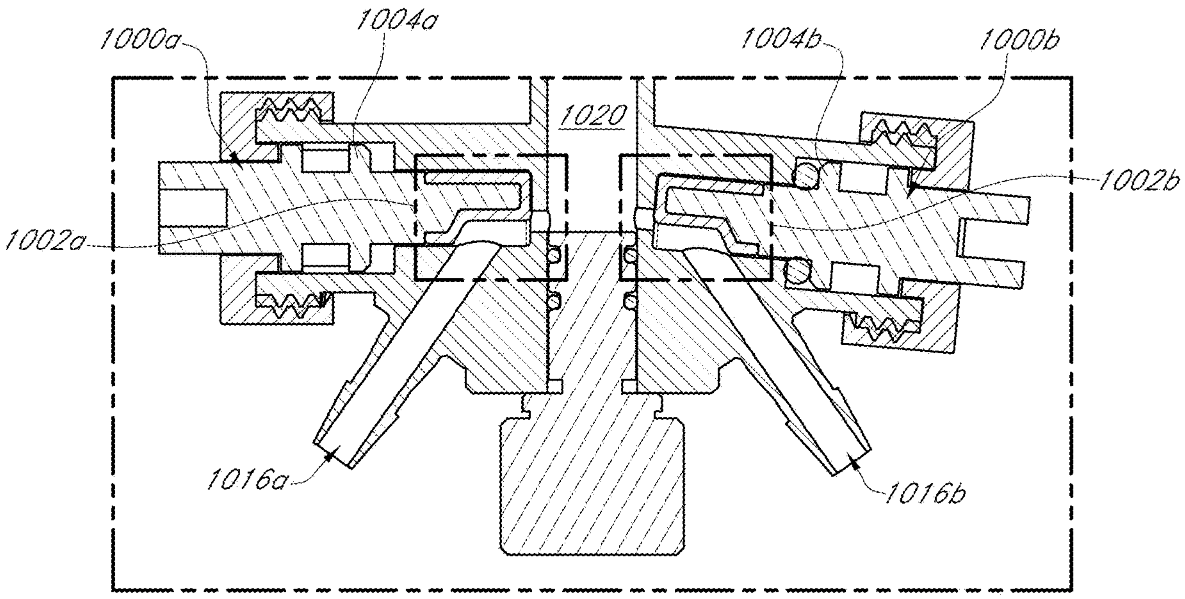

FIGS. 22E-22G illustrate an alternative embodiment to the plungers of FIGS. 22C and 22D. As shown, the sealing mechanism can include a rotatable sealing mechanism 1000 having a hemi-cylindrical head 1002 that can be rotated to selectively block or allow ingress through the inlet **1018*a* to the electroporation chamber 1020 and/or to selectively prevent egress from the electroporation chamber 1020 through the outlet 1018*b*. In an exemplary operation, the body 1006*a* of the sealing mechanism 1000 can engage a rotary piston 1014*a* operable by the electroporation system and cause the head 1002*a* to rotate into an open position (e.g., as shown in FIGS. 22F and 22G). Fluid can enter via the inlet port 1016 and through inlet 1018*a* into electroporation chamber 1020. An opposing sealing mechanism 1000*b* can be engaged by a complementary rotary piston 1014*b* and rotated into closed position (e.g., as shown in FIG. 22G), thereby allowing fluid to fill electroporation chamber 1020. Once filled, the sealing mechanism 1000*a* can be rotated such that the head 1002*a* occludes the inlet 1018*a*. Electroporation can then occur as described herein. The electroporated cells can be removed from electroporation chamber 1020 by rotating the head 1002*b* of the sealing mechanism 1000*b* associated with the outlet 1018*b* into an open position. The electroporated cells can then be removed through outlet port 1016*b***.

In some embodiments, the sealing mechanism 1000 includes a sealing ring 1004 configured to form a fluid tight seal between the body of the sealing mechanism and the cartridge 1010, which can prevent sample leakage and safeguard sterility of the consumable. The cartridge 1010 illustrated in FIG. 22F can also include an authentication chip 1012 as described above with respect to FIG. 5 and FIGS. 6A-6D.

Figure 22H:
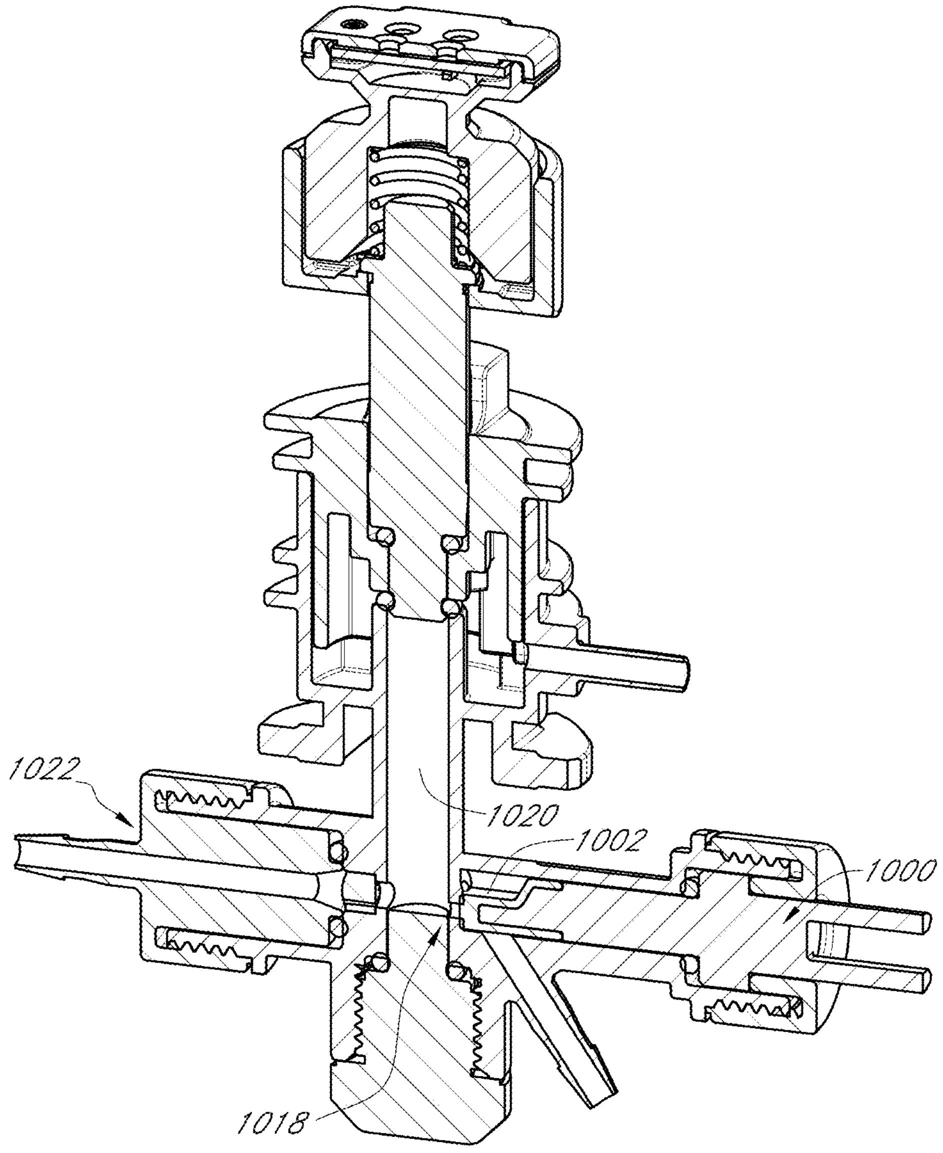
FIGS. 22H and 22I illustrate an exemplary flow-through electroporation cartridge that includes a sealing mechanism as depicted in FIG. 22E associated with the outlet port and in open and closed configurations, according to one embodiment.

Electroporation systems of the present disclosure can include linear pistons, rotary pistons, or a combination thereof. For example, as shown in FIG. 22H, a linear piston 1022 is associated with the inlet 1018 and a rotary piston is associated with the outlet 1016. In FIG. 22H, the linear piston is actuated to plug the inlet and the rotary piston is actuated to move the head 1002 into a closed position over the outlet 1016. In this configuration, cells within the chamber 1020 can be retained for electroporation. To vent the chamber 1020 and release the cells therefrom, the rotatable sealing mechanism 1000 can be rotated such that the head is oriented in an open position, thereby opening the outlet 1016, as shown in FIG. 22I.

Figure 22I:
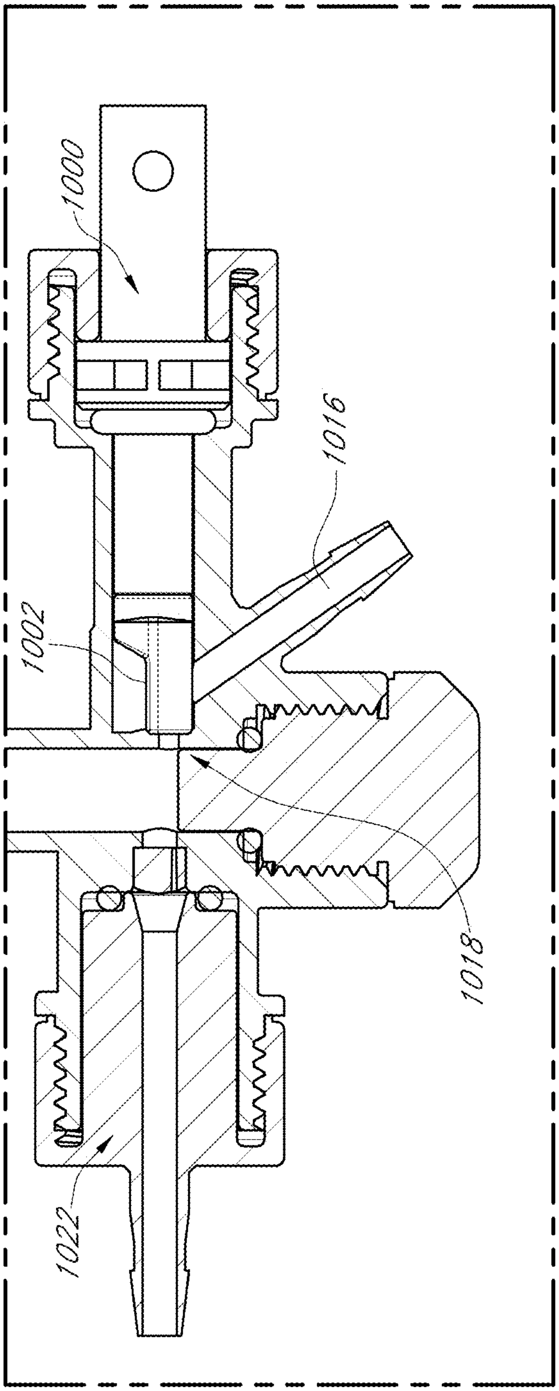

In some embodiments, the ports can be angled to allow for a more efficient flow into and/or out of the chamber, such as those inlet ports and outlet ports of FIG. 22F-22I shown in association with rotatable sealing mechanisms. In contrast to the right angle formed between the inlet of FIG. 22I, which can cause bubbles to form and hinder or prevent flow therethrough, the outlet port 1016 of FIG. 22I is angled, which can allow for more efficient flow of fluid therethrough and decrease bubble formation between the interface.

Figure 22J:
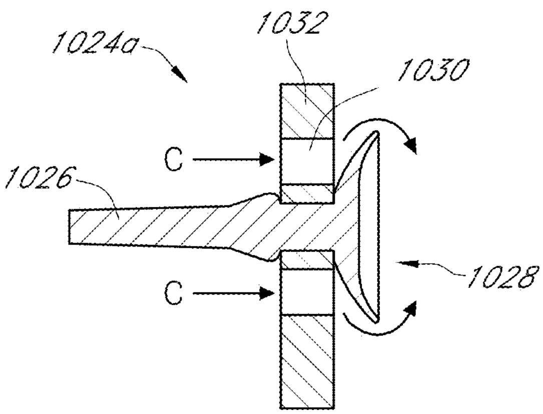
FIGS. 22J and 22K illustrate an umbrella valve in open and closed configurations, respectively, for use as a sealing mechanism, according to one embodiment of the present disclosure.
Figure 22K:
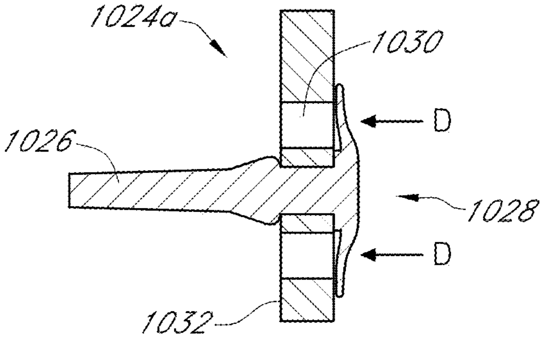

In some embodiments, the inlet can be associated with a valve, such as the umbrella valve 1026 illustrated in FIGS. 22J and 22K. Under pressure (e.g., from fluid flow) in a first direction, as shown by arrows C of FIG. 22J, the umbrella valve moves to an open position **1024*a* by flexibly deforming the head portion 1028 away from the apertures 1030 that are formed by the inlet 1032. As shown in FIGS. 22J and 22K, the umbrella valve 1026 allows fluid to flow in a single direction through the inlet. When pressure is applied against the head portion 1028 (as shown by arrows D in FIG. 22K), the head portion presses against the apertures 1030, the valve is in a closed position 1024*b*, retaining a seal over the apertures 1030 of the inlet 1032**.

Figure 22L:
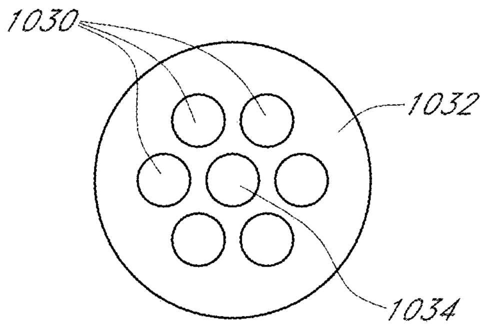
FIG. 22L illustrates a top view of the inlet port of FIGS. 22J and 22K with the corresponding umbrella valve removed from view.

FIG. 22L illustrates a top view of an exemplary inlet 1032 having a plurality of peripheral apertures 1030 formed around a central aperture 1034. The central aperture 1034 is sized and shaped to receive the umbrella valve with the head portion thereof extending over the peripheral apertures 1030 when in a closed position. It should be appreciated that the apertures 1030 can be in any number or configuration insofar as they are covered—and sealed—by the head portion of the complementary umbrella valve when in a closed position.

Figure 22M:
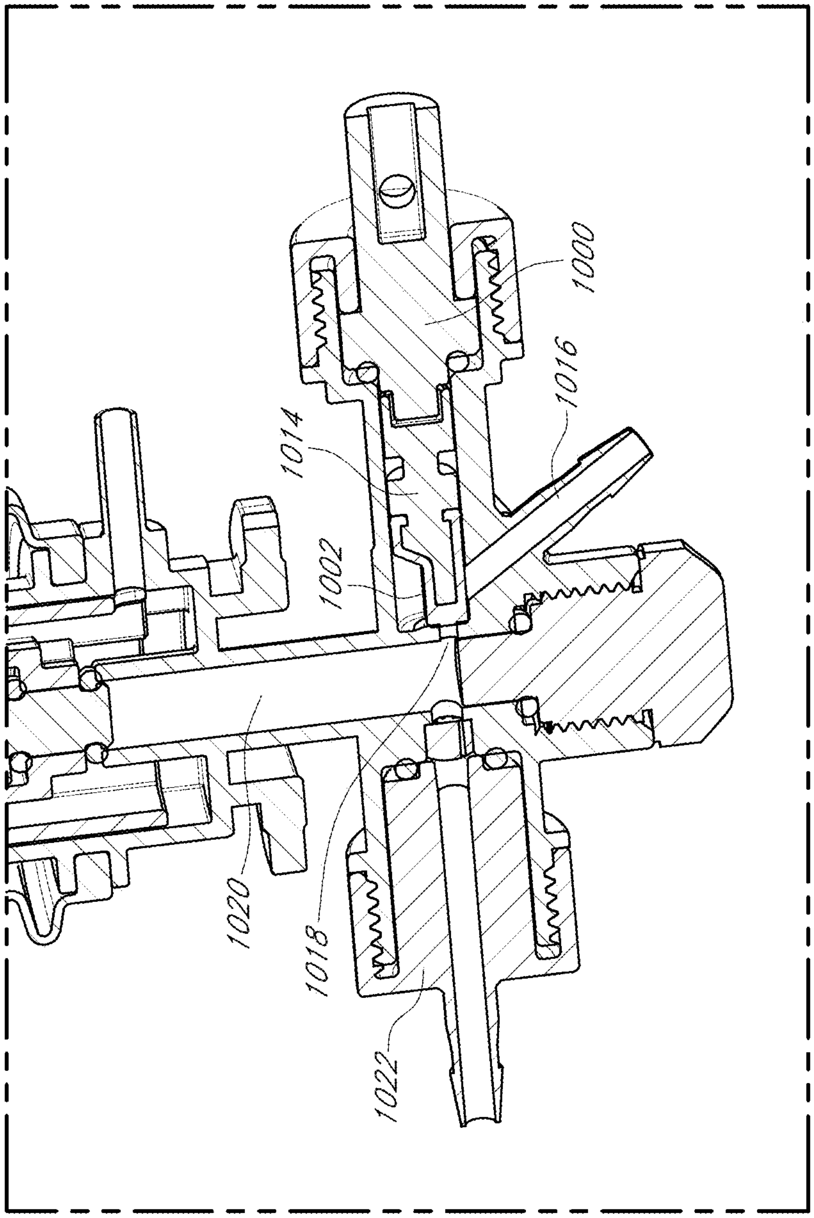
FIGS. 22M-22S illustrates an example setup to pressurize and seal an outlet port installed with a one-way valve (such as a minivalve) of an exemplary electroporation cartridge, according to one embodiment.
Figure 22N:
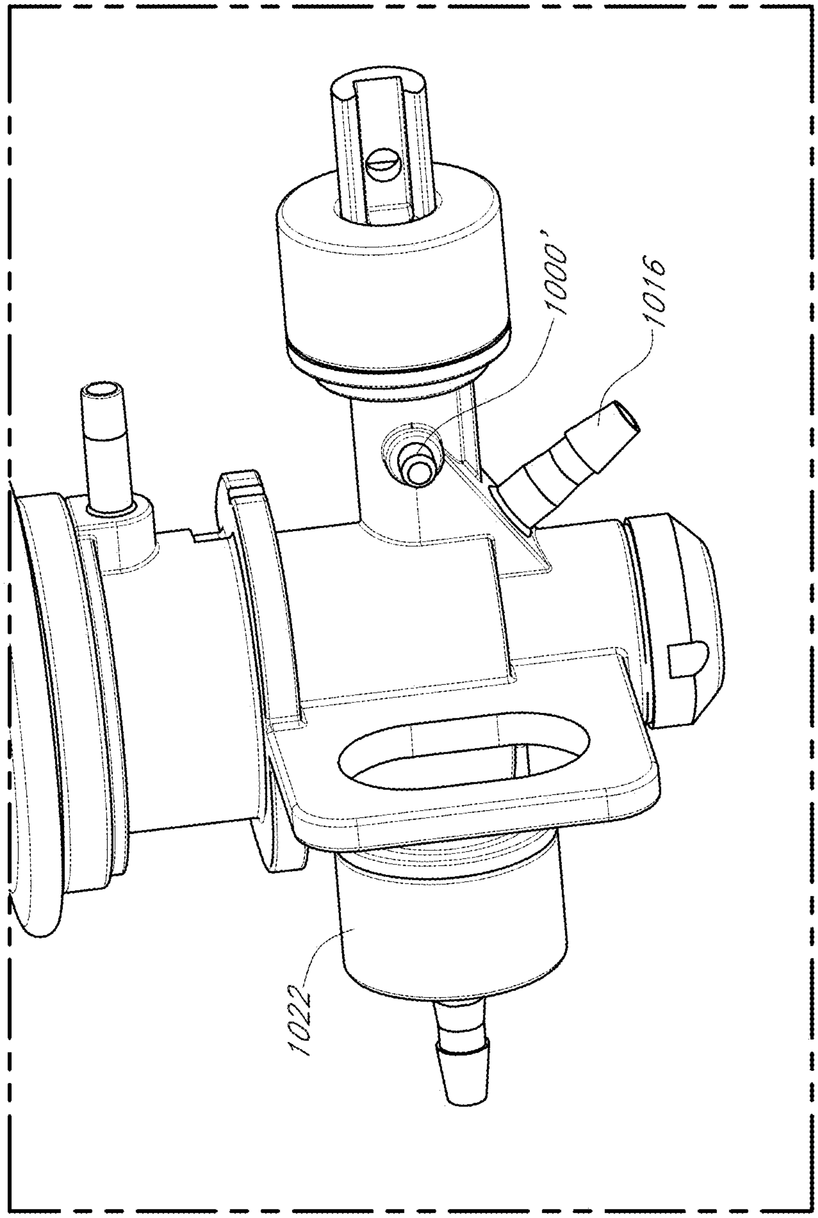

FIG. 22M illustrates an example setup to pressurize and seal an outlet port installed with a one-way valve (such as a minivalve). As shown in FIG. 22M, a rotational and translating piston 1014 with 1002 attached is associated with the inlet 1018 and a rotary piston 1014 is associated with the outlet 1016. In FIG. 22N, the rotational and translating piston is actuated to plug the inlet 1018 and the rotational and translating piston 1014 is actuated to move the head 1002 into a closed position over the outlet 1016. In this configuration, cells within the chamber 1020 can be retained for electroporation. To vent the chamber 1020 and release the cells therefrom, the rotatable sealing mechanism 1000 of rotary piston 1014 can be rotated such that the head is oriented in an open position, thereby opening the outlet 1016. 1022 is a rubber plug that is assembled to 1014.

Figure 22O:
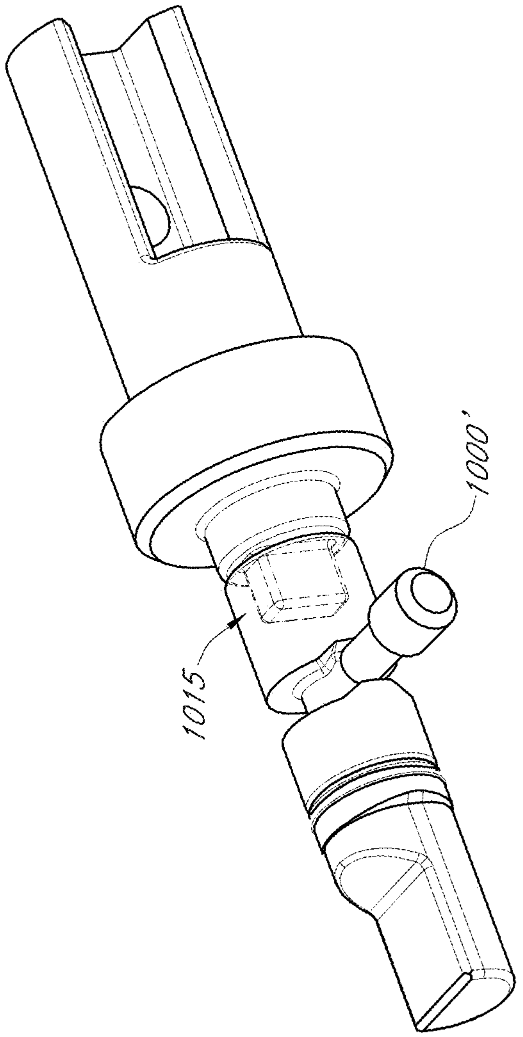

Rotatable sealing mechanism 1000 of rotational and translating piston 1014 in FIG. 22M is also referred to as a catch. Catch or rotatable sealing mechanism 1000 interfaces with an adaptor attached to a rotary motor. A pin 1000' (e.g. a dowel pin) can act as a cam to guide the movement of rotary piston 1014 as shown in FIG. 22N. According to one embodiment, during operation, driven by a rotary motor on instrument, catch or rotatable sealing mechanism 1000 rotates. As shown in FIG. 22O, piston 1014 latches onto catch 1000 by an "I" feature 1015. Piston 1014 is driven by catch 1000 as the catch 1000 rotates.

Figure 22P:
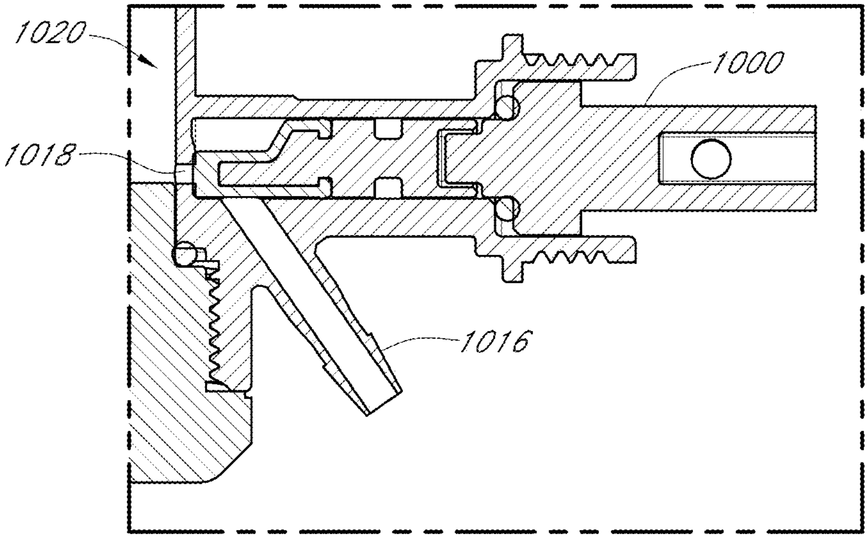
Figure 22Q:
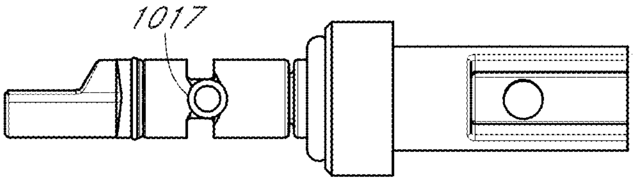
Figure 22R:
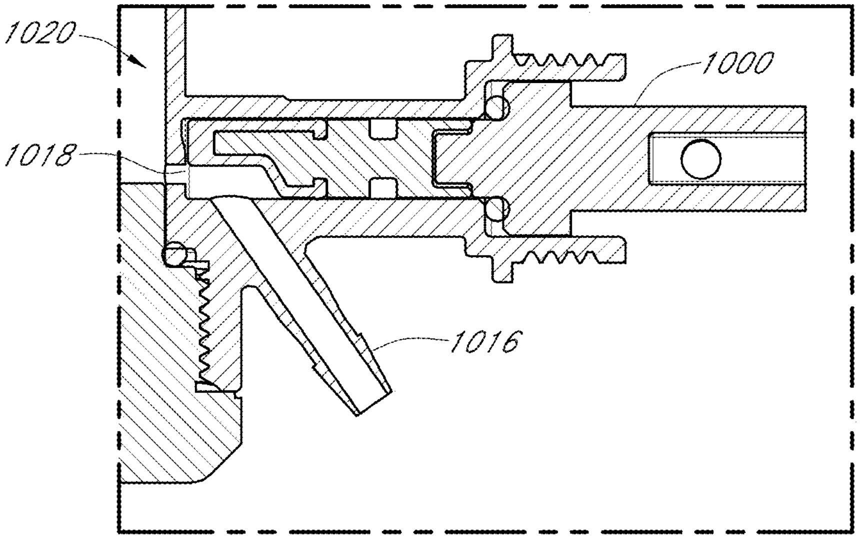
Figure 22S:
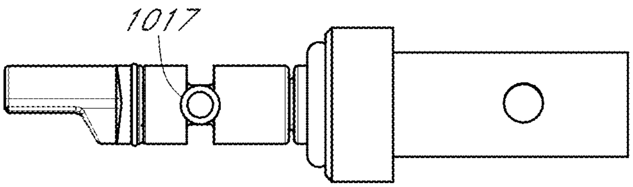

As shown in FIGS. 22P and 22Q, when protrusion 1017 is in-line with the pin 1000' inlet 1018 is plugged and electroporation chamber 1020 is sealed. As shown in FIG. 22R and FIG. 22S, catch 1000 is rotated to 180 degree to open inlet 1018. The linear position of piston 1014 is guided by the groove and pin 1000'. Piston 1014 and head 1002 moves away from chamber surface of electroporation chamber 1020.

It should be appreciated that in some embodiments the electroporation chamber of the cartridge is under pressure (even if slightly above atmospheric pressure) during electroporation, and as such, the umbrella valve is preferably utilized, if ever, on the inlet side where increased pressure in the chamber would press against the head portion of the valve to encourage the closed configuration. If an umbrella valve is used on the outlet, the pressure required to open the valve should ideally be greater than the pressure exerted on the valve during electroporation.

Arc Detection & Prevention

Arcing negatively affects both cell viability and transfection efficiency. Often, samples intended for electroporation are valuable, so it is desirable to keep waste and/or yield loss to a minimum. The major cause of arcing is bubble formation. The systems and methods of the present invention beneficially include features that reduce the occurrence of arcing or that at least detect the risk of arcing and allow sample recovery prior to wasting a portion of sample as a result of arcing.

Figure 23:
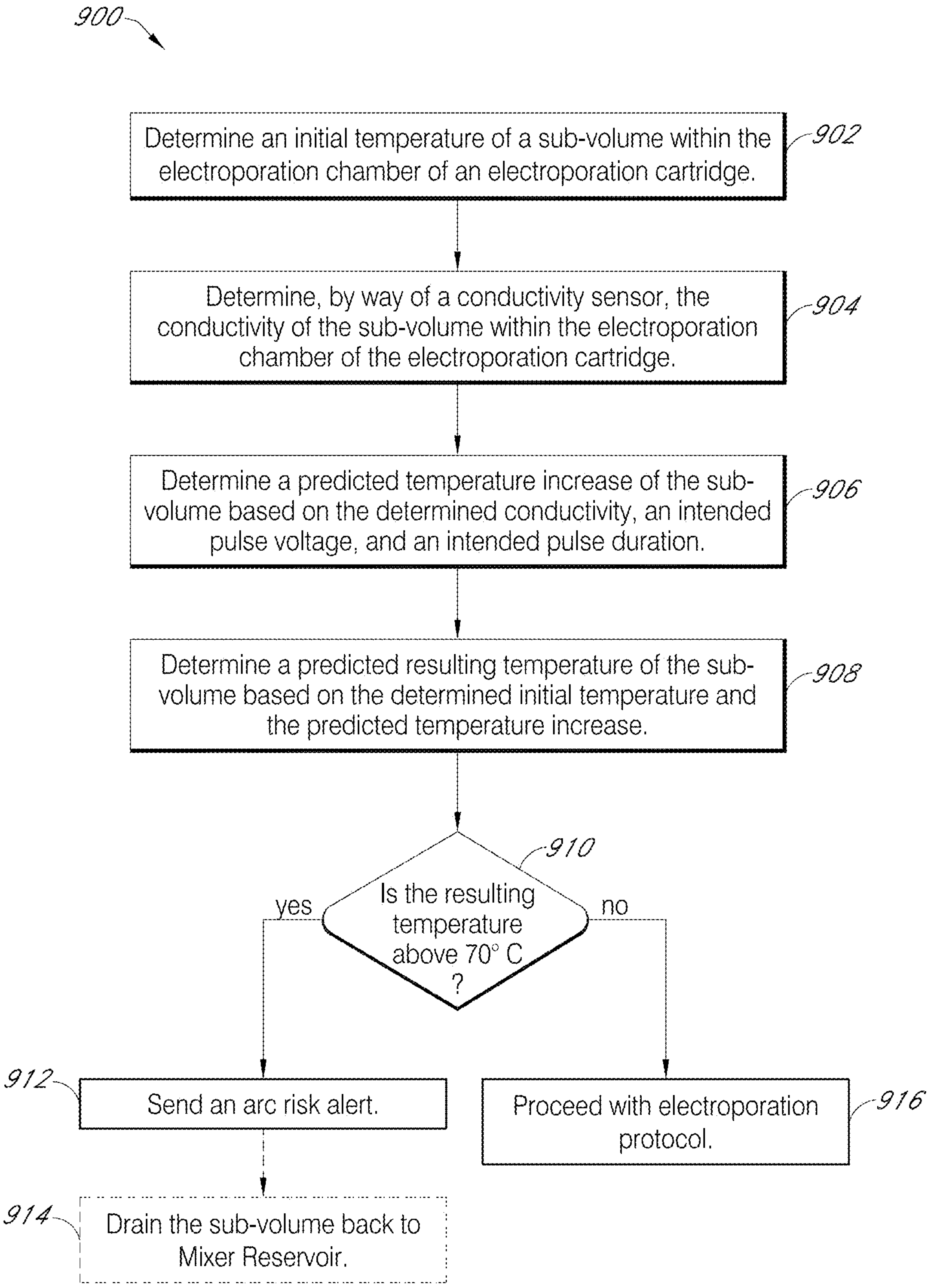
FIG. 23 illustrates a method for predicting the risk of arcing during an electroporation operation based on a predicted temperature change of the sample sub-volume, according to one embodiment.

FIG. 23 illustrates a method 900 for predicting the risk of arcing during an electroporation operation. The method 900 may be performed as a computer-implemented method performed by the controller 601 (see FIG. 10B) using data received from the one or more communicatively coupled system components and/or through the sending of instructions to the one or more communicatively coupled system components.

In an initial step of the method 900, the controller determines an initial temperature of a sub-volume within the electroporation chamber of an electroporation cartridge (step 902). Determination of the temperature of the sub-volume is preferably accomplished non-invasively. That is, the determination of the initial temperature is preferably accomplished without the use of a temperature probe. Use of a temperature probe has been found to interfere with the uniformity of the electric field within the electroporation chamber. Temperature probes and associated sensing circuitry have also been found to have limited lifespan in the high voltage environment of the chamber. External infrared temperature sensors are also less preferred because such measurements will be affected by the chamber sidewall.

In a preferred embodiment, the initial temperature of the sub-volume is determined indirectly through a pre-determined correlation between conductivity and temperature. For a given, known chamber geometry, estimating temperature by measuring conductivity and converting using a pre-determined correlation has been shown to provide temperature with accuracy of ±2° C.

If it has not done so already, the controller may then determine, by way of the conductivity sensor, the conductivity of the sub-volume within the electroporation chamber of the electroporation cartridge (step 904). The controller may then determine a predicted temperature increase of the sub-volume based on the determined conductivity, an intended pulse voltage, and an intended pulse duration (step 906). Arcing risk is related to the voltage level, temperature, bubble generation, and total the energy transferred into the sub-volume. As temperature rises, bubbles are more likely to be generated as portions of the sub-volume undergo phase change from liquid to vapor.

Using known electrical principles, the total energy delivered by a given electrical pulse can be calculated from the voltage used to deliver the pulse, the resistance of the sub-volume between the electrodes (determined by the conductivity sensor), and the intended pulse duration. The law of conservation of energy may then be applied by assuming that all of the electrical energy applied to the sub-volume is converted into heat (the Joule heating effect). The specific heat capacity of the sub-volume may be measured or alternatively assumed to be substantially similar to water. Using the specific heat capacity, the predicted temperature increase is readily determined.

The controller may then determine a predicted resulting temperature of the sub-volume based on the determined initial temperature and the predicted temperature increase (step 908). The controller may then determine whether the resulting temperature is above a pre-determined threshold (step 910). The threshold may be, for example, about 60° C., or about 70° C. If the determination is yes, the controller may send an arc risk alert (step 912), which may include an alarm sent to an input/output device with which the user may interact, a shutdown instruction, a process pause that must be manually overridden, or the like. Optionally, the controller may be configured to cause the sub-volume to be drained back to the mixer reservoir (step 914) so as to allow further cooling or other interventional steps to occur.

If instead the determination is that the predicted temperature will not exceed the threshold, the controller may then cause the system to proceed with the electroporation protocol (step 916).

Figure 24:
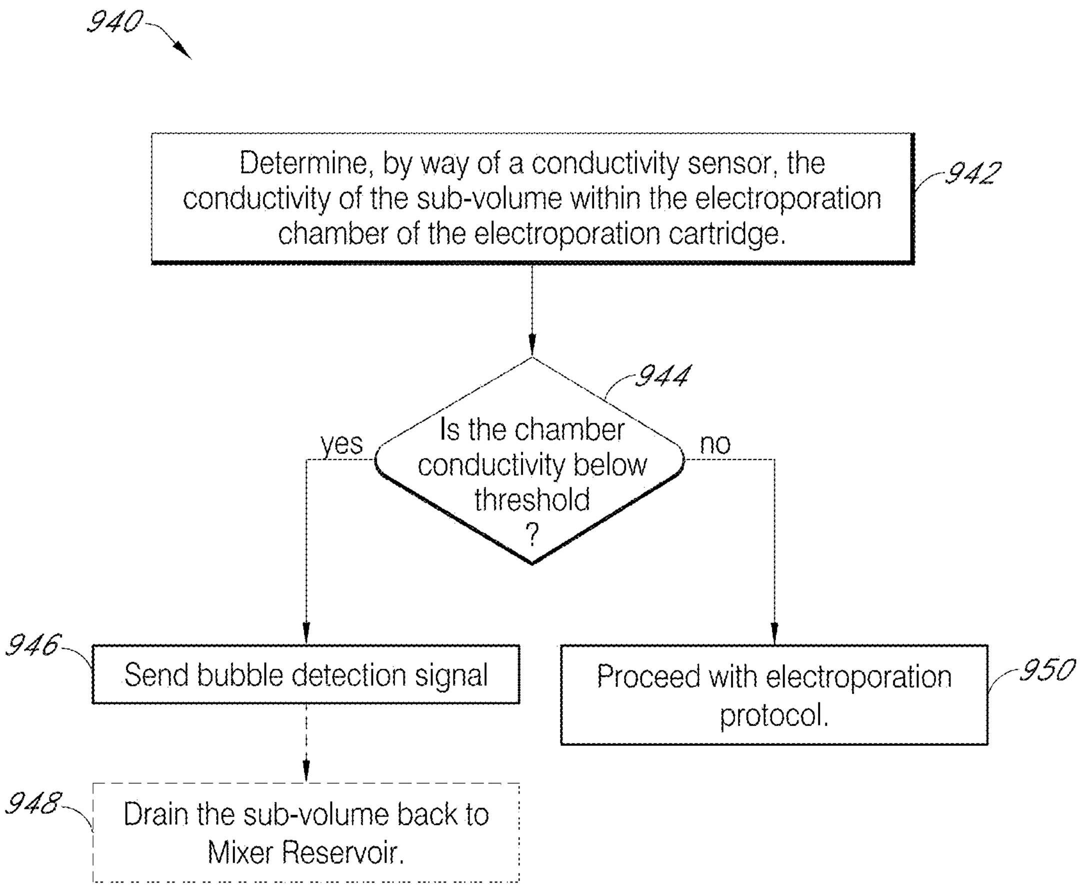
FIG. 24 illustrates a method for preventing arcing in the electroporation chamber based on an initial conductivity measurement of the sub-volume, according to one embodiment.

FIG. 24 illustrates a related method 940 for preventing arcing in the electroporation chamber. As with the method 900, the method 940 may be implemented by the controller 601 (see FIG. 10). In the illustrated method, the controller determines, by way of a conductivity sensor, the conductivity of the sub-volume within the electroporation chamber of the electroporation cartridge (step 942). The controller may then determine whether the measured conductivity is below a pre-determined threshold (step 944). Large bubbles will lower the conductivity to an appreciable degree such that they may be readily detected via measuring conductivity.

If the determination is that yes, the conductivity of the sub-volume is below the threshold, the controller may send a bubble detection signal (step 946). As with step 912 of method 900, this may include an alarm sent to an input/output device with which the user may interact, a shutdown instruction, a process pause that must be manually overridden, or the like. Optionally, the controller may be configured to drain the sub-volume back to the mixer reservoir to preserve the sample (step 948).

If instead the determination is that the conductivity is not below the threshold, the controller may then cause the system to proceed with the electroporation protocol (step 950).

Electroporation Pulse Optimization

Figure 25:
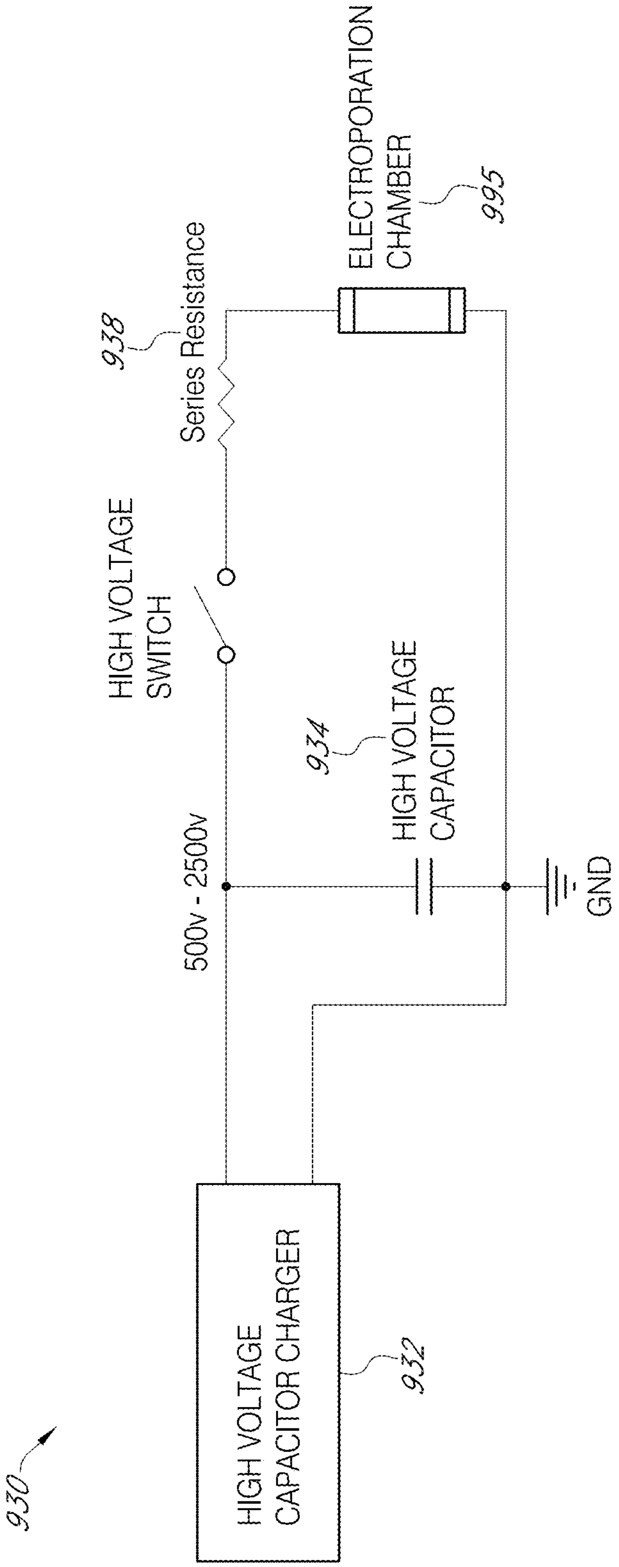
FIG. 25 illustrates a schematic of an electroporation circuit, according to one embodiment.

FIG. 25 illustrates a schematic of an electroporation circuit 930 comprising a charger 932 and capacitor 934 electrically connected to the electroporation chamber 995. A high voltage electroporation system may utilize a voltage pulse in the range of about 500 V to about 2,500 V. achieving electrical pulses based on such high voltages with repeatability and accuracy is desirable.

Calibration of the charger 932 and/or capacitor 934 may reduce some variability. However, as indicated in the schematic circuit 930, there will be an inherent amount of inherent circuit resistance 938. This may be due to circuit protection components, discharge resistors or other safety features of the circuit, and/or the resistance of the high voltage switch when in the on position, for example.

In addition, the resistance of the electroporation chamber 995 will vary according to the sub-volume properties and temperature. For example, for a chamber volume of 1 mL, the resistance may commonly vary from about 500 Ohm to 2,000 Ohm. The variability in resistance from one sub-volume to another can lead to inconsistent electrical pulses, which in turn can lead to inconsistent electroporation results.

FIG. 26 illustrates a method 960, which may be implemented by a computer system such as controller 601, for generating repeatable and consistent electrical pulses across the electroporation chamber. In the method 960, the controller may cause the system to determine, by way of a conductivity sensor, the conductivity of the sub-volume within the electroporation chamber of the electroporation cartridge (step 962), and to utilize the determined conductivity to determine a voltage drop across the electroporation chamber (step 964). The controller may then determine the resistance in the electroporation circuit between the capacitor and the electroporation chamber (step 966). This represents the inherent, fixed circuit resistance.

The controller may then charge the capacitor to a voltage level above the determined drop in voltage across the electroporation chamber to compensate for the additional resistance between the capacitor and the electroporation chamber (step 968). That is, the controller may add the series resistance and the measured resistance across the electroporation chamber to determine a total circuit resistance, and then cause the capacitor to be charged accordingly. Taking into account both the fixed portions of circuit resistance and the variable resistance of the electroporation chamber enables a more fine-tuned voltage charge to be determined so that the actual electrical pulse delivered remains more consistent from one sample sub-volume to the next.

The method may also optionally include the step of iteratively ramping the charger voltage based on a previous input voltage and a corresponding previous measured actual voltage as applied to the electroporation chamber (step 970). Charger output tolerances can vary by ±100 V, so rather than simply operating the charger based on an intended voltage level, the controller may apply an iterative voltage compensation method to successively lower the voltage error (e.g., to within about ±5 V) without sudden adjustments that could risk drastically altering outcomes.

The iterative voltage compensation method may proceed by first selecting a target pulse voltage (e.g., 2,500 V) and offsetting the input voltage by a predetermined amount (e.g., 200 V). The actual pulse voltage as delivered to the electroporation chamber is then measured. In the following iterations, the input voltage is varied according to the following:

$$\text{Charger input } V = (\text{Previous input } V / \text{Previous measured output } V) \times (\text{Target } V - \text{offset})$$

The "offset" can be ramped down from one iteration to the next. For example, if the initial offset was 200 V, as mentioned above, the offset in the next iteration may be 100

V, and then may be 5 V, and then eventually is reduced to 0. These offsets are exemplary only, and other implementations may ramp the offset down faster or slower according to application needs and/or preferences. In addition, the offset may be applied as a positive offset or a negative offset, depending, for example, on whether the charger error is initially expected to be result in charges that are greater than or less than the target.

Calibration of Electroporation Chamber Fill

The high-throughput electroporation systems described herein include many different components operating in conjunction with one another. Accordingly, multiple mechanical tolerances will be stacked on top of one another, which may lead to volume variations in the electroporation chamber across different consumable sets and/or even across different sub-volumes within the same consumable set. As described above, the negative consequences of failing to properly fill the electroporation chamber include underfill, which causes arcing, and overfill, which causes yield loss.

Figure 27A:
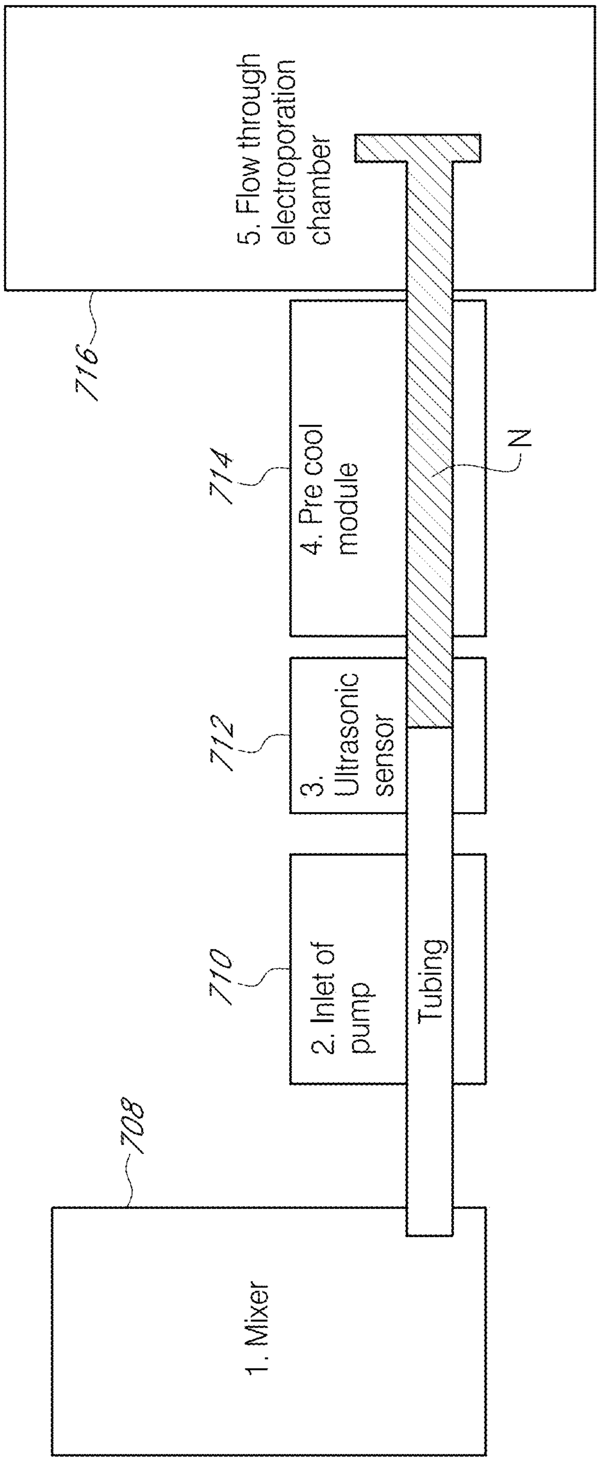
FIGS. 27A-27D illustrate a method for calibrating the fill volume of an electroporation chamber, according to one embodiment.
Figure 27B:
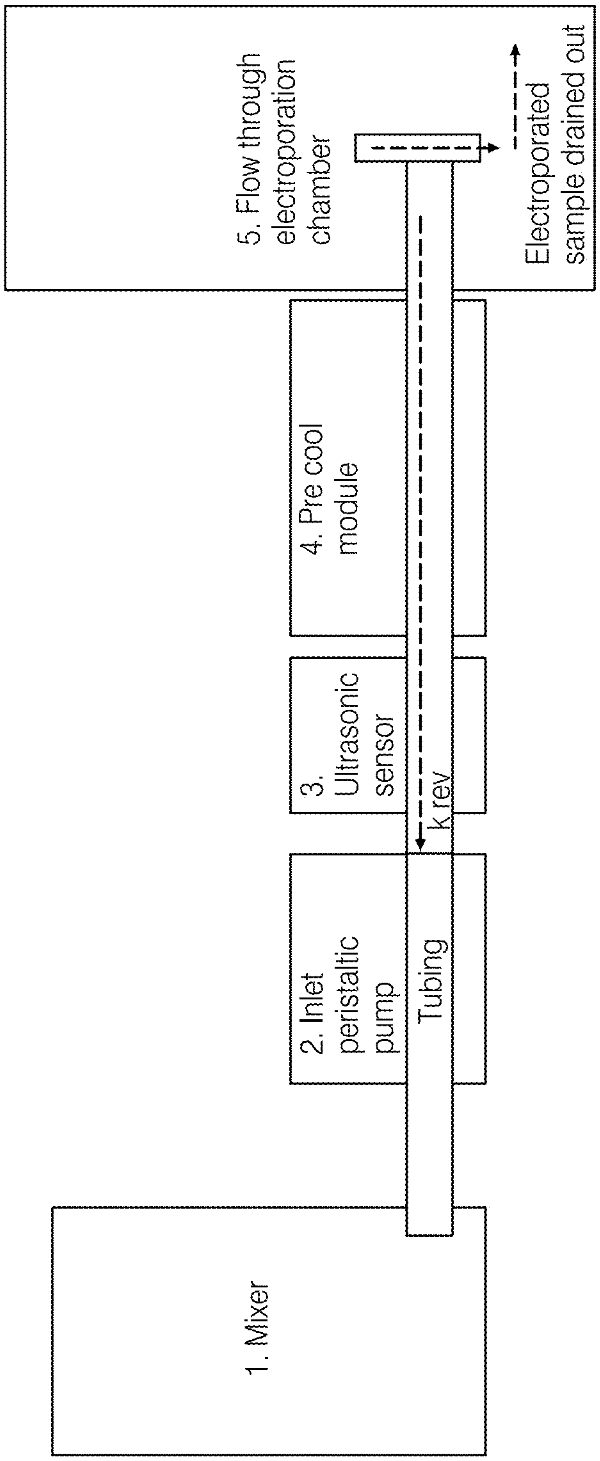
Figure 27C:
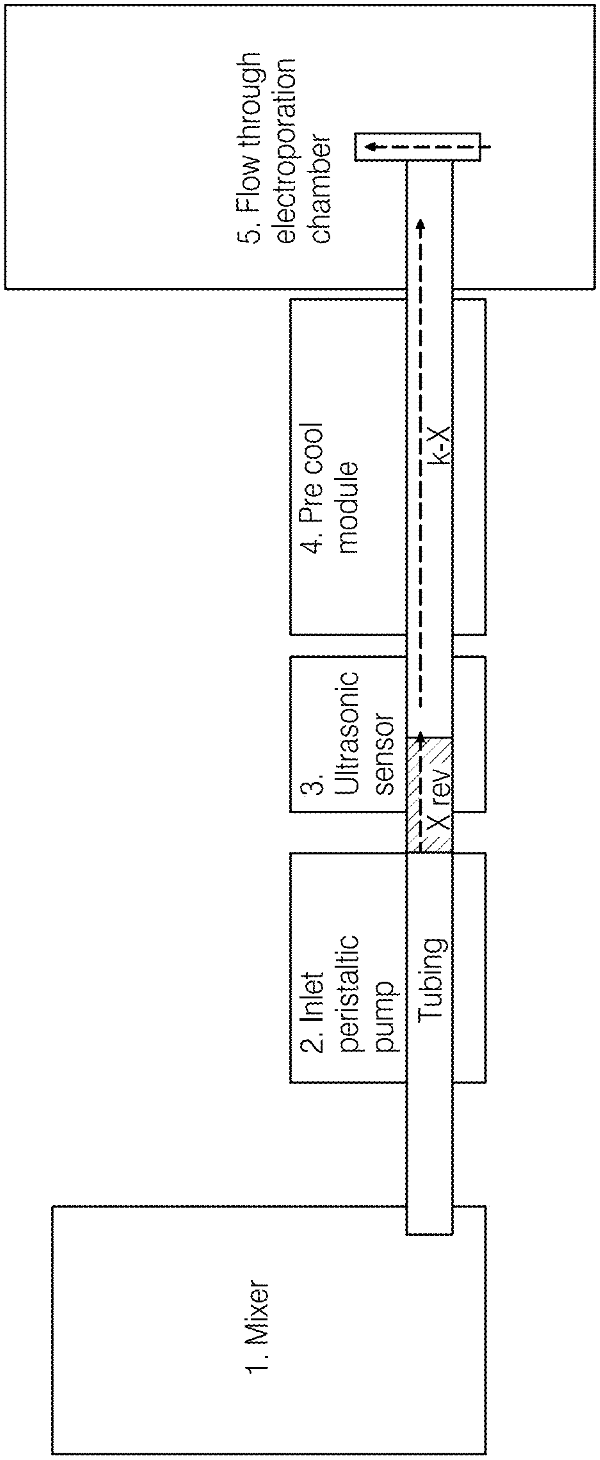
Figure 27D:
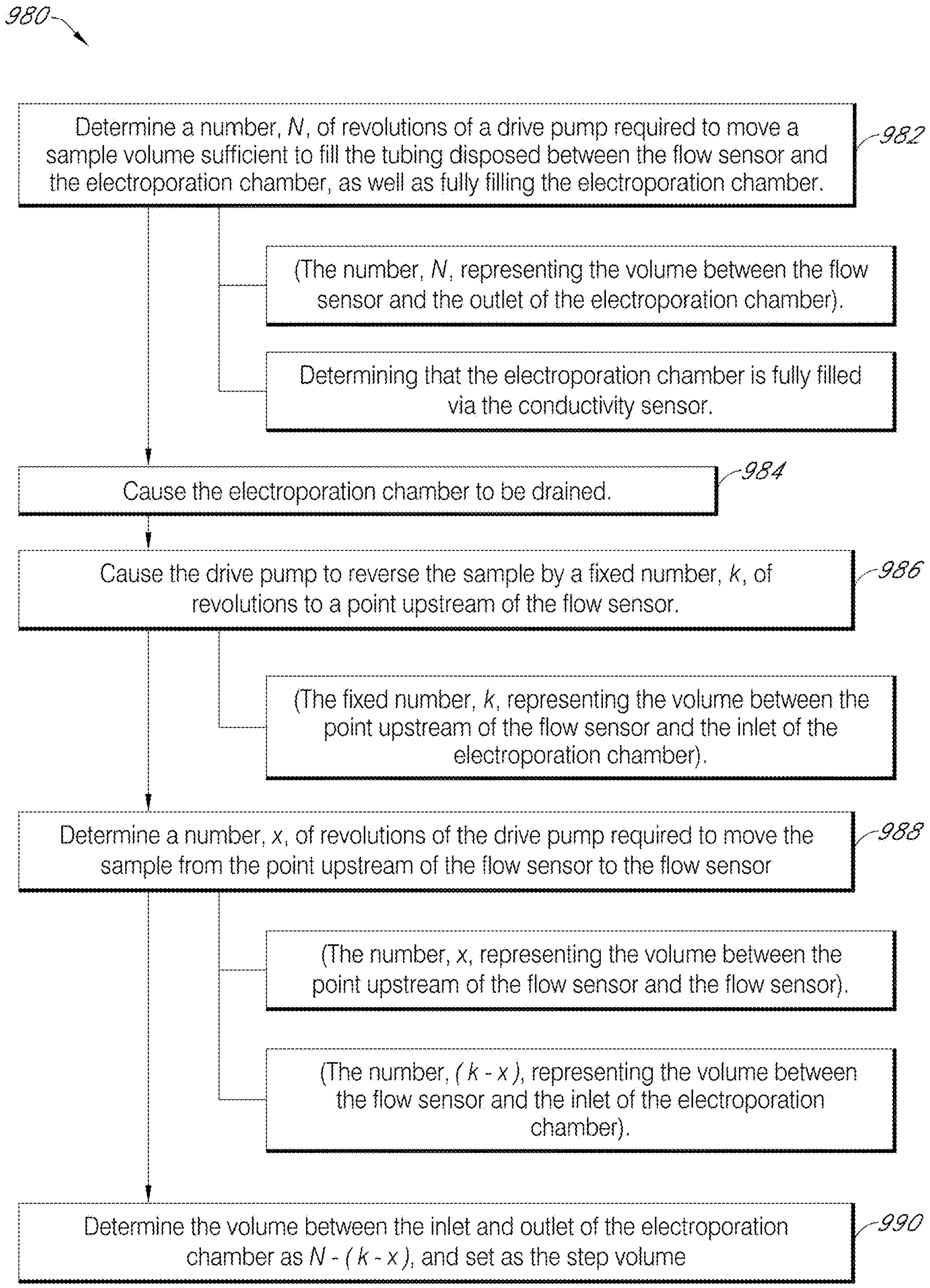

FIGS. 27A, 27B and 27C graphically illustrate a method for calibrating the fill volume of an electroporation chamber. The mixer reservoir 708, second pump 710, second flow sensor 712, pre-cooling module 714, and electroporation cartridge 716 are shown. A flowchart of the method 980 is illustrated in FIG. 27D. The method 980 may be implemented by a computer system, such as the controller 601.

In a first step, the controller may determine a number, N, of revolutions of a drive pump required to move a sample volume sufficient to fill the tubing disposed between the flow sensor and the electroporation chamber, as well as fully filling the electroporation chamber (step 982). This is shown graphically by FIG. 27A. The number N represents the volume between the flow sensor and the outlet of the electroporation chamber. The determination that the electroporation chamber has been filled may be made by using the conductivity sensor. That is, the electroporation chamber may be determined to be filled once the conductivity sensor measures a conductivity indicative that fluid extends from the lower electrode all the way to the upper electrode.

The controller may then cause the electroporation chamber to be drained (step 984). At this point, the controller may cause the drive pump to reverse the sample by a fixed number, k, of revolutions to a point upstream of the flow sensor (step 986). This is graphically shown in FIG. 27B. The fixed number, k, representing the volume between the point upstream of the flow sensor and the inlet of the electroporation chamber. The controller may then determine a number, x, of revolutions of the drive pump required to move the sample from the point upstream of the flow sensor to a point where it is detected by the flow sensor (step 988). This is represented graphically by FIG. 27C. The number, x, represents the volume between the point upstream of the flow sensor and the flow sensor. The number, (k−x) thus represents the volume between the flow sensor and the inlet of the electroporation chamber. The volume between the inlet and outlet of the electroporation chamber (i.e., the volume of the electroporation chamber) is therefore equal to N−(k−x). The controller may then set this volume as the step volume (step 990) such that the relevant pump performs N−(k−x) number of reps between each successive sub-volume electroporation.

Figure 27E:
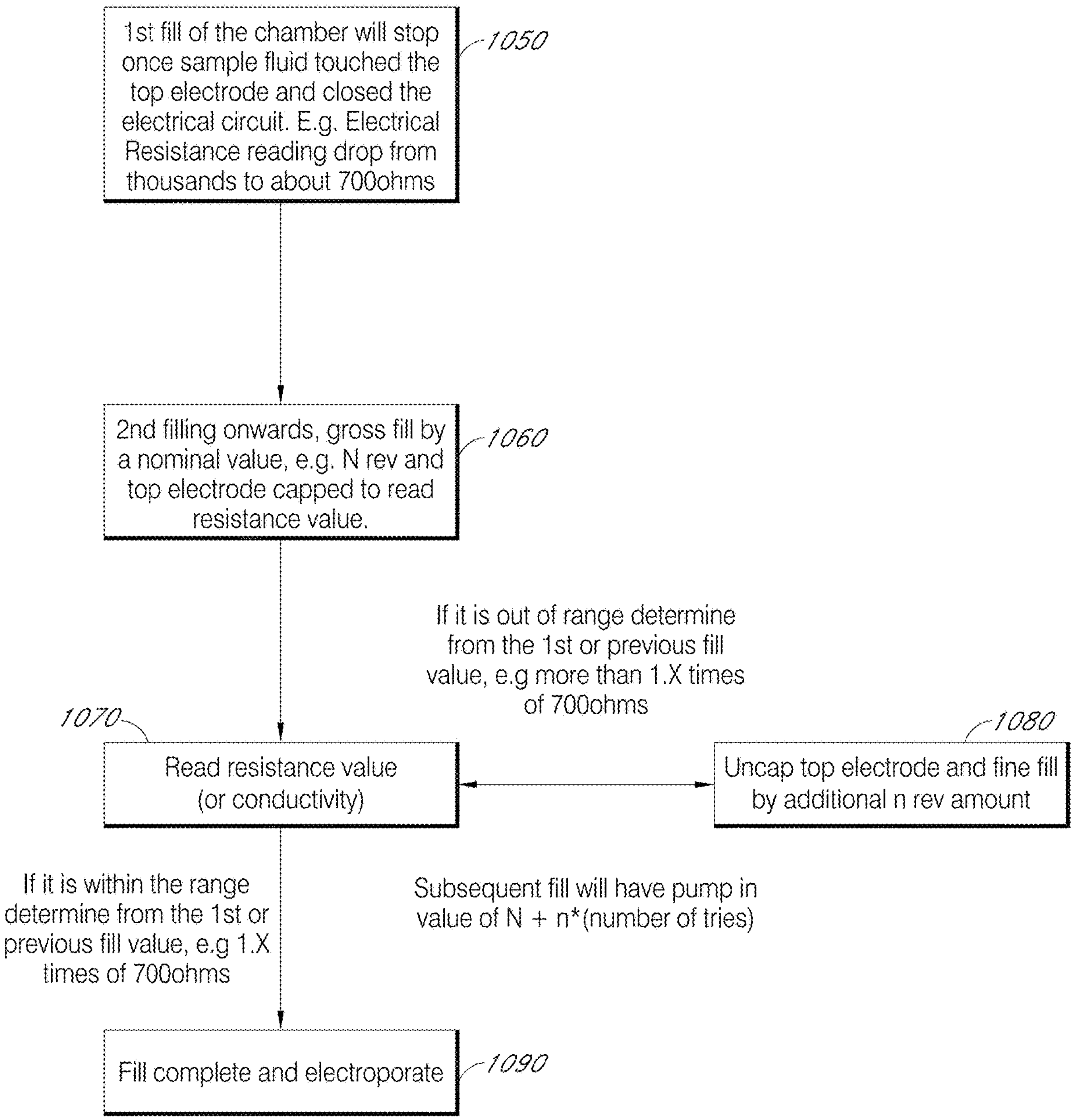
FIG. 27E illustrate a method for calibrating the fill volume of an electroporation chamber, according to one embodiment.

FIG. 27E illustrates another method of filling a flow-through electroporation chamber of the disclosure. As illustrated, In the first step (1050), the first filling of a chamber will stop once a sample fluid touches the top electrode and closes the electrical circuit. For example, this is when the Electrical Resistance reading drops from thousands to about 700 ohms (or in the range of 600-800 ohms).

In the second step (1060), for the second filling of the chamber and for subsequent filling, gross fill is done by a nominal value, e.g. $N_{rev}$ and top electrode capped to read resistance value.

At this stage, in a third step (1070), the electrical resistance value (or conductivity) is read. If the electrical resistance or conductivity is within the range determine from the first or any previous fill value, e.g. 1× times of 700 ohms, then the second fill is complete and one can proceed to electroporate the sample (step 1090).

However, if it is out of range, determine from the first or any previous fill value, e.g more than 1× times of 700 ohms, then proceed to step 1080 which comprises Uncap top electrode and fine fill by additional $n_{rev}$ amount. Subsequent fill will have pump in value of $N_{rev}$+$n_{rev}$x (where x=number of tries).

Accordingly, in some embodiments in an electroporation system of the disclosure, comprising a controller having one or more processors and one or more hardware storage devices, wherein the one or more hardware storage devices have stored thereon computer-executable instructions that when executed by the one or more processors configure the controller to determine a step volume to be moved by the system between each electroporation event, the calibration being carried out by performing at least the following: perform a first fill of the electroporation chamber by monitoring a drop in the electrical resistance in the electroporation chamber during the first fill from several thousand ohms to a stable value in the range of from about 600-800 ohms. Stopping the first fill when this stable range of voltage is reached.

This is then followed by a step of gross filling the electroporation chamber for the second fill based on a calculated value, such as $N_{rev}$ from the peristaltic pump (e.g., number of revolutions of the peristaltic pump to fill the chamber till the stable resistance volume is reached). In some embodiments, the step of gross filling the electroporation chamber for the second fill is further based on calculations using one or more empirical value such as the inner tube diameter of tubing, the number of rollers of the pump, the diameter of the electroporation chamber, and/or the height of the electroporation chamber in addition to the $N_{rev}$ value.

Gross filling the electroporation chamber for the second fill for the $N_{rev}$ revolutions is followed by measuring the electrical resistance after capping the top electrode after the second fill; if the electrical resistance is within the stable value range determined from the first fill, then the second fill is complete and one can proceed to electroporate the sample; if the electrical resistance is not within the stable value range determined from the first fill, then uncap the top electrode and fine fill by an additional $n_{rev}$ amount; measuring the electrical resistance after capping the top electrode after the first fine fill; if the electrical resistance is within the stable value range determined from the first fill, then the second fill is complete and one can proceed to electroporate the sample; if not repeat the fine fill and measure the electrical resistance steps as described above till the electrical resistance is within the stable value range determine from the first fill; subsequent fills (third fill, fourth fill and so on) are done for pump revolutions of $N_{rev}$+$n_{rev}$ x (number of tries of the fine fill). In some embodiments, a stable value of electrical resistance is about 700 ohms.

In some of these aspects, a controller is configured to implement a method for determining a calibrated step volume to be moved by the system between each electroporation event into a flow-through electroporation chamber, corresponding to a fill volume of the flow-through electroporation chamber. In one embodiment, such a method can comprise a first fill of a flow-through electroporation chamber till the sample makes contact (touches) the top electrode (first electrode as described in some embodiments) of the electroporation chamber. At this time (i.e., during the first fill), the electroporation system monitors a drop in the electrical resistance in the electroporation chamber from several thousand ohms to a stable value in the range of from about 600-800 ohms. The first fill is stopped when this stable electrical resistance value is reached.

For the second fill (and subsequent fills) the gross filling sample volume is derived from a combination of empirical data and theoretical calculation. Accordingly, for a second fill (and subsequent fills), the electroporation system (for e.g., a controller therein) determines a number of revolutions, "$N_{rev}$," i.e., number of revolutions of a drive pump that are required to move a sample volume sufficient to fully fill the electroporation chamber (i.e., the number of revolutions are counted from the time a sample fluid enters an electroporation chamber from a fixed entry point till the sample fluid makes contact with the top electrode (reaches its sample volume). In addition, an empirical determination of the inner tubing diameter "$d_i$" of the pump tubing and the number of rollers of the pump "n" are made. In a non-limiting example, the pump can be a peristaltic pump, which in some embodiments can have six rollers (e.g., n=6).

Determining the $N_{rev}$ value comprises measuring one or more of the following: revolutions of a peristaltic pump needed to fill an electroporation chamber from an entry point till it reaches the top electrode (which corresponds to the drop in resistance of the sample fluid to 600-800 ohms); inner diameter "$d_i$" of tubing in the pump; number of pump rollers "n"; volume of fluid per one complete revolution of the pump ("a" μL); fluid volume per one roller movement "b" smallest diameter of the electroporation chamber area where the electroporation sample resides; and/or electrical resistance or conductivity (using a voltmeter, a conductivity sensor, etc.) of the fluid in the electroporation chamber followed by theoretical calculations to arrive at $N_{rev}$.

Following this, is a step of measuring electrical resistance after capping the top electrode after the second fill (and subsequent fill); if the electrical resistance is within the stable value range determine from the first fill (i.e., in the range of from about 600-800 ohms), then the fill is complete and one can proceed to electroporate the sample. However, if after the second fill, the electrical resistance is not within the stable value range determine from the first fill (i.e., not in the range of from about 600-800 ohms), then the step of uncapping the top electrode and fine filling the electroporation chamber with a fluid by an additional $n_{rev}$ amount ($n_{rev}$ of the pump) is performed. This is followed by measuring the electrical resistance after capping the top electrode after the fine fill. If the electrical resistance is within the stable value range determine from the first fill (i.e., in the range of from about 600-800 ohms), then the second fill is complete and one can proceed to electroporate the sample. If not, repeat the file fill and electrical resistance steps above till the electrical resistance is within the stable value range determine from the first fill (i.e., in the range of from about 600-800 ohms). Subsequent fills (third fill, fourth fill and so on) are done for pump revolutions of $N_{rev}$+$n_{rev}$ x (number of tries of the fine fill). In some embodiments, the stable value of electrical resistance is about 700 ohms, such as for example in the range of 650-750 ohms and any values therebetween.

In one example embodiment, $N_{rev}$ is calculated as follows: in one embodiment system of the disclosure, having a peristaltic pump with six rollers and a tubing having an inner diameter 2.4 mm, empirical data of 172 μL of fluid was dispensed per full complete revolution of the pump. From empirically determined data, 28 μL of fluid was dispensed per rotation movement by one roller distance (in this case, 60 degree) of the pump. This was followed by a theoretical calculation to determine the volume of fluid the electroporation chamber can contain. With a nominal diameter of 6.4 mm (2r, where r=radius of the electroporation chamber), with a lower limit of 6.3 mm and an upper limit of 6.5 mm, together with the height of the electroporation chamber being 30 mm (h), using the formula of $\pi r^2 h$, the nominal sample volume was determined to be 965 μL with lower limit at 935 μL and upper limit at 995 μL. Variation of height (h), with the design tolerance of 0.2 mm is deemed to be insignificant as it contributes to at a maximum of 70 μL variations. To reduce sample loss from gross fill due to overfilling of the chamber, lower limit of the chamber diameter 6.3 mm was used in the calculation. Based on the calculated volume of 935 μL divided by the empirical data of 172 μL, the peristaltic pump revolution was determined to be 5.4, however to introduce a convex meniscus, a round up to 5.5 revolution was recommended. Therefore in this case, "$N_{rev}$" equals 5.5 revolution. The difference in chamber diameter from 6.3 mm to 6.5 mm resulted in about 30 μL sample volume difference for every 0.1 mm diameter change. This is quite close to the empirical data of 28 μL of fluid that was dispensed per rotation movement by one roller distance (in this case, 60 degree) of the pump, which is term as fine fill "$n_{rev}$" in the equation. Upon the gross fill of 5.5 revolution ($N_{rev}$), instrument will read the conductivity and if the fill is incomplete, the fine fill "$n_{rev}$" will commence. Depending on the number of tries, "x", for the fine fill, the second fill (and subsequent fills) will be made up of "$N_{rev}$+$n_{rev}$ x".)

Computer Systems of the Present Disclosure

It will be appreciated that computer systems are increasingly taking a wide variety of forms. In this description and in the claims, the terms "controller," "computer system," or "computing system" are defined broadly as including any device or system—or combination thereof—that includes at least one physical and tangible processor and a physical and tangible memory capable of having thereon computer-executable instructions that may be executed by a processor. By way of example, not limitation, the term "computer system" or "computing system," as used herein is intended to include personal computers, desktop computers, laptop computers, tablets, hand-held devices (e.g., mobile telephones, PDAs, pagers), microprocessor-based or programmable consumer electronics, minicomputers, mainframe computers, multi-processor systems, network PCs, distributed computing systems, datacenters, message processors, routers, switches, and even devices that conventionally have not been considered a computing system, such as wearables (e.g., glasses).

The memory may take any form and may depend on the nature and form of the computing system. The memory can be physical system memory, which includes volatile memory, non-volatile memory, or some combination of the two. The term "memory" may also be used herein to refer to non-volatile mass storage such as physical storage media.

The computing system also has thereon multiple structures often referred to as an "executable component." For instance, the memory of a computing system can include an executable component. The term "executable component" is the name for a structure that is well understood to one of ordinary skill in the art in the field of computing as being a structure that can be software, hardware, or a combination thereof.

For instance, when implemented in software, one of ordinary skill in the art would understand that the structure of an executable component may include software objects, routines, methods, and so forth, that may be executed by one or more processors on the computing system, whether such an executable component exists in the heap of a computing system, or whether the executable component exists on computer-readable storage media. The structure of the executable component exists on a computer-readable medium in such a form that it is operable, when executed by one or more processors of the computing system, to cause the computing system to perform one or more functions, such as the functions and methods described herein. Such a structure may be computer-readable directly by a processor—as is the case if the executable component were binary. Alternatively, the structure may be structured to be interpretable and/or compiled whether in a single stage or in multiple stages—so as to generate such binary that is directly interpretable by a processor.

The term "executable component" is also well understood by one of ordinary skill as including structures that are implemented exclusively or near-exclusively in hardware logic components, such as within a field programmable gate array (FPGA), an application specific integrated circuit (ASIC), Program-specific Standard Products (ASSPs), System-on-a-chip systems (SOCs), Complex Programmable Logic Devices (CPLDs), or any other specialized circuit. Accordingly, the term "executable component" is a term for a structure that is well understood by those of ordinary skill in the art of computing, whether implemented in software, hardware, or a combination thereof.

The terms "component," "service," "engine," "module," "control," "generator," or the like may also be used in this description. As used in this description and in this case, these terms—whether expressed with or without a modifying clause—are also intended to be synonymous with the term "executable component" and thus also have a structure that is well understood by those of ordinary skill in the art of computing.

While not all computing systems require a user interface, in some embodiments a computing system includes a user interface for use in communicating information from/to a user. The user interface may include output mechanisms as well as input mechanisms. The principles described herein are not limited to the precise output mechanisms or input mechanisms as such will depend on the nature of the device. However, output mechanisms might include, for instance, speakers, displays, tactile output, projections, holograms, and so forth. Examples of input mechanisms might include, for instance, microphones, touchscreens, projections, holograms, cameras, keyboards, stylus, mouse, or other pointer input, sensors of any type, and so forth.

Accordingly, embodiments described herein may comprise or utilize a special purpose or general-purpose computing system. Embodiments described herein also include physical and other computer-readable media for carrying or storing computer-executable instructions and/or data structures. Such computer-readable media can be any available media that can be accessed by a general purpose or special purpose computing system. Computer-readable media that store computer-executable instructions are physical storage media. Computer-readable media that carry computer-executable instructions are transmission media. Thus, by way of example—not limitation—embodiments disclosed or envisioned herein can comprise at least two distinctly different kinds of computer-readable media: storage media and transmission media.

Computer-readable storage media include RAM, ROM, EEPROM, solid state drives ("SSDs"), flash memory, phase-change memory ("PCM"), CD-ROM or other optical disk storage, magnetic disk storage or other magnetic storage devices, or any other physical and tangible storage medium that can be used to store desired program code in the form of computer-executable instructions or data structures and that can be accessed and executed by a general purpose or special purpose computing system to implement the disclosed functionality of the invention. For example, computer-executable instructions may be embodied on one or more computer-readable storage media to form a computer program product.

Transmission media can include a network and/or data links that can be used to carry desired program code in the form of computer-executable instructions or data structures and that can be accessed and executed by a general purpose or special purpose computing system. Combinations of the above should also be included within the scope of computer-readable media.

Further, upon reaching various computing system components, program code in the form of computer-executable instructions or data structures can be transferred automatically from transmission media to storage media (or vice versa). For example, computer-executable instructions or data structures received over a network or data link can be buffered in RAM within a network interface module (e.g., a "NIC") and then eventually transferred to computing system RAM and/or to less volatile storage media at a computing system. Thus, it should be understood that storage media can be included in computing system components that also—or even primarily—utilize transmission media.

Those skilled in the art will further appreciate that a computing system may also contain communication channels that allow the computing system to communicate with other computing systems over, for example, a network. Accordingly, the methods described herein may be practiced in network computing environments with many types of computing systems and computing system configurations. The disclosed methods may also be practiced in distributed system environments where local and/or remote computing systems, which are linked through a network (either by hardwired data links, wireless data links, or by a combination of hardwired and wireless data links), both perform tasks. In a distributed system environment, the processing, memory, and/or storage capability may be distributed as well.

Those skilled in the art will also appreciate that the disclosed methods may be practiced in a cloud computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

A cloud-computing model can be composed of various characteristics, such as on-demand self-service, broad network access, resource pooling, rapid elasticity, measured service, and so forth. A cloud-computing model may also come in the form of various service models such as, for example, Software as a Service ("SaaS"), Platform as a Service ("PaaS"), and Infrastructure as a Service ("IaaS"). The cloud-computing model may also be deployed using different deployment models such as private cloud, community cloud, public cloud, hybrid cloud, and so forth.

Abbreviated List of Defined Terms

To assist in understanding the scope and content of this written description and the appended claims, a select few terms are defined directly below. Unless defined otherwise, all technical and scientific terms used herein have the same meaning as commonly understood by one of ordinary skill in the art to which the present disclosure pertains.

The terms "approximately," "about," and "substantially," as used herein, represent an amount or condition close to the specific stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a specifically stated amount or condition.

As used herein, the term "electroporation" is intended to include the process of exposing cells to an electric field, typically a short duration, high voltage electric field, to cause the uptake of an electroporation target from the surrounding electroporation media into the electroporated cell. The cell can be any living cell, and it should be appreciated that the electroporation systems and methods disclosed herein can be used with prokaryotic and/or eukaryotic cells. As known to those skilled in the art, the process of electroporating a target into a prokaryotic organism, such as a bacterium, is termed "transformation," whereas electroporating a target into a eukaryotic organism, such as primary cells or cell lines, is typically termed "transfection." For the purposes of this disclosure, the terms "transformation" and "transfection" are interchangeable and agnostic to the type or kind of organism being transformed, unless specifically stated otherwise. Accordingly, the term "electroporation," or forms thereof, is intended to include the transformation/transfection of living cells—prokaryotic or eukaryotic—with an electroporation target.

The term "electroporation target," as used herein, is intended to be understood as any molecule, compound, or substance intended to be introduced to a target cell via electroporation. By way of example and not limitation, an electroporation target can include, proteins, peptides, nucleic acid, drug, or another compound. Proteins can include purified, folded, or unfolded proteins having a native, mutated, or engineered sequence, and peptides are understood to include any string of amino acids and may comprise portions of a protein sequence. Nucleic acid includes those sequences derived from a biological or environmental source and can be one or more of a gene, a regulatory sequence, intergenic sequence, genomic DNA, plasmid DNA, cDNA, or any of the various known forms of RNA. As is outlined herein, the electroporation target may take any of the foregoing forms, although in a preferred embodiment, the electroporation target constitutes a nucleic acid for transfecting primary cells or cell line.

As used herein, the term "primary cell" is intended to denote cells isolated directly from the tissue or bodily fluid of an organism that, without intervention, have a finite lifespan and limited in vitro expansion capacity using standard cell culture techniques. Primary cells are typically not associated with homogenous genotypic and phenotypic characteristics. In contrast to primary cells, the term "cell line" is intended to include those cells that that have acquired homogenous genotypic and phenotypic characteristics (e.g., from continual passaging over a long period of time). As known by those having skill in the art, cell lines include finite or continuous cell lines. An immortalized or continuous cell line has acquired the ability to proliferate indefinitely, either through genetic mutations or artificial modifications.

The term "sealing member," as used herein, is intended to include any structural element or mechanism known in the art that facilitates, forms, or acts to seal the junction between two surfaces. The sealing members disclosed herein preferably include O-rings or other gaskets that selectively allow the disclosed and associated electroporation cartridges to act as a functionally closed environment. The O-rings or similar gaskets provided within the scope of this disclosure can be made of or include any suitable material known in the art, including by way of example and not limitation, a non-conductive material, such as rubber or silicone.

Various aspects of the present disclosure, including devices, systems, and methods may be illustrated with reference to one or more embodiments or implementations, which are exemplary in nature. As used herein, the term "exemplary" means "serving as an example, instance, or illustration," and should not necessarily be construed as preferred or advantageous over other embodiments disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the following description.

As used in the specification, a word appearing in the singular encompasses its plural counterpart, and a word appearing in the plural encompasses its singular counterpart, unless implicitly or explicitly understood or stated otherwise. Thus, it will be noted that, as used in this specification and the appended claims, the singular forms "a," "an" and "the" include plural referents unless the context clearly dictates otherwise. For example, reference to a singular referent (e.g., "a widget") includes one, two, or more referents unless implicitly or explicitly understood or stated otherwise. Similarly, reference to a plurality of referents should be interpreted as comprising a single referent and/or a plurality of referents unless the content and/or context clearly dictate otherwise. For example, reference to referents in the plural form (e.g., "widgets") does not necessarily require a plurality of such referents. Instead, it will be appreciated that independent of the inferred number of referents, one or more referents are contemplated herein unless stated otherwise.

As used herein, directional terms, such as "top," "bottom," "left," "right," "up," "down," "upper," "lower," "proximal," "distal," "adjacent," and the like are used herein solely to indicate relative directions and are not otherwise intended to limit the scope of the disclosure and/or claimed invention.

SUMMARY OF EXEMPLARY EMBODIMENTS

An itemized list of some non-limiting exemplary embodiments of the disclosure are provided below:

1. An electroporation cartridge, comprising: an electroporation chamber defined by an elongate body; a first electrode disposed at a proximal end of the electroporation chamber; and a second electrode disposed at an opposite, distal end of the electroporation chamber, wherein at least one of the first electrode or the second electrode is moveable between a capped position for electroporation and an uncapped position for loading a sample and/or the electroporation cartridge is configurable between sealed and unsealed states.
2. The electroporation cartridge of item 1, wherein the elongate body is made of or includes one or more of a non-conductive plastic, glass, or ceramic and is configured to receive a cell-containing liquid to be electroporated within the electroporation chamber defined by the elongate body.
3. The electroporation cartridge of item 2, wherein the electroporation chamber is made of or comprises glass and/or ceramic.
4. The electroporation cartridge of item 2 or item 3, wherein the electroporation chamber is made of or comprises polycarbonate or other non-conductive irradiation-stable plastic.
5. The electroporation cartridge of any one of items 1-4, wherein at least a portion of the electroporation chamber is tapered between the first electrode and the second electrode.
6. The electroporation cartridge of item 5, wherein the tapered portion of the electroporation chamber does not substantially interfere with generation of a uniform electric field between the first and second electrodes.
7. The electroporation cartridge of any one of items 1-6, wherein the electroporation chamber comprises a uniform cross section along a length of the reaction chamber.
8. The electroporation cartridge of item 7, wherein the uniform cross section extends an entire length of the electroporation chamber between the first and second electrodes such that the electroporation cartridge is configured to produce a uniform electric field within the electroporation chamber disposed between the first and second electrodes.
9. The electroporation cartridge of item 7 or item 8, wherein the electroporation chamber comprises a cylindrical cavity and the uniform cross section comprises a circle.
10. The electroporation cartridge of any one of items 1-7, further comprising a proximal sidewall defined between a proximal opening of the elongate body and an inflection point of the sidewall defining the electroporation chamber, wherein the proximal sidewall narrows from a first diameter defined by the proximal opening to a second, smaller diameter defined at a position distal to the inflection point.
11. The electroporation cartridge of any one of items 1-10, wherein the first electrode comprises a bulbous extension having a substantially flat distal surface.
12. The electroporation cartridge of any one of items 1-10, wherein the first electrode comprises a bulbous extension having a distal surface with a convex or angled contour.
13. The electroporation cartridge of item 11 or item 12, wherein the bulbous extension is separated from a base portion of the first electrode by a narrow stem.
14. The electroporation cartridge of any one of items 11-13, wherein the bulbous extension is operable to displace one or more bubbles associated with a cell-containing liquid to be electroporated within the electroporation chamber upon securing the first electrode within the electroporation chamber.
15. The electroporation cartridge of any one of items 1-14, further comprising a sealing member disposed between the first electrode and a proximal surface of the elongate body, the sealing member operable to form a fluid tight connection between the first electrode and the elongate body.
16. The electroporation cartridge of item 15, wherein the first electrode comprises a first electrode flange and the elongate body comprises a proximal body flange, the proximal body flange oriented in a plane substantially parallel to the first electrode flange, the sealing member being disposed between the first electrode flange and the proximal body flange, forming the fluid tight connection therebetween.
17. The electroporation cartridge of any one of items 1-16, wherein the first electrode is operable to configure the electroporation cartridge between sealed and unsealed states.
18. The electroporation cartridge of item 17, wherein the first electrode is operable to configure the electroporation cartridge between sealed and unsealed states without an additional removable cap piece.
19. The electroporation cartridge of item 17 or item 18, wherein the first electrode is a removable cap.
20. The electroporation cartridge of any one of items 1-17, further comprising a removable cap secured to the first electrode, the removable cap comprising a coupling member for selectively securing the first electrode to the elongate body.
21. The electroporation cartridge of any one of items 1-20, wherein a diameter of a proximal end of the second electrode is substantially equal to a cross section of the electroporation chamber.
22. The electroporation cartridge of any one of items 1-21, wherein the second electrode comprises a protruding portion that extends into the electroporation chamber from a distal end of the elongate body.
23. The electroporation cartridge of item 22, wherein a circumference of the protruding portion comprises a complementary shape of an inner surface of the elongate body defining the electroporation chamber.
24. The electroporation cartridge of any item 22 or item 23, wherein the second electrode additionally comprises a first sealing member disposed between the second electrode and a distal surface of the elongate body, the first sealing member operable to form a fluid tight connection between the second electrode and the distal surface of the elongate body.
25. The electroporation cartridge of item 24, wherein the second electrode comprises an electrode flange and the elongate body comprises a distal body flange, the distal body flange oriented in a plane substantially parallel to the electrode flange, the sealing member being disposed between the electrode flange and the distal body flange, forming the fluid tight connection therebetween.
26. The electroporation cartridge of any one of items 22-25, wherein the second electrode additionally comprises a second sealing member disposed about the protruding portion of the second electrode and positioned distal to the proximal surface of the second electrode, the second sealing member operable to form a fluid tight connection between the protruding portion and an inner surface of the elongate body defining the electroporation chamber.

27. The electroporation cartridge of any one of items 22-26, wherein the proximal surface of the second electrode comprises a flat, uniform surface.
28. The electroporation cartridge of any one of items 22-27, wherein the proximal surface of the second electrode is orthogonal to a longitudinal axis of the electroporation chamber.
29. The electroporation cartridge of any one of items 1-28, further comprising a fixing pin associated with the second electrode and configured to secure the second electrode to the elongate body.
30. The electroporation cartridge of item 29, wherein the second electrode defines a channel configured in size and shape to receive the fixing pin, the channel being aligned with a pair of apertures defined by the sidewall of the elongate body and configured to receive the fixing pin, thereby securing the second electrode at a fixed position relative to the elongate body.
31. The electroporation cartridge of item 30, wherein the channel is formed through a central region of the protruding portion of the second electrode distal to the first sealing member and/or second sealing member.
32. The electroporation cartridge of any one of items 1-31, wherein a volume of the electroporation chamber is less than about 5 mL, preferably less than about 3 mL, more preferably less than about 1 mL or between about 100 μL-1 mL.
33. The electroporation cartridge of any one of items 1-32, further comprising a volume reducing sleeve configured in size and shape to fit within the electroporation chamber.
34. The electroporation cartridge of item 33, wherein the volume reducing sleeve defines a secondary electroporation chamber having a smaller volume than the electroporation chamber.
35. The electroporation cartridge of item 33 or item 34, wherein the volume reducing sleeve comprises a distal opening configured to interface with the second electrode when secured within the electroporation chamber.
36. The electroporation cartridge of any one of items 33-35, wherein the volume reducing sleeve comprises air vents disposed adjacent to the proximal end of the volume reducing sleeve that are configured to allow air to pass therethrough during introduction or extraction of the volume reducing sleeve with the electroporation chamber, thereby preventing formation of a vacuum between the secondary electroporation chamber and the electroporation chamber, thereby allowing the electroporated cell-containing fluid to fill the secondary electroporation chamber upon introduction of the volume reducing sleeve and to exit the secondary electroporation chamber upon introduction upon extraction of the volume reducing sleeve.
37. The electroporation cartridge of any one of items 33-36, wherein the volume reducing sleeve includes a radial sealing member configured to secure the volume reducing sleeve within the electroporation chamber.
38. The electroporation cartridge of item 37, wherein the radial sealing member forms a fluid tight seal with the sidewall defining the electroporation chamber to prevent leakage of cell containing fluid within the secondary electroporation chamber through the distal opening of the volume reducing sleeve.
39. The electroporation cartridge of any one of items 33-38, wherein the first electrode is configured to selectively associate with and form a fluid tight seal with the volume reducing sleeve.
40. The electroporation cartridge of any one of items 33-39, wherein a space is defined between an outer surface of the volume reducing sleeve and the inner sidewall of the elongate body, forming a fluid overfill space configured to receive a volume of overfill displaced by the first electrode upon sealing the electroporation chamber.
41. The electroporation cartridge of any one of items 1-40, further comprising a fluid overfill space associated with a proximal region of the electroporation chamber and configured to receive a volume of overfill displaced by the first electrode upon sealing the electroporation chamber.
42. The electroporation cartridge of any one of items 1-41, further comprising one or more springs longitudinally disposed on a proximal side of the elongate body and configured to situate the first electrode a distance away from the electroporation chamber in the uncapped position.
43. The electroporation cartridge of item 42, wherein the electroporation cartridge being in the capped position configures the one or more springs to be compressed and the first electrode to be disposed within the electrode chamber and operable to electroporate a cell-containing fluid disposed therein.
44. The electroporation cartridge of any one of items 1-43, wherein the electroporation cartridge comprises a flow-through electroporation cartridge.
45. The electroporation cartridge of item 44, further comprising a port associated with the first electrode, the port defining a lumen within the first electrode such that the lumen is fluidically connected to the electroporation chamber.
46. The electroporation cartridge of item 44, further comprising a port associated with a proximal portion of the elongate body, the port configured to exhaust displaced air from the electroporation chamber when the electroporation chamber is being filled and/or introduce filtered or purified air into the electroporation chamber when the electroporation chamber is being drained.
47. The electroporation cartridge of any one of items 44-46, further comprising a chamber inlet and a chamber outlet, each of the chamber inlet and chamber outlet being fluidically connected to the electroporation chamber.
48. The electroporation cartridge of item 47, wherein one or more of the chamber inlet or chamber outlet is disposed above a proximal surface of the second electrode.
49. The electroporation cartridge of item 47 or item 48, wherein a lumen of the chamber inlet and/or chamber outlet is substantially parallel to the proximal surface of the second electrode.
50. The electroporation cartridge of any one of items 47-49, wherein one or more of the chamber inlet or chamber outlet is associated with a plug and/or valve to control an inward flow of cell-containing fluid to be electroporated within the electroporation chamber and/or to control an outward flow of electroporated cell-containing fluid from the electroporation chamber.
51. The electroporation cartridge of any one of items 44-50, further comprising a fluid overfill space associated with the first electrode and/or the elongate body, the fluid overfill space configured to receive a volume of overfill displaced from the electroporation chamber when filling the electroporation chamber.

52. The electroporation cartridge of any one of items 44-50, further comprising a fluid overfill space associated with a sealing cap, the fluid overfill space configured to receive a volume of overfill displaced from the electroporation chamber when sealing the electroporation chamber with the sealing cap.
53. An electroporation system configured to provide flow-through electroporation of a sample, the electroporation system comprising: a modular casing having a plurality of compartments for holding and arranging a plurality of electroporation system components, the electroporation system components including: one or more pumps configured for moving the sample through the system; an electroporation compartment configured to receive a flow-through electroporation cartridge configured for holding a sub-volume of the sample within an electroporation chamber for electroporation of the sub-volume; and tubing having an inlet end and an outlet end, the tubing being routed through the casing so as to fluidically connect the plurality of electroporation system components.
54. The electroporation system of item 53, further comprising a bag compartment configured for receiving and supporting an input bag and/or output bag.
55. The electroporation system of item 54, wherein the bag compartment comprises an insert that is slidably connected to the bag compartment so as to be capable of being selectively drawn out from the casing or enclosed within the casing.
56. The electroporation system of item 55, wherein the bag compartment comprises one or more magnetic latches for holding the bag compartment in an enclosed position within the casing.
57. The electroporation system of any one of items 53-56, further comprising a cooling module in thermal contact with the electroporation chamber and configured to regulate the temperature of the electroporation chamber.
58. The electroporation system of item 57, wherein the cooling module comprises a ceramic block.
59. The electroporation system of item 57 or 58, wherein the cooling module is cooled via thermoelectric cooling.
60. The electroporation system of any one of items 53-59, further comprising a mixer reservoir disposed downstream of the inlet and upstream of the electroporation cartridge, the mixer reservoir comprising a mixing element configured to provide mixing to a portion of the sample contained within the mixing reservoir.
61. The electroporation system of item 60, wherein the mixing element comprises a mixing blade.
62. The electroporation system of item 60 or 61, wherein the mixer reservoir includes a mixer magnet assembly mechanically coupled to the mixing element, the mixer magnet assembly being disposed so as not to contact the portion of the sample contained within the mixer reservoir.
63. The electroporation system of item 62, further comprising a mixer driver having a magnet magnetically coupled to the mixer magnet assembly and configured to indirectly drive rotation of the mixer magnet assembly via magnetic connection to the mixer magnetic assembly.
64. The electroporation system of item 62 or 63, wherein the mixer reservoir comprises a cover, and wherein the mixer magnet assembly is disposed at or near the cover.
65. The electroporation system of any one of items 60-64, further comprising a sample input assembly configured to aid in transfer of sample between an input and the mixer reservoir, the sample input assembly including a main section of tubing disposed between the input and the mixer reservoir, and an intermediate section of tubing pneumatically coupled to the main section of tubing and extending therefrom to a terminal end having access to air, the intermediate section thereby allowing passage of air into the main section of tubing upon sufficient pressure drop in the main section of tubing.
66. The electroporation system of item 65, wherein the terminal end of the intermediate section couples to an air reservoir that has a variable volume, and wherein the sample input assembly is configured to detect a threshold reduction of the variable volume to thereby determine that the sample has been moved into the mixer reservoir.
67. The electroporation system of item 66, wherein the sample input sensor assembly comprises a syringe having a barrel and a plunger disposed within the barrel, the variable volume being defined by the position of the plunger within the barrel and the threshold reduction of the variable volume being detected as a result of movement of the plunger.
68. The electroporation system of any one of items 53-67, further comprising a chamber sealing assembly operatively coupled to the electroporation chamber and configured to regulate pressure within the electroporation chamber during electroporation and thereby limit bubble formation.
69. The electroporation system of item 68, wherein the chamber sealing assembly comprises one or more linear actuators configured to advance plungers toward or retract plungers away from the electroporation chamber to thereby regulate pressure within the electroporation chamber.
70. The electroporation system of any one of items 53-69, further comprising a pre-cooling assembly disposed upstream of the electroporation chamber and configured for cooling a sub-volume of the sample prior to electroporation of the sub-volume.
71. The electroporation system of item 70, wherein the pre-cooling assembly comprises a cooling block and a section of tubing disposed within or adjacent to the cooling block.
72. The electroporation system of item 70 or 71, wherein the cooling block of the pre-cooling assembly is cooled via thermoelectric cooling.
73. The electroporation system of any one of items 70-72, wherein the pre-cooling assembly comprises a flexible biasing element that biases the cooling block against the section of tubing disposed adjacent the cooling block.
74. The electroporation system of any one of items 53-73, further comprising at least one flow sensor, wherein the at least one flow sensor is disposed between the mixer reservoir and the electroporation chamber.
75. The electroporation system of item 74, wherein the flow sensor is an ultrasonic sensor.
76. The electroporation system of item 74 or 75, the flow sensor comprising an actuatable trigger that when actuated, positions a corresponding section of tubing within the flow sensor for detection of flow through the section of tubing.

77. The electroporation system of any one of items 53-76, further comprising one or more flow indicators that route a corresponding section of tubing to a position on an exterior of the casing to enable visualization of flow through the section of tubing.
78. The electroporation system of any one of items 53-77, wherein the casing includes one or more handles.
79. The electroporation system of item 78, wherein the one or more handles include a handle having a catch configured to engage with an instrument panel to attach the instrument panel to the casing.
80. The electroporation system of any one of items 53-79, further comprising an electroporation cartridge attachment feature coupled to the electroporation cartridge, the attachment feature including a flexible biasing element that biases the electroporation cartridge toward a cooling module integrated within the casing.
81. The electroporation system of any one of items 53-80, further comprising a capping mechanism configured to engage with the electroporation cartridge, wherein the electroporation cartridge comprises a first electrode and a second electrode, each disposed at opposite ends of an electroporation chamber, wherein at least one of the first electrode or second electrode is engageable with the capping mechanism and is moveable between a capped position for electroporation and an uncapped position for venting as a result of actuation of the capping mechanism.
82. The electroporation system of item 81, wherein the electroporation cartridge comprises a spring mechanism that allows for overtravel of the capping mechanism relative to displacement of the electrode moved as a result of actuation of the capping mechanism.
83. The electroporation system of any one of items 53-81, wherein the electroporation chamber comprises a chamber inlet and a chamber outlet, wherein the chamber outlet is coupled to an outlet plunger moveable between an advanced position that prevents outflow of the sub-volume from the electroporation chamber and a retracted position that allows outflow of the sub-volume from the electroporation chamber.
84. The electroporation system of any one of items 53-83, wherein the electroporation cartridge comprises one or more bellows structures each configured to encase a moveable component of the electroporation chamber.
85. The electroporation system of any one of items 53-84, wherein the electroporation chamber comprises the flow-through electroporation cartridge as in any one of items 44-52.
86. The electroporation system of any one of items 53-85, further comprising an electroporation assembly electrically coupled to the electroporation chamber, the electroporation assembly comprising a conductivity sensor for measuring conductivity across the electroporation chamber, the electroporation assembly being communicatively coupled to a controller having one or more processors and one or more hardware storage devices.
87. The electroporation system of item 86, wherein the one or more hardware storage devices have stored thereon computer-executable instructions that when executed by the one or more processors configure the controller to perform at least the following: determine, by way of the conductivity sensor, the conductivity of the sub-volume within the electroporation chamber; based on the determined conductivity, determine a voltage drop across the electroporation chamber; and charge a capacitor, which is in an electroporation circuit with the electroporation chamber, to a voltage level above the determined voltage drop across the electroporation chamber to compensate for other voltage drops between the capacitor and the electroporation chamber.
88. The electroporation system of item 86 or 87, wherein the one or more hardware storage devices have stored thereon computer-executable instructions that when executed by the one or more processors configure the controller to perform at least the following: determine, by way of the conductivity sensor, the conductivity of the sub-volume within the electroporation chamber; determine a predicted temperature increase of the sub-volume based on the determined conductivity, an intended pulse voltage, and an intended pulse duration; and if the predicted temperature increase leads to a temperature of the sub-volume that is greater than a predetermined threshold temperature, perform one or more of: send an ark risk alert; and/or withdraw the sample sub-volume to preserve the sample sub-volume, and/or tune cooling accordingly to decrease temperature of the electroporation chamber.
89. The electroporation system of item 88, wherein the computer-executable instructions further configure the controller to determine an initial temperature of the sub-volume within the electroporation chamber by correlating the determined conductivity to a temperature.
90. The electroporation system of any one of item 86-89, wherein the one or more hardware storage devices have stored thereon computer-executable instructions that when executed by the one or more processors configure the controller to perform at least the following: determine, by way of the conductivity sensor, the conductivity of the sub-volume within the electroporation chamber; and if the determined conductivity falls below a pre-determined threshold indicative of the presence of one or more bubbles within the electroporation chamber, to drain the sub-volume from the electroporation chamber.
91. The electroporation system of any one of items 53-90, further comprising a controller having one or more processors and one or more hardware storage devices, wherein the one or more hardware storage devices have stored thereon computer-executable instructions that when executed by the one or more processors configure the controller to iteratively ramp charger voltage based on a previous input voltage and a corresponding previous measured actual voltage applied to the electroporation chamber.
92. The electroporation system of any one of items 74-91, further comprising a controller having one or more processors and one or more hardware storage devices, wherein the one or more hardware storage devices have stored thereon computer-executable instructions that when executed by the one or more processors configure the controller to determine a step volume to be moved by the system between each electroporation event, the calibration being carried out by performing at least the following: determine a number, N, of revolutions of a drive pump required to move a sample volume sufficient to fill the tubing disposed between the flow sensor and the electroporation chamber, as well as fully filling the electroporation chamber, the number, N, representing the volume between the flow sensor and the outlet of the electroporation chamber; cause the electroporation chamber to be drained; cause the drive pump to reverse the sample by a fixed number, k, of revolutions to a point upstream of the flow sensor, the fixed number, k, representing the volume between the point upstream of the flow sensor and the inlet of the electroporation chamber; determine a number, x, of revolutions of the drive pump required to move the sample from the point upstream of the flow sensor to the flow sensor, the number, x, representing the volume between the point upstream of the flow sensor and the flow sensor, and the number, (k−x), representing the volume between the flow sensor and the inlet of the electroporation chamber; and determine the volume between the inlet and outlet of the electroporation chamber as N−(k−x), and set this volume as the step volume.

93. The electroporation system of any one of items 53-92, further comprising a safety door configured to mechanically open the electroporation circuit to prevent voltage discharge while the safety door is open.

94. The electroporation system of any one of items 53-93, wherein the capacitor circuit comprises one or more discharge resistors so as to discharge the capacitor when the capacitor circuit is not electrically connected to the electroporation cartridge.

95. The electroporation system of any one of items 74-91, further comprising a controller having one or more processors and one or more hardware storage devices, wherein the one or more hardware storage devices have stored thereon computer-executable instructions that when executed by the one or more processors configure the controller to determine a step volume to be moved by the system between each electroporation event, the calibration being carried out by performing at least the following:

perform a first fill of the electroporation chamber by monitoring a drop in the electrical resistance of a sample fluid in the electroporation chamber during the first fill from several thousand ohms to a stable value in the range of from about 600-800 ohms, stopping the first fill when the stable value of resistance is reached;

gross filling the electroporation chamber for the second fill based on a calculated value, such as $N_{rev}$ from the peristaltic pump;

measuring the electrical resistance after capping the top electrode after the second fill; if the electrical resistance is within the stable value range determine from the first fill, then the second fill is complete and one can proceed to electroporate the sample;

if the electrical resistance is not within the stable value range determine from the first fill, then uncap the top electrode and fine fill by an additional $n_{rev}$ amount;

measuring the electrical resistance after capping the top electrode after the fine fill; if the electrical resistance is within the stable value range as determined from the first fill, then the second fill is complete and one can proceed to electroporate the sample;

if not repeat the fine fill and measuring the electrical resistance steps above till the electrical resistance is within the stable value range as determined from the first fill, subsequent fills (third fill, fourth fill and so on) are done for pump revolutions of $N_{rev}$+$n_{rev}$ x (where x is equal to the number of tries of the fine fill).

96. The system of item 95, wherein the stable value of electrical resistance is about 700 ohms.

97. The system of item 95, wherein the step of gross filling the electroporation chamber for the second fill is further based on calculations using one or more parameters such as the inner tube diameter of tubing, the number of rollers of the pump, the diameter of the electroporation chamber, and/or the height of the electroporation chamber.

CONCLUSION

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention itemed. Thus, it should be understood that although the present invention has been specifically disclosed in part by preferred embodiments, exemplary embodiments, and optional features, modification and variation of the concepts herein disclosed may be resorted to by those skilled in the art, and such modifications and variations are considered to be within the scope of this invention as defined by the appended items. The specific embodiments provided herein are examples of useful embodiments of the present invention and various alterations and/or modifications of the inventive features illustrated herein, and additional applications of the principles illustrated herein that would occur to one skilled in the relevant art and having possession of this disclosure, can be made to the illustrated embodiments without departing from the spirit and scope of the invention as defined by the items and are to be considered within the scope of this disclosure.

It will also be appreciated that systems, devices, products, kits, methods, and/or processes, according to certain embodiments of the present disclosure may include, incorporate, or otherwise comprise properties or features (e.g., components, members, elements, parts, and/or portions) described in other embodiments disclosed and/or described herein. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include said features, members, elements, parts, and/or portions without necessarily departing from the scope of the present disclosure.

Moreover, unless a feature is described as requiring another feature in combination therewith, any feature herein may be combined with any other feature of a same or different embodiment disclosed herein. Furthermore, various well-known aspects of illustrative systems, methods, apparatus, and the like are not described herein in particular detail in order to avoid obscuring aspects of the example embodiments. Such aspects are, however, also contemplated herein.

All references cited in this application are hereby incorporated in their entireties by reference to the extent that they are not inconsistent with the disclosure in this application. It will be apparent to one of ordinary skill in the art that methods, devices, device elements, materials, procedures, and techniques other than those specifically described herein can be applied to the practice of the invention as broadly disclosed herein without resort to undue experimentation. All art-known functional equivalents of methods, devices, device elements, materials, procedures, and techniques specifically described herein are intended to be encompassed by this invention.

When a group of materials, compositions, components, or compounds is disclosed herein, it is understood that all individual members of those groups and all subgroups thereof are disclosed separately. When a Markush group or other grouping is used herein, all individual members of the group and all combinations and sub-combinations possible of the group are intended to be individually included in the disclosure. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure.

All changes which come within the meaning and range of equivalency of the items are to be embraced within their scope.

EXAMPLES

The following examples are provided to illustrate implementations of various exemplary embodiments disclosed herein. While a general paradigm or method flow is set forth in the following examples, it is appreciated by those having skill in the art that the disclosed method acts can be altered, excluded, or substituted with alternative or additional acts as known in the art. Accordingly, the following examples are intended to be exemplary in nature and not unnecessarily limiting of the scope and/or content of the disclosure provided herewith.

Example 1

Figure 28:
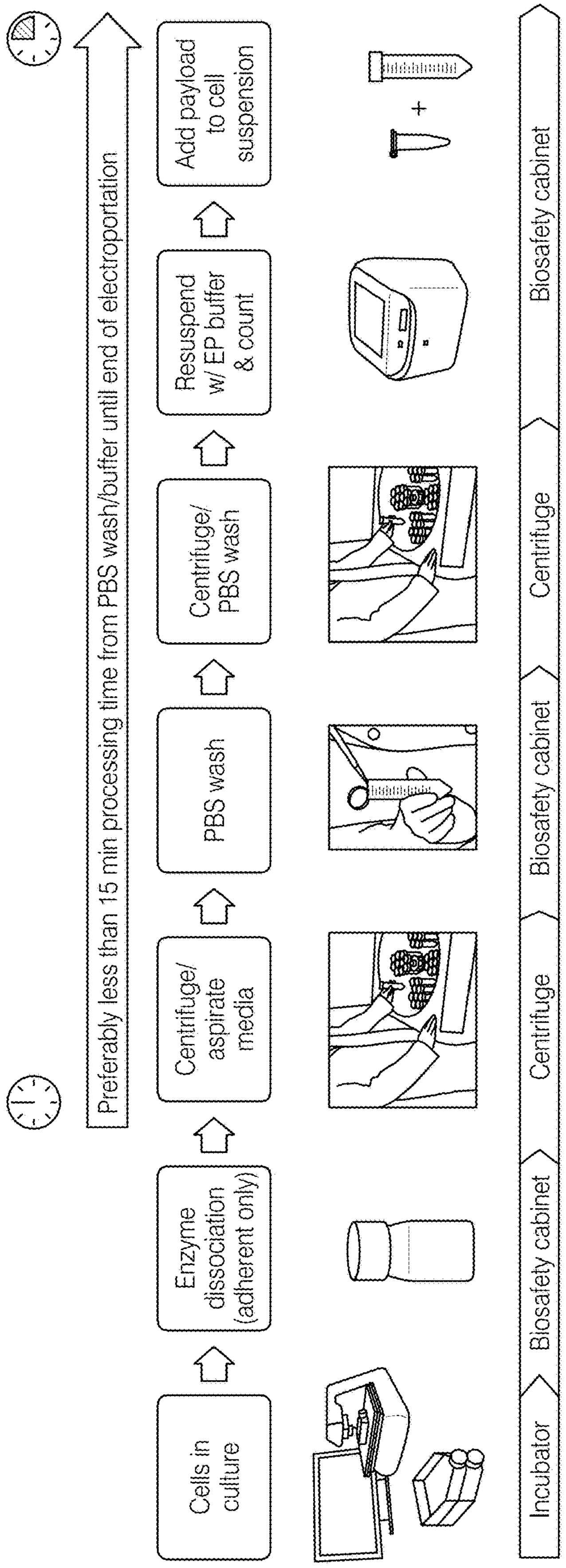
FIG. 28 illustrates an exemplary method flow for preparing cells for transformation via one or more electroporation systems disclosed herein in accordance with one or more embodiments of the present disclosure.
Figure 29A:
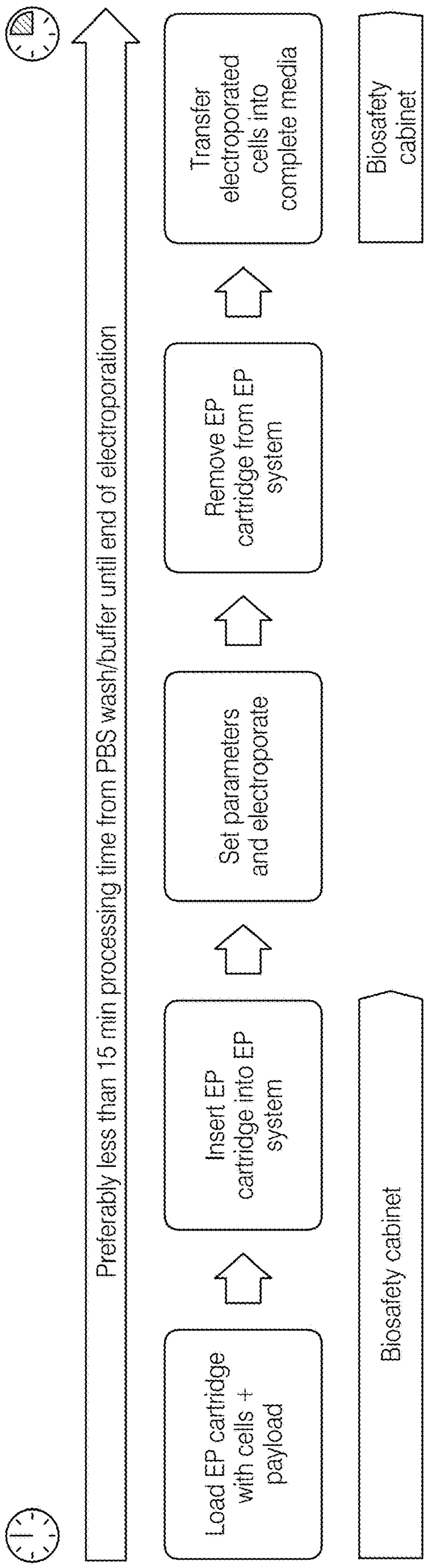
FIG. 29A illustrates an exemplary method flow for batch processing and transformation of cells prepared, for example, by the exemplary method outlined in FIG. 28 and in accordance with one or more embodiments of the present disclosure.
Figure 30A:
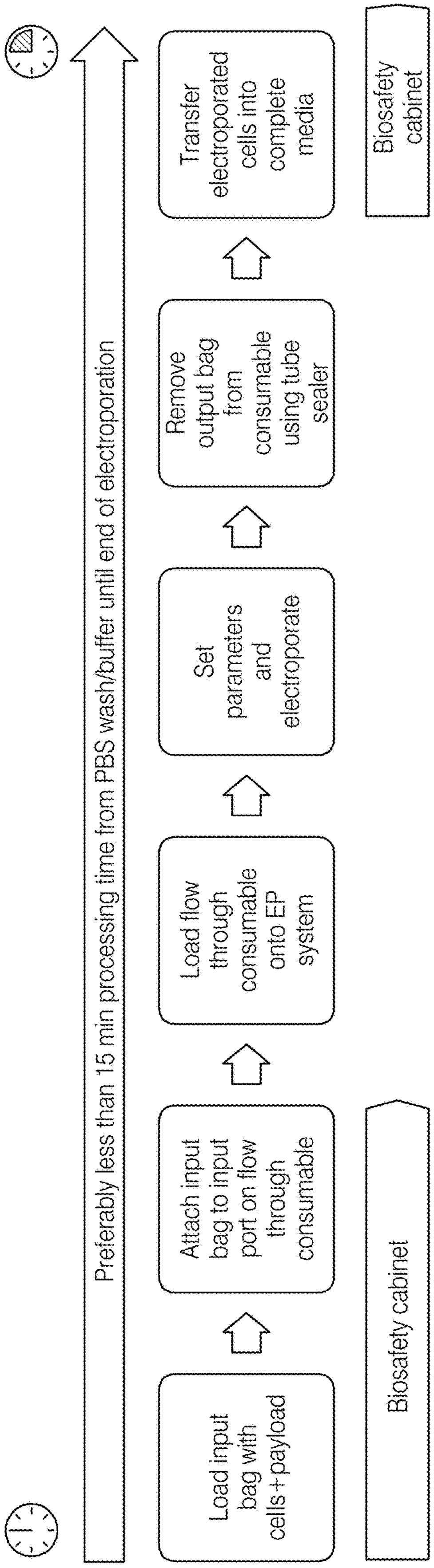
FIG. 30A illustrates an exemplary method for flow through processing and transformation of cells prepared, for example, by the exemplary method outlined in FIG. 28 and in accordance with one or more embodiments of the present disclosure.

To illustrate aspects of the functionality of the cartridges, systems and methods of the disclosure for electroporating cells, exemplary cellular preparation and processing methods were performed, as provided by the illustrative embodiments of FIG. 28, FIG. 29A, and FIG. 30A.

With reference to FIG. 28, illustrated is an exemplary method flow for preparing cells for transformation via a batch or flow-through electroporation system and associated cartridges (as disclosed above). As illustrated, the exemplary pre-electroporation method can include obtaining cultured cells. This can include, for example, expanding a stock of immortalized cell culture cells and/or isolating primary cells from a patient and culturing them in vitro to stabilize the cells prior to electroporation, to expand the cells to confluency, and/or to expand the cells by serial passaging. This act can be performed in an incubator with appropriate growth media, as known in the art.

The method of FIG. 28 additionally includes a gentle enzyme treatment, as known in the art, to release any cells that are adherent to the surface of the growth chamber. This method act can be performed in a sterile environment, such as a biological safety cabinet or other enclosed, ventilated laboratory workspace to reduce the likelihood of contamination.

The method of FIG. 28 further provides acts to remove the growth media and wash the cells with a wash solution (e.g., phosphate buffered saline, (PBS)) followed by resuspension and titration to a desired cellular density. These acts can be accomplished by any method using any materials known and used in the art for such purposes. Of note, however, FIG. 28 provides a canonical approach, including centrifugation and pipette-based washing and resuspension. The cells to be electroporated can be resuspended to a desired concentration by diluting the washed cells in a calculated volume of electroporation buffer (e.g., from a known concentration of cultured cells and/or through use of a cytometer or other cell counting mechanism/system). A "payload" or electroporation target, as that term is defined herein, can be added to the entire volume of resuspended cells or into desired aliquots of appropriate volume for batch or flow-through processing, as described herein.

In the preparation protocol illustrated in FIG. 28, it is noted that with some primary and/or immortalized cell lines, cell viability decreases about 15 minutes after the cells are removed from growth media and/or resuspended in electroporation buffer. As such it is noted that addition of the washed and/or resuspended cells to the electroporation systems and/or cartridges for transformation using the systems and methods disclosed above is preferably carried out within 15 minutes of washing and/or resuspending the cells. It should be appreciated that this time can vary between different cell and buffer types and between processing conditions.

Referring now to FIG. 29A, illustrated is an exemplary protocol for batch processing of processing and transformation of cells prepared, for example, by the exemplary method outlined in FIG. 28 above. As shown in the exemplary electroporation protocol of FIG. 29A, an aliquot or total volume of cells prepared in accordance with the method outlined and discussed with respect to FIG. 28 is loaded into an electroporation (EP) cartridge along with a desired payload or electroporation target. The EP cartridge is inserted into an electroporation system, such as those described herein configured to batch process samples, electroporation parameters are set and executed on the system, and the EP cartridge is removed from the system. The electroporated cells can then be transferred into complete media or other recovery media and incubated for a period of time (e.g., 24-72 hours). The electroporated cells can then be interrogated for viability and electroporation efficiency using an appropriate biochemical, optical, or molecular readout (e.g., Western blot for protein concentration/expression, flow cytometry for expression of transformed fluorescent protein, qPCR for molecular analysis, etc.).

Figure 29B:
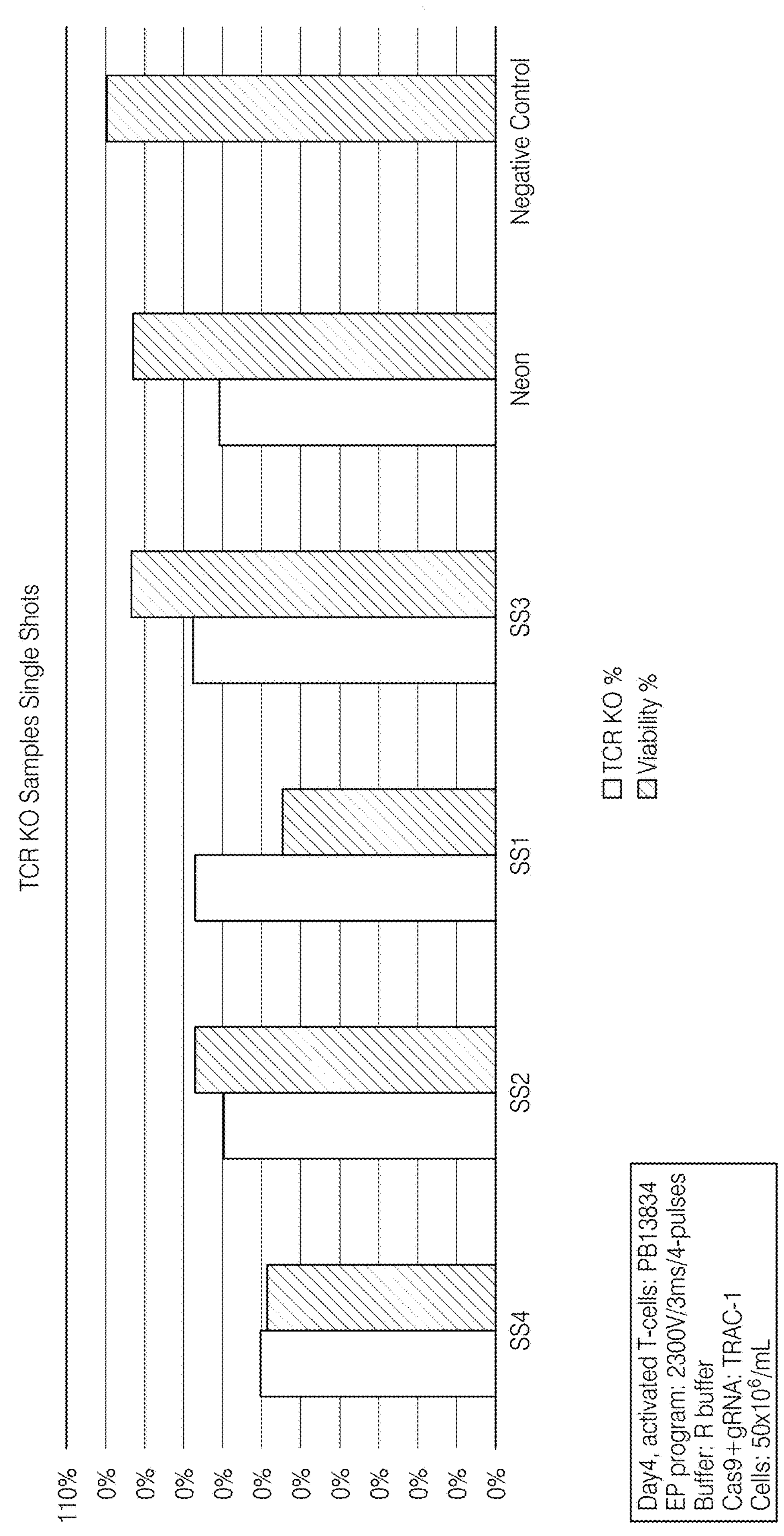
FIG. 29B is a graph illustrating the exemplary viability and transformation efficiency of primary cells prepared according to the protocols outlined in FIGS. 28 and 29A.

For example, as shown in FIG. 29B, primary T cells that were activated using CD3/CD28 Dynabeads™ were cultured for 4 days followed by preparation for electroporation according to the protocols disclosed and illustrated in FIGS. 28 and 29A. The washed primary cells were resuspended to a concentration of $50\times10^6$ cells/mL in R buffer and provided with a payload of Cas9+gRNA targeting TRAC-1. Electroporation was completed using a batch processing method and associated EP cartridge with electroporation parameters of 2300V/3 ms for each of 4 pulses. Following electroporation, the cells were transferred to complete media and incubated for 48 hours. The electroporated cells were then stained with a TCR$\alpha$/$\beta$ antibody and assessed for remaining expression via flow cytometry as compared to non-electroporation control cells (negative control). As shown in FIG. 29B, the transformation efficiency enabled by the disclosed systems were within expected limits as compared to commercially available platforms. Cells were also not significantly affected by electroporation as determined by sytox viability staining, which was also determined via flow cytometry.

Referring now to FIG. 30A, illustrated is an exemplary protocol for flow through processing and transformation of cells prepared, for example, by the exemplary method outlined in FIG. 28 above. As shown in the exemplary electroporation protocol of FIG. 30A, the resuspended cells are transferred or resuspended in an input bag along with a desired payload or electroporation target. The input bag is attached to an input port on a flow through consumable, as described above. The flow through consumable cartridge is then loaded into an electroporation system, such as those flow through electroporation systems described above. Electroporation parameters are set and executed (e.g., using an associated computing system and/or user interface on the electroporation system), and the output bag containing electroporated cells is removed from the consumable cartridge using, for example, a tube sealer. The electroporated cells can then be transferred into complete media or other recovery media and incubated for a period of time (e.g., 24-72 hours). The electroporated cells can then be interrogated for viability and electroporation efficiency using an appropriate biochemical, optical, or molecular readout (e.g., Western blot for protein concentration/expression, flow cytometry for expression of transformed fluorescent protein, qPCR for molecular analysis, etc.).

Figure 30B:
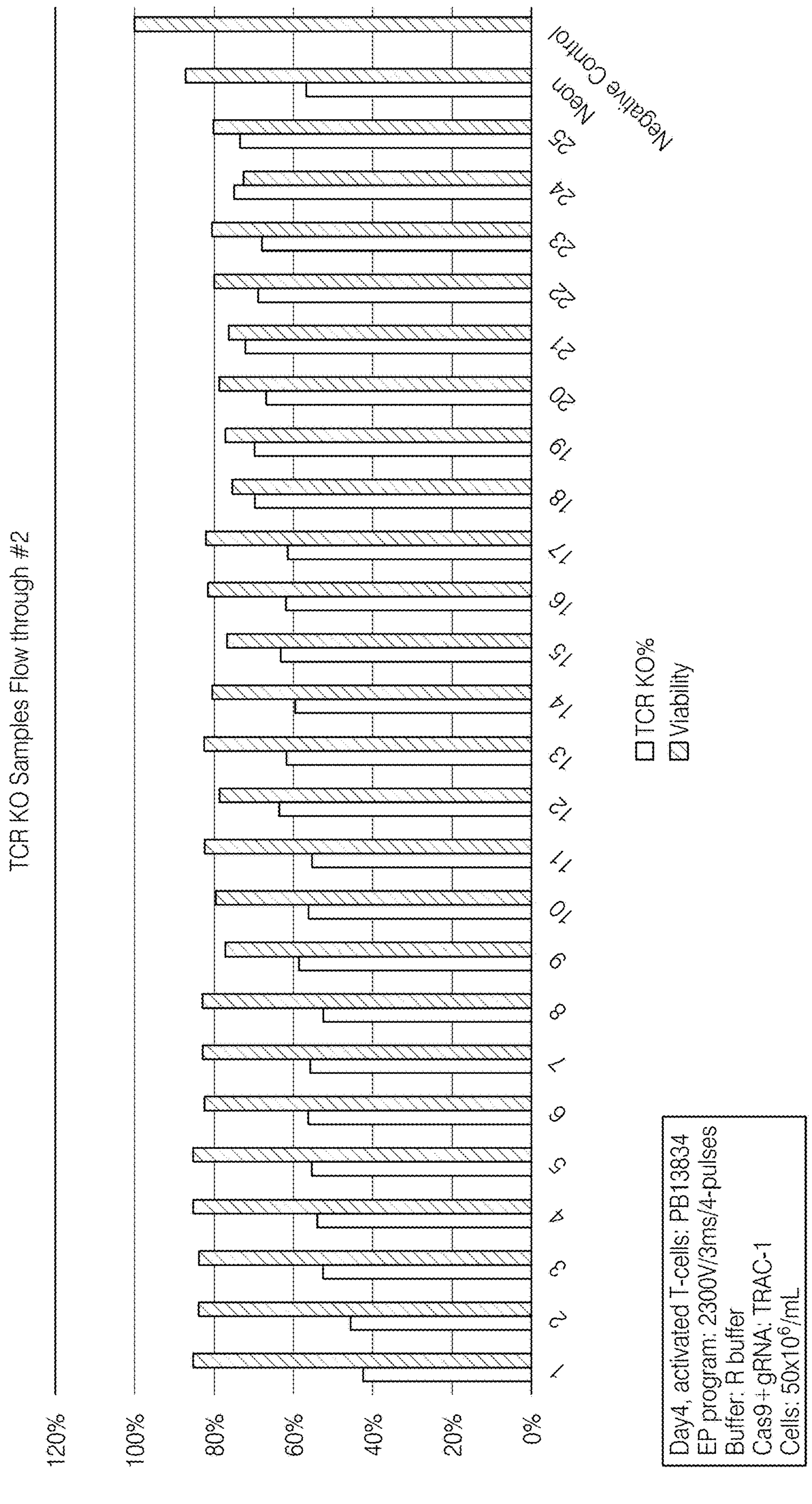
FIG. 30B is a graph illustrating the exemplary viability and transformation efficiency of primary cells prepared according to the protocols outlined in FIGS. 28 and 30A.

For example, as shown in FIG. 30B, primary T cells that were activated using CD3/CD28 Dynabeads™ were cultured for 4 days followed by preparation for electroporation according to the protocols disclosed and illustrated in FIG. 28 and FIG. 30A. The washed primary cells were resuspended to a concentration of $50\times10^6$ cells/mL in R buffer and provided with a payload of Cas9+gRNA targeting TRAC-1. Electroporation was completed using a flow through processing method and associated flow through consumable with electroporation parameters of 2300V/3 ms for each of 4 pulses. Following electroporation of each sample in the automated batch processing (e.g., "flow through" method), the cells were collected to assess variability, if any, between samples. Each isolated sample was transferred to complete media and incubated for 48 hours. The electroporated cells were then stained with a TCRα/β antibody and assessed for remaining expression via flow cytometry as compared to non-electroporation control cells (negative control). The results of each sample in the automated batch processing or flow-through method are shown in FIG. 30B. As clearly illustrated by the data, the transformation efficiency enabled by the disclosed systems were within expected limits as compared to commercially available platforms. Cells were also not significantly affected by electroporation as determined by sytox viability staining, which was also determined via flow cytometry.

Figure 31:
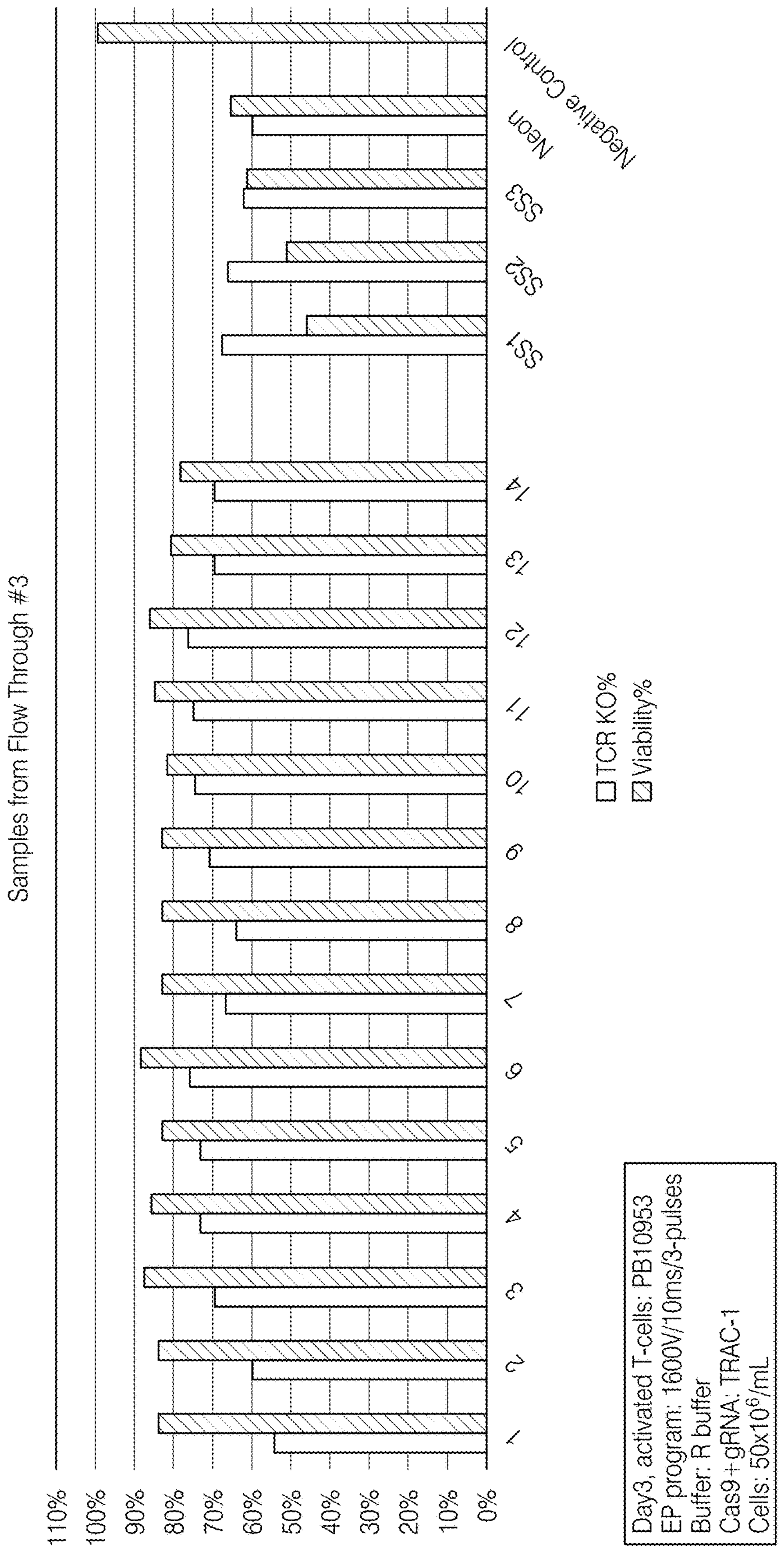
FIG. 31 is a graph illustrating the results of batch and flow through processing and electroporation of primary cells in accordance with one or more embodiments of the present disclosure.

A comparison of cell viability and electroporation efficiency was conducted between single batch processed samples and flow through or automated batch processed samples of the same culture of cells prepared as described above with respect to FIGS. 28, 29A, and 30A. As shown in FIG. 31, the flow through or automated batch processed samples have a greater viability and electroporation efficiency than prior art systems, whereas the single batch processed samples have a similar transformation efficiency and cell viability.

Figure 32:
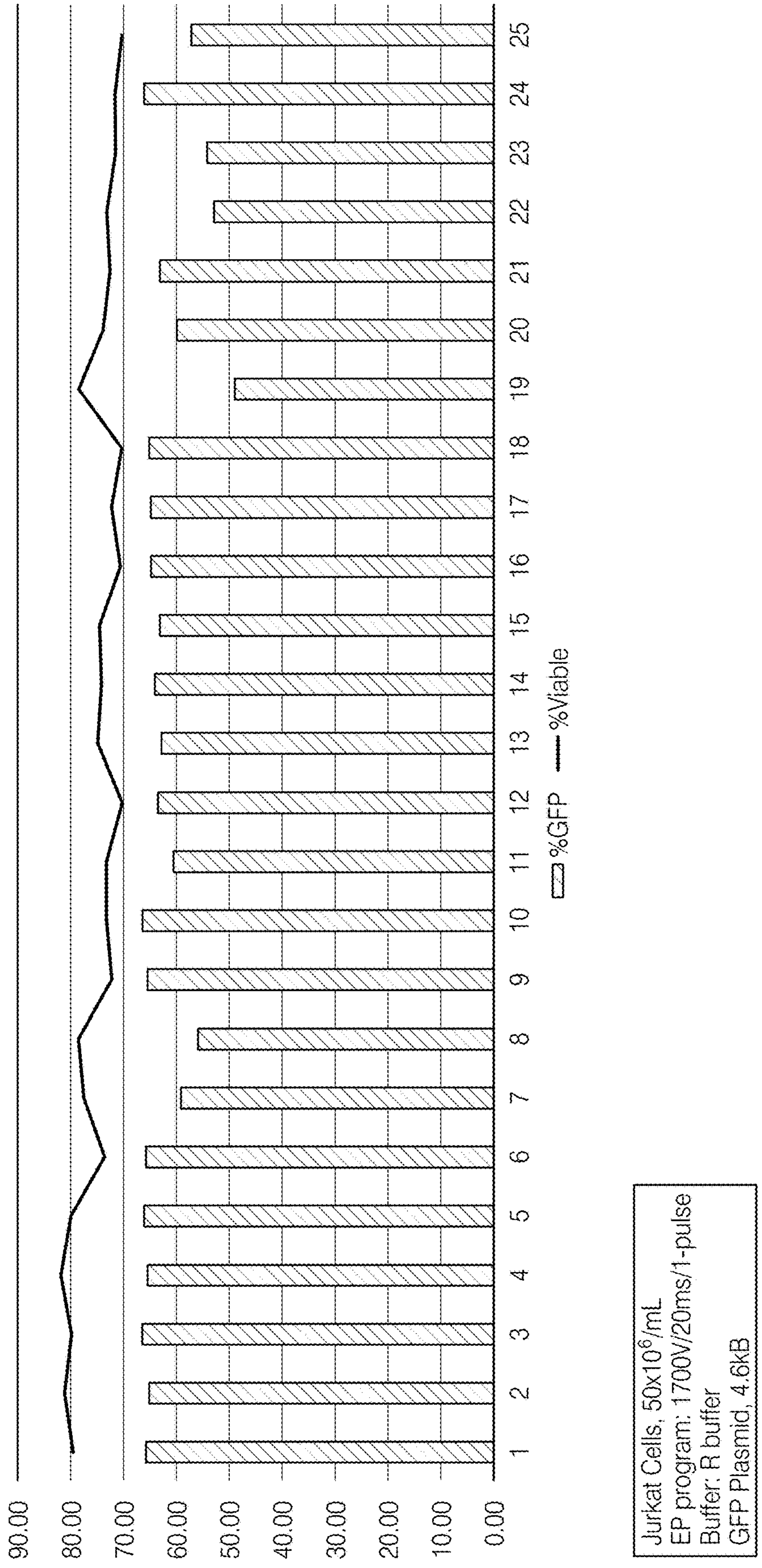
FIG. 32 is a graph illustrating the viability and transformation efficiency of exemplary flow through systems and methods for transforming immortalized cell culture cells via electroporation in accordance with one or more embodiments of the present disclosure.

The disclosed electroporation systems and methods were also shown to work using immortalized cell culture cells. Referring now to FIG. 32, illustrated is a graph showing the viability and transformation efficiency of exemplary flow through systems and methods using Jurkat cells. In particular, Jurkat cells that had been established for 4 passages post thaw were prepared for electroporation according to the protocol outlined in FIGS. 28 and 30A. Electroporation was completed using an exemplary flow through consumable and each individual electroporation was collected to assess variability between samples.

Figure 33:
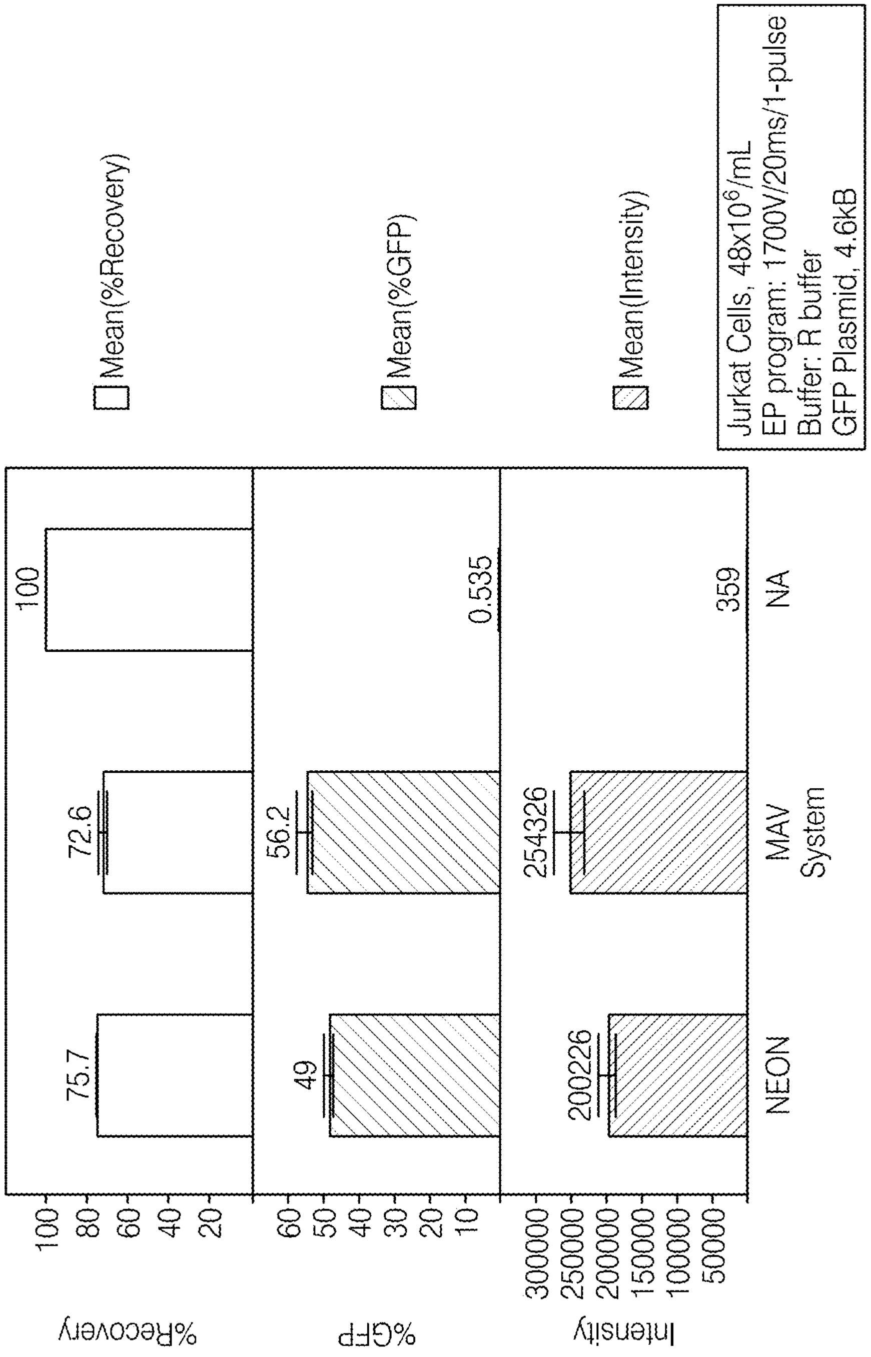
FIG. 33 is a series of graphs providing an exemplary comparison of the transformation efficiency and cell viability of immortalized cell culture cells electroporated using systems and methods disclosed herein versus a prior art electroporation system.

The washed Jurkat cells were resuspended to a concentration of $50\times10^6$ cells/mL in R buffer and provided with a payload of a 4.6 kB GFP plasmid. Electroporation was completed using a flow through processing method and associated flow through consumable with electroporation parameters of 1700V/20 ms for a single pulse. Following electroporation of each sample in the automated batch processing/flow through method, the cells were collected to assess variability, if any, between samples. Each isolated sample was transferred to complete media and incubated for 24 hours. The electroporated cells were then assessed for expression of GFP via flow cytometry as compared to non-electroporation control. The results of each sample in the automated batch processing or flow-through method are shown in FIGS. 32 and 33 (negative control data not shown on FIG. 32). As clearly illustrated by the data, the transformation efficiency enabled by the disclosed systems were within expected limits as compared to commercially available platforms, and the cells were also not significantly affected by electroporation as determined by sytox viability staining, which was also determined via flow cytometry.

Example 2

To illustrate aspects of functionality of electroporation cartridges, instruments, systems and methods of the disclosure for electroporating cells, exemplary cellular preparation and processing methods were performed, as provided by illustrative embodiments described herein.

Cell Source and Culture Conditions: Peripheral blood mononuclear cells (PBMC) were isolated from healthy donor leukopaks using standard Ficoll-Paque methods and cryopreserved. Upon thawing, PBMC were activated with CD3/CD28 Dynabeads™, cultured with OpTmizer™ media containing either 2% human serum or 5% Immune Cell Serum Replacement and maintained at 37 C, 5% $CO_2$. Activated primary human T-Cells were thus generated.

Electroporation: Three-days post activation, cells were prepared for electroporation by centrifugation and resuspended in a standard electroporation buffer or a gene editing buffer. Ribonucleoprotein (RNP) was formed by combining Invitrogen™ TrueCut™ Cas9 Protein v2 and Invitrogen™ TrueGuide™ Synthetic gRNA (from Thermo Fisher Scientific). Prepared cells and RNP were combined, incubated for five minutes, donor DNA template added and then electroporated using the newly developed large-scale electroporation system in a single use cartridge or a flowthrough cartridge of the present disclosure as described below. Cells were returned to complete media immediately after electroporation and cultured for 48-72 hrs. Analysis was performed with Invitrogen™ Attune™ NxT Flow Cytometer (from Thermo Fisher Scientific) with locus specific antibody targets.

In one exemplary embodiment, activated primary human T-cells were generated and electroporated with a Cas9 RNP targeted delivery of a homology directed repair transfection of either a Rab11a and a TRAC locus. Activated primary human T-cells were prepared as described in the method above (under the title Cell Source and Culture Conditions). The activated primary human T-cells were then resuspended with a gene editing buffer under the following conditions: cells=$2\times10^7$ c/mL; Cas9=80 μg/mL; gRNA=20 μg/mL; and dsDNA=80 μg/mL. Cells were immediately electroporated to deliver Cas9:gRNARNP targeting either the Rab11a or TRAC locus and a linear dsDNA template (1.4 kb) encoding for GFP with 100 bp homology arms using either Electroporation Condition A (i.e, 1700V/10 ms/1-pulse) or Electroporation Condition F (i.e., 2300V/3 ms/4-pulses) using the newly developed large-scale electroporation system in a single use cartridge of the present disclosure. Knock-in efficiency (KI efficiency in FIG. 34) and cell viability was analyzed 48-hours post-electroporation via flow cytometry. The results are shown in FIG. 34.

Figure 34:
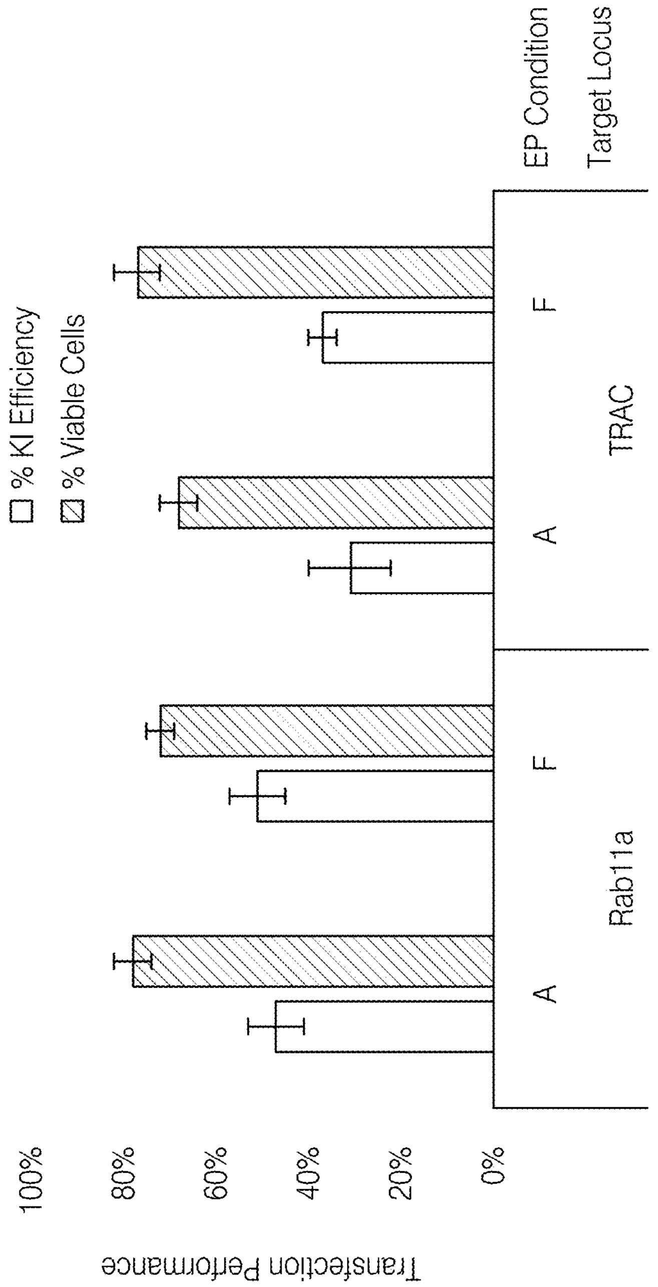
FIG. 34 is a graph illustrating the viability and transformation efficiency for transforming cells with a knock-in gene using an exemplary single use consumable and electroporation systems and methods for via electroporation, in accordance with one or more embodiments of the present disclosure.

FIG. 34 illustrates cell viability, transformation efficiency and knock-in efficiency of the transformed activated primary human T-cells as described above and demonstrates successful use of exemplary single use consumables and electroporation systems and methods for electroporation, in accordance with one or more embodiments of the present disclosure.

In another exemplary embodiment, activated primary human T-cells were generated and electroporated with a Cas9:gRNA RNP targeted delivery a TRAC locus to generate CAR-T cells. Activated primary human T-cells were prepared as described in the method above (under the title Cell Source and Culture Conditions). The activated primary human T-cells were then resuspended with a gene editing buffer under the following reagent conditions: cells=$2.5\times10^7$ c/mL; Cas9=100 μg/mL; gRNA=25 μg/mL; and dsDNA=80 μg/mL. Cells were electroporated to deliver Cas9:gRNA RNP targeting the TRAC locus and a linear dsDNA template (2.8 kb) encoding for an Anti-CD19 CAR with 100 bp homology arms using Electroporation Condition F (2300V/3 ms/4-pulses) both a 1 mL single use electroporation cartridge of the disclosure (described as "small scale EP" in FIG. 35) and in a 1 mL flow-through electroporation cartridge of the disclosure (described as "large scale EP" in FIG. 35). Knock-in efficiency (KI efficiency in FIG. 35) and cell viability was analyzed 96-hours post-electroporation via flow cytometry. The results are shown in FIG. 35.

Figure 35:
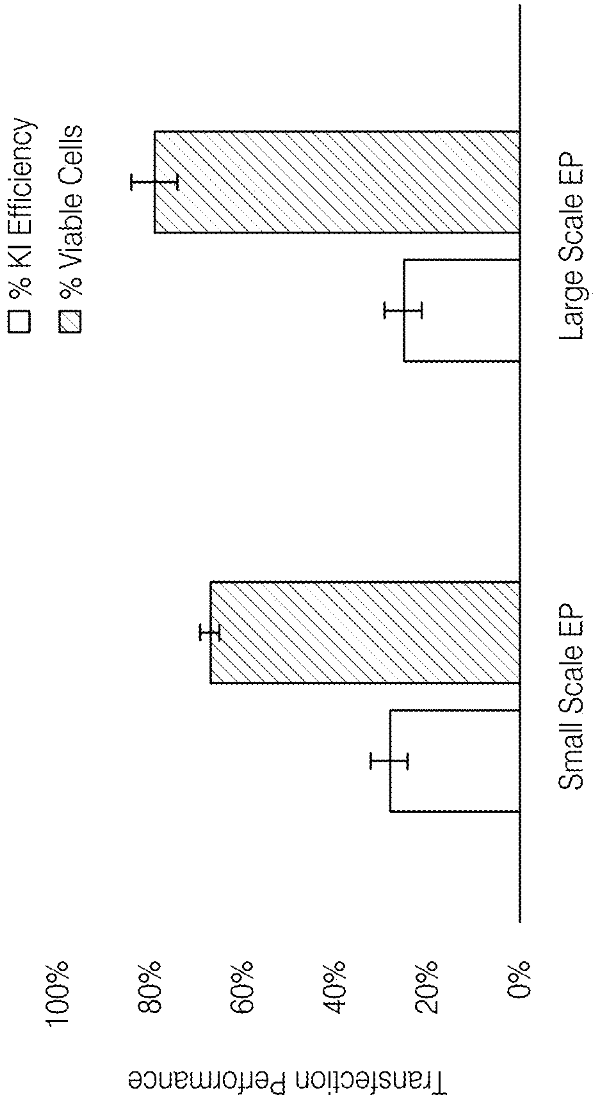
FIG. 35 is a graph illustrating transformation efficiency and cell viability during the generation of CAR-T cells using flow-through and single use cartridges and electroporation systems and methods disclosed herein, in accordance with one or more embodiments of the present disclosure.

FIG. 35 illustrates transformation efficiency, knock-in efficiency, and cell viability during the generation of CAR-T cells using flow-through and single use cartridges and electroporation systems and methods disclosed herein, in accordance with one or more embodiments of the present disclosure.

What is claimed is:

1. An electroporation cartridge, comprising:

an electroporation chamber having an elongate body;

a first electrode disposed at a proximal end of the electroporation chamber;

a second electrode disposed at a distal end of the electroporation chamber opposite the proximal end, wherein the first electrode is moveable from an uncapped position to a capped position, the proximal end of the electroporation chamber being sealed in the capped position;

a fluid overfill space disposed at a proximal region of the electroporation chamber configured to receive a volume of overfill fluid displaced upon moving the first electrode to the capped position; and one or more stabilizers extending from an outer surface of the elongate body of the electroporation chamber that extends between the first and second electrodes, the one or more stabilizers being configured to stabilize the electroporation cartridge in a standing position, facilitate manipulation of the electroporation cartridge, and facilitate positioning of the electroporation cartridge on an electroporation system.

2. The electroporation cartridge of claim 1, wherein the electroporation cartridge comprises 2 stabilizers.

3. The electroporation cartridge of claim 2, wherein the stabilizers comprise one or more feet operable to stabilize a longitudinal axis of the electroporation chamber in a vertical position.

4. The electroporation cartridge of claim 1, wherein the electroporation chamber comprises a uniform cross section along a length of the electroporation chamber.

5. The electroporation cartridge of claim 4, wherein the uniform cross section extends an entire length of the electroporation chamber between the first and second electrodes.

6. The electroporation cartridge of claim 1, wherein the first electrode comprises a bulbous extension having a distal surface with a convex or angled contour configured to contact a sample within the electroporation chamber.

7. The electroporation cartridge of claim 6, wherein the bulbous extension is separated from a base portion of the first electrode by a stem, a sealing member is disposed about the stem and the stem is disposed exterior to the electroporation chamber in the capped position.

8. The electroporation cartridge of claim 1, wherein the proximal surface of the second electrode comprises a flat, uniform surface orthogonal to a longitudinal axis of the electroporation chamber.

9. The electroporation cartridge of claim 1, wherein a volume of the electroporation chamber is less than 5 mL.

10. The electroporation cartridge of claim 1, wherein a volume of the electroporation chamber is less than 3 mL.

11. The electroporation cartridge of claim 1, wherein a volume of the electroporation chamber is less than 1 mL.

12. The electroporation cartridge of claim 1, wherein a volume of the electroporation chamber is between 100 pL to about 1 mL.

* * * * *